US012686668B2

(12) United States Patent
Burgoyne et al.

(10) Patent No.: US 12,686,668 B2
(45) **Date of Patent: *Jul. 21, 2026**

(54) LEUKOTRIENE SYNTHESIS INHIBITORS

(71) Applicant: Naegis Pharmaceuticals Inc., Vancouver (CA)

(72) Inventors: David L. Burgoyne, Delta (CA); Erin DeBruin, Port Coquitlam (CA); Julia Fonarev, Richmond (CA); James Gee Ken Yee, Port Moody (CA); John Michael Langlands, Richmond (CA)

(73) Assignee: Naegis Pharmaceuticals Inc., Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/590,523

(22) Filed: Feb. 28, 2024

(65) Prior Publication Data

US 2025/0011293 A1 Jan. 9, 2025

Related U.S. Application Data

(63) Continuation of application No. 17/420,885, filed as application No. PCT/US2020/013217 on Jan. 10, 2020, now Pat. No. 11,976,052.

(60) Provisional application No. 62/791,641, filed on Jan. 11, 2019.

(51) Int. Cl.
*C07D 277/68* (2006.01)

(52) U.S. Cl.
CPC .................................. *C07D 277/68* (2013.01)

(58) Field of Classification Search
CPC .................................................... C07D 277/68
See application file for complete search history.

(56) References Cited

U.S. PATENT DOCUMENTS

| | | | | |
|---|---|---|---|---|
| 4,661,499 | A | 4/1987 | Young et al. | |
| 5,410,061 | A | 4/1995 | Gilmore et al. | |
| 5,420,131 | A | 5/1995 | Carceller et al. | |
| 5,486,612 | A | 1/1996 | Sawyer | |
| 5,698,567 | A | 12/1997 | Guillonneau et al. | |
| 5,712,274 | A | 1/1998 | Sueoka et al. | |
| 6,277,849 | B1 * | 8/2001 | Zeller .................. | C07D 231/12 514/378 |
| 6,544,979 | B1 | 4/2003 | Snoeck | |
| 2001/0025040 | A1 | 9/2001 | Poppe et al. | |
| 2003/0203946 | A1 | 10/2003 | Behrens et al. | |
| 2004/0198768 | A1 | 10/2004 | Park Choo et al. | |
| 2006/0154931 | A1 | 7/2006 | Verhoest et al. | |
| 2007/0049622 | A1 | 3/2007 | Dimitroff et al. | |
| 2009/0126806 | A1 | 5/2009 | Hamza | |
| 2009/0286778 | A1 | 11/2009 | Combs et al. | |
| 2013/0310555 | A1 | 11/2013 | Chong | |
| 2015/0307497 | A1 | 10/2015 | Sugimoto et al. | |
| 2017/0252352 | A1 | 9/2017 | Chekler et al. | |
| 2018/0311255 | A1 | 11/2018 | Fatheree et al. | |

FOREIGN PATENT DOCUMENTS

| | | | |
|---|---|---|---|
| CN | 104045552 | A | 9/2014 |
| CN | 107383014 | A | 11/2017 |
| DE | 10 2006 021 878 | A1 | 11/2007 |
| JP | 7680955 | B2 | 7/2020 |
| WO | WO-98/14429 | A1 | 4/1998 |
| WO | WO-02/00612 | A1 | 1/2002 |
| WO | WO-02/40445 | A1 | 5/2002 |
| WO | WO-03/061567 | A2 | 7/2003 |
| WO | WO-2004/063147 | A1 | 7/2004 |
| WO | WO-2005/012296 | A1 | 2/2005 |
| WO | WO-2006/105304 | A2 | 10/2006 |
| WO | WO-2007/047397 | A2 | 4/2007 |
| WO | WO-2008/057280 | A1 | 5/2008 |
| WO | WO-2008/100564 | A1 | 8/2008 |
| WO | WO-2008/147782 | A1 | 12/2008 |
| WO | WO-2009/058347 | A1 | 5/2009 |
| WO | WO-2009/126806 | A8 | 10/2009 |
| WO | WO-2009/152288 | A1 | 12/2009 |
| WO | WO-2010/018874 | A1 | 2/2010 |
| WO | WO-2010/088335 | A1 | 8/2010 |
| WO | WO-2014/129796 | A1 | 8/2014 |
| WO | WO-2014/182643 | A2 | 11/2014 |
| WO | WO-2014/198594 | A1 | 12/2014 |
| WO | WO-2015/119998 | A1 | 8/2015 |
| WO | WO-2017/017096 | A1 | 2/2017 |
| WO | WO-2017/035438 | A1 | 3/2017 |

OTHER PUBLICATIONS

Registry No. 871550-08-2, entered in STN on Jan. 10, 2006; retrieved from the Chemical Library in CHEMCATS.*

Extended European Search Report on EP 20738780.4 dated Aug. 30, 2022 (20 pages).

Final Office Action on U.S. Appl. No. 17/420,885 DTD Aug. 31, 2023.

International Search Report and Written Opinion on PCT/US2020/013217 dated May 7, 2020 (18 pages).

Japanese Office Action on JP Patent Appln No. 2021-538484, dated Dec. 19, 2023 (4 pages, including English translation).

Kolasa et al., "Heteroarylmethoxyphenylalkoxyiminoalkylcarboxylic Acids as Leukotriene Biosynthesis Inhibitors", J. Med. Chem., vol. 43, 2000, pp. 690-705.

Luo et al., "Synthesis, Antifungal Activities and Molecular Docking Studies of Benzoxazole and Benzothiazole Derivatives", Molecules, vol. 23, 2018, 16 pages.

Murru et al., "Copper(I)-Catalyzed Cascade Synthesis of 2-Substituted 1,3-Benzothiazoles: Direct Access to Benzothiazolones", Eur. J. Org. Chem., 2009, pp. 5406-5413.

(Continued)

*Primary Examiner* — Shawquia Jackson

(74) *Attorney, Agent, or Firm* — Foley & Lardner LLP

(57) ABSTRACT

Provided are specific leukotriene synthesis inhibitor compounds and pharmaceutical compositions comprising the compounds and methods of using the compounds and the pharmaceutical compositions in treating, for example, inflammatory diseases or conditions.

20 Claims, 6 Drawing Sheets

(56) References Cited

OTHER PUBLICATIONS

Murru, S., et al., "Copper(I)-Catalyzed Cascade Synthesis of 2-Substituted 1,3-Benzothiazoles: Direct Access to Benzothiazolones," J. Org. Chem., 5406-5413 (2009) (8 pages).
Non-Final Office Action on U.S. Appl. No. 17/420,885 DTD Apr. 11, 2023.
Notice of Allowance on U.S. Appl. No. 17/420,885 DTD Nov. 29, 2023.
Palmer et al., "Antimicrobials. 2. Substituted Benzothiazolylbenzylamines and Related Compounds", J. Med. Chem., vol. 14, 1971, pp. 1226-1227.
Search Report and Written Opinion on SG Appl No. 11202107080V, dated Dec. 23, 2022 (11 pages).
Teodozyj Kolasa, et al., "Symmetrical Bis(heteroarylmethoxyphenyl)alkylcarboxylic Acids as Inhibitors of Leukotriene Biosynthesis," Journal of Medicinal Chemistry, vol. 43, No. 17, pp. 3322-3334, Apr. 25, 2000.
Aspiotis et al., "The discovery and synthesis of highly potent subtype selective phosphodiesterase 4D inhibitors", Bioorganic & Medicinal Chemistry Letters, 2010, 20, pp. 5502-5505.
CAS Registry No. 859534-60-4; STN Entry Date Aug. 11, 2005; Ethanone, 1-[2-[6-[4-(1-hydroxyethyl)phenoxy]-2-(2-pyridinyl)-1H-benzimidazol-5-yl]-1-pyrrolidinyl].
STN Registry RN 1208774-22-4 (Mar. 11, 2010).
STN Registry RN 1324554-80-4 (Sep. 28, 2011).
STN Registry RN 1481810-65-4 (Nov. 27, 2013).
STN Registry RN 1488912-40-8 (Dec. 6, 2013).
STN Registry RN 1708518-79-9 (May 20, 2015).
STN Registry RN 1710370-19-6 (May 22, 2015).
STN Registry RN 1775887-41-6 (Jun. 8, 2015).
STN Registry RN 1786658-14-7 (Jun. 23, 2015).
STN Registry RN 1786771-76-3 (Jun. 23, 2015).
STN Registry RN 1913371-71-7 (Apr. 19, 2016).
STN Registry RN 1913830-07-5 (May 19, 2016).
STN Registry RN 1913830-21-3 (May 19, 2016).
STN Registry RN 1915424-53-1 (May 22, 2016).
STN Registry RN 1915424-56-4 (May 22, 2016).
STN Registry RN 1915424-64-4 (May 22, 2016).
STN Registry RN 1915832-82-4 (May 23, 2016).
STN Registry RN 1917415-48-5 (May 25, 2016).
STN Registry RN 1917835-47-2 (May 25, 2016).
STN Registry RN 1917835-82-5 (May 25, 2016).
STN Registry RN 1917835-88-1 (May 25, 2016).
STN Registry RN 1917835-93-8 (May 25, 2016).
STN Registry RN 1918534-15-2 (May 26, 2016).
STN Registry RN 1918534-83-4 (May 26, 2016).
STN Registry RN 1920047-69-3 (May 29, 2016).
STN Registry RN 1920047-75-1 (May 29, 2016).
STN Registry RN 1921005-21-1 (May 30, 2016).
STN Registry RN 1921342-87-1 (May 30, 2016).
STN Registry RN 380644-81-5 (Jan. 7, 2002).
STN Registry RN 59080-85-2 (Nov. 16, 1984).
STN Registry RN 879152-04-2 (Apr. 4, 2006).
STN Registry RN 924212-90-8 (Mar. 1, 2007).
STN Registry RN 929338-90-9 (Apr. 8, 2007).
CAS Registry No. 1291494-75-1; STN Entry Date May 8, 2011; Benzenemethanamine, 4-(2-benzothiazolyloxy)-3-ethoxy-.
CAS Registry No. 1308122-30-6; STN Entry Date Jun. 9, 2011; Benzenemethanamine, 4-(2-benzoxazolyloxy)-3-methoxy-.
CAS Registry No. 1309213-53-3; STN Entry Date Jun. 13, 2011; Isoquinoline, 5-[2methoxy-4-(1- pyrrolidinylmethyl)phenoxy]-.
CAS Registry No. 1913371-71-7; STN Entry Date May 19, 2016; Benzenemethanol, 4-(2-benzothiazolylmethoxy)-α,3-dimethyl-[.
CAS Registry No. 1917415-48-5; STN Entry Date May 25, 2016; Benzeneethanol, 4-(2-benzothiazolylmethoxy)-α-methyl-.
CAS Registry No. 1917835-47-2; STN Entry Date May 25, 2016; Benzenemethanol, 4-(2-benzothiazolylmethoxy)-α-ethyl-[.
CAS Registry No. 1928589-07-4; STN Entry Date Jun. 9, 2016; Benzeneethanamine, 3-methyl-4-(3-quinolinyloxy)-.
STN Registry RN 1285956-86-6(Apr. 26, 2011).
STN Registry RN 1286890-58-1(Apr. 28, 2011).

* cited by examiner

LEUKOTRIENE SYNTHESIS INHIBITORS

CROSS-REFERENCE TO RELATED APPLICATIONS

This application claims the benefit of priority under 35 U.S.C. § 120 as a continuation of U.S. Non-Provisional patent application Ser. No. 17/420,885, filed Jul. 6, 2021, which is a U.S. National Phase Application under 35 U.S.C. § 371 of International Application No. PCT/US2020/013217, filed Jan. 10, 2020, which claims the benefit of and priority to U.S. Provisional Patent Application No. 62/791,641, filed Jan. 11, 2019, where each application is herein incorporated by reference in its entirety for all purposes.

FIELD OF THE DISCLOSURE

The present disclosure is directed to specific leukotriene synthesis inhibitor compounds and pharmaceutical compositions comprising the compounds and methods of using the compounds and the pharmaceutical compositions in treating, for example, inflammatory diseases or conditions

BACKGROUND OF THE DISCLOSURE

5-Lipoxygenase (5-LO) is a key enzyme in the production of leukotrienes, proinflammatory mediators of disease. With the assistance of 5-lipoxygenase activating protein (FLAP), 5-LO oxidizes substrate arachidonic acid to HPETE, a transient intermediate that degrades to leukotriene $A_4$ ($LTA_4$), the immediate precursor of the biologically active molecules, leukotriene $C_4$ ($LTC_4$) and leukotriene $B_4$ ($LTB_4$). Leukotriene $A_4$ is converted by $LTA_4$ hydrolase to $LTB_4$, or it can be conjugated with reduced glutathione by LTC4 synthase to yield $LTC_4$. $LTC_4$ is converted to leukotriene $D_4$ ($LTD_4$) which undergoes conversion to leukotriene $E_4$ ($LTE_4$) by sequential amino acid hydrolysis. Leukotrienes $C_4$, $D_4$ and $E_4$ are collectively known as the cysteinyl leukotrienes. Leukotrienes are largely, though not exclusively, produced by leukocytes. $LTB_4$ is produced, for example, by neutrophils, macrophages and mast cells. $LTC_4$ is produced, for example, by macrophages, eosinophils, basophils, and mast cells. Transcellular biosynthesis can also occur. For example, $LTA_4$ produced in neutrophils can be delivered to endothelial cells which lack 5-lipoxygenase but express $LTC_4$ synthase, wherein the endothelial cells metabolize $LTA_4$ to $LTC_4$. The amounts of $LTB_4$ and cysteinyl leukotrienes that various types of cells produce depend on the distal enzymes $LTA_4$ hydrolase and $LTC_4$ synthase respectively. Other factors that influence leukotriene synthesis include intracellullar localization of 5-lipoxygeanse.

Leukotrienes act by binding to specific G-protein coupled receptors that are located on the outer plasma membrane of structural and inflammatory cells. This binding activates signalling pathways within the cells leading to a host of biological responses present in, e.g., inflammatory diseases and conditions. Leukotrienes have a broad array of functional roles in disease including recruitment of leukocytes, increase in mucous release, increase in vascular permeability, and increased proliferation, among others.

Numerous strategies have been attempted to develop compounds that either inhibit the synthesis of leukotrienes or block the receptors through which they exert their function. 5-LO is an important drug target for disease indications wherein either or both of $LTB_4$ and the cysteinyl leukotrienes are involved. 5-LO inhibitors in development can be grouped by mechanism of inhibition. Redox inhibitors reduce the active site iron of the enzyme into the inactive ferrous form. However, general redox inhibitors interfere with multiple biological redox systems thereby leading to side effects. Another group of inhibitors are the iron ligand chelators. These compounds bind to the catalytic iron in the 5-LO enzyme such that it is hindered from catalysing the conversion of arachidonic acid to its products. Examples of compounds within this group includes hydroxamic acid and N-hydroxyurea derivatives. Potential for side effects of the iron chelators render them a less favorable therapeutic option. Non-redox competitive inhibitors offer specific inhibition of the 5-LO enzyme without the potential for side effects associated with the redox and iron chelator classes. Zileuton, a compound approved for the treatment of asthma, inhibits an estimated 26-86% of endogenous leukotriene production. Its clinical use, however, is limited by the need to monitor hepatic enzyme levels and to administer multiple times per day. FLAP was initially discovered as a target for MK886, and since then a number of compounds targeting FLAP have entered the clinic to treat respiratory and cardiovascular disease, but none have reached the market (D. Petterson et al., *Bioorg. Med. Chemm Lett.* (2015), v25(13) pp. 2607-2612).

In addition, targeted inhibition of $LTB_4$ through blocking leukotriene $A_4$ hydrolase ($LTA_4H$) has been an attractive drug target in diseases where primarily $LTB_4$ is involved. Leukotriene $A_4$ hydrolase ($LTA_4H$) is a bifunctional enzyme that is pivotal in leukotriene $B_4$ synthesis. The enzyme is classically known as an epoxide hydrolase activity responsible for generating of $LTB_4$ from $LTA_4$. It also possesses an aminopeptidase activity responsible for the breakdown of the tripeptides formed during destruction of collagen and is also chemotactic to neutrophils (A. Gaggar et al., *J. Immunol* (2008) v. 180(3) pp. 5662-5669; P. O'Reilly et al., *J. Neuroimmunol* (2009) v. 217(1-2) pp. 51-54; R. Snelgrove, *Thorax* (2011) v. 66(6) pp. 550-551). While $LTA_4H$ is classically recognized for its hydrolase activity for the synthesis of pro-inflammatory $LTB_4$ production, the aminopeptidase activity of this enzyme may play a compensatory mechanism to resolve inflammation. Therefore, a therapy that aimed at inhibiting $LTB_4$ production through inhibiting LTA4H must also maintain the aminopeptidase activity of the enzyme would be advantageous in the treatment of inflammatory diseases.

There remains a need for leukotriene inhibitors for the treatment of, e.g., inflammatory diseases or conditions.

All of the subject matter discussed in the Background section is not necessarily prior art and should not be assumed to be prior art merely as a result of its discussion in the Background section. Along these lines, any recognition of problems in the prior art discussed in the Background section or associated with such subject matter should not be treated as prior art unless expressly stated to be prior art. Instead, the discussion of any subject matter in the Background section should be treated as part of the inventor's approach to the particular problem, which in and of itself may also be inventive.

SUMMARY OF THE DISCLOSURE

In one aspect, the present disclosure provides compounds of formula (1). In another aspect, the present disclosure provides compositions comprising a compound of formula (1), e.g., pharmaceutical compositions. In another aspect, the present disclosure provides methods of treating various diseases and conditions, where the method comprises administering a therapeutically effective amount of a compound of formula (1) or a composition comprising a compound of formula (1).

Exemplary embodiments of the present disclosure include the compounds set forth in Table 1, and the following embodiments which are numbered for convenience of reference.

1) A compound of formula (1)

(1)

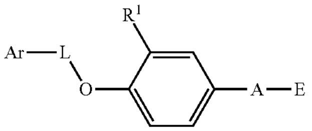

or a pharmaceutically acceptable enantiomer, diastereomer, salt, or solvate thereof, wherein:

Ar is a 9- or 10-membered bicyclic aromatic ring system, where Ar is optionally substituted with one, two or three substituents;

L is selected from a direct bond and methylene;

$R^1$ is selected from hydrogen, halide, $C_1$-$C_6$alkyl, $C_1$-$C_6$haloalkyl, $C_1$-$C_6$alkoxy, $C_3$-$C_6$cycloalkoxy, and $C_1$-$C_6$alkoxy substituted with $C_3$-$C_6$cycloalkyl;

A is selected from a direct bond, —$CH_2$— and —$CH_2CH_2$—;

E is selected from —C(O)—$R^2$, C($OR^3$)$R^4R^5$ and CH($R^6$)$NR^7R^8$;

$R^2$ is selected from methyl, ethyl and phenyl;

$R^3$ is selected from H, alkyl and substituted alkyl;

$R^4$ is selected from hydrogen, alkyl and phenyl;

$R^5$ is selected from $C_1$-$C_7$alkyl, $C_1$-$C_7$haloalkyl, phenyl and substituted phenyl;

$R^6$ is selected from hydrogen, methyl, halogenated methyl and ethyl;

$R^7$ is hydrogen; and $R^8$ is hydrogen, methyl or ethyl;

with the proviso that together, $R^7$ and $R^8$ may form a 5 or 6-membered, optionally substituted, heterocycle.

2) The compound of embodiment 1 wherein Ar is an unsubstituted 9-membered bicyclic aromatic ring system.

3) The compound of embodiment 1 wherein Ar is a mono-substituted 9-membered bicyclic aromatic ring.

4) The compound of embodiment 1 wherein Ar is a di-substituted 9-membered bicyclic aromatic ring.

5) The compound of embodiment 1 wherein Ar is a tri-substituted 9-membered bicyclic aromatic ring.

6) The compound of embodiment 1 wherein Ar is an unsubstituted 10-membered bicyclic aromatic ring system.

7) The compound of embodiment 1 wherein Ar is a mono-substituted 10-membered bicyclic aromatic ring.

8) The compound of embodiment 1 wherein Ar is a di-substituted 10-membered bicyclic aromatic ring.

9) The compound of embodiment 1 wherein Ar is a tri-substituted 10-membered bicyclic aromatic ring.

10) The compound of embodiment 1 wherein Ar is selected from 1,3-benzoxazole, 2-methylquinoline, and 1,3-benzothiazole.

11) The compound of embodiment 1 wherein Ar is naphthalene or a nitrogen-substituted analog thereof selected from 1,5-naphthyridine, 1,6-naphthyridine, 1,7-naphthyridine, 1,8-naphthyridine, isoquinoline, phthalazine, 2,6-naphthyridine and 2,7-naphthyridine.

12) The compound of embodiment 1 wherein Ar is substituted with a single —S—$CH_3$.

13) The compound of any of embodiments 1-12 wherein L is a direct bond.

14) The compound of any of embodiments 1-12 wherein L is methylene.

15) The compound of any of embodiments 1-14 wherein $R^1$ is hydrogen.

16) The compound of any of embodiments 1-14 wherein $R^1$ is halogen.

17) The compound of any of embodiments 1-14 wherein $R^1$ is $C_1$-$C_6$alkyl.

18) The compound of any of embodiments 1-14 wherein $R^1$ is $C_1$-$C_6$haloalkyl.

19) The compound of any of embodiments 1-14 wherein $R^1$ is $C_1$-$C_6$alkoxy.

20) The compound of any of embodiments 1-19 wherein A is a direct bond.

21) The compound of any of embodiments 1-19 wherein A is —$CH_2$—.

22) The compound of any of embodiments 1-19 wherein A is —$CH_2CH_2$—.

23) The compound of any of embodiments 1-22 wherein E is —C(O)—$R^2$.

24) The compound of any of embodiments 1-23 wherein $R^2$ is methyl.

25) The compound of any of embodiments 1-23 wherein $R^2$ is ethyl.

26) The compound of any of embodiments 1-23 wherein $R^2$ is phenyl.

27) The compound of any of embodiments 1-26 wherein E is —C($OR^3$)$R^4R^5$.

28) The compound of any of embodiments 1-27 wherein $R^3$ is hydrogen.

29) The compound of any of embodiments 1-28 wherein $R^3$ is alkyl.

30) The compound of any of embodiments 1-28 wherein $R^3$ is substituted alkyl.

31) The compound of any of embodiments 1-30 wherein $R^4$ is hydrogen.

32) The compound of any of embodiments 1-30 wherein $R^4$ is alkyl.

33) The compound of any of embodiments 1-30 wherein $R^4$ is phenyl.

34) The compound of any of embodiments 1-33 wherein $R^5$ is $C_1$-$C_7$alkyl.

35) The compound of any of embodiments 1-34 wherein $R^5$ is $C_1$-$C_7$haloalkyl, e.g., $R^5$ is trifluoromethyl.

36) The compound of any of embodiments 1-34 wherein $R^5$ is phenyl.

37) The compound of any of embodiments 1-34 wherein $R^5$ is substituted phenyl.

38) The compound of any of embodiments 1-37 wherein E is —CH($R^6$)$NR^7R^8$.

39) The compound of any of embodiments 1-38 wherein $R^6$ is hydrogen.

40) The compound of any of embodiments 1-38 wherein $R^6$ is methyl.

41) The compound of any of embodiments 1-38 wherein $R^6$ is halogenated methyl.

42) The compound of any of embodiments 1-38 wherein $R^6$ is ethyl.

43) The compound of any of embodiments 1-38 wherein $R^8$ is hydrogen.

44) The compound of any of embodiments 1-38 wherein $R^8$ is methyl.

45) The compound of any of embodiments 1-38 wherein $R^8$ is ethyl.

46) The compound of any of embodiments 1-45 wherein $R^7$ and $R^8$ together form a 5 membered heterocycle.

47) The compound of any of embodiments 1-45 wherein $R^7$ and $R^8$ together form a substituted 5 membered heterocycle.

48) The compound of any of embodiments 1-45 wherein $R^7$ and $R^8$ together form a 6 membered heterocycle.

49) The compound of any of embodiments 1-45 wherein $R^7$ and $R^8$ together form a substituted 6 membered heterocycle.

50) The compound of embodiment 1 selected from the group consisting of:

1-[4-(1,3-benzothiazol-2-yloxy)-3-methoxyphenyl]pentan-3-one;
1-[4-(1,3-benzoxazol-2-yloxy)-3-methoxyphenyl]pentan-3-one;
1-[4-(1,3-benzothiazol-2-yloxy)-3-methoxyphenyl]-3-(trifluoromethyl)pentan-3-ol;
1-{3-methoxy-4-[(4-methylsulfanyl-1,3-benzothiazol-2-yl)oxy]phenyl}-3-(trifluoromethyl)pentan-3-ol;
1-[4-(1-methyl-1H-benzimidazol-2-yloxy)-3-methoxyphenyl]-3-(trifluoromethyl)pentan-3-ol;
1-{3-methoxy-4-[(6-methylsulfonyl-1,3-benzothiazol-2-yl)oxy]phenyl}-3-(trifluoromethyl)pentan-3-ol;
1-{4-[(4,6-difluoro-1,3-benzothiazol-2-yl)oxy]-3-methoxyphenyl}-3-(trifluoromethyl)pentan-3-ol;
1-{4-[(6-fluoro-1,3-benzothiazol-2-yl)oxy]-3-methoxyphenyl}-3-(trifluoromethyl)pentan-3-ol;
1-{4-[(6-methoxy-1,3-benzothiazol-2-yl)oxy]-3-methoxyphenyl}-3-(trifluoromethyl)pentan-3-ol;
4-[4-(1,3-benzothiazol-2-yloxy)-3-methoxyphenyl]butan-2-one;
4-[4-(1,3-benzothiazol-2-yloxy)-3-methoxyphenyl]-1,1,1-trifluoro-2-methylbutan-2-ol;
1-[4-(1,3-benzothiazol-2-yloxy)-3-(iso-propyloxy)-phenyl]pentan-3-one;
1-[4-(1,3-benzothiazol-2-yloxy)-3-(cyclopentyloxy)-phenyl]pentan-3-one;
1-[4-(1,3-benzothiazol-2-yloxy)-3-(cyclopropyl-methoxy)-phenyl]pentan-3-one;
1-[4-(1,3-benzothiazol-2-yloxy)-3-(iso-propyloxy)phenyl]-3-(trifluoromethyl)pentan-3-ol
1-[4-(1,3-benzothiazol-2-yloxy)-3-(cyclopentyloxy)-phenyl]-3-(trifluoromethyl)-pentan-3-ol;
1-[4-(1,3-benzothiazol-2-yloxy)-3-(cyclopropyl-methoxy)-phenyl]-3-(trifluoromethyl)-pentan-3-ol;
4-(3-methoxy-4-{[4-(methylsulfanyl)-1,3-benzothiazol-2-yl]oxy}phenyl)butan-2-one;
1,1,1-trifluoro-4-(3-methoxy-4-{[4-(methylsulfanyl)-1,3-benzothiazol-2-yl]oxy}phenyl)-2-methylbutan-2-ol;
1-[4-(1,3-benzothiazol-2-yloxy)-3-ethoxyphenyl]-pentan-3-one;
1-[4-(1,3-benzothiazol-2-yloxy)-3-ethoxyphenyl]-3-(trifluoromethyl)pentan-3-ol;
4-[4-(1,3-benzothiazol-2-yloxy)-3-methoxyphenyl]-butan-2-ol;
4-[4-(1,3-benzothiazol-2-yloxy)-3-methoxyphenyl]-2-(phenyl)butan-2-ol;
4-[4-(1,3-benzothiazol-2-yloxy)-3-methoxyphenyl]-2-methylbutan-2-ol;
4-[4-(1,3-benzoxazol-2-yloxy)-3-methoxyphenyl]butan-2-one;
4-[4-(1,3-benzoxazol-2-yloxy)-3-methoxyphenyl]-2-methylbutan-2-ol;
1-[4-(1,3-benzoxazol-2-yloxy)-3-methoxyphenyl]-3-methylpentan-3-ol;
4-[4-(1,3-benzoxazol-2-yloxy)-3-methoxyphenyl]-2-phenylbutan-2-ol;
3-[4-(1,3-benzothiazol-2-yloxy)-3-ethoxyphenyl]-1-phenylpropan-1-one;
4-[3-ethoxy-4-(1,3-benzothiazol-2-yloxy)phenyl]-1,1,1-trifluoro-2-phenylbutan-2-ol;
3-[4-(1,3-benzothiazol-2-yloxy)-3-methoxyphenyl]-1-phenylpropan-1-one;
3-[4-(1,3-benzothiazol-2-yloxy)-3-methoxyphenyl]-1-phenylpropan-1-ol;
3-[4-(1,3-benzothiazol-2-yloxy)-3-methoxyphenyl]-1-(trifluoromethyl)-1-phenylpropan-1-ol;
2-{2-methoxyl-4-[3-phenyl-3-(pyrrolidin-1-yl)propyl]phenoxy}-1,3-benzothiazole;
1-[4-(1,3-benzothiazol-2-yloxy)-3-methoxyphenyl]pentan-3-amine;
4-{1-[3-methoxy-4-(1,3-benzothiazol-2-yloxy)phenyl]pentan-3-yl}morpholine;
1-[4-(1,3-benzothiazol-2-yloxy)-3-methoxyphenyl]-2,2,2-trifluoroethanol;
1-[4-(1,3-benzothiazol-2-yloxy)-3-methoxyphenyl]-N-ethyl-2,2,2-trifluoroethanamine;
2,2,2-trifluoro-1-(3-methoxy-4-{[4-(methylsulfanyl)-1,3-benzothiazol-2-yl]oxy}phenyl)ethanol;
4-[4-(1,3-benzothiazol-2-yloxy)phenyl]-1,1,1-trifluoro-2-methylbutan-2-ol;
4-[4-(1,3-benzothiazol-2-yloxy)phenyl]butan-2-ol;
1-[4-(1,3-benzothiazol-2-yloxy)phenyl]-3,4-dimethylpentan-3-ol;
1-[4-(1,3-benzothiazol-2-yloxy)phenyl]-3-methylpentan-3-ol;
4-[4-(1,3-benzothiazol-2-yloxy)phenyl]-2-phenylbutan-2-ol;
4-[4-(1,3-benzothiazol-2-yloxy)phenyl]-2-(4-fluorophenyl)butan-2-ol;
1-[4-(1,3-benzoxazol-2-yloxy)phenyl]-3-methylpentan-3-ol;
4-[4-(1,3-benzoxazol-2-yloxy)phenyl]-2-phenylbutan-2-ol;
1-[4-(1,3-benzothiazol-2-yloxy)phenyl]pentan-3-one;
1-[4-(1,3-benzothiazol-2-yloxy)-3-chlorophenyl]pentan-3-one;
1-[4-(1,3-benzothiazol-2-yloxy)phenyl]-3-(trifluoromethyl)pentan-3-ol;
1-[4-(1,3-benzothiazol-2-yloxy)-3-chlorophenyl]-3-(trifluoromethyl)pentan-3-ol;
1-[4-(1,3-benzothiazol-2-yloxy)-3-fluorophenyl]-pentan-3-one;
1-[4-(1,3-benzothiazol-2-yloxy)-3-(trifluoromethyl)-phenyl]pentan-3-one;
1-[4-(1,3-benzothiazol-2-yloxy)-3-fluorophenyl]-3-(trifluoromethyl)pentan-3-ol;
1-[4-(1,3-benzothiazol-2-yloxy)-3-(trifluoromethyl)-phenyl]-3-(trifluoromethyl)-pentan-3-ol;
2-{4-[3-(pyrrolidin-1-yl)butyl]phenoxy}-1,3-benzothiazole;
1-{4-[4-(1,3-benzothiazol-2-yloxy)phenyl]butan-2-yl}pyrrolidine-2-carboxylic acid;
2-{4-[3-(pyrrolidin-1-yl)pentyl]phenoxy}-1,3-benzothiazole;
1-[4-(1,3-benzothiazol-2-yloxy)phenyl]ethanone;
1-[4-(1,3-benzothiazol-2-yloxy)phenyl]ethanol;
2-[4-(1,3-benzothiazol-2-yloxy)phenyl]butan-2-ol;
2-{4-[1-(pyrrolidin-1-yl)ethyl]phenoxy}-1,3-benzothiazole;

2-[4-(1,3-benzothiazol-2-yloxy)phenyl]-1,1,1-trifluoropropan-2-ol;
2-[4-(pyrrolidin-1-ylmethyl)phenoxy]-1,3-benzothiazole;
1-[4-(1,3-benzothiazol-2-yloxy)benzyl]pyrrolidine-2-carboxylic acid;
1-[4-(1,3-benzothiazol-2-yloxy)phenyl]-2,2,2-trifluoroethanol;
1-[4-(1,3-benzothiazol-2-yloxy)-3-chlorophenyl]-2,2,2-trifluoroethanol;
1-[4-(1,3-benzothiazol-2-yloxy)phenyl]-N-ethyl-2,2,2-trifluoroethanamine;
1-{4-[(2-methyl-1,3-benzothiazol-6-yl)oxy]phenyl}ethanone;
1,1,1-trifluoro-2-{4-[(2-methyl-1,3-benzothiazol-6-yl)oxy]phenyl}propan-2-ol;
1-{4-[(2-methyl-1,3-benzothiazol-6-yl)oxy]phenyl}ethanol;
1-[4-(1,3-benzothiazol-2-yloxy)-3-methoxyphenyl]-ethanone;
2-[4-(1,3-benzothiazol-2-yloxy)-3-methoxyphenyl]-1,1,1-trifluoropropan-2-ol;
4-[4-(1,3-benzothiazol-2-yloxy)-3-chlorophenyl]butan-2-one;
4-[4-(1,3-benzothiazol-2-yloxy)-3-chlorophenyl]-1,1,1-trifluoro-2-methylbutan-2-ol;
1-(4-{[4-(methylsulfanyl)-1,3-benzothiazol-2-yl]oxy}phenyl)ethanol;
2-[4-(1,3-benzothiazol-2-yloxy)phenyl]propan-2-ol;
1-[4-(1,3-benzothiazol-2-yloxy)phenyl]-2,2,2-trifluoro-N-methylethanamine;
1-{4-[(4,6-difluoro-1,3-benzothiazol-2-yl)oxy]phenyl}-2,2,2-trifluoroethanol;
1-{4-[(4,6-difluoro-1,3-benzothiazol-2-yl)oxy]phenyl}ethanol;
2-{4-[(4,6-difluoro-1,3-benzothiazol-2-yl)oxy]phenyl}-1,1,1-trifluoropropan-2-ol;
1-{4-[(1,3-benzothiazol-2-yl}oxy]-2-methoxyphenyl}-2,2,2-trifluoroethan-1-ol;
1,1,1-trifluoro-2-methyl-4-[4-(quinolin-2-ylmethoxy)phenyl]butan-2-ol;
1,1,1-trifluoro-4-[3-methoxy-4-(quinolin-2-ylmethoxy)phenyl]-2-methylbutan-2-ol;
1-[4-(quinolin-2-ylmethoxy)-phenyl]-3-(trifluoromethyl)-pentan-3-ol;
1-[4-(1,3-benzothiazol-2-yloxy)-3-(cyclopentyloxy)-phenyl]pentan-3-ol;
1-[4-(1,3-benzothiazol-2-yloxy)-3-(cyclopropylmethoxy)-phenyl]-pentan-3-ol;
1-[4-(1,3-benzothiazol-2-yloxy)-3-methoxyphenyl]-3-(4-methylpiperazinyl-1yl)pentane;
4-{4-[(quinolinyl-2-yl)methoxy]phenyl}butan-2-one;
4-{4-[(quinoline-2-yl)methoxy]phenyl}butan-2-pyrrolidine;
1-(3-methoxy-4-{[4-(methylsulfanyl)-1,3-benzothiazol-2-yl]oxy}phenyl)pentan-3-methyl-3-ol;
1-(3-methoxy-4-{[4-(methylsulfanyl)-1,3-benzothiazol-2-yl]oxy}phenyl)pentan-3-one;
1-(3-methoxy-4-{[4-(methylsulfanyl)-1,3-benzothiazol-2-yl]oxy}phenyl)pentan-3-ol;
1-(4-{[4-(methylsulfanyl)-1,3-benzothiazol-2-yl]oxy}phenyl)pentan-3-one;
1-(4-{[4-(methylsulfanyl)-1,3-benzothiazol-2-yl]oxy}phenyl)-3-(trifluoromethyl)pentan-3-ol;
1-[4-(1,3-benzothiazol-2-yloxy)-3-methoxyphenyl]pentan-3-ol;
1,1,1-trifluoro-2-[4-(quinolin-2-ylmethoxy)phenyl]propan-2-ol;
1,1,1-trifluoro-2-[3-methoxy-4-(quinolin-2-ylmethoxy)phenyl]butan-3-ol; and
1,1,1-trifluoro-2-[3-methoxy-4-(quinolin-2-ylmethoxy)phenyl]propan-2-ol.

51) The compound of embodiment 1 as a racemic mixture of enantiomers of compounds of formula (1).

52) The compound of any of embodiments 1-51 as a non-racemic mixture of enantiomers of compounds of formula (1).

53) The compound of any of embodiments 1-51 as an isolated (S) enantiomer.

54) The compound of any of embodiments 1-51 as an isolated (R) enantiomer.

55) The compound of embodiment 1 wherein:

Ar is a 9- or 10-membered bicyclic ring system comprising two aromatic rings, where Ar is unsubstituted or is substituted with one substituent selected from halide, $C_{1-6}$alkyl; —S—$C_{1-6}$alkyl; —O—$C_{1-6}$alkyl; and —$SO_2$—$C_{1-6}$alkyl;

L is selected from a direct bond and —$CH_2$— (methylene);

$R^1$ is selected from hydrogen, halide, $C_1$-$C_6$alkyl, $C_1$-$C_6$haloalkyl, $C_1$-$C_6$alkoxy, $C_3$-$C_6$cycloalkoxy and $C_1$-$C_6$alkoxy substituted with $C_3$-$C_6$cycloalkyl;

A is selected from a direct bond, —$CH_2$— and —$CH_2CH_2$—;

E is selected from —C(O)—$R^2$, $C(OR^3)R^4R^5$ and $CH(R^6)NR^7R^8$;

$R^2$ is selected from methyl, ethyl and phenyl;

$R^3$ is H;

$R^4$ is selected from hydrogen, $C_1$-$C_7$alkyl and phenyl;

$R^5$ is selected from $C_1$-$C_7$alkyl, $C_1$-$C_7$haloalkyl, phenyl and halophenyl;

$R^6$ is selected from hydrogen, methyl, halogenated methyl and ethyl; and $R^7$ is hydrogen and $R^8$ is hydrogen, methyl or ethyl; or $R^7$ and $R^8$ together form a 5- or 6-membered heterocycle which is optionally substituted with a substituent selected from $C_1$-$C_6$alkyl and carboxylic acid.

56) The compound of embodiment 55 wherein Ar is 1,3-benzothiazole.

57) The compound of embodiment 55 wherein Ar is selected from 1,3-benzoxazole and quinoline.

58) The compound of embodiment 55 wherein Ar is substituted with a single substituent which is —S—$CH_3$.

59) The compound of any of embodiments 55-58 wherein L is a direct bond.

60) The compound of any of embodiments 55-58 wherein L is methylene.

61) The compound of any of embodiments 55-60 wherein $R^1$ is hydrogen or $C_1$-$C_6$alkoxy.

62) The compound of any of embodiments 55-61 wherein A is a direct bond.

63) The compound of any of embodiments 55-61 wherein A is —$CH_2CH_2$—.

64) The compound of any of embodiments 55-63 wherein E is —$C(OR^3)R^4R^5$.

65) The compound of any of embodiments 55-64 as a non-racemic mixture of enantiomers of compounds of formula (1).

66) The compound of embodiment 55 selected from the group consisting of:

1-[4-(1,3-benzothiazol-2-yloxy)-3-methoxyphenyl]-3-(trifluoromethyl)pentan-3-ol;
1-{3-methoxy-4-[(4-methylsulfanyl-1,3-benzothiazol-2-yl)oxy]phenyl}-3-(trifluoromethyl)pentan-3-ol;

1-{4-[(4,6-difluoro-1,3-benzothiazol-2-yl)oxy]-3-methoxyphenyl}-3-(trifluoromethyl)pentan-3-ol;

1-{4-[(6-fluoro-1,3-benzothiazol-2-yl)oxy]-3-methoxyphenyl}-3-(trifluoromethyl)pentan-3-ol;

4-[4-(1,3-benzothiazol-2-yloxy)-3-methoxyphenyl]-1,1,1-trifluoro-2-methylbutan-2-ol;

1,1,1-trifluoro-4-(3-methoxy-4-{[4-(methylsulfanyl)-1,3-benzothiazol-2-yl]oxy}phenyl)-2-methylbutan-2-ol;

1,1,1-trifluoro-2-{4-[(2-methyl-1,3-benzothiazol-6-yl)oxy]phenyl}propan-2-ol;

1,1,1-trifluoro-2-methyl-4-[4-(quinolin-2-ylmethoxy)phenyl]butan-2-ol;

1,1,1-trifluoro-4-[3-methoxy-4-(quinolin-2-ylmethoxy)phenyl]-2-methylbutan-2-ol;

1-[4-(quinolin-2-ylmethoxy)-phenyl]-3-(trifluoromethyl)-pentan-3-ol;

1-(3-methoxy-4-{[4-(methylsulfanyl)-1,3-benzothiazol-2-yl]oxy}phenyl)pentan-3-ol; and 1-(4-{[4-(methylsulfanyl)-1,3-benzothiazol-2-yl]oxy}phenyl)-3-(trifluoromethyl)pentan-3-ol.

67) A pharmaceutical composition comprising a compound of any of embodiments 1-66, or a pharmaceutically acceptable enantiomer, salt or solvate thereof, and at least one pharmaceutically acceptable carrier, diluent, excipient and/or adjuvant.

68) The pharmaceutical composition of embodiment 67 in the form of an eyedrop.

69) A method of treating an inflammatory disease or inflammatory condition comprising administrating to a subject in need thereof an effective amount of a compound of any of embodiments 1-66 or a composition of embodiment 67.

70) The method of embodiment 69 for treating an ocular inflammatory disease or an ocular inflammatory condition.

71) A method of treating a respiratory disease or condition comprising administering to a subject in need thereof a therapeutically-effective amount of a compound of any of embodiments 1-66 or a composition of embodiment 67.

72) A method of treating a neurodegenerative disease, condition or disorder comprising administering to a subject in need thereof a therapeutically-effective amount of a compound of any of embodiments 1-66 or a composition of embodiment 67.

73) A method of treating respiratory disease, lung dysfunction or lung conditions, such as asthma, chronic obstructive pulmonary disease (COPD), cystic fibrosis, bronchopulmonary dysplasia and Idiopathic pulmonary fibrosis (IPF), comprising administrating to a subject in need thereof an effective amount of a compound of any of embodiments 1-66 or a composition of embodiment 67.

74) A method of treating an autoimmune disease or autoimmune condition such as arthritis, Otis, and multiple sclerosis, comprising administrating to a subject in need thereof an effective amount of a compound of any of any of embodiments 1-66 or a composition of embodiment 67.

75) A method of treating an allergic disease comprising administrating to a subject in need thereof an effective amount of a compound of any of any of embodiments 1-66 or a composition of embodiment 67.

76) A method of treating a conjunctivitis comprising administrating to a subject in need thereof an effective amount of a compound of any of any of embodiments 1-66 or a composition of embodiment 67.

77) A method of treating uveitis comprising administrating to a subject in need thereof an effective amount of a compound of any of any of embodiments 1-66 or a composition of embodiment 67.

78) A method of treating dry eye comprising administrating to a subject in need thereof an effective amount of a compound of any of any of embodiments 1-66 or a composition of embodiment 67.

79) A method of treating diabetic retinopathy comprising administering to a subject in need thereof a therapeutically-effective amount of a compound of any of any of embodiments 1-66 or a composition of embodiment 67.

80) A method of treating age-related macular degeneration comprising administering to a subject in need thereof a therapeutically-effective amount of a compound of any of any of embodiments 1-66 or a composition of embodiment 67.

81) A method of treating diabetic macular edema comprising administering to a subject in need thereof a therapeutically-effective amount of a compound of any of any of embodiments 1-66 or a composition of embodiment 67.

82) A method of treating skin disorders or skin conditions, such as atopic dermatitis, psoriasis, and acne vulgaris comprising administrating to a subject in need thereof an effective amount of a compound of any of any of embodiments 1-66 or a composition of embodiment 67.

83) A method of treating cancer comprising administrating to a subject in need thereof an effective amount of a compound of any of any of embodiments 1-66 or a composition of embodiment 67.

84) A method of treating a neuroinflammatory disease or neurodegenerative disease, such as Alzheimer's disease, comprising administrating to a subject in need thereof an effective amount of a compound of any of any of embodiments 1-66 or a composition of embodiment 67.

85) A method of treating Sjogren-Larsson-Syndrome comprising administrating to a subject in need thereof an effective amount of a compound of any of any of embodiments 1-66 or a composition of embodiment 67.

86) A method of treating cardiovascular (CV) disease comprising administrating to a subject in need thereof an effective amount of a compound of any of any of embodiments 1-66 or a composition of embodiment 67.

Any two or more of the embodiments disclosed herein may be combined in order to describe compounds, compositions and methods of the present disclosure.

This Brief Summary has been provided to introduce certain concepts in a simplified form that are further described in detail below in the Detailed Description. Except where otherwise expressly stated, this Brief Summary is not intended to identify key or essential features of the claimed subject matter, nor is it intended to limit the scope of the claimed subject matter.

The details of one or more embodiments are set forth in the description below. The features illustrated or described in connection with one exemplary embodiment may be combined with the features of other embodiments. Thus, any of the various embodiments described herein can be combined to provide further embodiments. Aspects of the embodiments can be modified, if necessary to employ concepts of the various patents, applications and publications as identified herein to provide yet further embodiments. Other features, objects and advantages will be apparent from the description, the drawings, and the claims.

BRIEF DESCRIPTION OF THE DRAWINGS

FIG. 4B shows histological scores that were obtained 10 days post immunization.

FIG. 4C shows retinal thickness measurements that were determined from histological slides 10 days post immunization.

DETAILED DESCRIPTION

Figure 1:
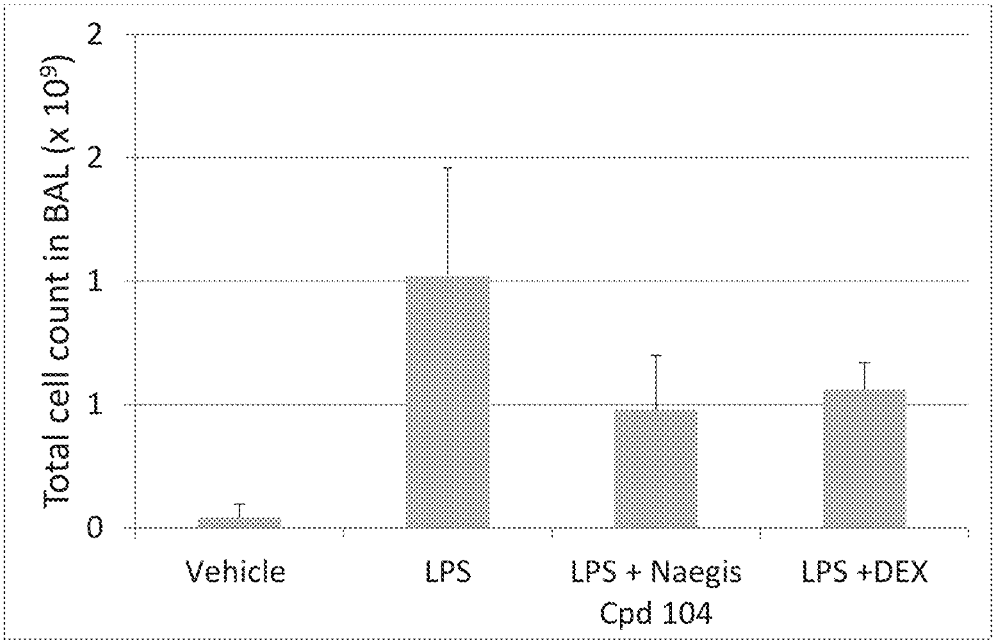
FIG. 1 shows the effect of Compound 104 on LPS-induced neutrophil infiltration into the lung. Animals were treated orally with 10 mg/kg of Compound 104, 1 mg/kg Dexamethasone or dosing vehicle 1 hr before and 2 hrs after 2.5 mg/kg LPS was administered intratracheally. Animals were euthanized 6 hr post-LPS and the BAL was collected from the lung. Values represent the mean±standard deviation, n=7-10 animals per group.

The present invention may be understood more readily by reference to the following detailed description of the preferred embodiments of the invention and the Examples included herein. Before describing the invention in further detail, certain definitions as used herein are provided with the following definitions, and certain conventions used herein are also set forth.

The terms used herein should be understood to have their ordinary meaning to the person of ordinary skill in the art of organic chemicals. That notwithstanding, and except where otherwise stated, the following definitions apply through the specification and claims. These definitions apply regardless of whether a term is used by itself or is instead used as part of a larger name. For example, the definition of "alkyl" applies to the term "alkyl" used by itself as well as the "alkyl" portion of words that incorporate the alkyl concept, e.g., "hydroxyalkyl", "haloalkyl", "O-alkyl", etc.

Chemical names, common names, and chemical structures may be used interchangeably to describe the same compound. For example, the compounds of formula (1) may be referred to herein by chemical structure and/or by chemical name. In an instance where both the structure and the name of a compound are provided and there is a discrepancy between the name and the structure, then it is to be understood that the structural representation of the compound controls.

As discussed further herein, the term "substituted" means that one or more hydrogens on a designated or selected atom is replaced with a selection from an indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" it is meant that a compound is sufficiently robust to survive isolation to a useful degree of purity from a reaction mixture, and formulation into an efficacious therapeutic composition. It should also be noted that any carbon as well as heteroatom with unsatisfied valences in the text, schemes, examples and tables herein is assumed to have the sufficient number of hydrogen atom(s) to satisfy the atom's normal valence.

"Alkyl" refers to a straight or branched hydrocarbon chain radical consisting solely of carbon and hydrogen atoms, containing no unsaturation, having from one to the specified number of carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, and the like. In one embodiment the alkyl group has 1 carbon. In one embodiment the alkyl group has 2 carbons. In one embodiment the alkyl group has 3 carbons. In one embodiment the alkyl group has 4 carbons. In one embodiment the alkyl group has 4 carbons. In one embodiment the alkyl group has 5 carbons. In one embodiment the alkyl group has 6 carbons. Two or more of these embodiments may be combined to describe compounds of the disclosure. "Alkoxy" refers to —O-alkyl. "Cycloalkyl" refers to a cyclic aliphatic radical having no unsaturation such as cyclopropyl, cyclobutyl, cyclopentyl and cyclohexyl. "Cycloalkoxy" refers to —O—cycloalkyl.

"Aryl" refers to a hydrocarbon ring system radical comprising hydrogen, 6 to 18 carbon atoms and at least one aromatic ring. In one embodiment the aryl ring system has 6 to 12 carbon atoms. In one embodiment the aryl ring system has 6 to 10 carbon atoms. For purposes of this disclosure, the aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, an aryl group may be optionally substituted by one or more substituents independently selected at each occurrence.

"Compounds of the present disclosure" (unless specifically identified otherwise) and the equivalent term "compounds of the (or this) invention" (unless specifically identified otherwise) refer to compounds of Formula (1), including subsets thereof, and all pure and mixed stereoisomers (including diastereoisomers and enantiomers), tautomers and isotopically labeled compounds. Hydrates and solvates of the compounds of this invention/disclosure are also considered within the scope of the term compounds of this invention/disclosure. The compounds may exist in one or more crystalline states, i.e., as co-crystals or polymorphs, or they may exist as amorphous solids, or they may exist as oils. All such forms are encompassed by the invention and the claims. Compounds of "Formula (1)", "Formula 1", "formula (1)", "formula 1" and the like may be used interchangeably herein and no difference or distinction is meant.

"Effective amount," "therapeutic amount," "therapeutically effective amount," or "effective dose" refers to an amount or dose of the active compound as described herein sufficient to elicit a desired pharmacological or therapeutic effect in a subject. In the case of compounds to treat inflammation, an effective amount will be an anti-inflammatory amount. In this context, "effective amounts," "therapeutic amounts," "therapeutically effective amount," and "effective doses" can be readily determined by ordinarily skilled artisans following the teachings of this disclosure and employing tools and methods generally known in the art, often based on routine clinical or patient-specific factors. It will be understood, however, that the attending physician, within the scope of sound medical judgment, will decide the total daily dosage of the compound. The specific therapeutically effective dose level for any particular patient will depend upon a variety of factors including the disorder being treated and the severity of the disorder; the desired result to be obtained, the activity of the specific compound employed; the specific composition employed; the age, body weight, general health, gender and diet of the patient; the time of administration, route of administration, and rate of excretion of the specific compound employed; the duration of the treatment; drugs used in combination or coincidental with the specific compound employed; and like factors well known in the medical arts. As a general guideline however, the total daily dose will typically range from about 0.0001 mg/kg/day to about 100 mg/kg/day in single or in divided doses. Typically, dosages for humans will range from about 0.1 mg to about 4000 mg per day, in a single or multiple doses "Fused" refers to any ring system described herein which is fused to an existing ring structure in the compounds of the disclosure. When the fused ring system is a heterocyclyl or a heteroaryl, any carbon in the existing ring structure which becomes part of the fused ring system may be replaced with a nitrogen.

"Halo" refers to chloro, bromo, fluoro, and iodo. The term "halogen" refers to fluorine (which may be depicted as —F), chlorine (which may be depicted as —Cl), bromine (which may be depicted as —Br), or iodine (which may be depicted as —I). In one embodiment, the halogen is chlorine. In another embodiment, the halogen is fluorine. In another embodiment, the halogen is bromine. Thus, halophenyl refers to a phenyl group having at least one halogen substituent which replaces a hydrogen normally present on phenyl. Halogenated $CH_2$ refers to a $CH_2$ group that has at least one halogen substitution in place of hydrogen, e.g., CHF and $CF_2$.

"Haloalkyl" refers to an alkyl group having at least one halogen substitution in lieu of a C—H bond. In one embodiment, there is a single halogen substituent on the named group (e.g., phenyl, alkyl). In embodiments, there are two halogen substituents, or 1-2 halogen substituents, or three halogen substituents, or 1-3 halogen substituents, where as mentioned previously, the halogen may be fluorine, or selected from fluorine and chlorine. A subset of haloalkyl is "fluoroalkyl", which refers to alkyl groups that are substituted by one or more fluorine atoms, up to the total number of hydrogen atoms present on the alkyl moiety. Thus, $C_1$-$C_6$fluoroalkyl refers to fluorinated alkyl groups, e.g., trifluoromethyl or difluoroethyl (i.e., $CF_3$ and $CH_2CHF_2$). As used herein, "$C_1$-$C_6$fluoroalkyl" denotes a straight-chain or branched alkyl group containing from 1 to 6, e.g., 1, 2, 3, or 4 carbon atoms. Examples of suitable $C_1$-$C_6$fluoroalkyl radicals are methyl, ethyl, n-propyl, iso-propyl, n-butyl, iso-butyl, sec-butyl, tert-butyl, where the radical contains 1, 2, 3, 4, 5, 6, 7, 8, 9 or 10 or more fluorine substituents, for example, the radical may contain 1, 2 or 3 fluorine substituents.

"Heteroaryl" refers to "aryl" as defined herein, wherein the aromatic ring includes one or more heteroatoms, preferably selected from N, O and S. Thus, a heteroaryl radical refers to an aromatic ring system radical wherein the ring atoms are selected from carbon, nitrogen, oxygen and sulfur, and include at least one of nitrogen, oxygen and sulfur. For purposes of this disclosure, the heteroaryl radical may be a monocyclic, bicyclic, tricyclic or tetracyclic ring system, which may include fused or bridged ring systems. Optionally, the heteroaryl radical is a 5-, 6- or 7-membered heteroaryl group. When there are multiple O and S atoms in the heteroaryl ring system, the O atoms and/or S atoms are preferably not linked directly to one another. Exemplary heteroaryl groups include 5-membered rings, such as pyrrole, pyrazole, imidazole, 1,2,3-triazole, 1,2,4-triazole, tetrazole, furan, thiophene, selenophene, oxazole, isoxazole, 1,2-thiazole, 1,3-thiazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole. The heteroaryl group may be a 6-membered ring, such as pyridine, pyridazine, pyrimidine, pyrazine, 1,3,5-triazine, 1,2,4-triazine, 1,2,3-triazine, 1,2,4,5-tetrazine, 1,2,3,4-tetrazine, 1,2,3,5-tetrazine, or fused rings including a 6-membered ring such as indole, isoindole, indolizine, indazole, benzimidazole, benzotriazole, purine, naphthimidazole, phenanthrimidazole, pyridimidazole, pyrazinimidazole, quinoxalinimidazole, benzoxazole, naphthoxazole, anthroxazole, phenanthroxazole, isoxazole, benzothiazole, benzofuran, isobenzofuran, dibenzofuran, quinoline, isoquinoline, pteridine, benzo-5,6-quinoline, benzo-6,7-quinoline, benzo-7,8-quinoline, benzoisoquinoline, acridine, phenothiazine, phenoxazine, benzopyridazine, benzopyrimidine, quinoxaline, phenazine, naphthyridine, azacarbazole, benzocarboline, phenanthridine, phenanthroline, thieno[2,3b]thiophene, thieno[3,2b]thiophene, dithienothiophene, isobenzothiophene, dibenzothiophene, and benzothiadiazo-thiophene. Unless stated otherwise specifically in the specification, the ring atoms of a heteroaryl group may be optionally substituted by one or more substituents independently selected at each ring atom.

"Hydroxyalkyl" refers to an alkyl group having at least one hydroxyl (—OH; also called hydroxy) substitution in lieu of a C—H bond. In one embodiment, there is a single hydroxyl substituent on the named group (e.g., phenyl, alkyl). In embodiments, there are two hydroxyl substituents, or 1-2 hydroxyl substituents, or three hydroxyl substituents, or 1-3 hydroxyl substituents. As used herein, "$C_1$-$C_6$ hydroxyalkyl" denotes a straight-chain or branched alkyl group containing from 1 to 6, e.g., 1, 2, 3, 4, 5 or 6 carbon atoms. Examples of suitable $C_1$-$C_6$hydroxyalkyl radicals are methyl, ethyl, n-propyl, iso-propyl, n-butyl, iso-butyl, sec-butyl, tert-butyl, where the radical contains 1 or more hydroxyl substituents, for example, as in one embodiment, the radical may contain 1 hydroxyl substituent.

"Independently selected" in reference to a group of options, e.g., a group of substituents, indicates that each substituent is selected without regard to the selection that is made for any other substituent, i.e., each substituent is independently selected. Thus, each selected substituent may be identical to or different from the other substituent(s) selected from a group of substituents. For additional clarity, it will be explained that a disclosure that something is selected from a group means that the selection is independently done at each occurrence in the event that the selection is done multiple times. Unless otherwise explicitly stated, and regardless of whether the selection is explicitly stated to be made independently, selections of atoms and/or substituents are independently selected.

"Mammal" refers to human or animals including livestock and companion animals. The phrase "companion animal" or "companion animals" refers to animals kept as pets, e.g., cats, dogs, and horses. The term "livestock" refers to animals reared or raised in an agricultural setting to make products such as food or fiber, or for its labor, e.g., cattle, goats, horses, pigs, sheep, lambs, and rabbits, as well as birds, such as chickens, ducks and turkeys.

"Pharmaceutically acceptable" refers to being suitable for use in mammals, companion animals or livestock animals. Thus, a pharmaceutically acceptable substance or composition must be compatible chemically and/or toxicologically, with the other ingredients comprising a formulation, and/or the mammal being treated therewith.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salts" refers to either "pharmaceutically acceptable acid addition salts" or "pharmaceutically acceptable base addition salts" depending upon the actual structure of the compound. When a compound of Formula (I) has a basic functional group, e.g., an amine group, then a "pharmaceutically acceptable salt" may refer to an acid addition salt of the amine group. Such salts refer to any non-toxic organic or inorganic acid addition salt of the compounds of this disclosure or any of its intermediates. Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids, which form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxy-benzoic, phenylacetic, cinnamic, salicylic, 2-phenoxybenzoic, p-toluenesulfonic acid, and sulfonic acids such as methane sulfonic acid and 2-hydroxyethane sulfonic acid. Such salts can exist in either a hydrated or substantially anhydrous form. In general, the acid addition salts of these compounds are soluble in water and various hydrophilic organic solvents. Basic nitrogen containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others. When a compound of Formula (I) has an acidic functional group, e.g., a carboxylic acid group, then a "pharmaceutically acceptable salt" may refer to a base addition salt of the acid group. Such basic salts refer to any non-toxic organic or inorganic base addition salt of the compounds of this disclosure or any of its intermediates. Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. The counterion of the carboxylic or other acidic group may be a quarternized nitrogen-containing group.

"Prodrug" refers to a compound (e.g., a drug precursor) that is transformed in vivo to provide a compound of the present disclosure or a pharmaceutically acceptable salt of the compound. The transformation may occur by, for example, metabolic or chemical processes, such as through hydrolysis in blood. Prodrugs include a bio-reversible derivative of a compound of Formula I of the present disclosure. Prodrugs can alter the solubility, lipophilicity and in-vivo distribution of drugs. By deliberately altering these key properties, it may be possible to improve absorption, enhance onset time, reduce first pass metabolism, allow development of aqueous IV formulations and achieve targeted delivery. In addition, prodrugs are useful in improving transdermal delivery, masking taste, minimizing pain on injection, improving stability, etc. In situations where the pharmacophore itself leads to poor delivery properties, prodrugs are one of the few strategies that can be used to salvage the highly active compound.

Included within the scope of the present disclosure are all prodrugs of the compounds of Formula (1) that can be prepared by the standard methods known to one skilled in the art. Prodrugs of the compounds of Formula (1) may be prepared following the methods described in, e.g., "Prodrugs of phosphates, phosphonates, and phosphinates", Krise J P, Stella V J, *Advanced Drug Delivery Reviews,* 19: (2) 287-310 May 22, 1996; "Targeted Prodrug Design to Optimize Drug Delivery". Hyo-Kyung Han and Gordon Amidon. *AAPS PharmSci* 2000; 2 (1) article 6; "Prodrugs", L. Prokai and K. Prokai-Tatrai, Chapter 12 in Injectable Drug Development: Techniques to Reduce Pain and Irritation, Interpharm Press, Buffalo Grove, Ind., 1999; "Improved oral drug delivery: Solubility limitations overcome by the use of prodrugs", Fleisher D, Bong R, Stewart B H, Advanced Drug Delivery Reviews, 19: (2) 115-130 May 22, 1996; "Permeable, water-soluble, non-irritating prodrugs of chemotherapeutic agents with oxaalkanoic acids", PCT Int. Publication No. WO 00/67801; T. Higuchi and V. Stella, "Pro-drugs as Novel Delivery Systems" (1987) vol. 14 of the *A.C.S. Symposium Series*, and "Bioreversible Carriers in Drug Design", (1987) Edward B. Roche, ed., American Pharmaceutical Association and Pergamon Press.

"Solvate" refers to a physical association of a compound of this disclosure with one or more solvent molecules. One or more compound of the disclosure may exist in solvated as well as unsolvated forms, where solvated forms are associated with pharmaceutically acceptable solvents such as water, ethanol and the like. All such solvated and unsolvated forms are within the scope of the compounds of Formula (1). The physical association involves varying degrees of ionic and covalent bonding including hydrogen bonding. In certain instances the solvate will be capable of isolation. This may happen when the one or more solvent molecules are incorporated into the crystal lattice of a crystalline solid comprising a compound of the present disclosure. Reference to "solvate" encompasses both solution-phase and isolatable solvates. Reference to "solvate" encompasses hemisolvates. Non-limiting examples of solvates including methanolates, ethanolates and hydrates, where hydrates refer to solvates wherein the associated solvent molecule is water. A compound of the present disclosure may optionally be converted to a corresponding solvate form by methods known in the art. An exemplary, non-limiting process for preparing a solvate involves dissolving the inventive compound in a selected amount of a desired solvent (organic or water or mixtures thereof) at temperature that is higher than room temperature, and then cooling the solution at a rate that is sufficiently slow that crystals are formed, where the crystals may be isolated. See, e.g., M. Caira et al. *J. Pharmaceutical Science* (2004) v.93(3) pp. 601-611; E. C. Tonder et al. *AAPS Pharm. Sci. Tech.* (2004 Feb. 23), v.5(1) p.E12; and A. L. Bingham et al. *Chem. Commun.* (2001) pp. 603-604, each of which provides a process for preparing selected solvates.

"Subject" refers to mammals, e.g., humans, as well as livestock. The subject may also be referred to as a patient.

"Substituents" refer to monovalent groups that may be attached to a mentioned radical. For example, a "substituted phenyl" refers to a phenyl ring having 1, 2, 3 or 4 substituents attached to the phenyl ring. Substituents may be selected from halogen, $C_1$-$C_6$alkyl, $C_1$-$C_6$haloalkyl, $C_1$-$C_6$hydroxyalkyl, —OH, —O($C_1$-$C_6$alkyl), —O($C_1$-$C_6$haloalkyl), —O($C_1$-$C_6$hydroxyalkyl), —S($C_1$-$C_6$alkyl), —S($C_1$-$C_6$haloalkyl), —S($C_1$-$C_6$hydroxyalkyl), cyano, amino (—$NH_2$), formyl (—CHO), carboxylic acid (—COOH), carboxylate ester (—COOR where R is a $C_1$-$C_{10}$ alkyl group). Likewise, a 5- or 6-membered substituted heterocycle refers to a heterocyclic radical where at least one of the ring atoms is bonded to a substituent as defined herein.

"Therapeutically effective amount" refers to the amount of a compound that, when administered to a mammal for a therapeutic purpose, is sufficient to effect such therapy for the disease or condition. The "therapeutically effective amount" will vary depending on the compound, the condition and its severity and the age, weight, etc., of the mammal to be treated.

"Treating" or "treatment" of a condition includes: (1) preventing the condition, i.e. causing the clinical symptoms or signs of the disease not to develop in a mammal that may be exposed to or predisposed to the condition but does not yet experience or display symptoms/signs of the condition; (2) inhibiting the condition, i.e., arresting or reducing the development of the condition or its clinical symptoms/signs, such as stopping the recurrence of the condition in a subject that has the condition; or (3) relieving the condition, i.e., causing regression of the condition or its clinical symptoms/signs. Thus, "treating" or "treatment" means an alleviation of symptoms associated with a disease, disorder or condition, or halt of further progression or worsening of those symptoms. Depending on the disease and condition of the patient, the term "treatment" as used herein may include one or more of curative, palliative and prophylactic treatment. Treatment can also include administering a pharmaceutical formulation of the present disclosure in combination with other therapies. The compounds of the disclosure can also be administered in conjunction with other drugs and/or therapies.

It is to be understood that the terminology used herein is for the purpose of describing specific embodiments only and is not intended to be limiting. It is further to be understood that unless specifically defined herein, the terminology used herein is to be given its traditional meaning as known in the relevant art.

Reference throughout this specification to "one embodiment" or "an embodiment" and variations thereof means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents, i.e., one or more, unless the content and context clearly dictates otherwise. It should also be noted that the conjunctive terms, "and" and "or" are generally employed in the broadest sense to include "and/or" unless the content and context clearly dictates inclusivity or exclusivity as the case may be. Thus, the use of the alternative (e.g., "or") should be understood to mean either one, both, or any combination thereof of the alternatives. In addition, the composition of "and" and "or" when recited herein as "and/or" is intended to encompass an embodiment that includes all of the associated items or ideas and one or more other alternative embodiments that include fewer than all of the associated items or ideas.

Unless the context requires otherwise, throughout the specification and claims that follow, the word "comprise" and synonyms and variants thereof such as "have" and "include", as well as variations thereof such as "comprises" and "comprising" are to be construed in an open, inclusive sense, e.g., "including, but not limited to." The term "consisting essentially of" limits the scope of a claim to the specified materials or steps, or to those that do not materially affect the basic and novel characteristics of the claimed disclosure.

As described herein, for simplicity, a patient, clinician, or another human may in some cases be described in the context of the male gender. It is understood that a medical practitioner can be of any gender, and the terms "he," "his," "himself," and the like as used herein are to be interpreted broadly inclusive of all known gender definitions.

Any headings used within this document are only being utilized to expedite its review by the reader, and should not be construed as limiting the invention or disclosure or claims in any manner. Thus, the headings and Abstract of the Disclosure provided herein are for convenience only and do not interpret the scope or meaning of the embodiments.

In one aspect the present disclosure provides compounds of formula (1)

(1)

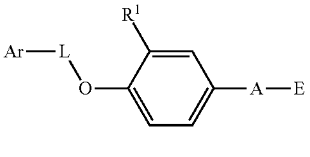

or a pharmaceutically acceptable enantiomer, diastereomer, salt, or solvate thereof, wherein:

Ar is a 9- or 10-membered bicyclic aromatic ring system, where Ar is optionally substituted with one, two or three substituents;

L is selected from a direct bond and methylene;

$R^1$ is selected from hydrogen, halide, $C_1$-$C_6$alkyl, $C_1$-$C_6$haloalkyl, $C_1$-$C_6$alkoxy, $C_3$-$C_6$cycloalkoxy and $C_1$-$C_6$alkoxy substituted with $C_3$-$C_6$cycloalkyl;

A is selected from a direct bond, —$CH_2$— and —$CH_2CH_2$—;

E is selected from —C(O)—$R^2$, C($OR^3$)$R^4R^5$ and CH($R^6$)$NR^7R^8$;

$R^2$ is selected from methyl, ethyl and phenyl;

$R^3$ is selected from hydrogen, alkyl and substituted alkyl;

$R^4$ is selected from hydrogen, alkyl and phenyl;

$R^5$ is selected from $C_1$-$C_7$alkyl, $C_1$-$C_7$haloalky, phenyl and substituted phenyl;

$R^6$ is selected from hydrogen, methyl, halogenated methyl and ethyl;

$R^7$ is hydrogen; and $R^8$ is hydrogen, methyl or ethyl;

with the proviso that together, $R^7$ and $R^8$ may form a 5 or 6-membered, optionally substituted, heterocycle.

For ease of discussion, formula (1) is sometimes written herein as:

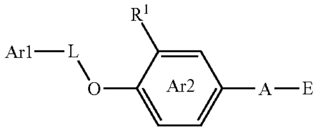

wherein Ar1 and Ar2 are used in order to refer distinctively to one of the two aromatic rings. Also for each of discussion, Ar1, which is 9- or 10-membered bicyclic aromatic ring system, may be referred to as an aromatic ring.

Included within the scope of compounds of formula (1) are pharmaceutically acceptable enantiomers, diastereomers, salts and solvates thereof. When a compound of formula (1) contains a chiral center, it may exist in either the (R) or (S) configuration and thus give rise to two enantiomeric forms. In one embodiment, the present disclosure provide a compound of claim 1 as a racemic mixture of two enantiomers of compounds of formula (1). In one embodiment, the present disclosure provides a compound of formula (1) as a non-racemic mixture of enantiomers of compounds of formula (1), i.e., both the (R) and (S) enantiomers are present together in admixture, but the molar (R):(S) ratio does not equal 1. In one embodiment, the present disclosure provides a compound of formula (1) as an isolated (S) enantiomer, i.e., not in admixture with the corresponding (R) enantiomer or in admixture with less than 1% of the (R) enantiomer. In one embodiment, the present disclosure provides a compound of formula (1) as an isolated (R) enantiomer, i.e., not in admixture with the corresponding (S) enantiomer or in admixture with less than 1% of the (S) enantiomer.

In compounds of formula (1), Ar (Ar1) represents a 9- or 10-membered bicyclic aromatic ring system, where Ar is optionally substituted with one, two or three substituents. A bicyclic ring system refers to a moiety having two rings that are fused to one another, and a bicyclic aromatic ring refers to a moiety having two rings fused together where at least one, and optionally two (both) of the rings is an aromatic ring. In one embodiment, only one of the two rings of the bicyclic aromatic ring system is an aromatic ring. In one embodiment, both rings of the bicyclic aromatic ring system are aromatic rings. That the ring system is 9- or 10-membered refers to the number of atoms that form the ring system. For example, a 6-membered ring fused to a 5-membered ring provides a 9-membered ring system, while a 6-membered ring fused to a 6-membered ring provides a 10-membered ring system.

In one embodiment, Ar1 is a 9-membered bicyclic aromatic ring system, wherein a five membered ring is fused to a six membered ring. Examples of 9-membered Ar groups according to the present disclosure include benzofuran, 1,3-benzoxazole, furo[3,2-b]pyridine, furo[3,2-c]pyridine, furo[2,3-c]pyridine, furo[2,3-b]pyridine, indole, 1H-benzimidazole, 1H-pyrrolo[3,2-b]pyridine, 1H-pyrrolo[3,2-c]pyridine, 1H-pyrrolo[2,3-c]pyridine, 1H-pyrrolo[2,3-b]pyridine, benzothiophene, 1,3-benzothiazole, thienol[3,2-b]pyridine, thieno[3,2-c]pyridine, thieno[2,3-c]pyridine, benzoxadiazole, benzothiadiazole, benzisoxazole, benzotriazole and thieno[2,3-b]pyridine. Each of the listed 9-membered ring systems may be an Ar group in compounds of formula (1), where each of these ring systems is optionally substituted with one, two or three substituents.

In another embodiment, Ar is a 10-membered bicyclic aromatic ring system wherein a six membered ring is fused to another six membered ring. Examples of 10-membered Ar groups according to the present disclosure include naphthalene, quinoline, quinazoline, quinoxaline, 1,5-naphthyridine, 1,6-naphthyridine, 1,7-naphthyridine, 1,8-naphthyridine, isoquinoline, phthalazine, 2,6-naphthyridine and 2,7-naphthyridine. Each of the listed 10-membered ring systems may be an Ar group in compounds of formula (1), where each of these ring systems is optionally substituted with one, two or three substituents.

In one optional embodiment, compounds of formula (1) have Ar as 1,3-benzothiazole. In another optional embodiment, compounds of formula (1) have Ar selected from 1,3-benzoxazole and quinoline.

A substituent on Ar refers to a monovalent group that may be attached to any of the ring atoms of the Ar group. In one embodiment, substituents may be selected from halide, $C_1$-$C_4$alkyl, $C_1$-$C_4$haloalkyl, $C_1$-$C_4$alkoxy, $C_1$-$C_4$haloalkoxy, $C_1$-$C_4$thioalkyl, $C_1$-$C_4$thiohaloalkyl, $C_1$-$C_4$hydroxyalkyl, —$SO_2$($C_1$-$C_4$alkyl), cyano, carboxylic acid and $C_1$-$C_4$carboxylic ester. In one embodiment, Ar does not have any substituents. In one embodiment, Ar is monosubstituted, where optionally the one substituent may be selected from those listed above. For example, in one embodiment, Ar contains a single substituent which is $C_1$-$C_4$thioalkyl, e.g., —S-methyl. In another embodiment, Ar is di-substituted, where optionally the two substituents may be independently selected from those listed above. In a further embodiment, Ar is tri-substituted, where optionally the three substituents may be independently selected from those listed above. In one optional embodiment, the compounds of formula (1) have a single substituent on Ar, where that single substituent is —S—$CH_3$.

The Ar group (sometimes referred to herein as Ar1) is joined to a central benzene ring (sometimes referred to herein as Ar2) in compounds of formula (1) via an -L-O— group. In one embodiment, L is a directed bond, so that the Ar group is joined to a central benzene ring in compounds of formula (1) via an ether (—O—) linkage. In another embodiment, L is methylene, so that the Ar group is joined to a central benzene ring in compounds of formula (1) via a —$CH_2$—O— linkage.

The central benzene ring in formula (1) is bonded to $R^1$, where $R^1$ is selected from hydrogen, halide, $C_1$-$C_6$alkyl, $C_1$-$C_6$haloalkyl, $C_1$-$C_6$alkoxy, and $C_1$-$C_6$alkoxy substituted with $C_3$-$C_6$cycloalkyl. In one embodiment, $R^1$ is hydrogen, so that the central benzene ring (Ar2) may be said to be unsubstituted. In another embodiment, $R^1$ is not hydrogen, so that the central benzene ring is substituted. In one embodiment $R^1$ is halide, e.g., fluoride. In another embodiment, $R^1$ is $C_1$-$C_6$alkyl, e.g., methyl or ethyl. In one embodiment, $R^1$ is $C_1$-$C_6$haloalkyl, e.g., trifluoromethyl. In one embodiment, $R^1$ is $C_1$-$C_6$alkoxy, e.g., methoxy or ethoxy. In one embodiment, $R^1$ is $C_3$-$C_6$cycloalkoxy, e.g., cyclopropyloxy, cyclobutyloxy or cyclopentyloxy. In one embodiment, $R^1$ is $C_1$-$C_6$alkoxy substituted with $C_3$-$C_6$cycloalkyl, such as —O—$CH_2$-cyclopropyl where —O—$CH_2$ is a $C_1$ alkoxy that is substituted with a $C_3$ cycloalkyl (cyclopropyl).

In compounds of formula (1), a central aromatic ring (benzene) is substituted with $R^1$ as descried above, as well as the group denoted as -A-E. In effect, A links together the E group and the central aromatic ring. The A group is selected from a direct bond, methylene and ethylene. Independent of the selection of the A group, the E group is selected from —C(O)—$R^2$, i.e., a carbonyl group bonded to $R^2$, $C(OR^3)R^4R^5$, i.e., a carbon to which each of $OR^3$, $R^4$ and $R^5$ is bonded, and $CH(R^6)NR^7R^8$, i.e., a carbon to which each of hydrogen, $R^6$ and $NR^7R^8$ is bonded. For example, A may be a direct bond while E is selected from —C(O)—$R^2$, $C(OR^3)R^4R^5$ and $CH(R^6)NR^7R^8$, i.e., in one embodiment A-E is —C(O)—$R^2$, while in another embodiment A-E is $C(OR^3)R^4R^5$, and in a further embodiment A-E is $CH(R^6)NR^7R^8$. Alternatively, A may be methylene while E is selected from —C(O)—$R^2$, $C(OR^3)R^4R^5$ and $CH(R^6)NR^7R^8$, i.e., in one embodiment A-E is $CH_2$—C(O)—$R^2$, while in another embodiment A-E is $CH_2$—$C(OR^3)R^4R^5$, and in a further embodiment A-E is $CH_2$—$CH(R^6)NR^7R^8$. As a further embodiment, A may be ethylene while E is selected from —C(O)—$R^2$, $C(OR^3)R^4R^5$ and $CH(R^6)NR^7R^8$, i.e., in one embodiment A-E is $CH_2CH_2$—C(O)—$R^2$, while in another embodiment A-E is $CH_2CH_2$—$C(OR^3)R^4R^5$, and in a further embodiment A-E is $CH_2CH_2$—$CH(R^6)NR^7R^8$. In one embodiment, A is a direct bond. In another embodiment, A is —$CH_2$—. In one embodiment, A is —$CH_2CH_2$—. In another embodiment, $R^5$ is trifluoromethyl.

In one embodiment, E is —C(O)—$R^2$, where $R^2$ is methyl, ethyl or phenyl, e.g., E may be any of $C(O)CH_3$, i.e., acetyl, $C(O)CH_2CH_3$, or C(O)phenyl, i.e., benzoyl. Thus, in one embodiment, -A-E is —C(O)—$R^2$ when A is a direct bond. In another embodiment, -A-E is $CH_2$—C(O)—$R^2$ when A is methylene, e.g., —$CH_2$—$C(O)CH_3$, or —$CH_2C(O)CH_2CH_3$, or —$CH_2$(C(O)phenyl. In a further embodiment, A-E is $CH_2CH_2C(O)$—$R^2$ when A is ethylene, e.g., —$CH_2CH_2C(O)CH_3$ or —$CH_2CH_2C(O)CH_2CH_3$ or $CH_2CH_2C(O)$phenyl.

In one embodiment, E is $C(OR^3)R^4R^5$, where $R^3$ is selected from hydrogen, alkyl and substituted alkyl; $R^4$ is selected from hydrogen, alkyl and phenyl; and $R^5$ is selected from $C_1$-$C_7$alkyl, $C_1$-$C_7$haloalky, phenyl and substituted phenyl. In one embodiment, $R^5$ is trifluoromethyl and $R^3$ is hydrogen.

In one embodiment, E is $CH(R^6)NR^7R^8$, where $R^6$ is selected from hydrogen, methyl, halogenated methyl and ethyl; $R^7$ is hydrogen; and $R^8$ is hydrogen, methyl or ethyl. For example, in one embodiment, E is selected from $CH(R^6)NH_2$, $CH(R^6)NH(CH_3)$ and $CH(R^6)NH(CH_2CH_3)$. In one embodiment, $R^7$ and $R^8$ together, along with the nitrogen atom to which they are both attached, may form a 5 or 6-membered, optionally substituted, heterocycle, where the heterocycle will include the nitrogen to which both $R^7$ and $R^8$ are attached, as well as one or more, e.g., two, non-carbon atoms, e.g., oxygen or nitrogen. Thus, optionally, $R^7$ and $R^8$ together form a 5 or 6-membered, optionally substituted, heterocyclic ring, which includes the nitrogen of the $NR^7R^8$ group. Exemplary 5-membered rings are pyrrolidine and unsaturated analogs thereof, e.g., 2,5-dihydro-1H-pyrrole. Thus, —$NR^7R^8$ may represent 2,5-dihydro-1H-pyrrole. Exemplary 6-membered heterocyclic rings are piperidine and unsaturated analogs thereof, e.g., 1,2,3,4-tetrahydropyridine, and piperazine. The 5-membered heterocyclic ring and 6-membered heterocyclic ring will each have at least one nitrogen atom, and optionally may have a second heteroatom ring atom, e.g., a heteroatom selected from oxygen, nitrogen and sulfur. The 5-membered heterocyclic ring and 6-membered heterocyclic ring may be substituted as described herein. In one embodiment, substituents may be selected from halogen, $C_1$-$C_6$alkyl, $C_1$-$C_6$haloalkyl, $C_1$-$C_6$hydroxyalkyl, hydroxyl (—OH), oxo (═O), —O($C_1$-$C_6$alkyl), —O($C_1$-$C_6$haloalkyl), —O($C_1$-$C_6$hydroxyalkyl), —S($C_1$-$C_6$alkyl), —S($C_1$-$C_6$haloalkyl), —S($C_1$-$C_6$hydroxyalkyl), cyano, amino (—$NH_2$), formyl (—CHO), carboxylic acid (—COOH), carboxylate ester (—COOR where R is a $C_1$-$C_{10}$ alkyl group). Thus, in one embodiment, E is $CH(R^6)NR^7R^8$, where (i) $R^6$ is selected from hydrogen, methyl, halogenated methyl and ethyl; and $R^7$ is hydrogen; and $R^8$ is selected from hydrogen, methyl and ethyl, or (ii) $R^7$ and $R^8$ together, along with the nitrogen atom to which they are both attached, form a 5 or 6-membered heterocycle, which is optionally substituted, where the heterocycle will include the nitrogen to which both $R^7$ and $R^8$ are attached, as well as one or more, e.g., two, non-carbon atoms, e.g., oxygen or nitrogen.

In compounds of formula (1), Ar may be unsubstituted aryl, or it may have one, two or three substituents. In one embodiment, Ar has no substituents. In another embodiment, Ar has one substituent. In yet another embodiment, Ar has two substituents. In a further embodiment, Ar has three substituents. When Ar has no substituents, the present disclosure provides compounds of formula (1)

(1)

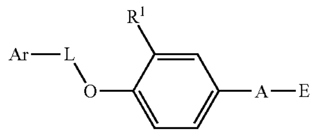

and pharmaceutically acceptable salts thereof, wherein: Ar is a 9- or 10-membered unsubstituted bicyclic aromatic ring system; L is selected from a direct bond and methylene; $R^1$ is selected from hydrogen, halide, $C_1$-$C_6$alkyl, $C_1$-$C_6$haloalkyl and $C_1$-$C_6$alkoxy; A is selected from a direct bond, —$CH_2$— and —$CH_2CH_2$—; E is selected from —C(O)—$R^2$, $C(OR^3)R^4R^5$ and $CH(R^6)NR^7R^8$; $R^2$ is selected from methyl, ethyl and phenyl; $R^3$ is selected from hydrogen, alkyl and substituted alkyl; $R^4$ is selected from hydrogen, alkyl and phenyl; $R^5$ is selected from $C_1$-$C_7$alkyl, $C_1$-$C_7$haloalkyl (e.g., trifluoromethyl), phenyl and substituted phenyl; $R^6$ is selected from hydrogen, methyl, halogenated methyl and ethyl; $R^7$ is hydrogen; and $R^8$ is hydrogen, methyl or ethyl; with the proviso that together, $R^7$ and $R^8$ may form a 5 or 6-membered, optionally substituted, heterocycle. In one such embodiment, A is ethylene and E is —C(O)—$R^2$, while $R^1$ is selected from halide and alkoxy so as to provide compound, when Ar-L-O is benzoxazol-2-yloxy so as to provide compounds of the formula

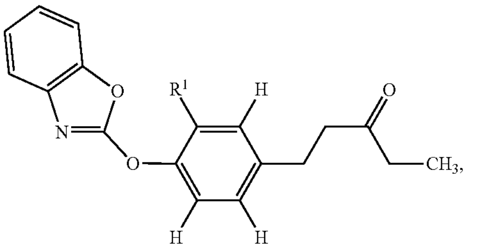

for example, a compound of the formula

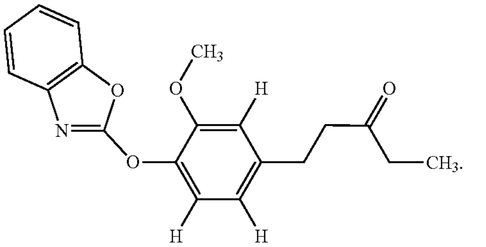 [SMILES: CCC(=O)CCc1ccc(Oc2nc3ccccc3o2)c(OC)c1]

In another such embodiment, A is ethylene and E is $C(OR^3)R^4R^5$ where $R^3$ is hydrogen, $R^4$ is alkyl, e.g., ethyl, and $R^5$ is $C_1$-$C_7$haloalky, e.g., trifluoromethyl, while $R^1$ is $C_1$-$C_4$alkoxy, so as to provide compounds, when Ar-L-O is 1,3-benzothiazol-2-yloxy, of the formula

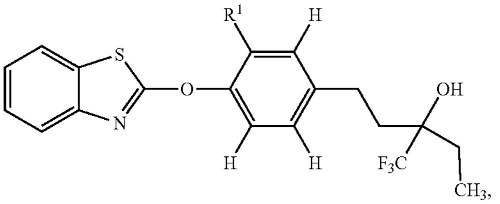

for example, the compounds

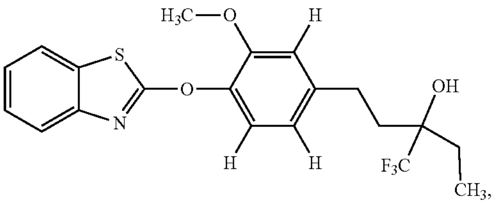

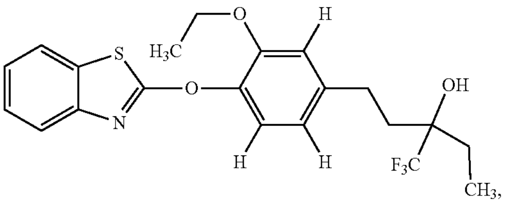

-continued

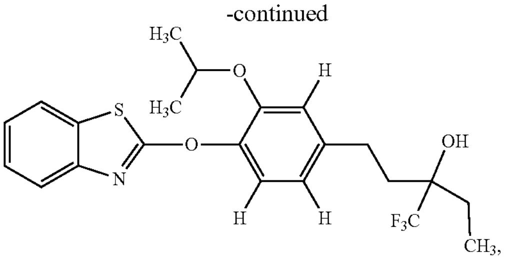

and

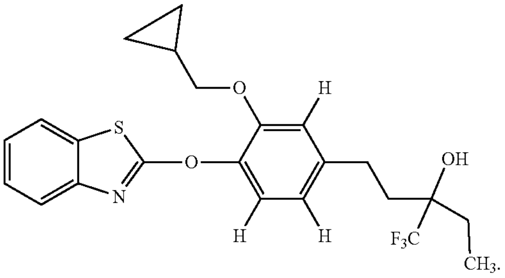

In another such embodiment, A is ethylene and E is $C(OR^3)R^4R^5$ where $R^3$ is hydrogen, $R^4$ is alkyl, e.g., methyl, and $R^5$ is $C_1$-$C_7$haloalky, e.g., trifluoromethyl, while $R^1$ is $C_1$-$C_4$alkoxy, so as to provide compounds, when Ar-L-O is 1,3-benzothiazol-2-yloxy, of the formula

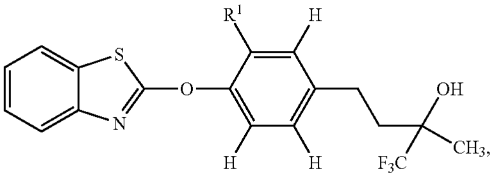

for example, a compound of the formula

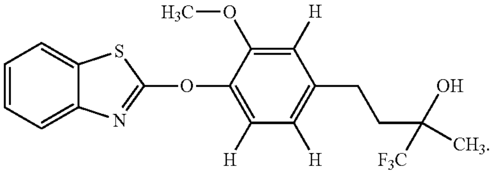 [SMILES: COc1cc(CCC(C)(O)C(F)(F)F)ccc1Oc1nc2ccccc2s1]

In another embodiment, A is ethylene and E is $C(OR^3)R^4R^5$ where $R^3$ is selected from hydrogen, alkyl and substituted alkyl; $R^4$ is hydrogen, and $R^5$ is selected from $C_1$-$C_7$alkyl, $C_1$-$C_7$haloalky, phenyl and substituted phenyl; while $R^1$ is selected from hydrogen, halide, $C_1$-$C_6$alkyl, $C_1$-$C_6$haloalkyl and $C_1$-$C_6$alkoxy, so as to provide compounds, e.g., when Ar-L-O is 1,3-benzothiazol-2-yloxy, of the formula

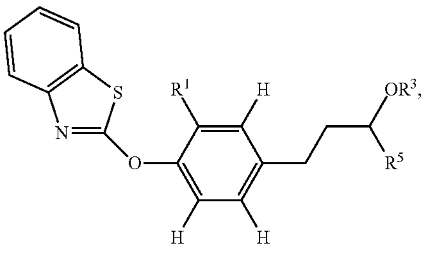

for instance compounds of the formula

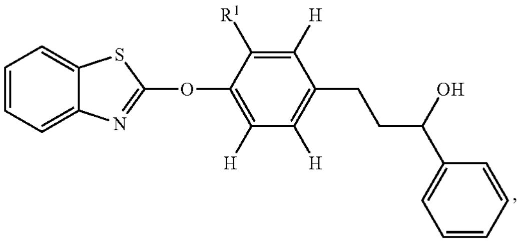

, e.g.,

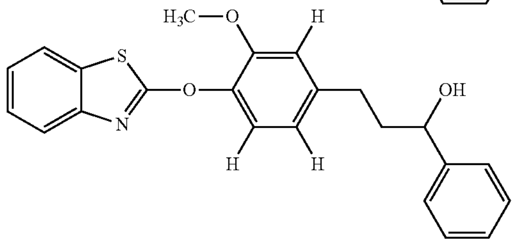

, and

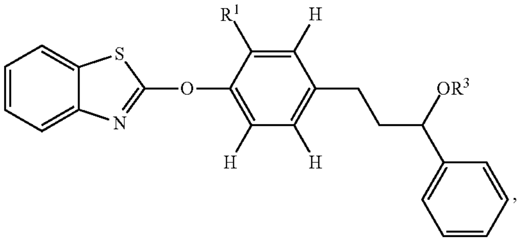

, e.g.,

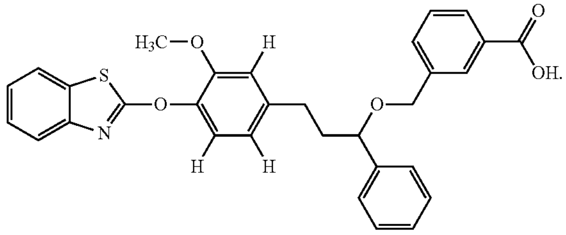

In another embodiment, $R^1$ may be hydrogen so as to provide compounds of the formula

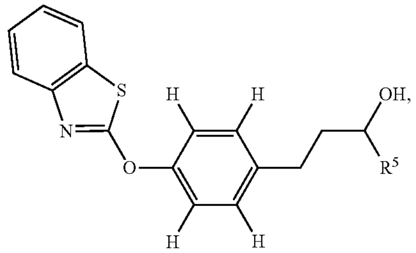

e.g.,

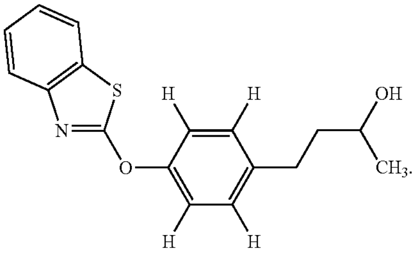

In another embodiment wherein Ar is unsubstituted, the present disclosure provides compounds having the formula

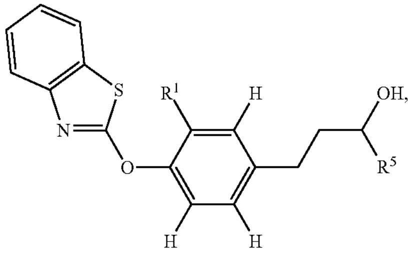

including those having the formula

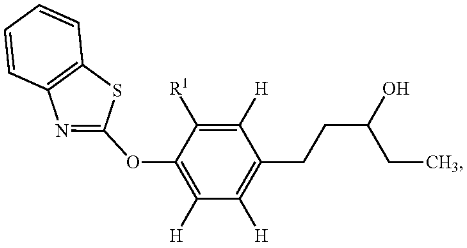

e.g., when $R^1$ is alkoxy, the compounds

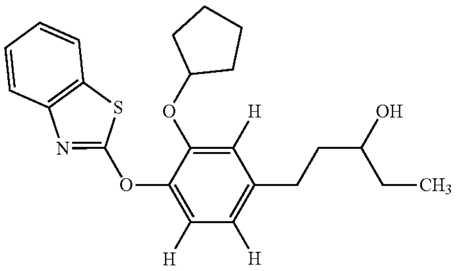

and

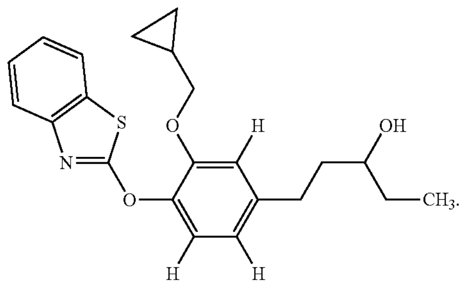

In another embodiment, Ar is unsubstituted, R1 is hydrogen, A is ethylene, E is $C(OR^3)R^4R^5$; $R^3$ is selected from hydrogen, alkyl and substituted alkyl; $R^4$ is selected from hydrogen, alkyl and phenyl; and $R^5$ is selected from $C_1$-$C_7$alkyl, $C_1$-$C_7$haloalkyl, phenyl and substituted phenyl; so as to provide compounds, e.g., of the formula

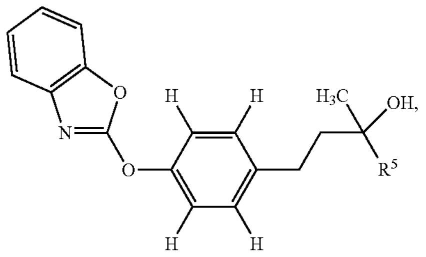

e.g., the compounds

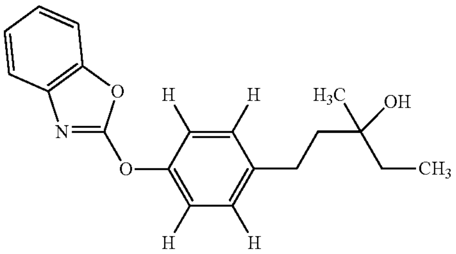

and

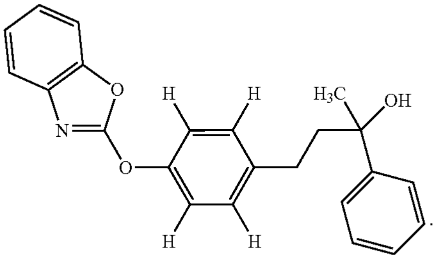

In another embodiment, Ar is unsubstituted and $R^1$ is $C_2$-$C_4$alkoxy, so as to provide compounds, e.g., of the formula.

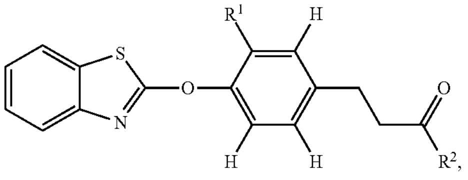

the compound

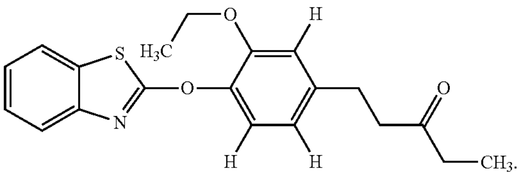 [SMILES: CCOc1cc(CCC(=O)CC)ccc1Oc1nc2ccccc2s1]

Other compounds of the present disclosure having an unsubstituted Ar group include:

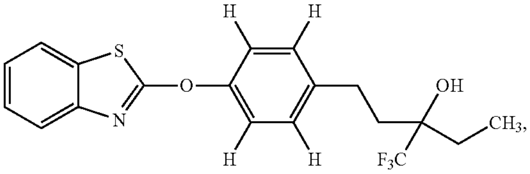

and

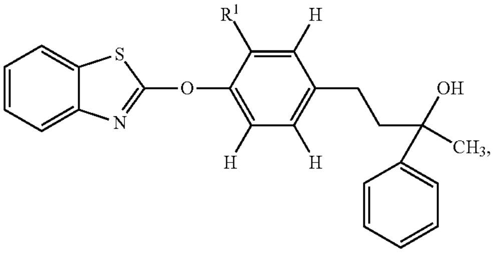

e.g.,

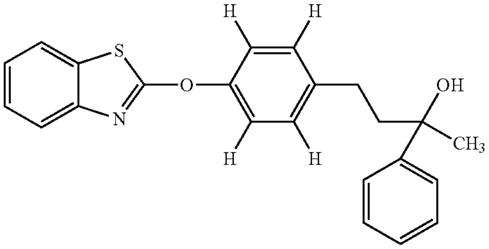

and

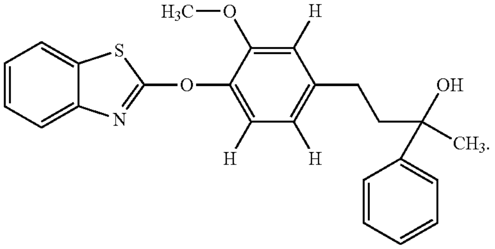

In another embodiment, Ar is unsubstituted and E is —$C(OH)(CF_3)(CH_2CH_3)$, so as to provide compounds of the formula

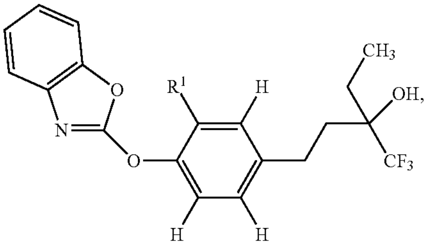

e.g., the compound

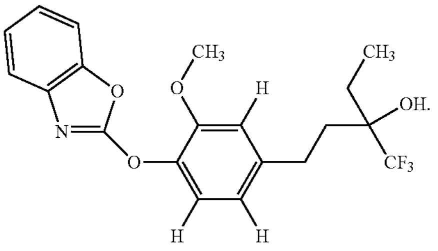 [SMILES: CCC(O)(CCc1ccc(Oc2nc3ccccc3o2)c(OC)c1)C(F)(F)F]

Other compound of the present disclosure having an unsubstituted Ar group have A equal to ethylene and E is C(O)-phenyl, for example, compounds of the formula

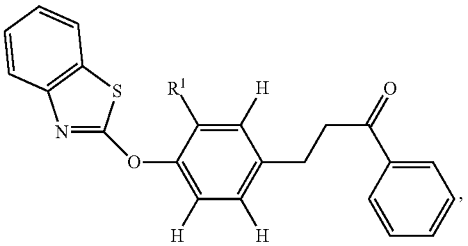

e.g., the compound

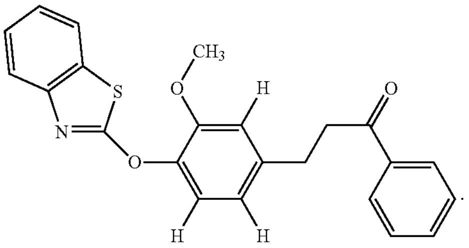 [SMILES: COc1cc(CCC(=O)c2ccccc2)ccc1Oc1nc2ccccc2s1]

In another embodiment, Ar is unsubstituted and A is a direct bond, to provide compounds, e.g., having the formula

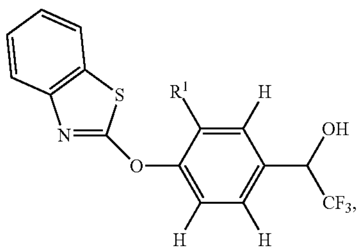

e.g., the compound

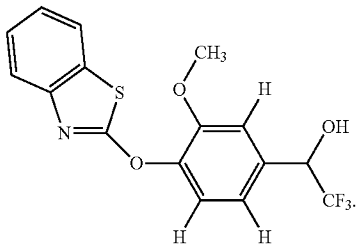 [SMILES: COc1cc(C(O)C(F)(F)F)ccc1Oc1nc2ccccc2s1]

Other compounds wherein A is a direct bond have R1 as hydrogen, so as to provide compounds having the formula

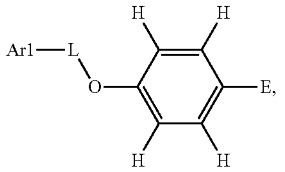

such as compounds having the formula

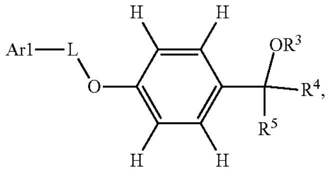

which includes compounds, using benzothiazole as an exemplary Ar group, having the formula

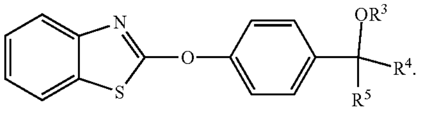

e.g., the compounds

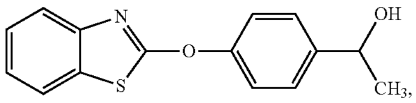

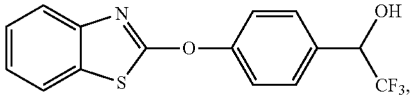

and

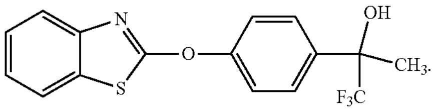

As mentioned above, in compounds of formula (1), Ar may be unsubstituted aryl, or it may have one, two or three substituents. When Ar has substituents, the present disclosure provides compounds of formula (1)

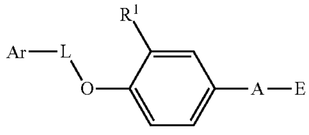

(1)

and pharmaceutically acceptable salts thereof, wherein: Ar is a 9- or 10-membered substituted bicyclic aromatic ring system, having one, two or three substituents; L is selected from a direct bond and methylene; $R^1$ is selected from hydrogen, halide, $C_1$-$C_6$alkyl, $C_1$-$C_6$haloalkyl and $C_1$-$C_6$alkoxy; A is selected from a direct bond, —$CH_2$— and —$CH_2CH_2$—; E is selected from —C(O)—$R^2$, C($OR^3$)$R^4R^5$ and CH($R^6$)$NR^7R^8$; $R^2$ is selected from methyl, ethyl and phenyl; $R^3$ is selected from hydrogen, alkyl and substituted alkyl; $R^4$ is selected from hydrogen, alkyl and phenyl; $R^5$ is selected from $C_1$-$C_7$alkyl, $C_1$-$C_7$haloalkyl (e.g., trifluoromethyl), phenyl and substituted phenyl; $R^6$ is selected from hydrogen, methyl, halogenated methyl and ethyl; $R^7$ is hydrogen; and $R^8$ is hydrogen, methyl or ethyl; with the proviso that together, $R^7$ and $R^8$ may form a 5 or 6-membered, optionally substituted, heterocycle. In one such embodiment, Ar has one or two substituents. Optionally, A is selected from $CH_2$ and $CH_2CH_2$ so as to provide, for example, compounds of the formula

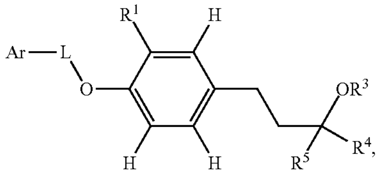

including compounds wherein L is a direct bond to provide compounds having the formula

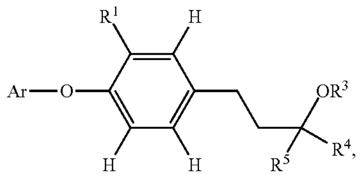

which includes compounds of the formula

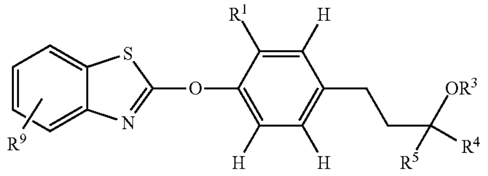

wherein $R^9$ represents one or two substituents on Ar, independently selected at each occurrence, where $R^3$ may be, for example, hydrogen, so as to provide compounds of the formula.

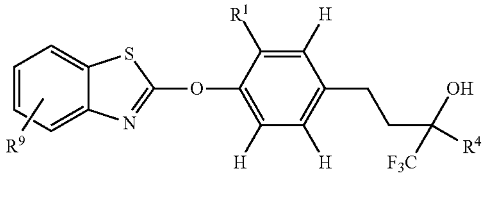

wherein $R^4$ is methyl or ethyl, and compounds of the formula

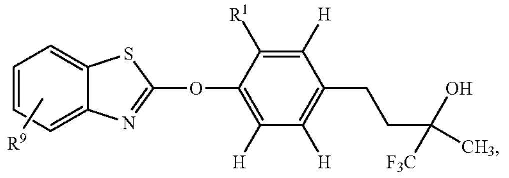

including compounds having the formula

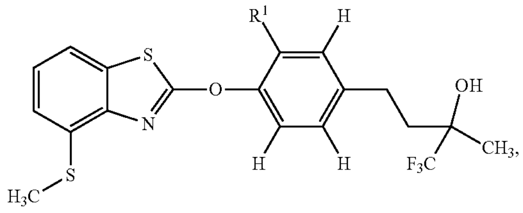

the compound

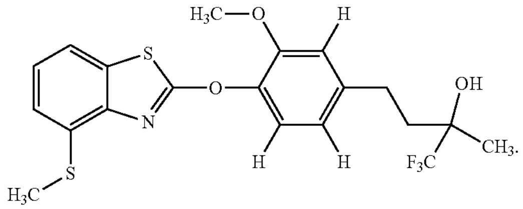 [SMILES: COc1cc(CCC(C)(O)C(F)(F)F)ccc1Oc1nc2c(SC)cccc2s1]

In one embodiment wherein Ar is substituted with one or two $R^9$ groups, the present disclosure provides compounds having the formula

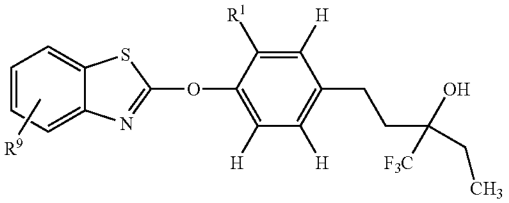

including compounds wherein $R^9$ is thiomethyl, to provide compounds having the formula

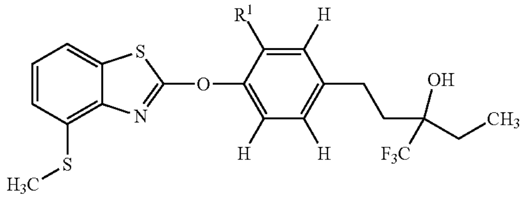

e.g., the compound

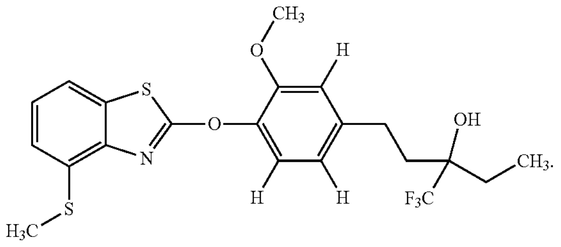 [SMILES: CCC(O)(CCc1ccc(Oc2nc3c(SC)cccc3s2)c(OC)c1)C(F)(F)F]

Other compounds of the present disclosure having methoxy as $R^1$ and substitution on Ar include those of the formula

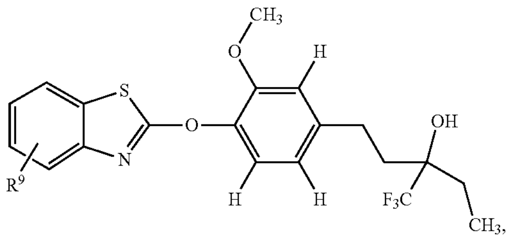

including the compounds

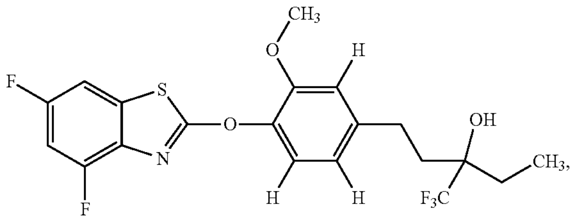

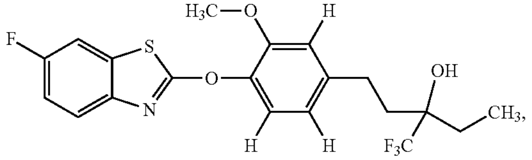

and

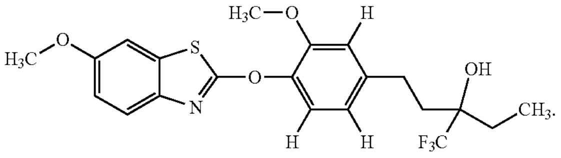

Further compounds of the present disclosure having substitution on Ar include compounds having the formula

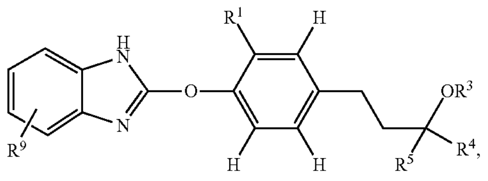

e.g., the compound

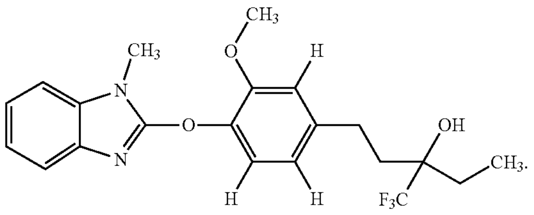

In other embodiments, Ar is substituted and $R^1$ is selected from halide and alkoxy to provide, e.g., a compounds of the formulae

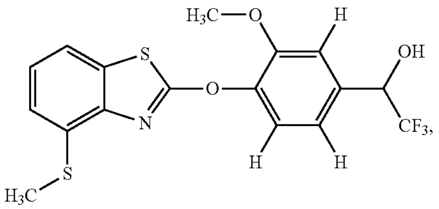

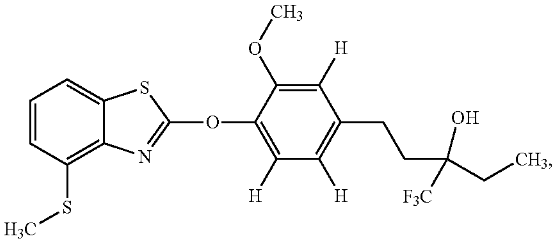

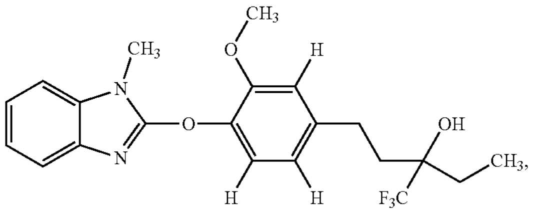 [SMILES: CCC(O)(CCc1ccc(Oc2nc3ccccc3n2C)c(OC)c1)C(F)(F)F]

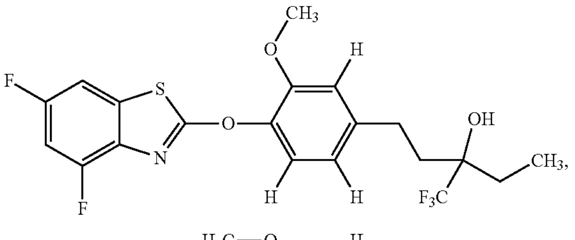

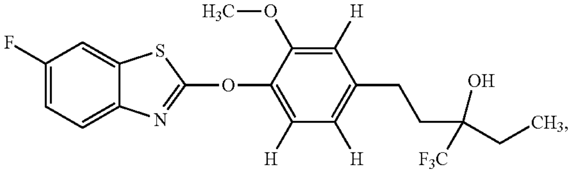

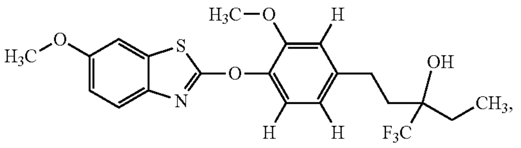

and

-continued

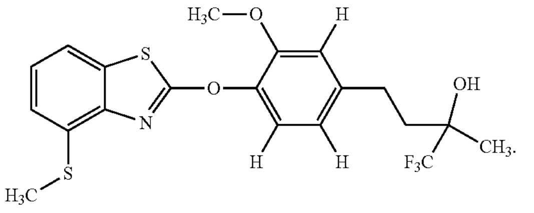

In one embodiment, the compounds of the disclosure include both of hydroxyl and trifluoromethyl as components of the "E" group. For example, the present disclosure provides compounds of the formula (1)

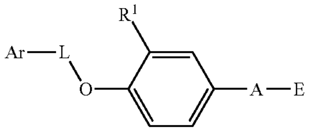

and pharmaceutically acceptable salts thereof, wherein: Ar is a 9- or 10-membered bicyclic aromatic ring system, where Ar is optionally substituted with one, two or three substituents; L is selected from a direct bond and methylene; $R^1$ is selected from hydrogen, halide, $C_1$-$C_4$alkyl, $C_1$-$C_4$haloalkyl and $C_1$-$C_4$alkoxy; A is selected from a direct bond, —$CH_2$— and —$CH_2CH_2$—; E is $C(OR^3)R^4R^5$ where $R^3$ is hydrogen while $R^5$ is trifluoromethyl, so that E is $C(OH)(CF_3)R^4$; and $R^4$ is selected from hydrogen, methyl and ethyl. Optionally, a compound of formula (1) may additionally be characterized by one or more of the following: $R^5$ is $C_1$-$C_7$alkyl; $R^5$ is methyl; $R^5$ is ethyl; $R^5$ is $C_1$-$C_7$haloalkyl; $R^5$ is phenyl; A is —$CH_2CH_2$— and $R^5$ is $C_1$-$C_7$alkyl; A is —$CH_2CH_2$— and $R^5$ is methyl; A is —$CH_2CH_2$— and $R^5$ is ethyl; A is —$CH_2CH_2$— and $R^5$ is $C_1$-$C_7$haloalkyl; A is —$CH_2CH_2$— and $R^5$ is phenyl; L is a direct bond, A is —$CH_2CH_2$— and $R^5$ is $C_1$-$C_7$alkyl; L is a direct bond, A is —$CH_2CH_2$— and $R^5$ is methyl; L is a direct bond, A is —$CH_2CH_2$— and $R^5$ is ethyl; L is a direct bond, A is —$CH_2CH_2$— and $R^5$ is $C_1$-$C_7$haloalkyl (e.g., trifluoromethyl); L is a direct bond, A is —$CH_2CH_2$— and $R^5$ is phenyl; Ar is unsubstituted benzothiazol-2-yl; Ar is benzothiazol-2-yl having one substituent; Ar is benzothiazol-2-yl having two substituents; and Ar is benzothiazol-2-yl having three substituents. In addition, the present disclosure provides the following exemplary compounds that include hydroxyl and trifluoromethyl as components of the "E" group:

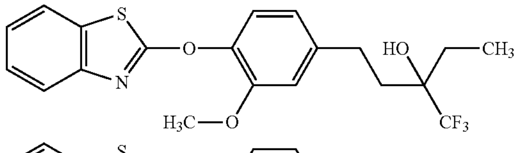

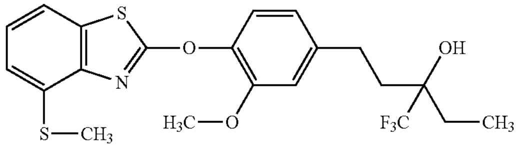

-continued

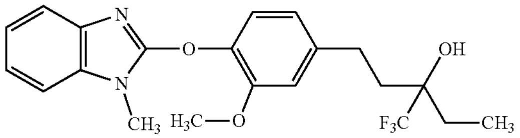

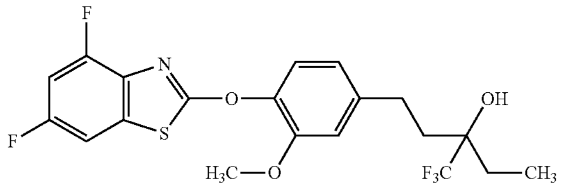

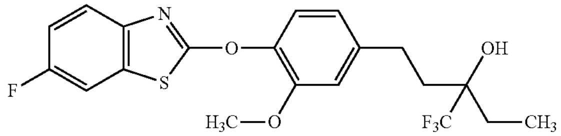

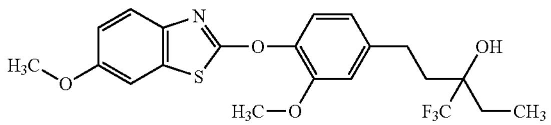

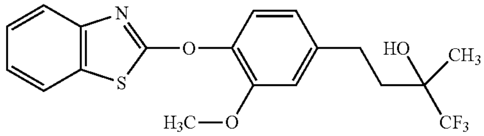

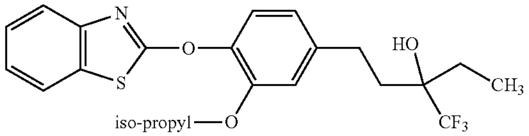

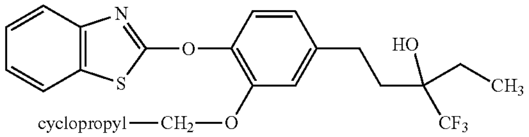

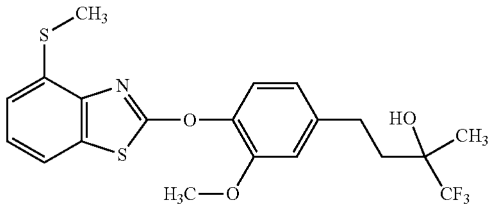

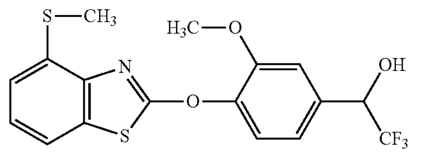

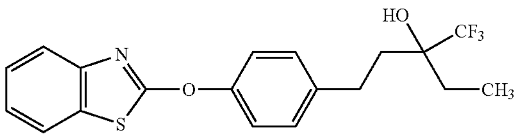

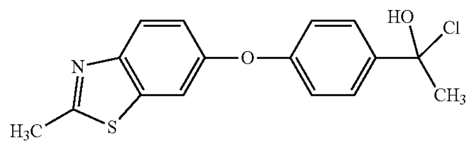

-continued

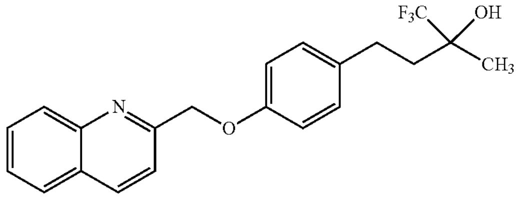

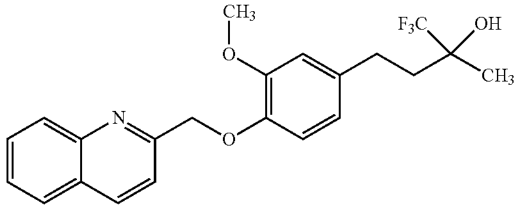

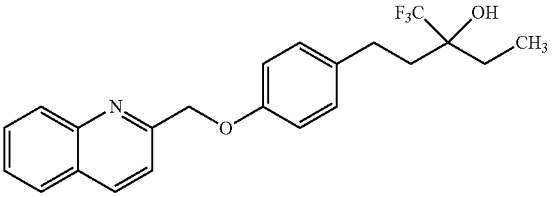

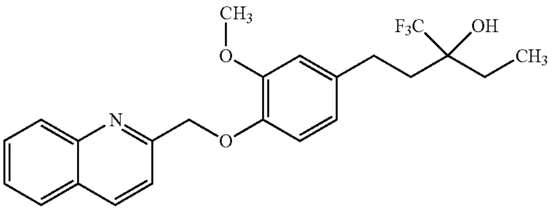

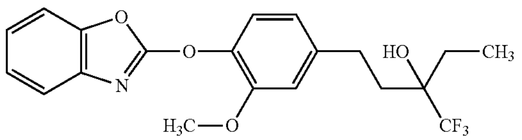

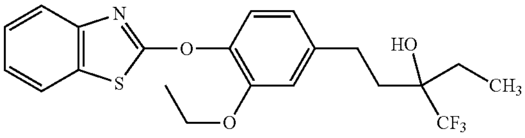

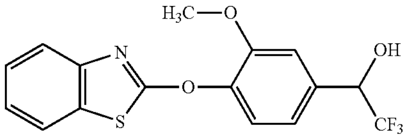

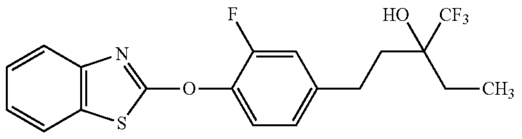

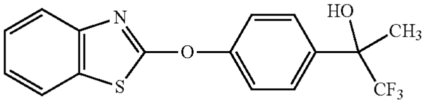

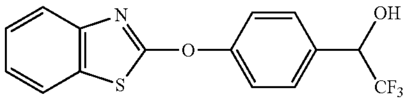

In another embodiment, the present disclosure provides compounds of formula (1)

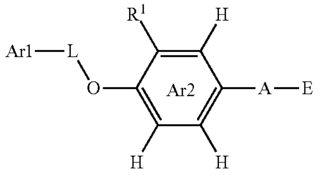

(1)

including pharmaceutically acceptable salts thereof, wherein Ar1 is a 6-benzothiazole, where Ar1 is optionally substituted with one or two substituents, and L is a direct bond, so that formula (1) has the structure;

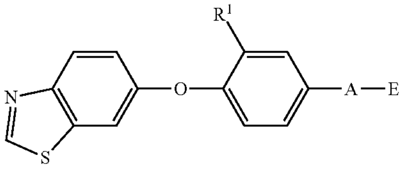

where $R^1$ is selected from hydrogen, halide and alkoxy; A is selected from a direct bond, —$CH_2$— and —$CH_2CH_2$—; E is selected from —C(O)—$R^2$, C($OR^3$)$R^4R^5$ and CH($R^6$)$NR^7R^8$; $R^2$ is selected from methyl, ethyl and phenyl; $R^3$ is selected from H and a hydroxyl protecting group; $R^4$ is selected from hydrogen, methyl and ethyl; $R^5$ is selected from methyl, halogenated methyl (e.g., trifluoromethyl) ethyl and phenyl; $R^6$ is selected from hydrogen, methyl, halogenated methyl and ethyl; $R^7$ is hydrogen; and $R^8$ is methyl or ethyl; with the proviso that together, $R^7$ and $R^8$ may form a 5 or 6-membered optionally substituted heterocycle. In addition, the present disclosure provides the following exemplary compounds that include 6-benzothiazole as the Ar group:

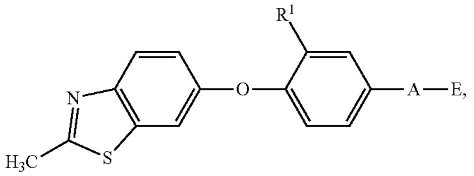

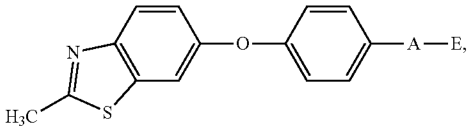

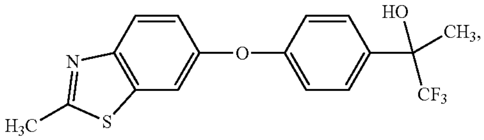

and

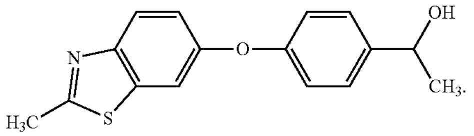

In another embodiment, the present disclosure provides compounds of formula (1)

(1)

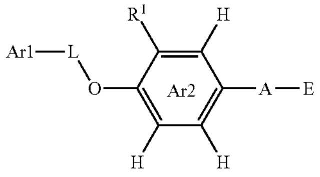

and pharmaceutically acceptable salts thereof, wherein Ar1 is a naphthalene radical, or a heterocyclic analog thereof, where Ar1 is optionally substituted with one or two substituents, and L is optionally a methylene group (—$CH_2$—), where $R^1$ is selected from hydrogen, halide and alkoxy; A is selected from a direct bond, —$CH_2$— and —$CH_2CH_2$—; E is selected from —C(O)—$R^2$, C($OR^3$)$R^4R^5$ and CH($R^6$) $NR^7R^8$; $R^2$ is selected from methyl, ethyl and phenyl; $R^3$ is selected from H and a hydroxyl protecting group; $R^4$ is selected from hydrogen, methyl and ethyl; $R^5$ is selected from methyl, halogenated methyl (e.g., trifluoromethyl), ethyl and phenyl; $R^6$ is selected from hydrogen, methyl, halogenated methyl and ethyl; $R^7$ is hydrogen; and $R^8$ is methyl or ethyl; with the proviso that together, $R^7$ and $R^8$ may form a 5 or 6-membered optionally substituted heterocycle. In addition, the present disclosure provides the following exemplary compounds that include naphthyl or heterocyclic analogs of naphthyl as the Ar group:

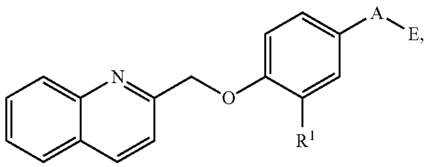

wherein $R^1$ is selected from hydrogen, halide and alkoxy; A is selected from a direct bond, —$CH_2$— and —$CH_2CH_2$—; E is selected from —C(O)—$R^2$, C($OR^3$)$R^4R^5$ and CH($R^6$) $NR^7R^8$; $R^2$ is selected from methyl, ethyl and phenyl; $R^3$ is selected from H and a hydroxyl protecting group; $R^4$ is selected from hydrogen, methyl and ethyl; $R^5$ is selected from methyl, halogenated methyl (e.g., trifluoromethyl), ethyl and phenyl; $R^6$ is selected from hydrogen, methyl, halogenated methyl and ethyl; $R^7$ is hydrogen; and $R^8$ is methyl or ethyl; with the proviso that together, $R^7$ and $R^8$ may form a 5 or 6-membered optionally substituted heterocycle, such as compounds of the formula

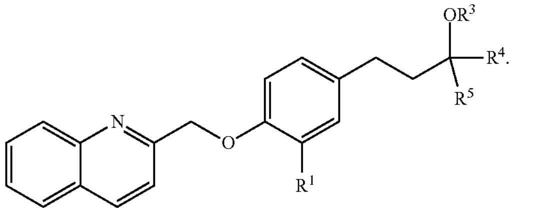

wherein $R^1$ is selected from hydrogen, halide and alkoxy; $R^3$ is selected from H and a hydroxyl protecting group; $R^4$ is selected from hydrogen, methyl and ethyl; $R^5$ is selected from methyl, halogenated methyl (e.g., trifluoromethyl), ethyl and phenyl, e.g.,

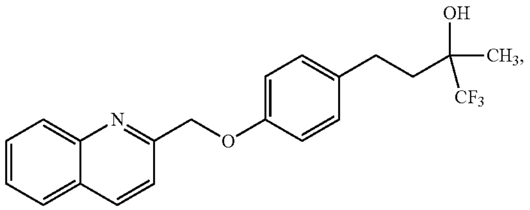

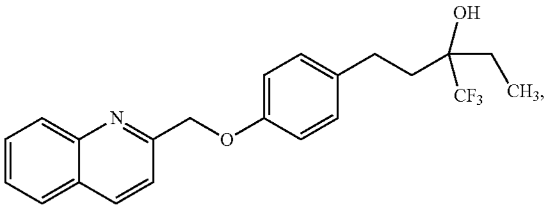

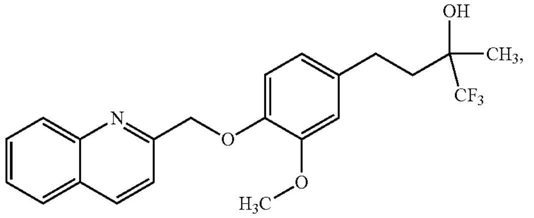

and

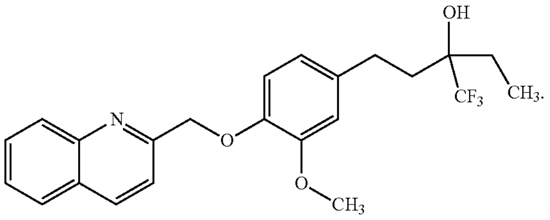

And in addition, the present disclosure provides the following exemplary compounds that include naphthyl or heterocyclic analogs of naphthyl as the Ar group, such as compounds of the formula:

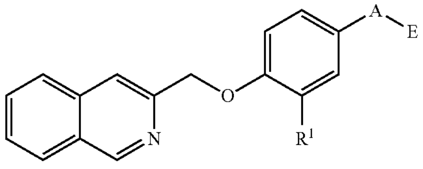

wherein $R^1$ is selected from hydrogen, halide and alkoxy; A is selected from a direct bond, —$CH_2$— and —$CH_2CH_2$—; E is selected from —C(O)—$R^2$, C($OR^3$)$R^4R^5$ and CH($R^6$) $NR^7R^8$; $R^2$ is selected from methyl, ethyl and phenyl; $R^3$ is selected from H and a hydroxyl protecting group; $R^4$ is selected from hydrogen, methyl and ethyl; $R^5$ is selected from methyl, halogenated methyl (e.g., trifluoromethyl), ethyl and phenyl; $R^6$ is selected from hydrogen, methyl, halogenated methyl and ethyl; $R^7$ is hydrogen; and $R^8$ is methyl or ethyl; with the proviso that together, $R^7$ and $R^8$ may form a 5 or 6-membered optionally substituted heterocycle, including compounds of the formula

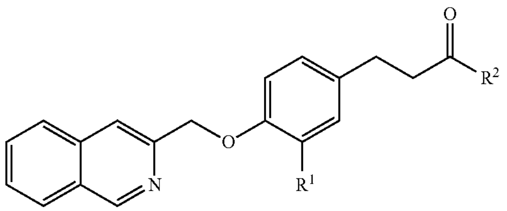

wherein $R^1$ is selected from hydrogen, halide and alkoxy and $R^2$ is selected from methyl, ethyl and phenyl, such as the compound of the formula

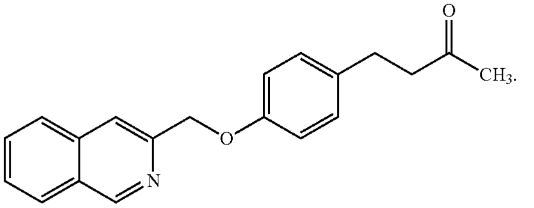 [SMILES: CC(=O)CCc1ccc(OCc2cc3ccccc3cn2)cc1]

In one embodiment, the compounds of the disclosure have a nitrogen atom as part of the E group, and more specifically have E is —$CH(R^6)NR^7R^8$. For example, the present disclosure provides compounds of the formula (1)

(1)

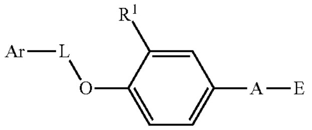

and pharmaceutically acceptable salts thereof, wherein: Ar is a 9- or 10-membered bicyclic aromatic ring system, where Ar is optionally substituted with one or two substituents; L is selected from a direct bond and methylene; $R^1$ is selected from hydrogen, halide and alkoxy; A is selected from a direct bond, —$CH_2$— and —$CH_2CH_2$—; E is $CH(R^6)NR^7R^8$; $R^6$ is selected from hydrogen, methyl, halogenated methyl and ethyl; $R^7$ is hydrogen; and $R^8$ is methyl or ethyl; with the proviso that together, $R^7$ and $R^8$ may form a 5 or 6-membered optionally substituted heterocycle. Optionally, a compound of formula (1) may additionally be characterized by one or more of the following: $R^7$ and $R^8$ form a 5 or 6-membered optionally substituted heterocycle, and $R^1$ is hydrogen; A is $CH_2CH_2$; $R^7$ and $R^8$ form a 5 or 6-membered optionally substituted heterocycle, $R^1$ is hydrogen and A is $CH_2CH_2$, to provide, for example, the following compounds:

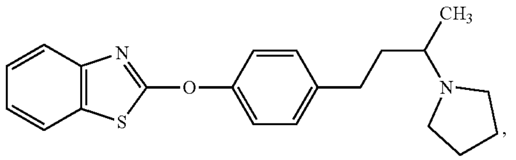

-continued

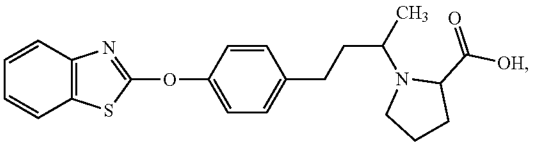

and

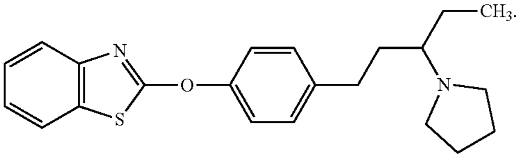

Optionally, such a compound of formula (1) may additionally be characterized by specifying that A is a direct bond, so as to provide, for example, compounds of the formula:

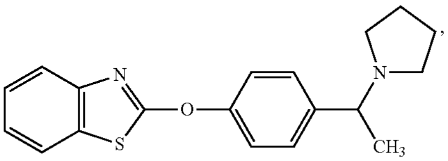

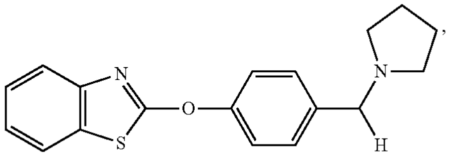

, and

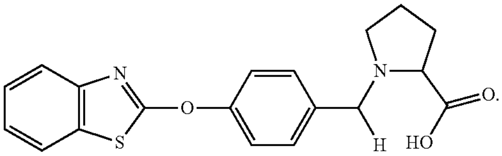

Optionally, such a compound of formula (1) may additionally be characterized by specifying that $R^1$ is not hydrogen, $R^7$ is hydrogen, and $R^8$ is methyl or ethyl, so as to provide, for example, a compound of the formula.

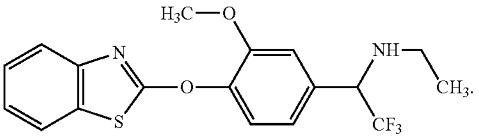

In one embodiment, the compounds of the disclosure have a carbonyl group (C(O)) as part of the E group, and more specifically have E is —$CH(R^6)NR^7R^8$. For example, the present disclosure provides compounds of the formula (1)

(1)

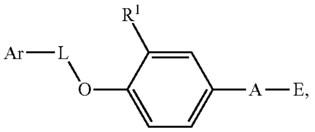

and pharmaceutically acceptable salts thereof, wherein: Ar is a 9- or 10-membered bicyclic aromatic ring system, where Ar is optionally substituted with one, two or three substituents; L is selected from a direct bond and methylene; $R^1$ is selected from hydrogen, halide, $C_1$-$C_6$alkyl, $C_1$-$C_6$haloalkyl and $C_1$-$C_6$alkoxy; A is selected from a direct bond, —$CH_2$— and —$CH_2CH_2$—; E is —C(O)—$R^2$; and $R^2$ is selected from methyl, ethyl and phenyl. For example, the present disclosure provides compounds of the formula

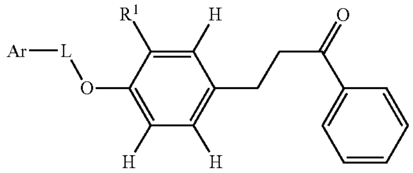

wherein Ar is a 9- or 10-membered bicyclic aromatic ring system, where Ar is optionally substituted with one, two or three substituents; L is selected from a direct bond and methylene; $R^1$ is selected from hydrogen, halide, $C_1$-$C_6$alkyl, $C_1$-$C_6$haloalkyl and $C_1$-$C_6$alkoxy; A is —$CH_2CH_2$—; E is —C(O)—$R^2$; and $R^2$ is phenyl, including compounds of the formula

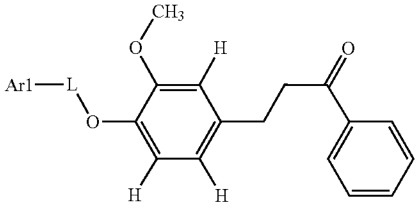

wherein Ar is a 9- or 10-membered bicyclic aromatic ring system, where Ar is optionally substituted with one, two or three substituents; L is selected from a direct bond and methylene; $R^1$ is $C_1$-$C_6$alkoxy and specifically methoxy; A is —$CH_2CH_2$—; E is —C(O)—$R^2$; and $R^2$ is phenyl, and including compounds of the formula

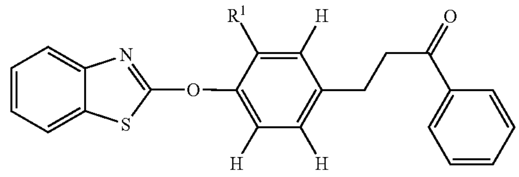

wherein $R^1$ is selected from hydrogen, halide, $C_1$-$C_6$alkyl, $C_1$-$C_6$haloalkyl and $C_1$-$C_6$alkoxy, such as the compound of the formula

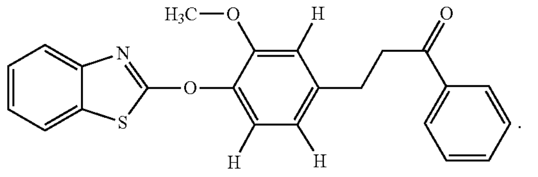 [SMILES: COc1cc(CCC(=O)c2ccccc2)ccc1Oc1nc2ccccc2s1]

In one embodiment, the compounds of the disclosure have halide substitution on the central aromatic ring, i.e., compounds of formula (1) wherein $R^1$ is halide. For example, the present disclosure provides compounds of the formula (1) In one aspect the present disclosure provides compounds of the formula (1)

(1)

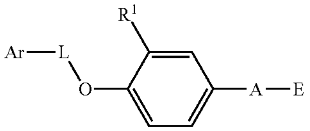

and pharmaceutically acceptable salts thereof, wherein: Ar is a 9- or 10-membered bicyclic aromatic ring system, where Ar is optionally substituted with one, two or three substituents; L is selected from a direct bond and methylene; $R^1$ is halide; A is selected from a direct bond, —$CH_2$— and —$CH_2CH_2$—; E is selected from —C(O)—$R^2$, C($OR^3$)$R^4R^5$ and CH($R^6$)$NR^7R^8$; $R^2$ is selected from methyl, ethyl and phenyl; $R^3$ is selected from hydrogen, alkyl and substituted alkyl; $R^4$ is selected from hydrogen, alkyl and phenyl; $R^5$ is selected from $C_1$-$C_7$alkyl, $C_1$-$C_7$haloalkyl (e.g., trifluoromethyl), phenyl and substituted phenyl; $R^6$ is selected from hydrogen, methyl, halogenated methyl and ethyl; $R^7$ is hydrogen; and $R^8$ is hydrogen, methyl or ethyl; with the proviso that together, $R^7$ and $R^8$ may form a 5 or 6-membered, optionally substituted, heterocycle. For example, the present disclosure provides compounds of the formula

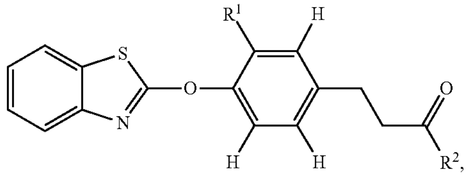

wherein $R^1$ is halide and $R^2$ is selected from methyl, ethyl and phenyl; such as

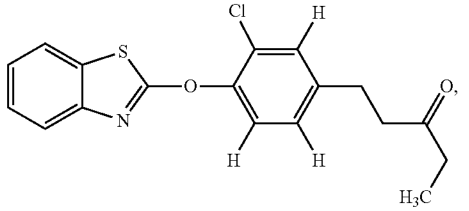

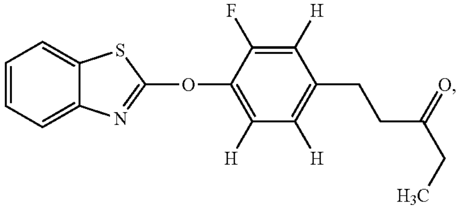

and

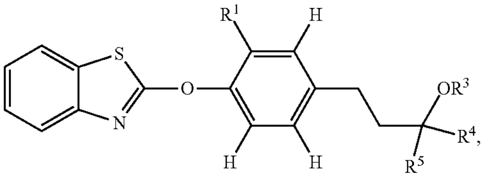

wherein $R^1$ is halide, $R^3$ is selected from hydrogen, alkyl and substituted alkyl; $R^4$ is selected from hydrogen, alkyl and phenyl; $R^5$ is selected from $C_1$-$C_7$alkyl, $C_1$-$C_7$haloalkyl (e.g., trifluoromethyl), phenyl and substituted phenyl; such as

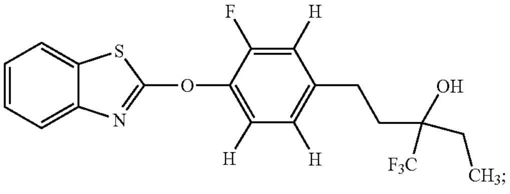

and

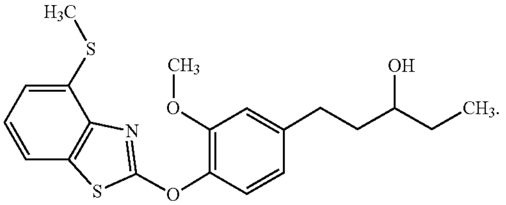

The compounds of the present disclosure are also meant to encompass all pharmaceutically acceptable compounds of formula (1) and subsets thereof, being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These radiolabeled compounds could be useful to help determine or measure the effectiveness of the compounds, by characterizing, for example, the site or mode of action, or binding affinity to a pharmacologically important site of action. Certain isotopically-labelled compounds of the disclosure, for example, those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection. Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labelled compounds of the disclosure can generally be prepared by conventional techniques known to those skilled in the art or by processes analogous to those described in the Preparations and Examples as set out below using an appropriate isotopically-labelled reagent in place of the non-labeled reagent previously employed.

Often crystallizations produce a solvate of the compound of the disclosure. As used herein, the term "solvate" refers to an aggregate that comprises one or more molecules of a compound of the disclosure with one or more molecules of solvent. The solvent may be water, in which case the solvate may be a hydrate. Alternatively, the solvent may be an organic solvent. Thus, the compounds of the present disclosure may exist as a hydrate, including a monohydrate, dihydrate, hemihydrate, sesquihydrate, trihydrate, tetrahydrate and the like, as well as the corresponding solvated forms. The compound of the disclosure may be true solvates, while in other cases, the compound of the disclosure may merely retain adventitious water or be a mixture of water plus some adventitious solvent.

Some specific compounds of the present disclosure are provided in Table 1, which identifies specific compounds by each of compound number (No.), compound structure and compound name:

TABLE 1

| No. | Compound Structure | Compound Name |
|---|---|---|
| 101 | 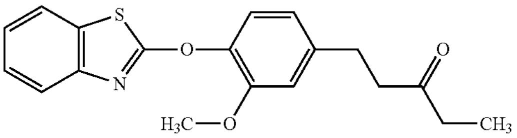 | 1-[4-(1,3-benzothiazol-2-yloxy)-3-methoxyphenyl]pentan-3-one |
| 102 | 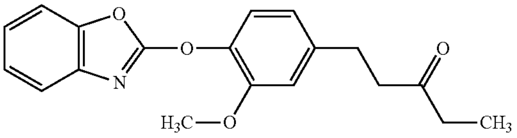 | 1-[4-(1,3-benzoxazol-2-yloxy)-3-methoxyphenyl]pentan-3-one |
| 103 | 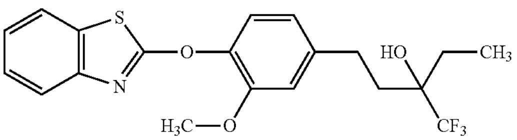 [SMILES: CCC(O)(CCc1ccc(Oc2nc3ccccc3s2)c(OC)c1)C(F)(F)F] | 1-[4-(1,3-benzothiazol-2-yloxy)-3-methoxyphenyl]-3-(trifluoromethyl)pentan-3-ol |
| 104 | 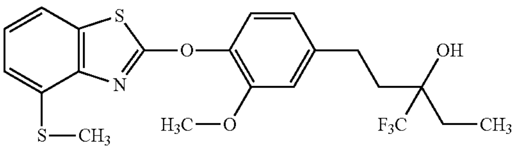 [SMILES: CCC(O)(CCc1ccc(Oc2nc3c(SC)cccc3s2)c(OC)c1)C(F)(F)F] | 1-{3-methoxy-4-[(4-methylsulfanyl-1,3-benzothiazol-2-yl)oxy]phenyl}-3-(trifluoromethyl)pentan-3-ol |

TABLE 1-continued

| No. | Compound Structure | Compound Name |
| --- | --- | --- |
| 105 | 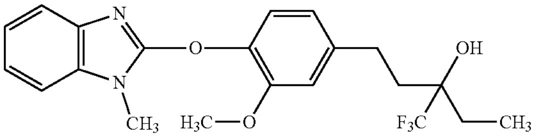 [SMILES: CCC(O)(CCc1ccc(Oc2nc3ccccc3n2C)c(OC)c1)C(F)(F)F] | 1-[4-(1-methyl-1H-benzimidazol-2-yloxy)-3-methoxyphenyl]-3-(trifluoromethyl)pentan-3-ol |
| 106 | 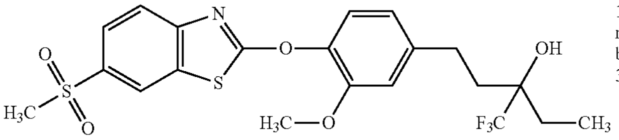 | 1-{3-methoxy-4-[(6-methylsulfonyl-1,3-benzothiazol-2-yl)oxy]phenyl}-3-(trifluoromethyl)pentan-3-ol |
| 107 | 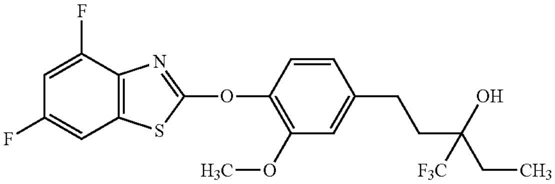 [SMILES: CCC(O)(CCc1ccc(Oc2nc3c(F)cc(F)cc3s2)c(OC)c1)C(F)(F)F] | 1-{4-[(4,6-difluoro-1,3-benzothiazol-2-yl)oxy]-3-methoxyphenyl}-3-(trifluoromethyl)pentan-3-ol |
| 108 | 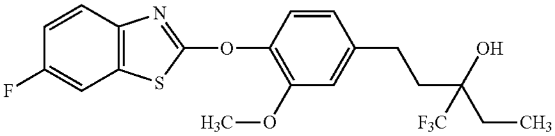 | 1-{4-[(6-fluoro-1,3-benzothiazol-2-yl)oxy]-3-methoxyphenyl}-3-(trifluoromethyl)pentan-3-ol |
| 109 | 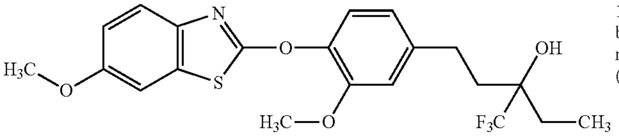 | 1-{4-[(6-methoxy-1,3-benzothiazol-2-yl)oxy]-3-methoxyphenyl}-3-(trifluoromethyl)pentan-3-ol |
| 110 | 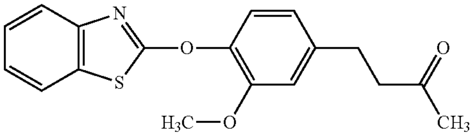 | 4-[4-(1,3-benzothiazol-2-yloxy)-3-methoxyphenyl]butan-2-one |
| 111 | 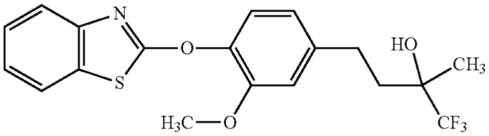 | 4-[4-(1,3-benzothiazol-2-yloxy)-3-methoxyphenyl]-1,1,1-trifluoro-2-methylbutan-2-ol |
| 112 | 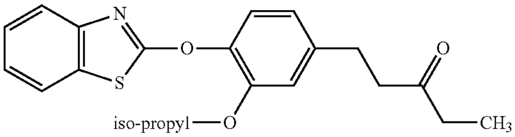 | 1-[4-(1,3-benzothiazol-2-yloxy)-3-(iso-propyloxy)-phenyl]pentan-3-one |
| 113 | 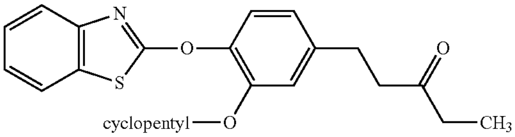 | 1-[4-(1,3-benzothiazol-2-yloxy)-3-(cyclopentyloxy)-phenyl]pentan-3-one |
| 114 | 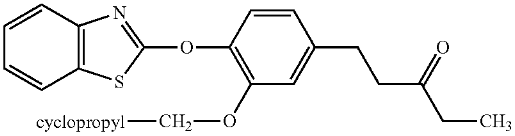 | 1-[4-(1,3-benzothiazol-2-yloxy)-3-(cyclopropyl-methoxy)-phenyl]pentan-3-one |

TABLE 1-continued

| No. | Compound Structure | Compound Name |
| --- | --- | --- |
| 115 | 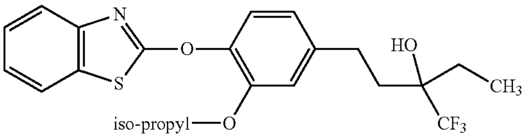 | 1-[4-(1,3-benzothiazol-2-yloxy)-3-(iso-propyloxy)phenyl]-3-(trifluoromethyl)pentan-3-ol |
| 116 | 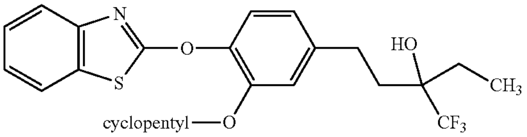 | 1-[4-(1,3-benzothiazol-2-yloxy)-3-(cyclopentyloxy)-phenyl]-3-(trifluoromethyl)-pentan-3-ol |
| 117 | 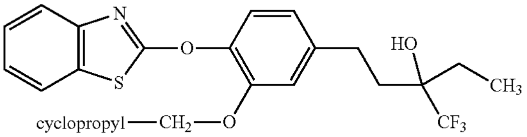 | 1-[4-(1,3-benzothiazol-2-yloxy)-3-(cyclopropyl-methoxy)-phenyl]-3-(trifluoromethyl)-pentan-3-ol |
| 118 | 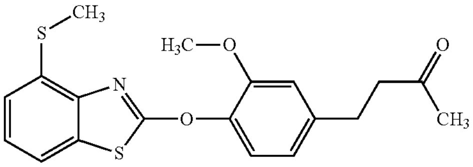 [SMILES: COc1cc(CCC(C)=O)ccc1Oc1nc2c(SC)cccc2s1] | 4-(3-methoxy-4-{[4-(methylsulfanyl)-1,3-benzothiazol-2-yl]oxy}phenyl)butan-2-one |
| 119 | 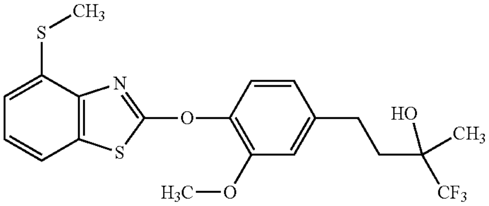 | 1,1,1-trifluoro-4-(3-methoxy-4-{[4-(methylsulfanyl)-1,3-benzothiazol-2-yl]oxy}phenyl)-2-methylbutan-2-ol |
| 120 | 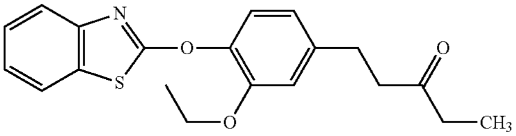 [SMILES: CCOc1cc(CCC(=O)CC)ccc1Oc1nc2ccccc2s1] | 1-[4-(1,3-benzothiazol-2-yloxy)-3-ethoxyphenyl]-pentan-3-one |
| 121 | 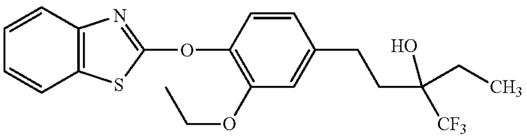 | 1-[4-(1,3-benzothiazol-2-yloxy)-3-ethoxyphenyl]-3-(trifluoromethyl)pentan-3-ol |
| 122 | 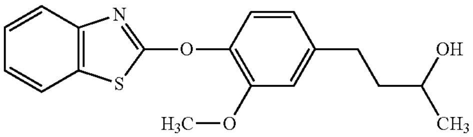 [SMILES: COc1cc(CCC(C)O)ccc1Oc1nc2ccccc2s1] | 4-[4-(1,3-benzothiazol-2-yloxy)-3-methoxyphenyl]-butan-2-ol |
| 123 | 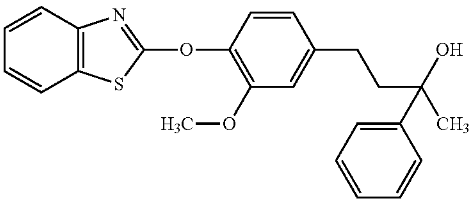 [SMILES: COc1cc(CCC(C)(O)c2ccccc2)ccc1Oc1nc2ccccc2s1] | 4-[4-(1,3-benzothiazol-2-yloxy)-3-methoxyphenyl]-2-(phenyl)butan-2-ol |

TABLE 1-continued

| No. | Compound Structure | Compound Name |
| --- | --- | --- |
| 124 | 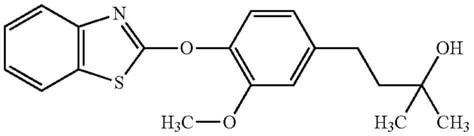 | 4-[4-(1,3-benzothiazol-2-yloxy)-3-methoxyphenyl]-2-methylbutan-2-ol |
| 125 | 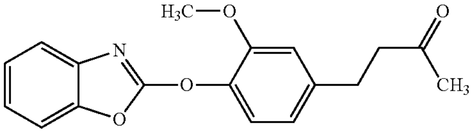 [SMILES: COc1cc(CCC(C)=O)ccc1Oc1nc2ccccc2o1] | 4-[4-(1,3-benzoxazol-2-yloxy)-3-methoxyphenyl]butan-2-one |
| 126 | 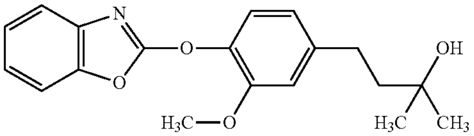 | 4-[4-(1,3-benzoxazol-2-yloxy)-3-methoxyphenyl]-2-methylbutan-2-ol |
| 127 | 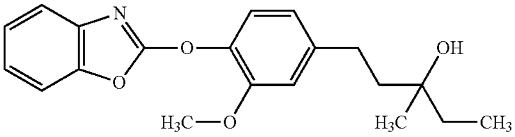 [SMILES: CCC(C)(O)CCc1ccc(Oc2nc3ccccc3o2)c(OC)c1] | 1-[4-(1,3-benzoxazol-2-yloxy)-3-methoxyphenyl]-3-methylpentan-3-ol |
| 128 | 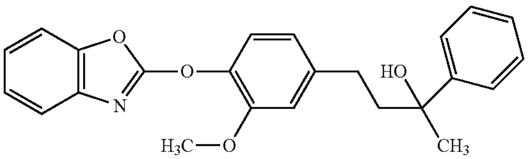 [SMILES: COc1cc(CCC(C)(O)c2ccccc2)ccc1Oc1nc2ccccc2o1] | 4-[4-(1,3-benzoxazol-2-yloxy)-3-methoxyphenyl]-2-phenylbutan-2-ol |
| 129 | 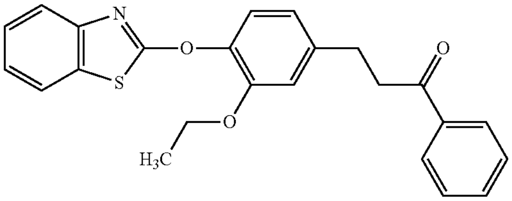 [SMILES: CCOc1cc(CCC(=O)c2ccccc2)ccc1Oc1nc2ccccc2s1] | 3-[4-(1,3-benzothiazol-2-yloxy)-3-ethoxyphenyl]-1-phenylpropan-1-one |
| 130 | 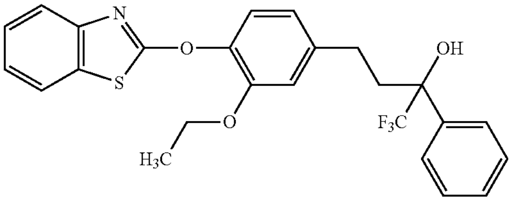 [SMILES: CCOc1cc(CCC(O)(c2ccccc2)C(F)(F)F)ccc1Oc1nc2ccccc2s1] | 4-[3-ethoxy-4-(1,3-benzothiazol-2-yloxy)phenyl]-1,1,1-trifluoro-2-phenylbutan-2-ol |
| 131 | 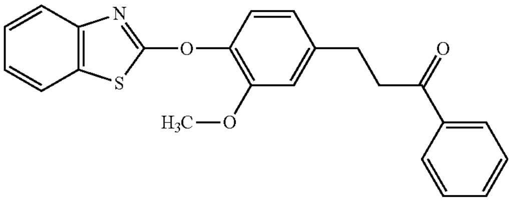 [SMILES: COc1cc(CCC(=O)c2ccccc2)ccc1Oc1nc2ccccc2s1] | 3-[4-(1,3-benzothiazol-2-yloxy)-3-methoxyphenyl]-1-phenylpropan-1-one |
| 132 | 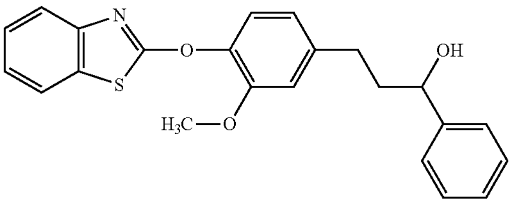 [SMILES: COc1cc(CCC(O)c2ccccc2)ccc1Oc1nc2ccccc2s1] | 3-[4-(1,3-benzothiazol-2-yloxy)-3-methoxyphenyl]-1-phenylpropan-1-ol |

TABLE 1-continued

| No. | Compound Structure | Compound Name |
| --- | --- | --- |
| 133 | 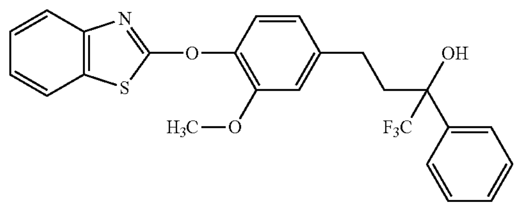 [SMILES: COc1cc(CCC(O)(c2ccccc2)C(F)(F)F)ccc1Oc1nc2ccccc2s1] | 3-[4-(1,3-benzothiazol-2-yloxy)-3-methoxyphenyl]-1-(trifluoromethyl)-1-phenylpropan-1-ol |
| 134 | 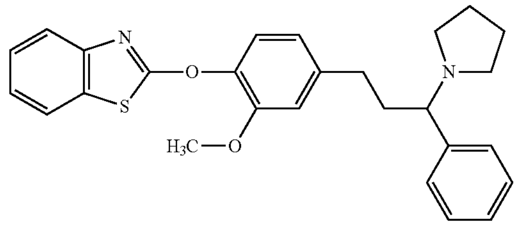 [SMILES: COc1cc(CCC(c2ccccc2)N2CCCC2)ccc1Oc1nc2ccccc2s1] | 2-{2-methoxyl-4-[3-phenyl-3-(pyrrolidin-1-yl)propyl]phenoxy}-1,3-benzothiazole |
| 135 | 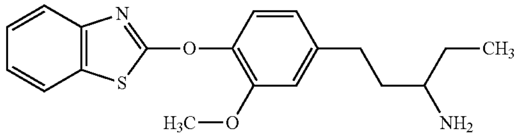 [SMILES: CCC(N)CCc1ccc(Oc2nc3ccccc3s2)c(OC)c1] | 1-[4-(1,3-benzothiazol-2-yloxy)-3-methoxyphenyl]pentan-3-amine |
| 136 | 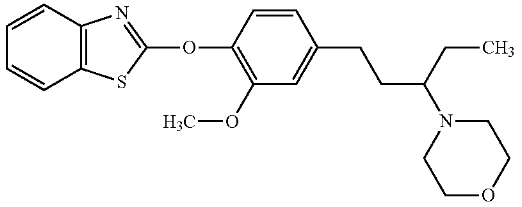 [SMILES: CCC(CCc1ccc(Oc2nc3ccccc3s2)c(OC)c1)N1CCOCC1] | 4-{1-[3-methoxy-4-(1,3-benzothiazol-2-yloxy)phenyl]pentan-3-yl}morpholine |
| 137 | 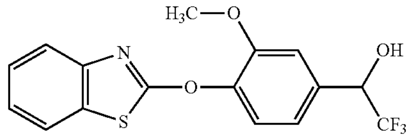 [SMILES: COc1cc(C(O)C(F)(F)F)ccc1Oc1nc2ccccc2s1] | 1-[4-(1,3-benzothiazol-2-yloxy)-3-methoxyphenyl]-2,2,2-trifluoroethanol |
| 138 | 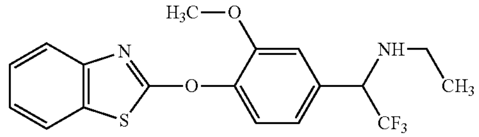 [SMILES: CCNC(c1ccc(Oc2nc3ccccc3s2)c(OC)c1)C(F)(F)F] | 1-[4-(1,3-benzothiazol-2-yloxy)-3-methoxyphenyl]-N-ethyl-2,2,2-trifluoroethanamine |
| 139 | 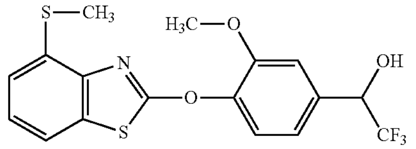 [SMILES: COc1cc(C(O)C(F)(F)F)ccc1Oc1nc2c(SC)cccc2s1] | 2,2,2-trifluoro-1-(3-methoxy-4-{[4-(methylsulfanyl)-1,3-benzothiazol-2-yl]oxy}phenyl)ethanol |
| 140 | 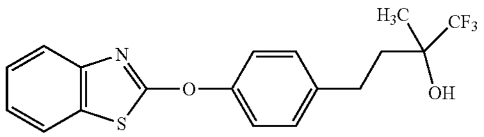 [SMILES: CC(O)(CCc1ccc(Oc2nc3ccccc3s2)cc1)C(F)(F)F] | 4-[4-(1,3-benzothiazol-2-yloxy)phenyl]-1,1,1-trifluoro-2-methylbutan-2-ol |
| 141 | 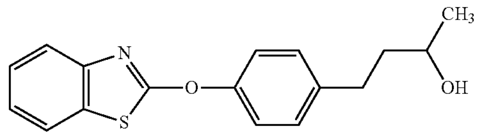 [SMILES: CC(O)CCc1ccc(Oc2nc3ccccc3s2)cc1] | 4-[4-(1,3-benzothiazol-2-yloxy)phenyl]butan-2-ol |

TABLE 1-continued

| No. | Compound Structure | Compound Name |
| --- | --- | --- |
| 142 | 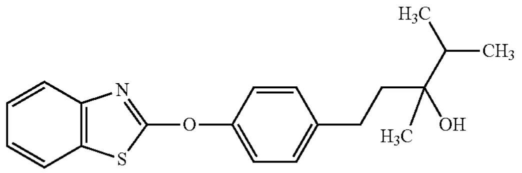 [SMILES: CC(C)C(C)(O)CCc1ccc(Oc2nc3ccccc3s2)cc1] | 1-[4-(1,3-benzothiazol-2-yloxy)phenyl]-3,4-dimethylpentan-3-ol |
| 143 | 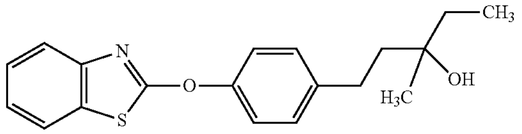 [SMILES: CCC(C)(O)CCc1ccc(Oc2nc3ccccc3s2)cc1] | 1-[4-(1,3-benzothiazol-2-yloxy)phenyl]-3-methylpentan-3-ol |
| 144 | 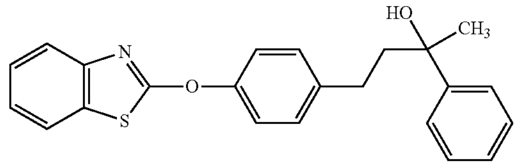 [SMILES: CC(O)(CCc1ccc(Oc2nc3ccccc3s2)cc1)c1ccccc1] | 4-[4-(1,3-benzothiazol-2-yloxy)phenyl]-2-phenylbutan-2-ol |
| 145 | 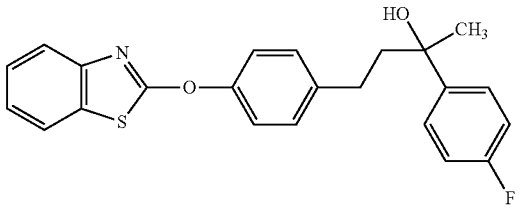 [SMILES: CC(O)(CCc1ccc(Oc2nc3ccccc3s2)cc1)c1ccc(F)cc1] | 4-[4-(1,3-benzothiazol-2-yloxy)phenyl]-2-(4-fluorophenyl)butan-2-ol |
| 146 | 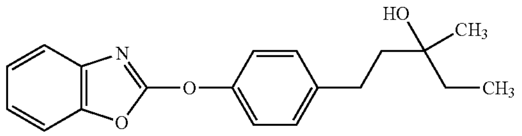 | 1-[4-(1,3-benzoxazol-2-yloxy)phenyl]-3-methylpentan-3-ol |
| 147 | 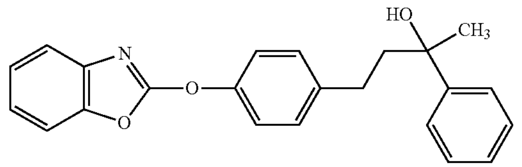 | 4-[4-(1,3-benzoxazol-2-yloxy)phenyl]-2-phenylbutan-2-ol |
| 148 | 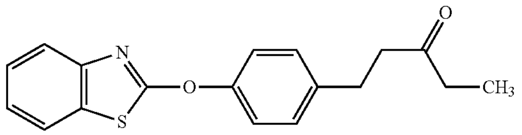 [SMILES: CCC(=O)CCc1ccc(Oc2nc3ccccc3s2)cc1] | 1-[4-(1,3-benzothiazol-2-yloxy)phenyl]pentan-3-one |
| 149 | 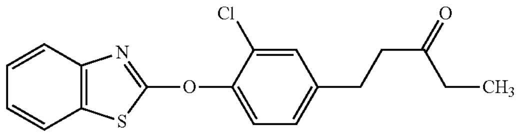 | 1-[4-(1,3-benzothiazol-2-yloxy)-3-chlorophenyl]pentan-3-one |
| 150 | 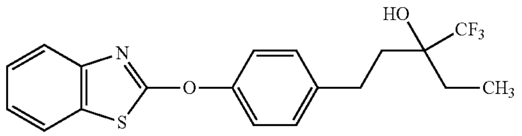 [SMILES: CCC(O)(CCc1ccc(Oc2nc3ccccc3s2)cc1)C(F)(F)F] | 1-[4-(1,3-benzothiazol-2-yloxy)phenyl]-3-(trifluoromethyl)pentan-3-ol |

TABLE 1-continued

| No. | Compound Structure | Compound Name |
| --- | --- | --- |
| 151 | 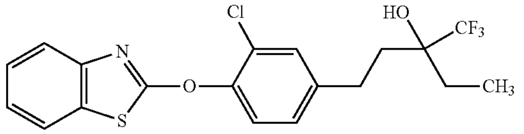 [SMILES: CCC(O)(CCc1ccc(Oc2nc3ccccc3s2)c(Cl)c1)C(F)(F)F] | 1-[4-(1,3-benzothiazol-2-yloxy)-3-chlorophenyl]-3-(trifluoromethyl)pentan-3-ol |
| 152 | 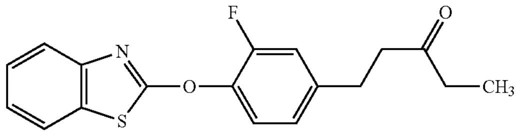 [SMILES: CCC(=O)CCc1ccc(Oc2nc3ccccc3s2)c(F)c1] | 1-[4-(1,3-benzothiazol-2-yloxy)-3-fluorophenyl]-pentan-3-one |
| 153 | 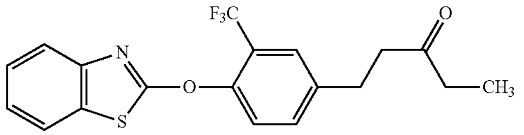 [SMILES: CCC(=O)CCc1ccc(Oc2nc3ccccc3s2)c(C(F)(F)F)c1] | 1-[4-(1,3-benzothiazol-2-yloxy)-3-(trifluoromethyl)-phenyl]pentan-3-one |
| 154 | 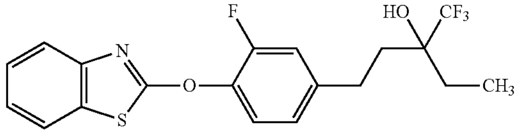 | 1-[4-(1,3-benzothiazol-2-yloxy)-3-fluorophenyl]-3-(trifluoromethyl)pentan-3-ol |
| 155 | 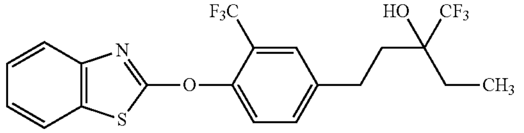 [SMILES: CCC(O)(CCc1ccc(Oc2nc3ccccc3s2)c(F)c1)C(F)(F)F] | 1-[4-(1,3-benzothiazol-2-yloxy)-3-(trifluoromethyl)-phenyl]-3-(trifluoromethyl)-pentan-3-ol |
| 156 | 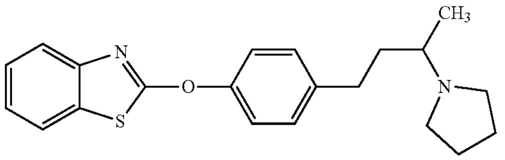 [SMILES: CC(CCc1ccc(Oc2nc3ccccc3s2)cc1)N1CCCC1] | 2-{4-[3-(pyrrolidin-1-yl)butyl]phenoxy}-1,3-benzothiazole |
| 157 | 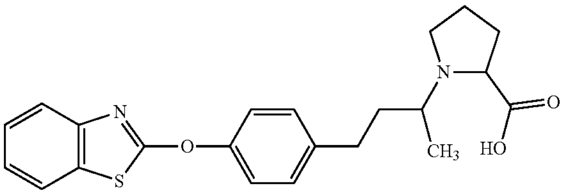 [SMILES: CC(CCc1ccc(Oc2nc3ccccc3s2)cc1)N1CCCC1C(=O)O] | 1-{4-[4-(1,3-benzothiazol-2-yloxy)phenyl]butan-2-yl}pyrrolidine-2-carboxylic acid |
| 158 | 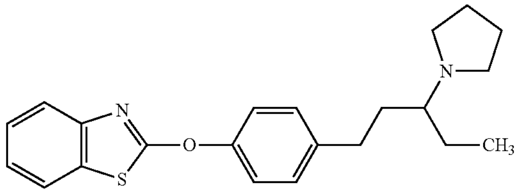 [SMILES: CCC(CCc1ccc(Oc2nc3ccccc3s2)cc1)N1CCCC1] | 2-{4-[3-(pyrrolidin-1-yl)pentyl]phenoxy}-1,3-benzothiazole |
| 159 | 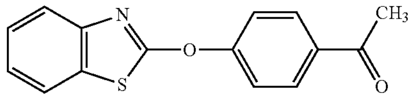 [SMILES: CC(=O)c1ccc(Oc2nc3ccccc3s2)cc1] | 1-[4-(1,3-benzothiazol-2-yloxy)phenyl]ethanone |
| 160 | 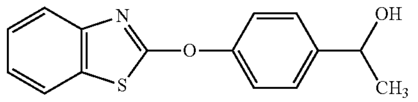 | 1-[4-(1,3-benzothiazol-2-yloxy)phenyl]ethanol |

TABLE 1-continued

| No. | Compound Structure | Compound Name |
|---|---|---|
| 161 | 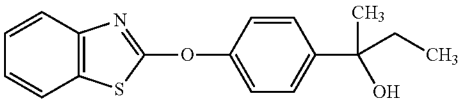 [SMILES: CCC(C)(O)c1ccc(Oc2nc3ccccc3s2)cc1] | 2-[4-(1,3-benzothiazol-2-yloxy)phenyl]butan-2-ol |
| 162 | 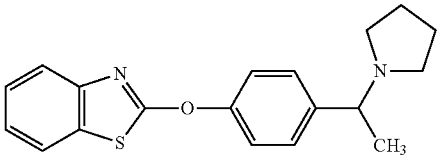 | 2-{4-[1-(pyrrolidin-1-yl)ethyl]phenoxy}-1,3-benzothiazole |
| 163 | 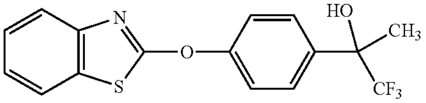 | 2-[4-(1,3-benzothiazol-2-yloxy)phenyl]-1,1,1-trifluoropropan-2-ol |
| 164 | 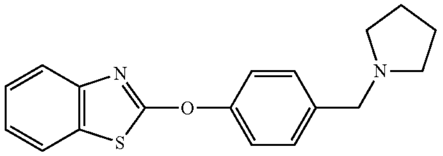 [SMILES: c1ccc2sc(Oc3ccc(CN4CCCC4)cc3)nc2c1] | 2-[4-(pyrrolidin-1-ylmethyl)phenoxy]-1,3-benzothiazole |
| 165 | 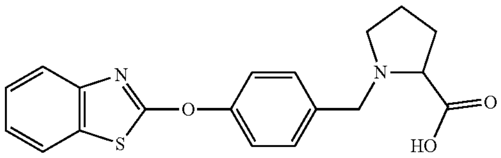 [SMILES: O=C(O)C1CCCN1Cc1ccc(Oc2nc3ccccc3s2)cc1] | 1-[4-(1,3-benzothiazol-2-yloxy)benzyl]pyrrolidine-2-carboxylic acid |
| 166 | 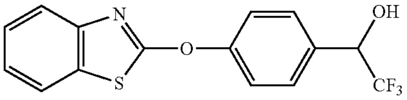 | 1-[4-(1,3-benzothiazol-2-yloxy)phenyl]-2,2,2-trifluoroethanol |
| 167 | 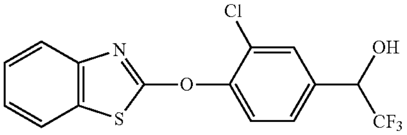 [SMILES: OC(c1ccc(Oc2nc3ccccc3s2)c(Cl)c1)C(F)(F)F] | 1-[4-(1,3-benzothiazol-2-yloxy)-3-chlorophenyl]-2,2,2-trifluoroethanol |
| 168 | 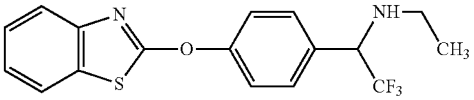 | 1-[4-(1,3-benzothiazol-2-yloxy)phenyl]-N-ethyl-2,2,2-trifluoroethanamine |
| 169 | 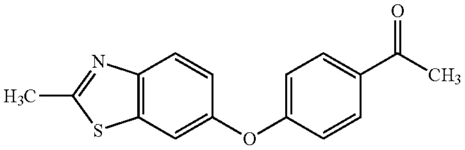 [SMILES: CC(=O)c1ccc(Oc2ccc3nc(C)sc3c2)cc1] | 1-{4-[(2-methyl-1,3-benzothiazol-6-yl)oxy]phenyl}ethanone |
| 170 | 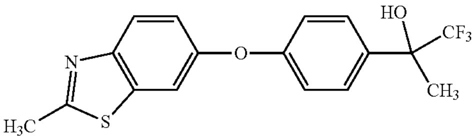 [SMILES: Cc1nc2ccc(Oc3ccc(C(C)(O)C(F)(F)F)cc3)cc2s1] | 1,1,1-trifluoro-2-{4-[(2-methyl-1,3-benzothiazol-6-yl)oxy]phenyl}propan-2-ol |
| 171 | 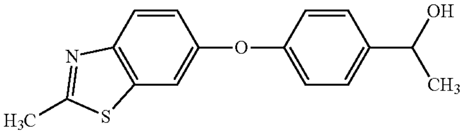 [SMILES: Cc1nc2ccc(Oc3ccc(C(C)O)cc3)cc2s1] | 1-{4-[(2-methyl-1,3-benzothiazol-6-yl)oxy]phenyl}ethanol |

TABLE 1-continued

| No. | Compound Structure | Compound Name |
|---|---|---|
| 172 | 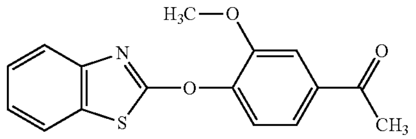 [SMILES: COc1cc(C(C)=O)ccc1Oc1nc2ccccc2s1] | 1-[4-(1,3-benzothiazol-2-yloxy)-3-methoxyphenyl]-ethanone |
| 173 | 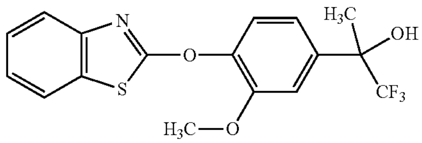 [SMILES: COc1cc(C(C)(O)C(F)(F)F)ccc1Oc1nc2ccccc2s1] | 2-[4-(1,3-benzothiazol-2-yloxy)-3-methoxyphenyl]-1,1,1-trifluoropropan-2-ol |
| 174 | 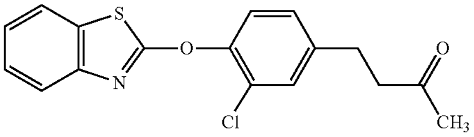 [SMILES: CC(=O)CCc1ccc(Oc2nc3ccccc3s2)c(Cl)c1] | 4-[4-(1,3-benzothiazol-2-yloxy)-3-chlorophenyl]butan-2-one |
| 175 | 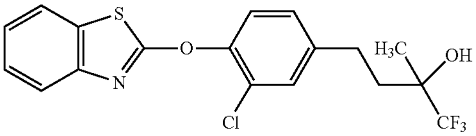 [SMILES: CC(O)(CCc1ccc(Oc2nc3ccccc3s2)c(Cl)c1)C(F)(F)F] | 4-[4-(1,3-benzothiazol-2-yloxy)-3-chlorophenyl]-1,1,1-trifluoro-2-methylbutan-2-ol |
| 176 | 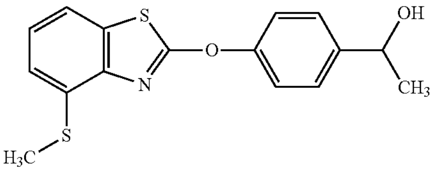 [SMILES: CSc1cccc2sc(Oc3ccc(C(C)O)cc3)nc12] | 1-(4-{[4-(methylsulfanyl)-1,3-benzothiazol-2-yl]oxy}phenyl)ethanol |
| 177 | 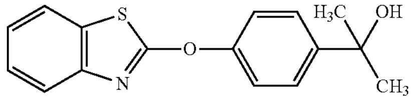 | 2-[4-(1,3-benzothiazol-2-yloxy)phenyl]propan-2-ol |
| 178 | 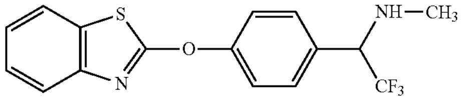 | 1-[4-(1,3-benzothiazol-2-yloxy)phenyl]-2,2,2-trifluoro-N-methylethanamine |
| 179 | 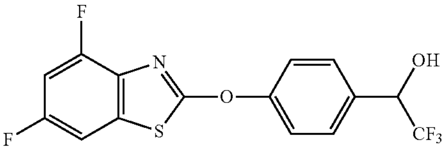 [SMILES: OC(c1ccc(Oc2nc3c(F)cc(F)cc3s2)cc1)C(F)(F)F] | 1-{4-[(4,6-difluoro-1,3-benzothiazol-2-yl)oxy]phenyl}-2,2,2-trifluoroethanol |
| 180 | 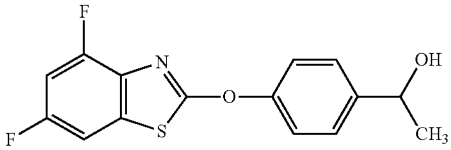 [SMILES: CC(O)c1ccc(Oc2nc3c(F)cc(F)cc3s2)cc1] | 1-{4-[(4,6-difluoro-1,3-benzothiazol-2-yl)oxy]phenyl}ethanol |
| 181 | 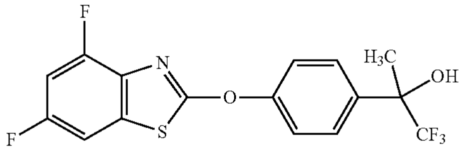 [SMILES: CC(O)(c1ccc(Oc2nc3c(F)cc(F)cc3s2)cc1)C(F)(F)F] | 2-{4-[(4,6-difluoro-1,3-benzothiazol-2-yl)oxy]phenyl}-1,1,1-trifluoropropan-2-ol |

TABLE 1-continued

| No. | Compound Structure | Compound Name |
|---|---|---|
| 182 | 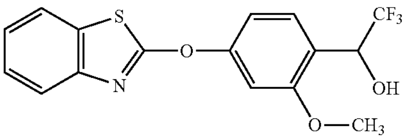 [SMILES: COc1cc(Oc2nc3ccccc3s2)ccc1C(O)C(F)(F)F] | 1-{4-[(1,3-benzothiazol-2-yl}oxy]-2-methoxyphenyl}-2,2,2-trifluoroethan-1-ol |
| 183 | 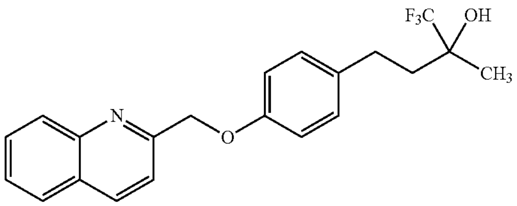 [SMILES: CC(O)(CCc1ccc(OCc2ccc3ccccc3n2)cc1)C(F)(F)F] | 1,1,1-trifluoro-2-methyl-4-[4-(quinolin-2-ylmethoxy)phenyl]butan-2-ol |
| 184 | 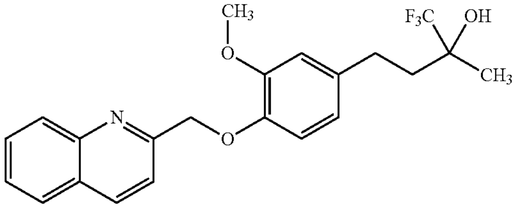 [SMILES: COc1cc(CCC(C)(O)C(F)(F)F)ccc1OCc1ccc2ccccc2n1] | 1,1,1-trifluoro-4-[3-methoxy-4-(quinolin-2-ylmethoxy)phenyl]-2-methylbutan-2-ol |
| 185 | 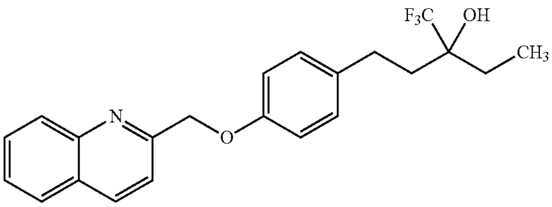 [SMILES: CCC(O)(CCc1ccc(OCc2ccc3ccccc3n2)cc1)C(F)(F)F] | 1-[4-(quinolin-2-ylmethoxy)-phenyl]-3-(trifluoromethyl)-pentan-3-ol |
| 186 | 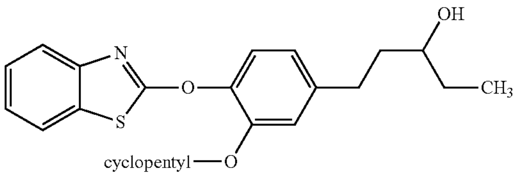 | 1-[4-(1,3-benzothiazol-2-yloxy)-3-(cyclopentyloxy)-phenyl]pentan-3-ol |
| 187 | 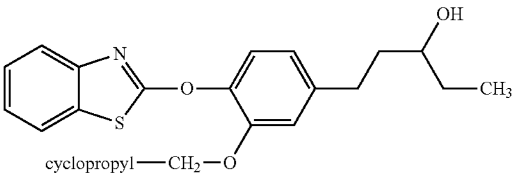 | 1-[4-(1,3-benzothiazol-2-yloxy)-3-(cyclopropylmethoxy)-phenyl]-pentan-3-ol |
| 188 | 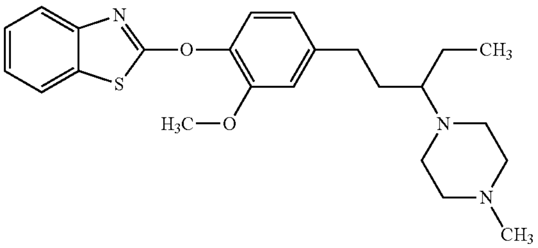 [SMILES: CCC(CCc1ccc(Oc2nc3ccccc3s2)c(OC)c1)N1CCN(C)CC1] | 1-[4-(1,3-benzothiazol-2-yloxy)-3-methoxyphenyl]-3-(4-methylpiperazinyl-1yl)pentane |

TABLE 1-continued

| No. | Compound Structure | Compound Name |
|---|---|---|
| 189 | 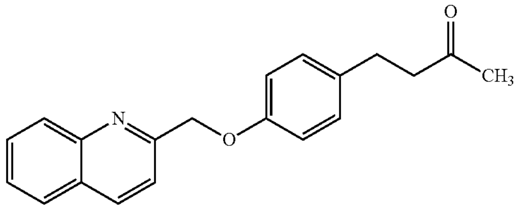 [SMILES: CC(=O)CCc1ccc(OCc2ccc3ccccc3n2)cc1] | 4-{4-[(quinolinyl-2-yl)methoxy]phenyl}butan-2-one |
| 190 | 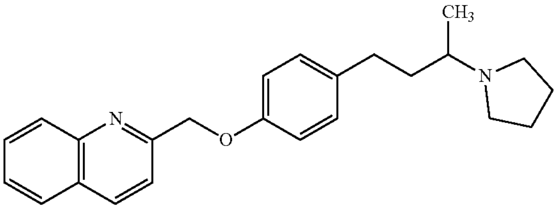 [SMILES: CC(CCc1ccc(OCc2ccc3ccccc3n2)cc1)N1CCCC1] | 4-{4-[(quinoline-2-yl)methoxyphenyl}butan-2-pyrrolidine |
| 191 | 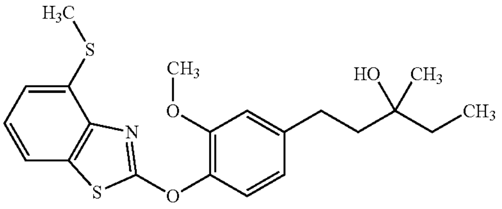 [SMILES: CCC(C)(O)CCc1ccc(Oc2nc3c(SC)cccc3s2)c(OC)c1] | 1-(3-methoxy-4-{[4-(methylsulfanyl)-1,3-benzothiazol-2-yl]oxy}phenyl)pentan-3-methyl-3-ol |
| 192 | 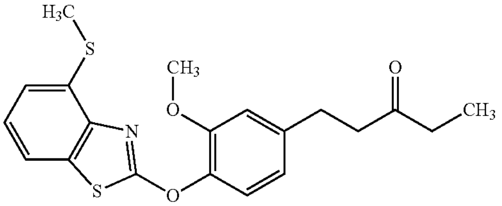 [SMILES: CCC(=O)CCc1ccc(Oc2nc3c(SC)cccc3s2)c(OC)c1] | 1-(3-methoxy-4-{[4-(methylsulfanyl)-1,3-benzothiazol-2-yl]oxy}phenyl)pentan-3-one |
| 193 | 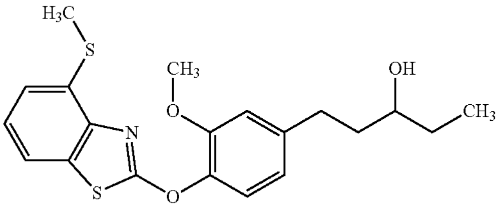 [SMILES: CCC(O)CCc1ccc(Oc2nc3c(SC)cccc3s2)c(OC)c1] | 1-(3-methoxy-4-{[4-(methylsulfanyl)-1,3-benzothiazol-2-yl]oxy}phenyl)pentan-3-ol |
| 194 | 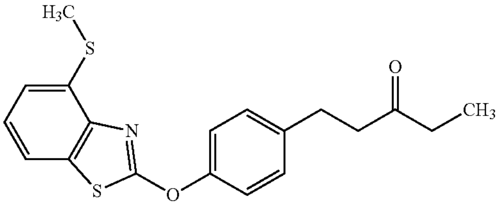 [SMILES: CCC(=O)CCc1ccc(Oc2nc3c(SC)cccc3s2)cc1] | 1-(4-{[4-(methylsulfanyl)-1,3-benzothiazol-2-yl]oxy}phenyl)pentan-3-one |
| 195 | 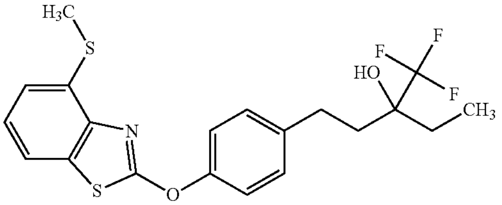 [SMILES: CCC(O)(CCc1ccc(Oc2nc3c(SC)cccc3s2)cc1)C(F)(F)F] | 1-(4-{[4-(methylsulfanyl)-1,3-benzothiazol-2-yl]oxy}phenyl)-3-(trifluoromethyl)pentan-3-ol |

TABLE 1-continued

| No. | Compound Structure | Compound Name |
|---|---|---|
| 196 | 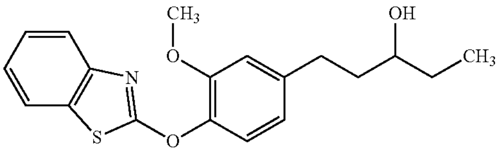 [SMILES: CCC(O)CCc1ccc(Oc2nc3ccccc3s2)c(OC)c1] | 1-[4-(1,3-benzothiazol-2-yloxy)-3-methoxyphenyl]pentan-3-ol |
| 197 | 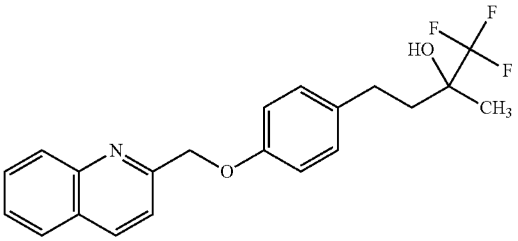 [SMILES: CC(O)(CCc1ccc(OCc2ccc3ccccc3n2)cc1)C(F)(F)F] | 1,1,1-trifluoro-2-[4-(quinolin-2-ylmethoxy)phenyl]propan-2-ol |
| 198 | 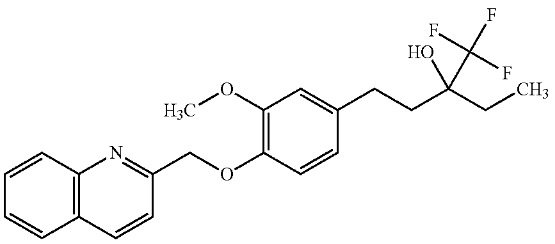 [SMILES: CCC(O)(CCc1ccc(OCc2ccc3ccccc3n2)c(OC)c1)C(F)(F)F] | 1,1,1-trifluoro-2-[3-methoxy-4-(quinolin-2-ylmethoxy)phenyl]butan-3-ol |
| 199 | 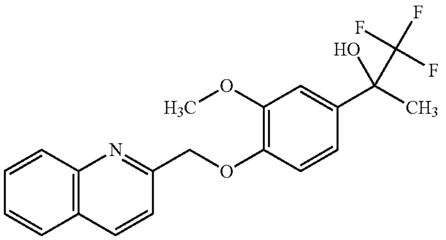 [SMILES: COc1cc(C(C)(O)C(F)(F)F)ccc1OCc1ccc2ccccc2n1] | 1,1,1-trifluoro-2-[3-methoxy-4-(quinolin-2-ylmethoxy)phenyl]propan-2-ol |

In embodiments, the present disclosure provides the compounds in Table 1, listed singly or in any combination, as well as a pharmaceutically acceptable enantiomer, diastereomer, salt, or solvate thereof.

In addition, the present disclosure provides compounds of formula (I) as described above and in the following exemplary numbered embodiments:

1) A compound of formula (1)

(1)

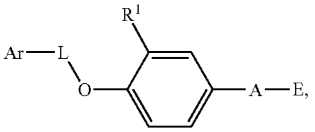

or a pharmaceutically acceptable enantiomer, diastereomer, salt, or solvate thereof, wherein:

Ar is a 9- or 10-membered bicyclic aromatic ring system, where Ar is optionally substituted with one, two or three substituents;

L is selected from a direct bond and methylene;

$R^1$ is selected from hydrogen, halide, $C_1$-$C_6$alkyl, $C_1$-$C_6$haloalkyl, $C_1$-$C_6$alkoxy, $C_3$-$C_6$cycloalkoxy and $C_1$-$C_6$alkoxy substituted with $C_3$-$C_6$cycloalkyl;

A is selected from a direct bond, —$CH_2$— and —$CH_2CH_2$—;

E is selected from —C(O)—$R^2$, $C(OR^3)R^4R^5$ and $CH(R^6)NR^7R^1$;

$R^2$ is selected from methyl, ethyl and phenyl;

$R^3$ is selected from H, alkyl and substituted alkyl;

$R^4$ is selected from hydrogen, alkyl and phenyl;

$R^5$ is selected from $C_1$-$C_7$alkyl, $C_1$-$C_7$haloalkyl, phenyl and substituted phenyl;

$R^6$ is selected from hydrogen, methyl, halogenated methyl and ethyl;

$R^7$ is hydrogen; and $R^8$ is hydrogen, methyl or ethyl; with the proviso that together, $R^7$ and $R^8$ may form a 5 or 6-membered, optionally substituted, heterocycle.

2) The compound of embodiment 1, or a pharmaceutically acceptable enantiomer, diastereomer, salt, or solvate thereof, wherein:

Ar is a 9- or 10-membered bicyclic ring system comprising two aromatic rings, where Ar is unsubstituted or is substituted with one substituent selected from halide, $C_{1-6}$alkyl; —S—$C_{1-6}$alkyl; —O—$C_{1-6}$alkyl; and —$SO_2$—$C_{1-6}$alkyl;

L is selected from a direct bond and —$CH_2$— (methylene);

$R^1$ is selected from hydrogen, halide, $C_1$-$C_6$alkyl, $C_1$-$C_6$haloalkyl and $C_1$-$C_6$alkoxy;

A is selected from a direct bond, $—CH_2—$ and $—CH_2CH_2—$;

E is selected from $—C(O)—R^2$, $C(OR^3)R^4R^5$ and $CH(R^6)NR^7R^8$;

$R^2$ is selected from methyl, ethyl and phenyl;

$R^3$ is H;

$R^4$ is selected from hydrogen, $C_1$-$C_7$alkyl and phenyl;

$R^5$ is selected from $C_1$-$C_7$alkyl, $C_1$-$C_7$haloalkyl, phenyl and halophenyl;

$R^6$ is selected from hydrogen, methyl, halogenated methyl and ethyl; and $R^7$ is hydrogen and $R^8$ is hydrogen, methyl or ethyl; or $R^7$ and $R^8$ together form a 5- or 6-membered heterocycle which is optionally substituted with a substituent selected from $C_1$-$C_6$alkyl and carboxylic acid.

3) The compound of embodiments 1 or 2 wherein Ar is 1,3-benzothiazole.

4) The compound of embodiments 1 or 2 wherein Ar is selected from 1,3-benzoxazole and quinoline.

5) The compound of embodiments 1 or 2 wherein Ar is substituted with a single substituent which is $—S—CH_3$.

6) The compound of embodiments 1 or 2 wherein L is a direct bond.

7) The compound of embodiments 1 or 2 wherein L is methylene.

8) The compound of embodiments 1 or 2 wherein $R^1$ is hydrogen or $C_1$-$C_6$alkoxy.

9) The compound of embodiments 1 or 2 wherein A is a direct bond.

10) The compound of embodiments 1 or 2 wherein A is $—CH_2CH_2—$.

11) The compound of embodiments 1 or 2 wherein E is $—C(OR^3)R^4R^5$.

12) The compound of embodiments 1 or 2 as a non-racemic mixture of enantiomers of compounds of formula (1).

13) The compound of embodiments 1 or 2 selected from:

1-[4-(1,3-benzothiazol-2-yloxy)-3-methoxyphenyl]-3-(trifluoromethyl)pentan-3-ol;

1-{3-methoxy-4-[(4-methylsulfanyl-1,3-benzothiazol-2-yl)oxy]phenyl}-3-(trifluoromethyl)pentan-3-ol;

1-{4-[(4,6-difluoro-1,3-benzothiazol-2-yl)oxy]-3-methoxyphenyl}-3-(trifluoromethyl)pentan-3-ol;

1-{4-[(6-fluoro-1,3-benzothiazol-2-yl)oxy]-3-methoxyphenyl}-3-(trifluoromethyl)pentan-3-ol;

4-[4-(1,3-benzothiazol-2-yloxy)-3-methoxyphenyl]-1,1,1-trifluoro-2-methylbutan-2-ol;

1,1,1-trifluoro-4-(3-methoxy-4-{[4-(methylsulfanyl)-1,3-benzothiazol-2-yl]oxy}phenyl)-2-methylbutan-2-ol;

1,1,1-trifluoro-2-{4-[(2-methyl-1,3-benzothiazol-6-yl)oxy]phenyl}propan-2-ol;

1,1,1-trifluoro-2-methyl-4-[4-(quinolin-2-ylmethoxy)phenyl]butan-2-ol;

1,1,1-trifluoro-4-[3-methoxy-4-(quinolin-2-ylmethoxy)phenyl]-2-methylbutan-2-ol;

1-[4-(quinolin-2-ylmethoxy)-phenyl]-3-(trifluoromethyl)-pentan-3-ol;

1-(3-methoxy-4-{[4-(methylsulfanyl)-1,3-benzothiazol-2-yl]oxy}phenyl)pentan-3-ol; and 1-(4-f{[4-(methylsulfanyl)-1,3-benzothiazol-2-yl]oxy}phenyl)-3-(trifluoromethyl)pentan-3-ol.

In addition to the above-listed compounds, the present disclosure also provides the following exemplary numbered embodiments directed to pharmaceutical compositions and therapeutic methods of use of the compounds.

14) A pharmaceutical composition comprising a compound of embodiments 1 or 2, or a pharmaceutically acceptable enantiomer, salt or solvate thereof, and at least one pharmaceutically acceptable carrier, diluent, excipient and/or adjuvant.

15) The pharmaceutical composition of embodiment 14 in a form of an eye drop.

16) A method of treating an inflammatory disease or inflammatory condition comprising administrating to a subject in need thereof an effective amount of a compound of embodiments 1 or 2, or a composition of embodiments 14 or 15.

17) The method of embodiment 16 wherein the inflammatory disease or inflammatory condition is an ocular inflammatory disease or an ocular inflammatory condition, respectively.

18) A method of treating a respiratory disease or condition comprising administering to a subject in need thereof a therapeutically-effective amount of a compound of embodiments 1 or 2, or a composition of embodiment 14.

19) A method of treating a neurodegenerative disease, condition or disorder comprising administering to a subject in need thereof a therapeutically-effective amount of a compound of embodiments 1 or 2, or a composition of embodiment 14.

As mentioned above, the compounds and compositions of the present disclosure as set forth above, e.g., compounds of formula (1), may be used in therapeutic methods. The therapeutic method may provide either a therapeutically effective amount of the compound/composition, or a prophylactically-effective amount of the compound/composition. For instance, when a patient will be undergoing surgery, a compound of the disclosure may be administered pre-surgery to minimize post-surgery trauma. The following are exemplary therapeutic methods where the compounds and compositions may be used.

In one aspect, the present disclosure provides a method of treating inflammation comprising administering to a subject in need thereof a therapeutically-effective amount of a compound as set forth above.

In another aspect, the present disclosure provides a method of treating inflammation prophylactically comprising administering to a subject in need thereof a prophylactically-effective amount of a compound as set forth above. For example, in conditions such as asthma and allergy, the compounds as set forth herein may be administered prophylactically to prevent exacerbation or flare of the condition.

In one aspect, the present disclosure provides a method of treating a respiratory disease or condition, comprising administering to a subject in need thereof a therapeutically-effective amount of a compound as set forth above.

In another aspect, the present disclosure provides a method of treating asthma comprising administering to a subject in need thereof a therapeutically-effective amount of a compound as set forth above. In one embodiment, the subject being treated has mild to moderate asthma. In another embodiment, the subject being treated has severe asthma.

In another aspect, the present disclosure provides a method of treating asthma comprising administering to a subject in need thereof a prophylactically-effective amount of a compound as set forth above. In one embodiment, the subject being treated has mild to moderate asthma. In another embodiment, the subject being treated has severe asthma.

In another aspect, the present disclosure provides a method of treating allergic disease including but not limited to dermal and ocular indications comprising administering to a subject in need thereof a therapeutically-effective amount of a compound as set forth above.

In another aspect, the present disclosure provides a method of treating allergic disease including but not limited to dermal and ocular indications comprising administering to a subject in need thereof a prophylactically-effective amount of a compound as set forth above.

In another aspect, the present disclosure provides a method of treating conjunctivitis. For example, the present disclosure provides a method of treating allergic conjunctivitis comprising administering to a subject in need thereof a therapeutically-effective amount of a compound as set forth above. Instead of allergic conjunctivitis, the conjunctivitis may be secondary to an infection such as a viral or bacterial infection. As another alternative, the conjunctivitis may be caused by contact lens use.

In another aspect, the present disclosure provides a method of treating conjunctivitis. For example, the present disclosure provides a method of treating allergic conjunctivitis comprising administering to a subject in need thereof a prophylactically-effective amount of a compound as set forth above. Instead of allergic conjunctivitis, the conjunctivitis may be secondary to an infection such as a viral or bacterial infection. As another alternative, the conjunctivitis may be caused by contact lens use.

In another aspect, the present disclosure provides a method of treating uveitis comprising administering to a subject in need thereof a therapeutically-effective amount of a compound as set forth above. The subject may have, for example, anterior, intermediate, posterior or pan uveitis.

In another aspect, the present disclosure provides a method of treating uveitis comprising administering to a subject in need thereof a prophylactically-effective amount of a compound as set forth above. The subject may have, for example, anterior, intermediate, posterior or pan uveitis.

In another aspect, the present disclosure provides a method of treating atopic dermatitis comprising administering to a subject in need thereof a therapeutically-effective amount of a compound as set forth above.

In another aspect, the present disclosure provides a method of treating atopic dermatitis comprising administering to a subject in need thereof a prophylactically-effective amount of a compound as set forth above.

In another aspect, the present disclosure provides a method of treating psoriasis comprising administering to a subject in need thereof a therapeutically-effective amount of a compound as set forth above.

In another aspect, the present disclosure provides a method of treating psoriasis comprising administering to a subject in need thereof a prophylactically-effective amount of a compound as set forth above.

In another aspect, the present disclosure provides a method of treating acne vulgaris comprising administering to a subject in need thereof a therapeutically-effective amount of a compound as set forth above.

In another aspect, the present disclosure provides a method of treating acne vulgaris comprising administering to a subject in need thereof a prophylactically-effective amount of a compound as set forth above.

In another aspect, the present disclosure provides a method of treating tendinopathy comprising administering to a subject in need thereof a therapeutically-effective amount of a compound as set forth above.

In another aspect, the present disclosure provides a method of treating tendinopathy comprising administering to a subject in need thereof a prophylactically-effective amount of a compound as set forth above.

In another aspect, the present disclosure provides a method of treating bronchopulmonary dysplasia comprising administering to a subject in need thereof a therapeutically-effective amount of a compound as set forth above.

In another aspect, the present disclosure provides a method of treating bronchopulmonary dysplasia comprising administering to a subject in need thereof a prophylactically-effective amount of a compound as set forth above.

In another aspect, the present disclosure provides a method of treating chronic obstructive pulmonary disease (COPD) comprising administering to a subject in need thereof a therapeutically-effective amount of a compound as set forth above. The subject may have, for example, early stage or mild/moderate COPD.

In another aspect, the present disclosure provides a method of treating chronic obstructive pulmonary disease (COPD) comprising administering to a subject in need thereof a prophylactically-effective amount of a compound as set forth above. The subject may have, for example, early stage or mild/moderate COPD.

In another aspect, the present disclosure provides a method of treating lung dysfunction comprising administering to a subject in need thereof a therapeutically-effective amount of a compound as set forth above. The subject may have, for example, occupational lung dysfunction related to environmental pollutants/hazards.

In another aspect, the present disclosure provides a method of treating lung dysfunction comprising administering to a subject in need thereof a prophylactically-effective amount of a compound as set forth above. The subject may have, for example, occupational lung dysfunction related to environmental pollutants/hazards.

In another aspect, the present disclosure provides a method of treating pulmonary hypertension (e.g., neonatal) comprising administering to a subject in need thereof a therapeutically-effective amount of a compound as set forth above.

In another aspect, the present disclosure provides a method of treating pulmonary hypertension (e.g., neonatal) comprising administering to a subject in need thereof a prophylactically-effective amount of a compound as set forth above.

In another aspect, the present disclosure provides a method of treating cancer comprising administering to a subject in need thereof a therapeutically-effective amount of a compound as set forth above. An exemplary cancer is a solid tumor. The cancer may be, for example breast cancer or ovarian cancer. The method may provide presentation of metastases of an existing cancer.

In another aspect, the present disclosure provides a method of treating neuroinflammatory disease comprising administering to a subject in need thereof a therapeutically-effective amount of a compound as set forth above.

In another aspect, the present disclosure provides a method of treating neuroinflammatory disease comprising administering to a subject in need thereof a prophylactically-effective amount of a compound as set forth above.

In one aspect, the present disclosure provides a method of treating a neurodegenerative disease, condition or disorder, comprising administering to a subject in need thereof a therapeutically-effective amount of a compound as set forth above.

In another aspect, the present disclosure provides a method of treating multiple sclerosis comprising administering to a subject in need thereof a therapeutically-effective amount of a compound as set forth above.

In another aspect, the present disclosure provides a method of treating multiple sclerosis comprising administering to a subject in need thereof a prophylactically-effective amount of a compound as set forth above.

In another aspect, the present disclosure provides a method of treating cystic fibrosis comprising administering to a subject in need thereof a therapeutically-effective amount of a compound as set forth above. The cystic fibrosis may be related to lung inflammation (e.g., be at a non-infectious stage).

In another aspect, the present disclosure provides a method of treating cystic fibrosis comprising administering to a subject in need thereof a prophylactically-effective amount of a compound as set forth above. The cystic fibrosis may be related to lung inflammation (e.g., be at a non-infectious stage).

In another aspect, the present disclosure provides a method of treating idiopathic pulmonary fibrosis (IPF) comprising administering to a subject in need thereof a therapeutically-effective amount of a compound as set forth above.

In another aspect, the present disclosure provides a method of treating idiopathic pulmonary fibrosis (IPF) comprising administering to a subject in need thereof a prophylactically-effective amount of a compound as set forth above.

In another aspect, the present disclosure provides a method of treating Alzheimer's disease, particularly early stage Alzheimer's disease, comprising administering to a subject in need thereof a therapeutically-effective amount of a compound as set forth above.

In another aspect, the present disclosure provides a method of treating Sjogren-Larsson-Syndrome comprising administering to a subject in need thereof a therapeutically-effective amount of a compound as set forth above.

In another aspect, the present disclosure provides a method of treating cardiovascular (CV) disease, e.g., ACS or plaque formation, comprising administering to a subject in need thereof a therapeutically-effective amount of a compound as set forth above. The population being treated may have an ischemia/reperfusion injury.

In another aspect, the present disclosure provides a method of treating otitis comprising administering to a subject in need thereof a therapeutically-effective amount of a compound as set forth above. The otitis may be, for example, secondary to an infection.

In another aspect, the present disclosure provides a method of treating inflammation that is associated with ocular surgery comprising administering to a subject in need thereof a therapeutically-effective amount of a compound as set forth above.

In another aspect, the present disclosure provides a method of treating inflammation that is associated with ocular surgery comprising administering to a subject in need thereof a prophylactically-effective amount of a compound as set forth above.

In another aspect, the present disclosure provides a method of treating dry eye, comprising administering to a subject in need thereof a therapeutically effective amount of a compound as set forth above.

In another aspect, the present disclosure provides a method of treating inflammation associated with cataract surgery comprising administering to a subject in need thereof a therapeutically-effective amount of a compound as set forth above.

In another aspect, the present disclosure provides a method of treating inflammation associated with cataract surgery comprising administering to a subject in need thereof a prophylactically-effective amount of a compound as set forth above.

In another aspect, the present disclosure provides a method of treating arthritis comprising administering to a subject in need thereof a therapeutically-effective amount of a compound as set forth above. The arthritis may be, for example, at the early onset stage.

In another aspect, the present disclosure provides a method of treating arthritis comprising administering to a subject in need thereof a prophylactically-effective amount of a compound as set forth above. The arthritis may be, for example, at the early onset stage.

In another aspect, the present disclosure provides a method of treating inflammation associated with laser eye surgery comprising administering to a subject in need thereof a therapeutically-effective amount of a compound as set forth above.

In another aspect, the present disclosure provides a method of treating inflammation associated with laser eye surgery comprising administering to a subject in need thereof a prophylactically-effective amount of a compound as set forth above.

In another aspect, the present disclosure provides a method of treating allograft rejection comprising administering to a subject in need thereof a therapeutically-effective amount of a compound as set forth above.

In another aspect, the present disclosure provides a method of treating allograft rejection comprising administering to a subject in need thereof a prophylactically-effective amount of a compound as set forth above.

In another aspect, the present disclosure provides a method of treating trauma, e.g., a cerebral ischemia, comprising administering to a subject in need thereof a therapeutically-effective amount of a compound as set forth above.

In another aspect, the present disclosure provides a method of treating diabetic retinopathy comprising administering to a subject in need thereof a therapeutically-effective amount of a compound as set forth above.

In another aspect, the present disclosure provides a method of treating age-related macular degeneration comprising administering to a subject in need thereof a therapeutically-effective amount of a compound as set forth above.

In another aspect, the present disclosure provides a method of treating diabetic macular edema comprising administering to a subject in need thereof a therapeutically-effective amount of a compound as set forth above.

As mentioned elsewhere herein, the present disclosure provides composition that may be used to treat the above-mentioned medical condition. Those compositions may optionally include one or more active agents other than compounds of formula (1), which, e.g., supplement, augment or complement the activity of a compound of formula (1).

In one aspect, the present disclosure provides pharmaceutical compositions comprising a compound of formula (1). In other words, the compounds of the present disclosure may be formulated into a pharmaceutical composition. In one aspect, the present disclosure provides a pharmaceutical composition comprising a compound of formula (1) as set forth above, and at least one pharmaceutically acceptable carrier, excipient or diluent.

Compounds of the disclosure can be formulated for administration for use in human or veterinary medicine, by analogy with other bioactive agents such as anti-inflammatory agents. Such methods are known in the art and include administration by any route known in the art, such as subdermal, by-inhalation, oral, topical or parenteral. Likewise, the compositions may be administered in intravenous (bolus or infusion), intraperitoneal, topical (e.g., ocular, eye drop), subcutaneous, intramuscular or transdermal (e.g., patch) form, all using forms well known to those of ordinary skill in the pharmaceutical arts.

The composition is formulated into a form suitable for the desired route of administration. In other words, a form of the compositions is selected, in part, based on the desired route of administration. The compositions may be in any form known in the art, including but not limited to tablets, capsules, powders, granules, lozenges, creams or liquid preparations. A brief summary includes oral administration, which is readily accomplished with solid (e.g., tablet, capsule, gel-cap, powder, granule, lozenge, delayed-release solid form, slow or sustained release solid form, encapsulated solid form) or liquid (e.g., liquid gel cap, suspension, solution, syrup, elixir, liposomal solution) compositions. As another example, for administration by inhalation, the composition may be in liquid (e.g., nebulized solution/suspension) or solid (e.g., metered dose inhaler, dry powder inhaler) form. As yet another example, the composition may be delivered via an implant, where examples are an ocular implant (e.g., a slow or sustained release depot solid form matrix) and a subcutaneous implant (e.g., a slow or sustained release depot pump). When intravenous administration is deemed appropriate by the health care provider, the composition may be a liquid (e.g., solution, nano-suspension, liposomal suspension, micellar suspension) or a solid (e.g., a lyophilized product) which may be reconstituted to provide a liquid form. When Intramuscular is the desired route of administration, the composition may be a liquid (e.g., solution, nano-suspension, liposomal suspension, micellar suspension, oil-based formulation) or a solid (e.g., a lyophilized product) which may be reconstituted to provide a liquid form. Intramuscular administration may also be accomplished with a suitably positioned implant. The composition may be administered subcutaneously, in which case the same forms that are suitable for intramuscular administration may be used for subcutaneous administration. Intraperitoneal administration may be used to deliver a compound or composition of the present disclosure, where a suitable form intraperitoneal administration is liquid (e.g., solution, nano-suspension, liposomal suspension, micellar suspension) or solid (Lyophilized product for reconstitution). Intrathecal is another suitable route of administration, in which case the formulation may be a liquid (e.g., solution, nano-suspension, liposomal suspension, micellar suspension) or solid (e.g., lyophilized product for reconstitution). The composition may be administered topically to the skin of the subject, where suitable forms are liquid (e.g., solution, suspension, emulsion, cream, gel, ointment—with carriers). Topical administration may also be for delivery to the eye of the subject, where suitable forms are liquid (e.g., solution, suspension, liposomal suspension, emulsion, ointment) or solid (e.g., coated implant, implant pump). For transdermal delivery, the compounds of the disclosure may be formulated into a transdermal patch, which may provide slow or sustained release of the compound to the subject. Rectal administration may be accomplished with a suppository, such as a solid/solid wax or solid oil-based; or solid/semi-solid wax oil based with semi-solid liquid or gel composition. The present disclosure also provides lyophilized preparations for reconstitution with a suitable vehicle. Lyophilization refers to the removal of liquid components of a formulation to provide a solid phase. Lyophilization may be accomplished by techniques known in the art, e.g., placing the composition under vacuum and moderate heating to evaporate the liquid components. Thus, the active ingredients will typically be administered in admixture with carrier materials selected with a view to the intended form of administration, such as oral tablets, capsules (either solid-filled, semi-solid filled or liquid filled), powders for constitution, oral gels, elixirs, dispersible granules, syrups, liquids, solutions and suspensions including sterile solutions or suspensions for topical administration. In one embodiment the composition is administered to an eye of the subject, and the composition may take the form of a liquid composition that may be dropped onto the surface of the eye. Each of such compositions may be made in a manner consistent with conventional pharmaceutical practices.

In one embodiment the composition is a solid form preparation. For example, for oral administration the composition may be in the form of tablets, dispersible granules, and capsules. In these compositions the active drug component may be combined with any oral non-toxic pharmaceutically acceptable inert carrier. Examples include saccharides such as lactose, mannitol, sucrose and other sugars, starches and cellulose; and inorganic compounds such as calcium sulfate, magnesium stearate and dicalcium phosphate. As another example, the solid may be formulated as a suppository. For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Other components that may be included in the solid formulation include conventional binders, lubricants, disintegrating agents and coloring agents. Suitable binders include starches, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starches, methylcellulose, guar gum, and the like. Sweetening and flavoring agents and preservatives may also be included where appropriate for a dosage form intended for oral administration. Conventional excipients may be included in the composition, such as binding agents, for example acacia, gelatin, sorbitol, tragacanth, or polyvinylpyrollidone; fillers, for example lactose, sugar, maize-starch, calcium phosphate, sorbitol or glycine; tableting lubricants, for example magnesium stearate, talc, polyethylene glycol or silica, disintegrants, for example potato starch; or acceptable wetting agents such as sodium lauryl sulphate.

The solid form preparation may contain from between about 0.5 to about 100 weight percent of active ingredient including a compound of formula (1).

The compounds of the present disclosure may be formulated into a liquid pharmaceutical compositions. Liquid form preparations include solutions, suspensions and emulsions. Liquid compositions include at least one material that is a liquid at room temperature, where water is one such material. Other liquid materials that may be included in the liquid composition include propylene glycol parenteral injection. Depending on the formulation, liquid compositions may be administered orally, topically, parenterally, intravenously and intranasally, to name a few.

Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerin, propylene glycol, or ethyl alcohol; preservatives, for example methyl or propyl p-hydroxybenzoate or sorbic acid, and, if desired, conventional flavoring or coloring agents.

The liquid form of the pharmaceutical composition may be formulated with the intent that the compositions will be delivered by topical administration, e.g., as an eyedrop. The eyedrop formulation may optionally contain one or more of cyclodextrin, methyl cellulose and EDTA in addition to a compound of formula (1), which may be present in the eyedrop at a concentration of between about 0.1% to 1% (weight basis) in the eyedrop solution. The eyedrop formulation may optionally contain hydroxypropyl-beta-cyclodextrin in a range of 1% to 40% and hydroxypropyl methyl cellulose in a range of 0.1% to 1%. In exemplary embodiments, the eye drop formulation may optionally contain 10%, 20%, or 30% by weight of hydroxypropyl-beta-cyclodextrin. The amount, timing and mode of delivery of compounds the disclosure will be routinely adjusted on an individual basis, depending on such factors as weight, age, gender, and condition of the individual, the condition being induced or treated, whether the administration is prophylactic or therapeutic, and on the basis of other factors known to effect drug delivery, absorption, pharmacokinetics, including half-life, and efficacy. In exemplary embodiments, the suitable ocular dose range for use is from about 0.01 mg to 1000 mg per day, or from 0.05 mg to about 1000 mg per day, about 0.1 mg to about 1000 mg a day, about 0.5 mg to about 1000 mg a day, about 2 mg to about 1000 mg a day, about 0.05 mg to about 500 mg per day, 0.10 mg to 300 mg per day, 0.10 mg to 100 mg per day, 75 mg to 450 mg per day, 150 mg to 400 mg per day, about 300 mg to about 1500 mg per day, about 600 to about 1500 mg per day. A topical dose is typically between 0.5 mg and 3 mg/day where a dose of 3 mg/day may be administered in the form of six applications of 0.5 mg each. A typical oral dose is between 100 mg and 3500 mg×2 per day.

For parenteral administration, fluid unit dosage forms are prepared utilizing the compound and a sterile vehicle, water being typical. The compound of formula (1), depending on the vehicle and concentration used, can be either suspended or dissolved in the vehicle or other suitable solvent. In preparing solutions, the compound can be dissolved in water for injection and filter sterilized before filling into a suitable vial or ampoule and sealing. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. A surfactant or wetting agent is included in the composition to facilitate uniform distribution of the compound. Parenteral solutions and suspensions may be used for topical administration.

The liquid form preparation may contain from between about 0.05 to about 95 weight percent of active ingredient including a compound of formula (1).

The pharmaceutical compositions of the present disclosure include solid form preparations which are intended to be converted, shortly before use, to liquid form preparations for either oral or parenteral administration. Such liquid forms include solutions, suspensions and emulsions.

Additionally, the compositions of the present disclosure may be formulated in a sustained release form to provide a rate controlled release of any one or more of the components or active ingredients to optimize therapeutic effects. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or more Compounds of Formula (1) are administered orally.

In another embodiment, the one or more Compounds of Formula (1) are administered topically.

In one embodiment, a pharmaceutical preparation comprising at least one compound of formula (1) is in unit dosage form. In such form, the preparation is subdivided into unit doses containing effective amounts of the active components.

Compositions can be prepared according to conventional mixing, granulating or coating methods, respectively, and the present compositions can contain, in one embodiment, from about 0.5 wt % to about 95 wt % of one or more compounds of formula (1). In various embodiments, the present compositions can contain, in one embodiment, from about 1% to about 70% or from about 5% to about 60% of the compound of formula (1).

The compounds of Formula I may be administered orally in a dosage range of 0.001 to 150 mg/kg of mammal (e.g., human) body weight per day in a single dose or in divided doses. One preferred dosage range is 0.01 to 100 mg/kg body weight per day orally in a single dose or in divided doses. Another preferred dosage range is 0.1 to 50 mg/kg body weight per day orally in single or divided doses. For oral administration, the compositions can be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the subject to be treated. The specific dose level and frequency of dosage for any particular subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of Formula I may be administered to the eye in the form of eye drops as dosage range of 0.01 to 50 mg per day in a single dose or in divided doses in the form of one or more eye drops as a solution of 0.1% to 2% by weight of compound. One preferred dosage range is 0.1 to 10 mg per day in a single dose or in divided doses in the form of one or more eye drops as a solution of 0.1% to 2% by weight of compound. Another preferred dosage range is 0.3 to 3 mg per day in a single dose or in divided doses in the form of one or more eye drops as a solution of 0.1% to 2% by weight of compound. The compositions can be provided in the form of eye drops containing 0.01 to 3 milligrams of the active ingredient, particularly 0.01, 0.05, 0.1, 0.2, 0.3, 0.4, 0.5, 0.6, 0.7, 0.8, 0.9, 1, 1.5, 2, and 3 milligrams of the active ingredient per eye drop for the symptomatic adjustment of the dosage to the subject to be treated. The specific dose level and frequency of dosage for any particular subject may be varied and will depend upon a variety of factors including the activity of the specific compound employed, the metabolic stability and duration of action of that compound, the age, body weight, general health, sex, diet, mode and time of administration, rate of excretion, drug combination, the severity of the particular condition, and the host undergoing therapy.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The amount and frequency of administration of the compounds of Formula (1) will be regulated according to the judgment of the attending clinician considering such factors as age, condition and size of the subject as well as severity of the symptoms being treated. The compositions of the disclosure can further comprise one or more additional therapeutic agents.

The compositions including one or more compounds of formula (1) may include additional active agents. The additional active agent may, for example, augment the biological activity of a compound of formula (1), or it may complement that activity, or it may supplement that biological activity.

The compounds of formula (1) may be prepared in a number of different ways from known or readily prepared starting materials. In describing suitable synthetic methodology, it is helpful to identify the Ar group of formula (1) as Ar1, and the central benzene ring of formula (1) as Ar2, as shown below.

(1)

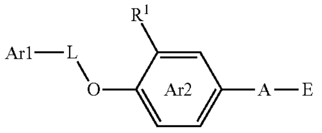

Several exemplary methods for preparing representative compounds of formula (1) are illustrated in the following Schemes and Examples. Alternative synthetic pathways and analogous structures useful in preparing compounds of formula (1) will be apparent to those skilled in the art of organic chemical synthesis. In some cases the final product may be further manipulated, for example, by manipulation of substituents. These manipulations may include, but are not limited to, reduction, oxidation, alkylation, acylation, and hydrolysis reactions which are well known to those of ordinary skill in the art and are discussed further later herein.

One factor that may be considered when preparing a compound of formula (1) is the identity of the group that links together the Ar1 and Ar2 groups. That linking group is represented in formula (1) by -L-O— where O is oxygen and L is selected from a direct bond and methylene (i.e., —$CH_2$—). Thus, the linking group may take the form of O or $CH_2O$.

These linking groups may be formed by reacting together appropriately substituted Ar1 and Ar2 containing compounds under suitable reaction conditions. For example, compounds of formula (1) where L is $CH_2$ may be prepared as shown in Scheme 1, where phenol or a $R_1$-substituted phenol (either of which is represented by hydroxyl substituted Ar2) is reacted with an X-substituted benzyl compound (having the Ar1 group) where X is a leaving group. This reaction may be conducted in the presence of a suitable base such as potassium carbonate in combination with sodium iodide, and in the presence of a suitable solvent such as acetone.

Scheme 1

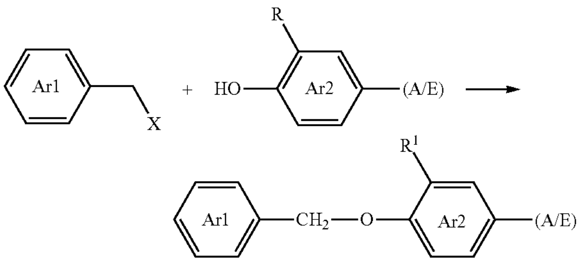

In Scheme 1, Ar1 is shown as a benzene ring, however that is for illustrative purposes only. In the compounds of the present disclosure, Ar1 is more generally identified as Ar, and represents a 9- or 10-membered bicyclic aromatic ring system which is optionally substituted with one, two or three substituents. For example, Ar1 may be quinoline (introduced via 2(chloromethyl)quinoline hydrochloride as the alkylating agent), naphthylene (introduced via 2(chloromethyl) naphthylene as the alkylating agent) or benzothiazole (introduced via 2(chloromethyl)benzothiazole as the alkylating agent, as well as many other choices. Also in Scheme 1, Ar2 is shown as substituted with (A/E) where this designation is meant to denote collectively e-A-E as identified herein, and precursors thereto which can be converted to an A-E group after the Ar1 and Ar2 rings are coupled together.

When the linking group -L-O— has L as a direct bond, then the linking group is oxygen (O). Such compounds may be prepared as illustrated in Scheme 2.

Scheme 2

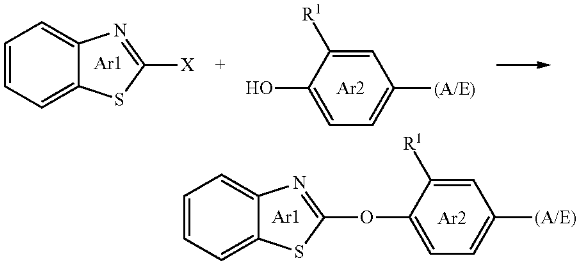

In Scheme 2, Ar1 is illustrated as a benzothiazole compound having a leaving group X at the 2-position, however other Ar1 groups may be used in this synthesis in lieu of benzothiazole. A few examples are 2-chlorobenzoxazole, 2-chloroquinoline and 3-chloroisoquinoline. Also in Scheme 2, Ar2 is shown as substituted with (A/E) where this designation is meant to denote collectively -A-E as identified herein, and precursors thereto which can be converted to an A-E group after the Ar1 and Ar2 rings are coupled together. The Ar1- and Ar2-containing compounds may be combined under suitable reaction conditions, e.g., in the presence of a suitable base such as potassium carbonate, and in a suitable solvent such as dimethylformamide, to provide the corresponding coupled compound of Formula (1).

In Scheme 2, Ar2 comprises a hydroxyl group while Ar1 comprises a leaving group X. Alternatively, compounds of the present disclosure may be prepared by a process wherein the relative placement of the hydroxyl group and the leaving group is switched between Ar1 and Ar2 as shown in Scheme 3. In Scheme 3, a phenolic compound comprising Ar1 is reacted with a fluoroaryl compound comprising Ar2 under suitable reaction conditions, such as in the presence of a suitable base such as potassium carbonate and in the presence of a suitable solvent such as dimethylsulfoxide, to provide compounds of formula (1). The process outlined in Scheme 3

Scheme 3

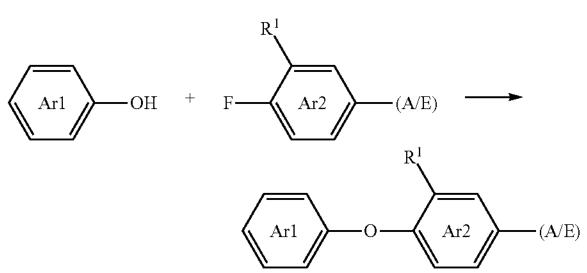

In Scheme 3, Ar1 is shown as a benzene ring, however that is for illustrative purposes only. In compounds of the present disclosure, Ar1 is more generally identified as Ar, and represents a 9- or 10-membered bicyclic aromatic ring system that is optionally substituted with one, two or three substituents. Also in Scheme 3, Ar2 is shown as substituted with (A/E) where this designation is meant to denote collectively -A-E as identified herein, and precursors thereto which can be converted to an A-E group after the Ar1 and Ar2 rings are coupled together. The reaction outlined in Scheme 3 is favored when A/E is an electron withdrawing group, e.g., carbonyl, in which case the (A/E) substituents in (F)($R^1$)Ar2(A/E) is a precursor to -A-E.

The compounds of the present disclosure may have a variety of substituents on the Ar1 and Ar2 moieties. These substituents may be prepared by standard methodology known in the art. Such methodology includes benzylation, condensation, hydrogenolysis, O-alkylation, Grignard reaction, trifluoromethylation, reduction, reductive amination of aromatic/aliphatic ketones, reductive amination of aliphatic ketones, and reductive amination of aromatic ketones, any one or more of which may optionally be used in the preparation of compounds of formula (1). These techniques may also be modified according to the knowledge of those skilled in the art. The following provides General Procedures that are further exemplified in the specific Examples which follow.

Benzylation: Phenolic compound (1 eq), benzyl bromide (1.5 eq) and $K_2CO_3$ (1.5 eq) in acetone are stirred at reflux for 3-18 h. The reaction mixture is allowed to cool to room temperature and filtered. The filter cake is washed with acetone, and the solvent is removed under reduced pressure. The material is purified by flash chromatography.

Condensation: To a stirred solution of aldehyde (1 eq) in $MeOH/H_2O$ is added ketone (4 to 8 eq), followed by 85% by weight KOH (4 to 6 eq). The mixture is stirred at room temperature for 7 days or at reflux for 3 h. The reaction is quenched with 1-5% aq. HCl or water and extracted with EtOAc. The organic layer is washed with water, dried ($MgSO_4$), filtered, and the solvent is removed under reduced pressure. The material is purified by trituration with ether/hexane or by flash chromatography.

Hydrogenolysis: A mixture of unsaturated ketone (1 eq) and 10% Pd/C (10% by weight) in methanol or ethyl acetate (with or without catalytic amount of acetic acid) is stirred under hydrogen for 1 to 18 h. The reaction is filtered, and the solvent is removed under reduced pressure. The material is purified by flash chromatography.

O-alkylation: Phenolic compound (1 eq), alkylating agent (1 to 1.5 eq), $K_2CO_3$ (1 to 1.5 eq), and dimethylformamide (DMF) are heated under argon to 90-150° C. for approximately 16-24 hours and cooled to room temperature. The reaction is diluted with water and ethyl acetate. The organic layer is washed with 5% aqueous sodium hydroxide and/or water, washed with brine, dried ($MgSO_4$), filtered, and the solvent is removed under reduced pressure. The material is purified using flash column chromatography.

Grignard reaction: Grignard reactions can be carried out using commercially available alkyl or aryl magnesium bromides or prepared freshly as follows. (1) Preparation of Grignard Reagent. To freshly crushed magnesium turnings (2.5 to 5.0 eq) under argon in THF (1.5 mmol of Mg per mL of tetrahydrofuran (THF)) is added 1,2 dibromoethane (50 μL) and stirred for 5 minutes and followed by ethyl magnesium bromide (50 μL, 3.0M in ether) and stirred for another 5 min. Alkyl or aryl bromide (1 eq) is then added and the reaction is cooled occasionally with a water bath over 1 hr. (2) Grignard Additions. To a 0° C. solution of ketone (1 eq) as a solution in dry THF under argon is added Grignard reagent (generally 1 to 2 eq). The reaction is stirred for approximately 1 hr. and quenched with water and/or 5% aqueous HCl. The mixture is extracted with water, washed with brine, dried ($MgSO_4$), filtered, and the solvent is removed under reduced pressure. The material is purified using flash column chromatography.

Trifluoromethylation: To a solution of ketone (1 eq) in dry DMF at room temperature or reduced temperature (e.g. 0° C.) is added $CF_3$-TMS (1.5 to 2 eq) followed by a catalytic amount of $K_2CO_3$ (~0.1 to 0.3 eq) and stirred under argon for a desired length of time, typically 18-72 hours. The reaction is diluted with water and washed with brine. The organic layer is dried ($MgSO_4$), filtered, and the solvent removed in vacuo. To the residue in methanol is added conc. HCl, and the solution is stirred until the reaction is complete (~1 hr). The reaction is diluted with ethyl acetate and extracted with brine. The organic layer is dried ($MgSO_4$), filtered, and the solvent removed under reduced pressure. The material is purified using flash column chromatography.

Reduction: To a solution of ketone (1 eq) in methanol under argon is added sodium borohydride (2 eq) and stirred for 1 h. Optionally, cerium (III) chloride heptahydrate (1 eq)

may be added. The reaction is diluted with water and 5% aqueous HCl and extracted once with ethyl acetate. The organic layer is washed with brine, dried ($MgSO_4$), filtered, and the solvent is removed under reduced pressure. The material is purified using flash column chromatography.

Reductive amination of aromatic/aliphatic ketones: To a stirred solution of aromatic or aliphatic ketone (1 eq) in THF at room temperature under argon is added $Ti(OiPr)_4$ (1.2 eq), followed by amine (1.4 eq). The reaction mixture is stirred at reflux for ~18 h, and then is allowed to cool to room temperature. $NaBH_4$ (1.5 eq) is added, and the reaction mixture is stirred for 1 to 3 h. It is then quenched with water and extracted three times with ethyl acetate (EtOAc). The organic layer is washed with water, dried ($MgSO_4$), filtered, and the solvent is removed under reduced pressure. The material is purified by flash chromatography.

Reductive amination of aliphatic ketones: To a stirred solution of aliphatic ketone (1 eq) in DCE at room temperature under argon is added amine (1.2 eq), followed by $NaBH(OAc)_3$ (2 eq) and acetic acid (AcOH, 2 eq) optionally with 4A molecular sieves. The reaction mixture is stirred for 18 h, quenched with water, and extracted three times with either $CH_2Cl_2$ or EtOAc. The organic layer is dried ($MgSO_4$), filtered, and the solvent is removed under reduced pressure. The material is purified by flash chromatography.

Reductive amination of aromatic aldehydes: To a stirred solution of aromatic aldehyde (1 eq) in DCE at room temperature under argon is added amine (1.2 eq), followed by $NaBH(OAc)_3$ (1.5 eq). The reaction mixture is stirred for 18 h, quenched with water, and extracted three times with either $CH_2Cl_2$ or EtOAC. The organic layer is dried ($MgSO_4$), filtered, and the solvent is removed under reduced pressure. The material is purified by flash chromatography.

Reductive amination to form primary and secondary alkyl amines: To a stirred mixture of $NH_4Cl$ (1 eq) in methanol (MeOH) at room temperature under argon are added $Et_3N$ (1 eq), ketone (1 eq), and $Ti(OiPr)_4$ (~2 eq). The reaction mixture is stirred for 18 h. Another 1 equivalent of $Et_3N$ and $NH_4Cl$ may be added and the reaction mixture then stirred for 3 h. $NaBH_4$ (1.2 eq) is added, and the reaction mixture is stirred for 1.5 h. Another portion of $NaBH_4$ (0.5 eq) may optionally be added, and the reaction mixture is stirred for 1 h. It is quenched with water and extracted with EtOAc. The organic layer is washed with water, dried over anhydrous $MgSO_4$, filtered, and the solvent is removed under reduced pressure. The residue is purified by flash chromatography.

Reductive amination and trifluoromethylation: To a stirred solution of ketone or aldehyde (1 eq) in THF under argon at room temperature is added 4A molecular sieves and ethylamine (~6 eq). The mixture is stirred under argon at room temperature for 3 h, filtered, and the solvent is removed under reduced pressure. To the residue is added $KHF_2$ (~0.75 eq), acetonitrile and DMF and the mixture is cooled to at 0° C. under argon. TFA (~1.3 eq) is added. The mixture is stirred for 5 minutes, and then $CF_3TMS$ (~1.5 eq) is added. The cooling bath is removed, and the reaction mixture is stirred for ~18 hours, diluted with saturated aqueous $Na_2CO_3$ and extracted with EtOAc. The organic layer is washed with water, dried over anhydrous $MgSO_4$, filtered, and the solvent is removed under reduced pressure. The residue is purified by flash chromatography. To the residue is added MeOH then $NaBH_4$ (0.67 eq), and the mixture is stirred under argon for 30 minutes. The reaction is quenched with water and extracted with EtOAc. The organic layer is dried over anhydrous $Na_2SO_4$, filtered, and the solvent is removed under reduced pressure. The residue is purified by flash chromatography.

In each case standard reactions may be monitored by thin layer chromatography (TLC) to determine progress of reaction. Temperature and/or reaction time may be increased or decreased to increase the conversion of starting material to product or to reduce formation of by-products.

The Examples and preparations provided below further illustrate and exemplify the compounds of the present disclosure and methods of preparing such compounds. It is to be understood that the scope of the present invention is not limited in any way by the scope of the following Examples and preparations. The starting materials and various reactants utilized or referenced in the examples may be obtained from commercial sources, or are readily prepared from commercially available organic compounds, using methods well-known to one skilled in the art.

In the following Examples, standard abbreviations are used including the following: AcOH=acetic acid; aq.=aqueous; BnBr=benzyl bromide; $CF_3TMS$=$TMSCF_3$=$CF_3$—$Si(CH_3)_3$; Conc.=concentrated; DCE=1,2-dichloroethane; DMF=N,N-dimethylformamide; DMSO—dimethylsulfoxide; dppp=1,3-Bis(diphenylphosphino)propane; EtOAc=ethyl acetate; $Et_2O$=diethyl ether; h=hour; Hex=hexanes; MeCN=acetonitrile; MeOH=methanol; mL=milliliters; TBS=tert-butyl dimethyl silyl; TBSCl=tert-butyl dimethyl silyl chloride; TFA=trifluoroacetic acid, i.e., $CF_3$—COOH; TLC=thin layer chromatography; wt %=percentage by weight, e.g., 5% EtOAc in Hex refers to 5 weight parts (e.g., grams) ethyl acetate in combination with 95 weight parts (e.g., grams) hexanes.

In the following Examples, molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art. For example, enantiomers may be separated from one another by HPLC using a chiral column such as a ChiralPak™ column (Daicel Corp., Japan), e.g., ChiralPak AD™ which has a size of 4.6×250 mm and contains particles having an average diameter of 5 □m. The mobile phase may be a mixture of iso-propanol in hexane, where the i-PrOH/hexane ratio may be varied to impact the degree of separation of the enantiomers. An exemplary flow rate is 1 mL/min and an exemplary injection volume is 50 □L, working with a sample concentration of 5 mg/mL. The run time may likewise be adjusted to enhance separation, where an exemplary run time is 11 minutes.

For selected compounds prepared according to the following examples, $^1$H NMR (nuclear magnetic resonance spectroscopy) was performed to obtain $^1$H NMR spectra, which are characterized as provided in Table 6, which follows these Examples.

EXAMPLES

Example 1

Preparation of Compound 101

To a stirred solution of 4-hydroxy-3-methoxybenzaldehyde (10 g, 65.8 mmol) in MeOH (85 mL)/$H_2O$ (13 mL) was added 2-butanone (50 mL, 556 mmol) followed by KOH (15 g, 214 mmol). The mixture was stirred at room temperature for 7 days. The reaction was quenched with the addition of water and aq. HCl (15 mL conc. HCl in 200 mL water) and extracted with EtOAc (300 mL). The organic layer was washed with water (2×150 mL), dried over anhydrous $MgSO_4$, filtered, and the solvent was removed under reduced pressure. The residue was triturated with $Et_2O$/Hex (1:3), filtered and washed with $Et_2O$/Hex (1:3) to yield 5.2 g of 1-(4-hydroxy-3-methoxyphenyl)pent-1-en-3-one as a yellow solid.

To a stirred solution of 1-(4-hydroxy-3-methoxyphenyl) pent-1-en-3-one (5.0 g, 24 mmol) in MeOH (75 mL) was added 10% Pd/C (250 mg). The reaction mixture was stirred under hydrogen for 1 h after which time an additional 10% Pd/C (250 mg) was added. Stirring under hydrogen was continued for an additional 2 h, and then the mixture was filtered. The solvent was removed under reduced pressure, and the residue was purified by flash chromatography (25% EtOAc in Hex) to yield 2.45 g of 1-(4-hydroxy-3-methoxyphenyl)pentan-3-one as a colourless oil.

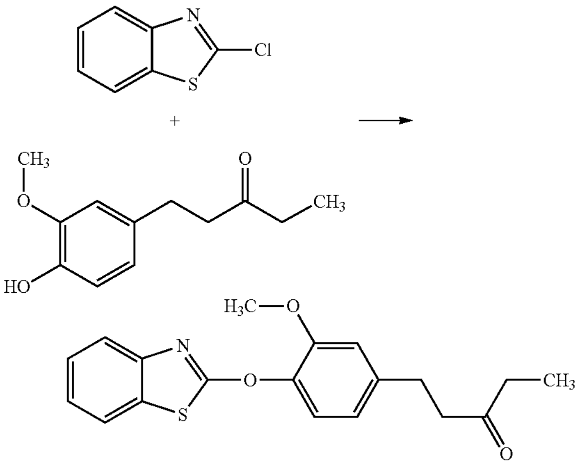

(101)

A mixture of 1-(4-hydroxy-3-methoxyphenyl)pentan-3-one (1.5 g, 7.20 mmol), $K_2CO_3$ (1.00 g, 7.24 mmol), and 2-chlorobenzothiazole (1.00 mL, 7.68 mmol) in DMF (15 mL) was stirred under argon at 100° C. for 18 h. The mixture was allowed to cool to room temperature, diluted with EtOAc (30 mL), washed with water (30 mL), brine (2×30 mL), dried over anhydrous $MgSO_4$, filtered, and the solvent was removed under reduced pressure. The residue was purified by flash chromatography (25% EtOAc in Hex) to yield 2.10 g of Compound 101 as a yellow solid.

Example 2

Preparation of Compound 102

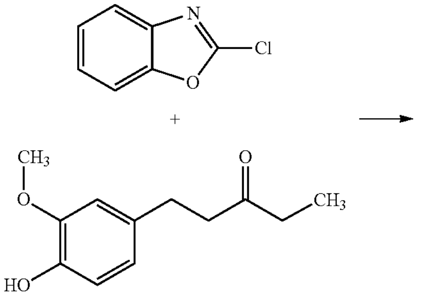

-continued

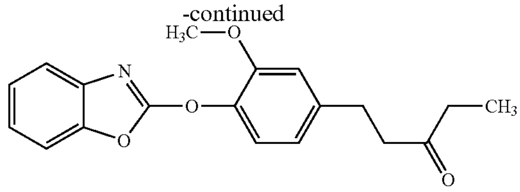

(102)

A mixture of 1-(4-hydroxy-3-methoxyphenyl)pentan-3-one (170 mg, 0.82 mmol, prepared as described in Example 1), $K_2CO_3$ (130 mg, 0.94 mmol), and 2-chlorobenzoxazole (100 μL, 0.87 mmol) in DMF (3 mL) was stirred in a sealed tube at 83° C. for 16 h. The mixture was allowed to cool to room temperature and water (10 mL), brine (10 mL) and EtOAc (20 mL) were added. The layers were separated, the aqueous layer extracted with EtOAc (10 mL) and the combined organic layers were washed with brine (10 mL), dried over anhydrous $MgSO_4$, filtered, and the solvent was removed under reduced pressure. The residue was purified by flash chromatography (30% EtOAc in Hex) to yield 130 mg of Compound 102 as an oil.

Example 3

Preparation of Compound 103

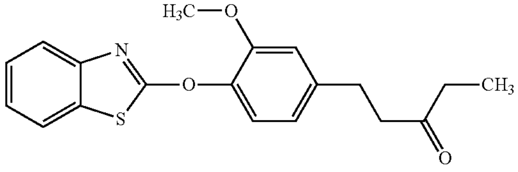

(101)

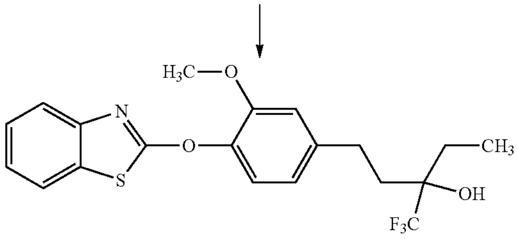

(103)

To a stirred mixture of Compound 101 (1.50 g, 3.98 mmol) and $K_2CO_3$ (60 mg, 0.434 mmol) in DMF (20 mL) under argon was added $CF_3TMS$ (1.30 mL, 8.80 mmol). The reaction mixture was stirred for 18 h at room temperature, and then was diluted with EtOAc (40 mL) and water (10 mL) and washed with brine (3×40 mL). The organic layer was dried over anhydrous $MgSO_4$, filtered, and the solvent was removed under reduced pressure. The residue was taken-up in MeOH (20 mL), combined with conc. HCl (2 mL) and stirred for 1 h. The solvent was removed under reduced pressure, the residue was taken-up in EtOAc (40 mL) and washed with water (2×40 mL) then brine (40 mL). The organic layer was dried over anhydrous $MgSO_4$, filtered, and the solvent was removed under reduced pressure. The residue was purified by flash chromatography (25% EtOAc in Hex) to yield 1.54 g of Compound 103 as a yellow oil.

Example 4

Preparation of Compound 104

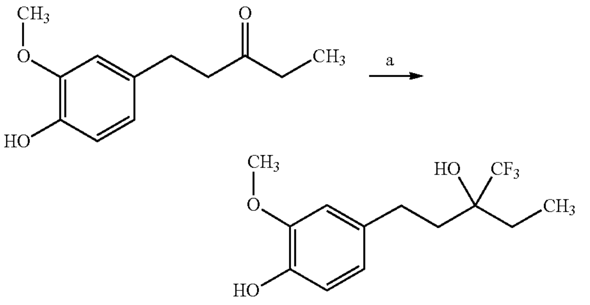

To a stirred mixture of 1-(4-hydroxy-3-methoxyphenyl) pentan-3-one (843 mg, 4.05 mmol, prepared as in Example 1) and $K_2CO_3$ (56 mg, 0.405 mmol) in DMF (8 mL) cooled in an ice bath to 0° C. under argon was added $CF_3TMS$ (1.50 mL, 10.2 mmol) dropwise. The cooling bath was removed and the reaction mixture was stirred at room temperature for 18 h. The mixture was diluted with EtOAc (40 mL) and washed with water (2×25 mL). The organic layer was dried over anhydrous $MgSO_4$, filtered, and the solvent was removed under reduced pressure. The residue was taken-up in MeOH (8 mL) and stirred with conc. HCl (0.6 mL) for 1 h. The mixture was diluted with EtOAc (40 mL) and washed with water (2×25 mL). The organic layer was dried over anhydrous $MgSO_4$, filtered, and the solvent was removed under reduced pressure. The residue was purified by flash chromatography (30% EtOAc in Hex) to yield 938 mg of 4-[3-hydroxy-3-(trifluoromethyl)pentyl]-2-methoxyphenol as a yellow oil.

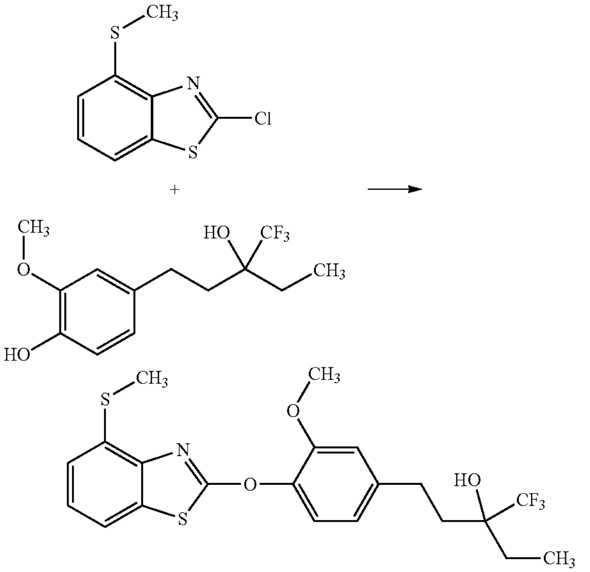

(104)

A mixture of 4-[3-hydroxy-3-(trifluoromethyl)pentyl]-2-methoxyphenol (150 mg, 0.539 mmol), $K_2CO_3$ (223 mg, 1.61 mmol), and 2-chloro-4-(methylthio)-benzothiazole (145 mg, 0.672 mmol) in DMF (3 mL) was stirred in a sealed tube at 100° C. for 18 h. The mixture was allowed to cool to room temperature, diluted with EtOAc (35 mL), washed with water (2×25 mL), dried over anhydrous $MgSO_4$, filtered, and the solvent was removed under reduced pressure. The residue was purified by flash chromatography (20% EtOAc in Hex) to yield 230 mg of Compound 104 as a yellow oil, which solidified at room temperature.

The two enantiomers of Compound 104 were separated from one another by HPLC using the following conditions: column: ChiralPak AD™, 5 □m particle size, 4.6×250 mm; mobile phase: 20% i-PrOH in hexane; flow rate: 1 mL/min; injection volume: 50 □L; sample concentration: 5 mg/mL; run time: 11 minutes; number of injections: 16. Each peak was manually collected, the fractions containing each enantiomer were combined, and the solvent was removed under reduced pressure to give 2 mg of each enantiomer.

Each set of combined fractions was examined for purity by HPLC at 1 mg/mL using the same column, mobile phase, and run time as mentioned above. Enantiomer 1 had a retention time of 7.633 min, and >99% purity. $^1$H NMR for enantiomer 1 (400 MHz, $CDCl_3$): □ 7.44-7.39 (m, 1H), 7.26 (d, 1H), 7.21 (d, 1H), 7.20 (s, 1H), 6.89-6.82 (m, 2H), 3.82 (s, 3H), 2.76 (t, 2H), 2.55 (s, 3H), 2.07-1.99 (m, 2H), 1.90-1.80 (m, 2H), 1.06 (t, 3H). Enantiomer 2 had a retention time of 9.368 min, and >99% purity. $^1$H NMR for enantiomer 2 (400 MHz, $CDCl_3$): □ 7.43-7.39 (m, 1H), 7.26 (d, 1H), 7.21 (d, 1H), 7.20 (s, 1H), 6.89-6.82 (m, 2H), 3.82 (s, 3H), 2.76 (t, 2H), 2.55 (s, 3H), 2.07-1.99 (m, 2H), 1.89-1.78 (m, 2H), 1.06 (t, 3H).

Example 5

Preparation of Compound 105

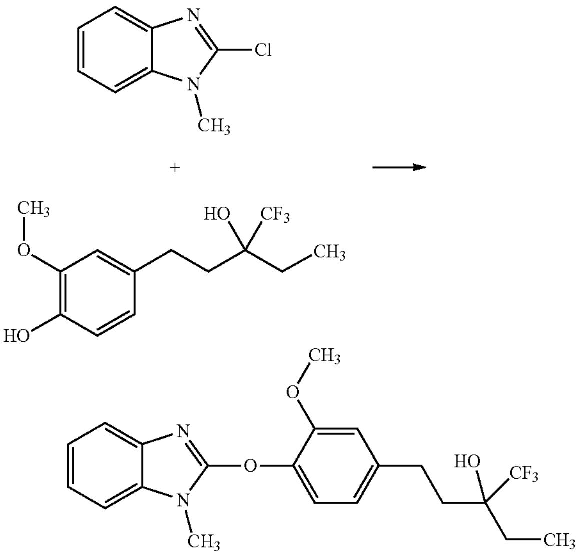

(105)

Following the procedure of Example 4 for making Compound 104 except using 2-chloro-1-methyl-1H-1,3-benzodiazole (112 mg, 0.672 mmol) instead of 2-chloro-4-(methylthio)-benzothiazole and stirring at 150° C. for 64 h yielded 112 mg of Compound 105 as a white solid.

The two enantiomers of Compound 105 were separated from one another by HPLC using the following conditions: ChiralPak AD™ column, 5 □m particle size, 4.6×250 mm column dimensions; mobile phase: 90% i-PrOH in hexane; flow rate: 1 mL/min; injection volume: 50 □L; sample concentration: 1 mg/mL; run time: 17 minutes; number of injections: 1. Each peak was manually collected to provide two fractions. 50 DL samples from each fraction were separately re-injected into the HPLC column. Enantiomer 1 had a retention time of 13.975 min and >99% purity. Enantiomer 2 had a retention time of 15.487 min and >99% purity.

Example 6

Preparation of Compound 106

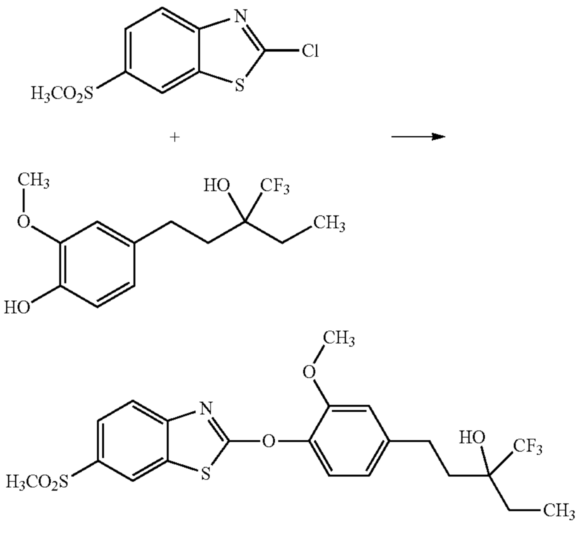

(106)

Following the procedure of Example 4 for making Compound 104 except using 2-chloro-6-(methylsulfonyl)benzothiazole (167 mg, 0.674 mmol) instead of 2-chloro-4-(methylthio)-benzothiazole yielded 145 mg of Compound 106 as a yellowish oil, which solidified at room temperature.

Example 7

Preparation of Compound 107

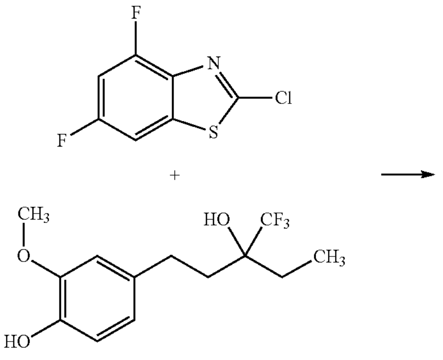

-continued

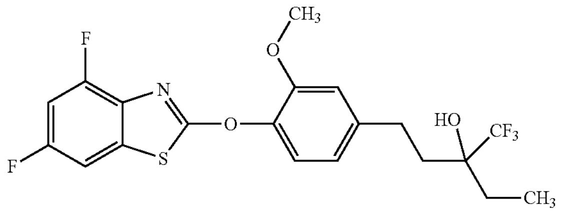

(107)

Following the procedure of Example 4 for preparing Compound 104 except using 2-chloro-4,6-difluorobenzothiazole (138 mg, 0.671 mmol) instead of 2-chloro-4-(methylthio)-benzothiazole yielded 231 mg of Compound 107 as a colourless oil.

Example 8

Preparation of Compound 108

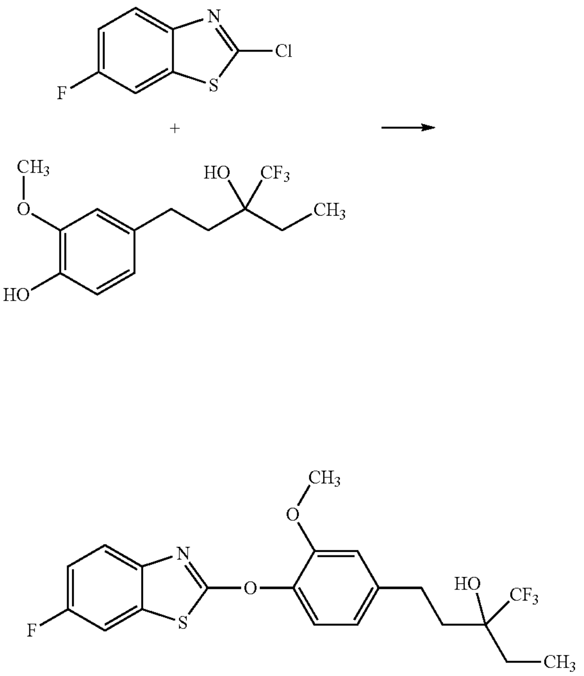

(108)

A mixture of 4-[3-hydroxy-3-(trifluoromethyl)pentyl]-2-methoxyphenol prepared as in Example 4 (124 mg, 0.45 mmol), $K_2CO_3$ (100 mg, 0.71 mmol), and 2-chloro-6-fluorobenzothiazole (166 mg, 0.88 mmol) in DMF (2.5 mL) was stirred in a sealed tube at 100° C. for 18 h. The mixture was allowed to cool to room temperature, diluted with EtOAc (15 mL) and $H_2O$ (15 mL). The layers were separated and the aqueous layer was extracted with EtOAc (20 mL). The organic layers were combined and washed with brine, dried over anhydrous $MgSO_4$, filtered, and the solvent was removed under reduced pressure. The residue was purified by flash chromatography (20% EtOAc in Hex) to yield 83 mg of Compound 108 as an oil.

Example 9

Preparation of Compound 109

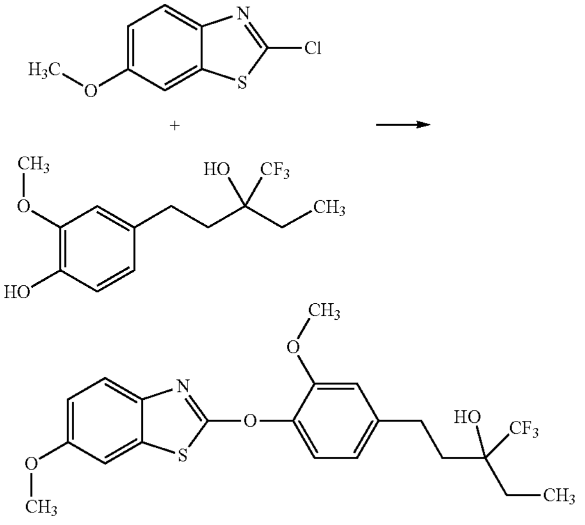

(109)

A mixture of 4-[3-hydroxy-3-(trifluoromethyl)pentyl]-2-methoxyphenol prepared as in Example 4 (124 mg, 0.45 mmol), $K_2CO_3$ (87 mg, 0.62 mmol), and 2-chloro-6-methoxy-benzothiazole (180 mg, 0.90 mmol) in DMF (2.5 mL) was stirred in a sealed tube at 100° C. for 18 h. The mixture was allowed to cool to room temperature, then diluted with EtOAc (15 mL) and $H_2O$ (15 mL). The layers were separated and the aqueous layer was extracted with EtOAc (20 mL). The organic layers were combined and washed with brine, dried over anhydrous $MgSO_4$, filtered, and the solvent was removed under reduced pressure. The residue was purified by flash chromatography (20% EtOAc in Hex) to yield 118 mg of Compound 109 as a colourless oil.

Example 10

Preparation of Compound 110

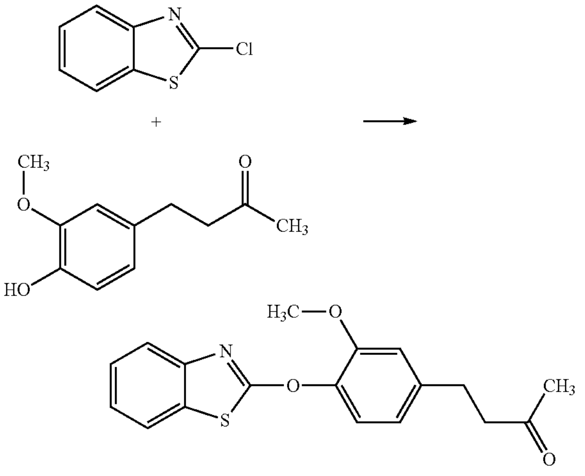

(110)

To a solution of vanillyl acetone (15, 250 mg, 1.29 mmol) in DMF (3 mL) under argon was added 2-chlorobenzothiazole (168 μl, 1.29 mmol) and $K_2CO_3$ (267 mg, 1.93 mmol). The reaction mixture was stirred in a sealed tube at 100° C. for 18 hours. The reaction mixture was diluted with water and ethyl acetate. The organic layer was then washed with 5% aqueous sodium hydroxide, water, and brine. The organic layer was dried ($MgSO_4$), filtered, and the solvent was removed under reduced pressure. Flash column chromatography on silica gel (30% EtOAc in Hex) yielded 321 mg of Compound 110 as a white solid.

Example 11

Preparation of Compound 111

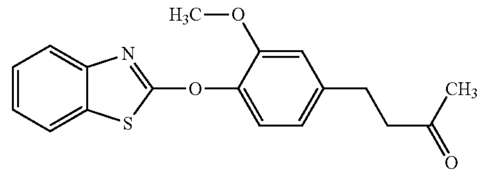

(110)

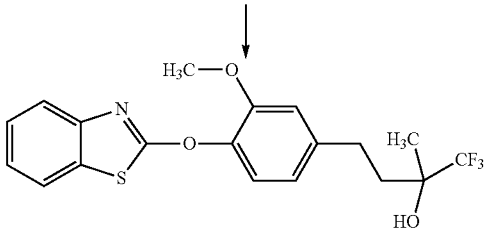

(111)

To a stirred mixture of Compound 110 (150 mg, 0.458 mmol) and $K_2CO_3$ (6 mg, 0.043 mmol) in DMF (2 mL) at 0° C. under argon was added $CF_3TMS$ (135 μL, 0.914 mmol) dropwise. The cooling bath was removed and the reaction mixture was stirred at room temperature for 18 h. The mixture was diluted with EtOAc (35 mL) and washed with water (25 mL). The organic layer was dried over anhydrous $Na_2SO_4$, filtered, and the solvent was removed under reduced pressure. The residue was taken-up in MeOH (3 mL), combined with conc. HCl (0.3 mL) and stirred for 1 h. The mixture was diluted with EtOAc (35 mL) and washed with water (25 mL). The organic layer was dried over anhydrous $Na_2SO_4$, filtered, and the solvent was removed under reduced pressure. The residue was purified by flash chromatography (20% EtOAc in Hex) to yield 100 mg of Compound 111 as a colourless oil.

Example 12

Preparation of Compound 112

3,4-Dihydroxybenzaldehyde (0.50 g, 3.62 mmol), benzyl bromide (0.43 mL, 3.62 mmol), $K_2CO_3$ (0.75 g, 5.43 mmol), NaI (0.054 g, 0.36 mmol), and acetone (10 mL) were combined, stirred under argon and brought to reflux. The reaction mixture was stirred at reflux for 18 hours, filtered and concentrated. The residue was purified by flash column chromatography on silica gel (20% EtOAc in Hex) to yield 483 mg of 4-(benzyloxy)-3-hydroxybenzaldehyde as a white solid.

To a stirred solution of 4-(benzyloxy)-3-hydroxybenzaldehyde (1.50 g, 6.57 mmol) in MeOH (14 mL)/$H_2O$ (1.4 mL) KOH (1.73 g, 26.2 mmol) was added followed by 2-butanone (5.3 mL, 58.80 mmol). The mixture was stirred at reflux for 2 h. The reaction was allowed to cool to room temperature then quenched with 10% aq. HCl (60 mL) and extracted with EtOAc (2×50 mL). The organic layer was washed with water (2×150 mL), dried over anhydrous $MgSO_4$, filtered, and the solvent was removed under reduced pressure. The residue was triturated with diethyl ether to yield 0.648 g of 1-[4-(benzyloxy)-3-hydroxyphenyl] pent-1-en-3-one as an off-white solid.

A mixture of 1-[4-(benzyloxy)-3-hydroxyphenyl]pent-1-en-3-one (0.5 g, 1.77 mmol), $K_2CO_3$ (0.734 g, 5.31 mmol), and 2-bromopropane (0.830 mL, 8.84 mmol) in DMF (5 mL) was stirred in a sealed tube at 90° C. for 18 h. The mixture was allowed to cool to room temperature, diluted with EtOAc (35 mL), washed with water (3×25 mL), dried over anhydrous $MgSO_4$, filtered, and the solvent was removed under reduced pressure to yield 0.531 g of 1-[4-(benzyloxy)-3-(propan-2-yloxy)phenyl]pent-1-en-3-one as an off-white solid.

To a stirred solution of 1-[4-(benzyloxy)-3-(propan-2-yloxy)phenyl]pent-1-en-3-one (0.400 g, 1.23 mmol) in EtOAc (12 mL) and AcOH (600 μL) 10% Pd/C (0.040 g) was added. The reaction mixture was stirred under hydrogen for 5 h and then filtered. The solvent was removed under reduced pressure, and the residue was purified by flash chromatography (30% EtOAc in Hex) to yield 0.193 g of 1-[4-(hydroxy)-3-(propan-2-yloxy)phenyl]pentan-3-one.

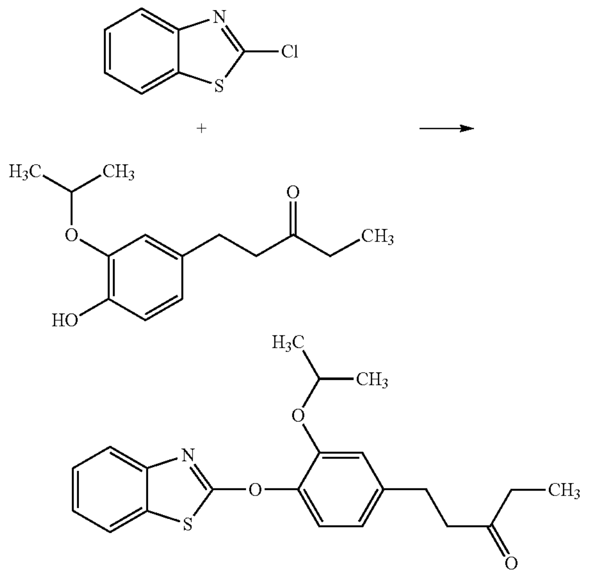

(112)

A mixture of 1-[4-(hydroxy)-3-(propan-2-yloxy)phenyl] pentan-3-one (236 mg, 1.00 mmol), $K_2CO_3$ (140 mg, 1.01 mmol), and 2-chlorobenzothiazole (0.145 mL, 1.1 mmol) in DMF (3 mL) was stirred in a sealed tube at 100° C. for 18 h. The mixture was allowed to cool to room temperature, diluted with EtOAc (35 mL), washed with water (2×25 mL), dried over anhydrous $MgSO_4$, filtered, and the solvent was removed under reduced pressure. The residue was purified by flash chromatography (20% EtOAc in Hex) to yield 245 mg of Compound 112 as a yellow oil.

Example 13

Preparation of Compound 113

A mixture of 1-[4-(benzyloxy)-3-hydroxyphenyl]pent-1-en-3-one (0.5 g, 1.77 mmol, prepared as in Example 12), $K_2CO_3$ (0.367 g, 2.66 mmol), and cyclopentylbromide (0.290 mL, 2.70 mmol) in DMF (5 mL) was stirred in a sealed tube at 90° C. for 18 h. The mixture was allowed to cool to room temperature, diluted with EtOAc (35 mL), washed with water (3×25 mL), dried over anhydrous $MgSO_4$, filtered, and the solvent was removed under reduced pressure. The residue was triturated with ether/Hex to yield 0.454 g of 1-[4-(benzyloxy)-3-(cyclopentyloxy) phenyl]pent-1-en-3-one as an off-white solid.

To a stirred solution of 1-[4-(benzyloxy)-3-(cyclopentyloxy)phenyl]pent-1-en-3-one (0.450 g, 1.28 mmol) in EtOAc (14 mL) and AcOH (700 μL) 10% Pd/C (0.045 g) was added. The reaction mixture was stirred under hydrogen for 23 h and then filtered. The solvent was removed under reduced pressure, and the residue was purified by flash chromatography (30% EtOAc in Hex) to yield 0.193 g of 1-[4-(hydroxy)-3-(cyclopentyloxy)phenyl]pentan-3-one.

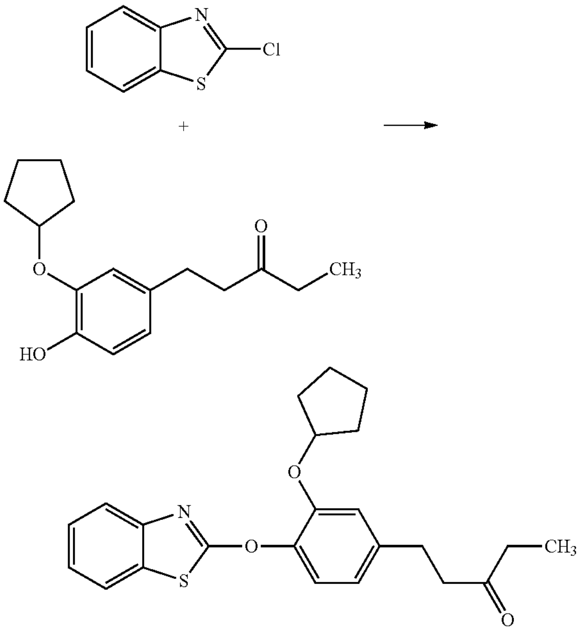

(113)

A mixture of 1-[4-(hydroxy)-3-(cyclopentyloxy)phenyl] pentan-3-one (0.234 mg, 0.892 mmol), $K_2CO_3$ (0.124 g, 0.897 mmol), and 2-chlorobenzothiazole (0.130 mL, 0.998 mmol) in DMF (3 mL) was stirred in a sealed tube at 100° C. for 18 h. The mixture was allowed to cool to room temperature, diluted with EtOAc (35 mL), washed with water (2×25 mL), dried over anhydrous $MgSO_4$, filtered, and the solvent was removed under reduced pressure. The residue was purified by flash chromatography (20% EtOAc in Hex) to yield 0.245 g of Compound 113 as a yellow oil.

Example 14

Preparation of Compound 114

A mixture of 1-[4-(benzyloxy)-3-hydroxyphenyl]pent-1-en-3-one (0.5 g, 1.77 mmol, prepared as in Example 12), $K_2CO_3$ (0.367 g, 2.66 mmol), and (bromomethyl)cyclopropane (0.260 mL, 2.68 mmol) in DMF (5 mL) was stirred in a sealed tube at 90° C. for 18 h. The mixture was allowed to cool to room temperature, diluted with EtOAc (35 mL), washed with water (3×25 mL), dried over anhydrous $MgSO_4$, filtered, and the solvent was removed under reduced pressure. The residue was triturated with ether/Hex to yield 0.440 g of 1-[4-(benzyloxy)-3-(cyclopropylmethoxy)phenyl]pent-1-en-3-one as a solid.

To a stirred solution of 1-[4-(benzyloxy)-3-(cyclopropylmethoxy)phenyl]pent-1-en-3-one (0.440 g, 1.31 mmol) in EtOAc (14 mL) and AcOH (700 μL) 10% Pd/C (0.044 g) was added. The reaction mixture was stirred under hydrogen for 18 h and then filtered. The solvent was removed under reduced pressure, and the residue was purified by flash chromatography (20% EtOAc in Hex) to yield 0.244 g of 1-[4-(hydroxy)-3-(cyclopropylmethoxy)phenyl]pentan-3-one.

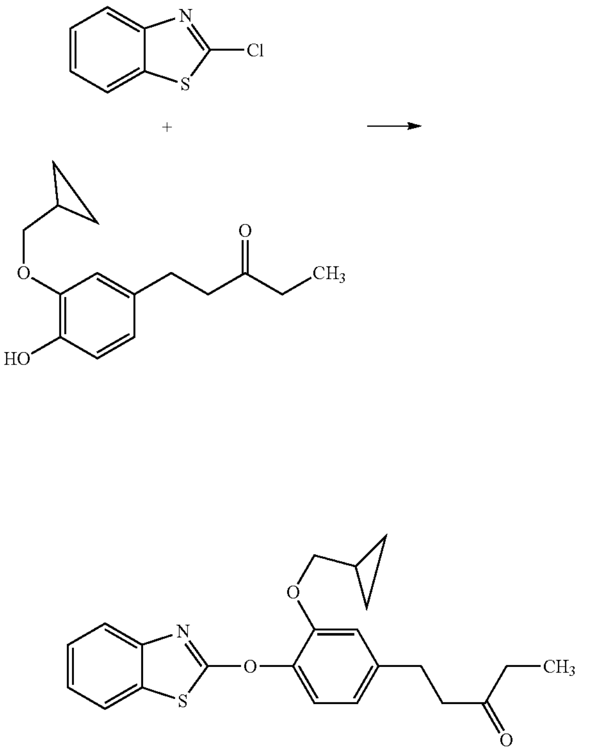

(114)

A mixture of 1-[4-(hydroxy)-3-(cyclopropylmethoxy)phenyl]pentan-3-one (0.244 mg, 0.983 mmol), $K_2CO_3$ (0.136 g, 0.984 mmol), and 2-chlorobenzothiazole (0.140 mL, 1.08 mmol) in DMF (4 mL) was stirred in a sealed tube at 100° C. for 18 h. The mixture was allowed to cool to room temperature, diluted with EtOAc (35 mL), washed with water (3×25 mL), dried over anhydrous $MgSO_4$, filtered, and the solvent was removed under reduced pressure. The residue was purified by flash chromatography (20% EtOAc in Hex) to yield 0.285 g of Compound 114 as a yellow oil.

Example 15

Preparation of Compound 115

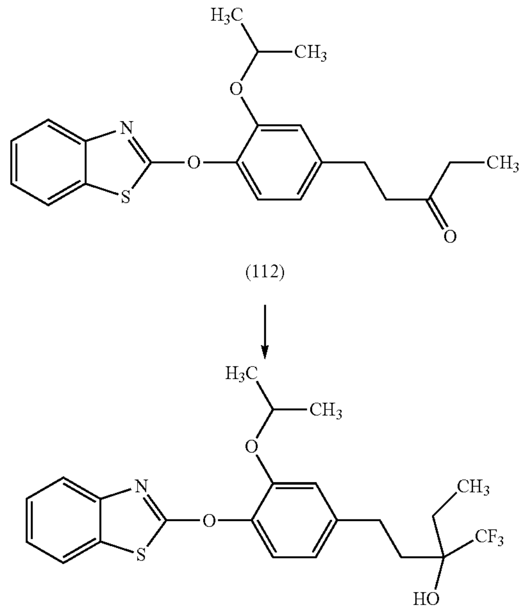

(112)

(115)

To a stirred mixture of Compound 112 (235 mg, 0.636 mmol) and $K_2CO_3$ (9 mg, 0.065 mmol) in DMF (3 mL) under argon was added $CF_3$TMS (0.120 mL, 0.813 mmol) dropwise. The reaction mixture was stirred at room temperature for 18 h. The mixture was partitioned between EtOAc (35 mL) and water (25 mL) and the aqueous layer was extracted with EtOAc (35 mL). The combined organic layers was dried over anhydrous $MgSO_4$, filtered, and concentrated. The residue was taken-up in MeOH (6 mL), conc. HCl (0.1 mL) was added and the mixture was stirred for 1 h. The mixture was diluted with EtOAc (35 mL) and washed with water (2×25 mL). The organic layer was dried over anhydrous $MgSO_4$, filtered, and concentrated. The residue was purified by flash chromatography (20% EtOAc in Hex) to yield 203 mg of Compound 115 as a white solid.

Example 16

Preparation of Compound 116

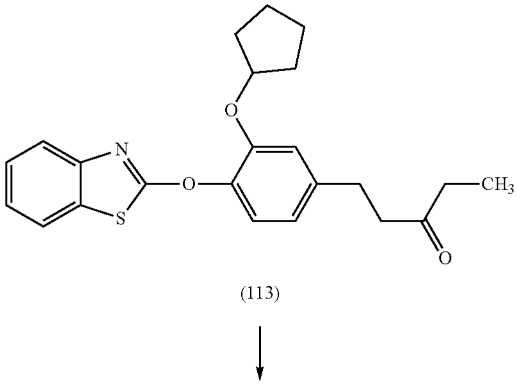

(113)

-continued

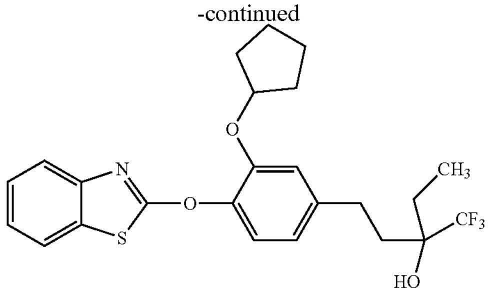

(116)

To a stirred mixture of Compound 113 (0.125 g, 0.316 mmol) and $K_2CO_3$ (0.004 g, 0.029 mmol) in DMF (1.5 mL) under argon was added $CF_3TMS$ (0.060 mL, 0.406 mmol) dropwise. The reaction mixture was stirred at room temperature for 18 h. The mixture was diluted with EtOAc (35 mL) and washed with water (2x25 mL). The organic layer was dried over anhydrous $MgSO_4$, filtered, and concentrated. The residue was taken-up in MeOH (3 mL), conc. HCl (0.05 mL) was added and the mixture was stirred for 1 h. The mixture was diluted with EtOAc (35 mL) and washed with water (2x25 mL). The organic layer was dried over anhydrous $MgSO_4$, filtered, and concentrated. The residue was purified by flash chromatography (20% EtOAc in Hex) to yield 0.106 g of Compound 116 as a white solid.

Example 17

Preparation of Compound 117

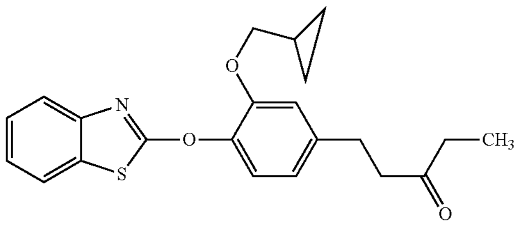

(114)

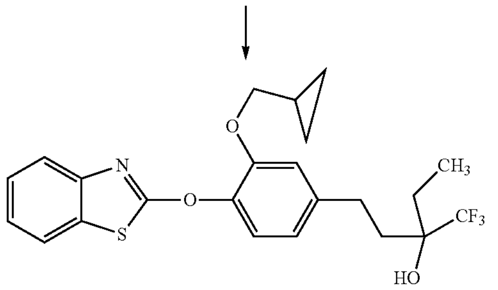

(117)

To a stirred mixture of Compound 114 (0.150 g, 0.393 mmol) and $K_2CO_3$ (0.006 g, 0.043 mmol) in DMF (2 mL) under argon was added $CF_3TMS$ (0.080 mL, 0.572 mmol) dropwise. The reaction mixture was stirred at room temperature for 18 h. The mixture was diluted with EtOAc (35 mL) and washed with water (2x25 mL). The organic layer was dried over anhydrous $MgSO_4$, filtered, and concentrated. The residue was taken-up in MeOH (3 mL), conc. HCl (0.05 mL) was added and the mixture was stirred for 1 h. The mixture was diluted with EtOAc (35 mL) and washed with water (2x25 mL). The organic layer was dried over anhydrous $MgSO_4$, filtered, and concentrated. The residue was purified by flash chromatography (20% EtOAc in Hex) to yield 0.121 g of Compound 117 as a white solid.

Example 18

Preparation of Compound 118

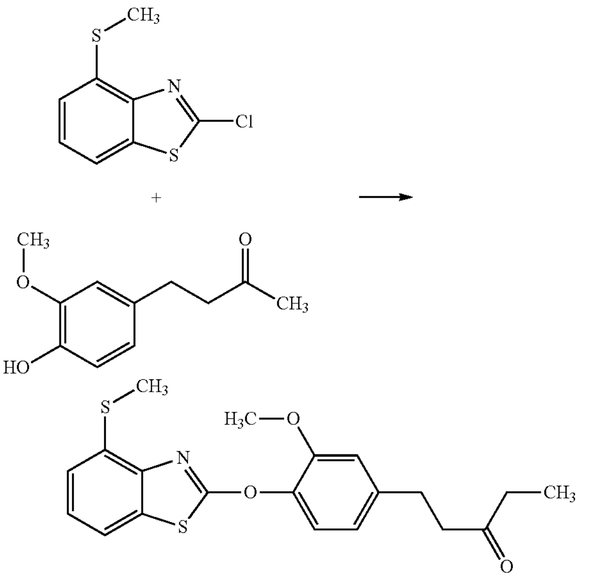

(118)

To a solution of vanillyl acetone (150 mg, 0.772 mmol), $K_2CO_3$ (160 mg, 1.16 mmol), and 2-chloro-4-(methylthio)-benzothiazole (208 mg, 0.964 mmol) in DMF (3 mL) was stirred in a sealed tube at 100° C. for 18 h. The mixture was allowed to cool to room temperature, diluted with EtOAc (35 mL), washed with water (2x25 mL), dried over anhydrous $MgSO_4$, filtered, and the solvent was removed under reduced pressure. The residue was purified by flash chromatography (20% EtOAc in Hex) to yield 214 mg of Compound 118 as a yellow oil.

Example 19

Preparation of Compound 119

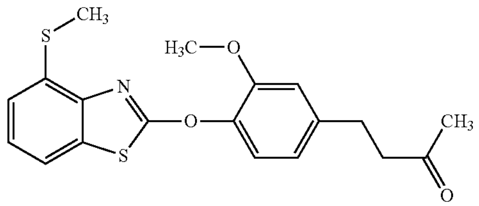

(118)

-continued

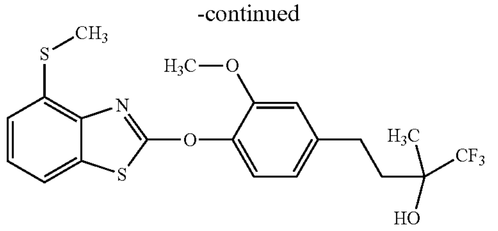

(119)

To a stirred mixture of Compound 118 (214 mg, 0.599 mmol) and $K_2CO_3$ (8 mg, 0.058 mmol) in DMF (3 mL) under argon was added $CF_3$TMS (133 μL, 0.901 mmol) dropwise. The mixture was stirred at room temperature for 18 h. The mixture was diluted with EtOAc (35 mL) and washed with water (2×25 mL). The organic layer was dried over anhydrous $MgSO_4$, filtered, and the solvent was removed under reduced pressure. The residue was taken-up in MeOH (3 mL) conc. HCl (0.3 mL) was added and the mixture was stirred for 1 h. The mixture was diluted with EtOAc (35 mL) and washed with water (2×25 mL). The organic layer was dried over anhydrous $MgSO_4$, filtered, and the solvent was removed under reduced pressure. The residue was purified by flash chromatography (20% EtOAc in Hex) to yield 95 mg of Compound 119 as a yellow oil.

Example 20

Preparation of Compound 120

To a stirred solution of 3-ethoxy-4-hydroxybenzaldehyde (2 g, 12 mmol) in MeOH (17 mL)/$H_2O$ (2.5 mL) 2-butanone (10 mL, 111 mmol) was added, followed by KOH (3 g, 45 mmol). The mixture was stirred at room temperature for 18 h. The reaction was quenched with 10% aq. HCl and extracted with EtOAc (3×30 mL). The organic layer was washed with brine (30 mL), dried over anhydrous $MgSO_4$, filtered, and the solvent was removed under reduced pressure. The residue was purified by flash column chromatography (20% EtOAc in Hex) to yield 2.09 g of 1-(3-ethoxy-4-hydroxyphenyl)pent-1-en-3-one as a solid.

To a stirred solution of 1-(3-ethoxy-4-hydroxyphenyl) pent-1-en-3-one (1.73 g, 7.86 mmol) in EtOAc (15 mL) 10% Pd/C (150 mg) was added. The reaction mixture was stirred under hydrogen for 1.5 h and then was filtered. The solvent was removed under reduced pressure, and the residue was purified by flash chromatography (40% EtOAc in Hex) to yield 0.720 g of 1-(3-ethoxy-4-hydroxyphenyl)pentan-3-one.

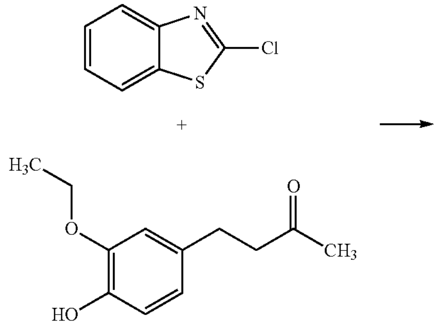

-continued

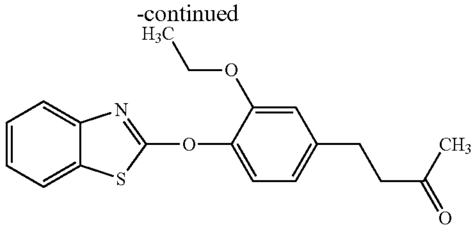

(120)

A mixture of 1-(3-ethoxy-4-hydroxyphenyl)pentan-3-one (0.430 g, 1.94 mmol), $K_2CO_3$ (0.266 g, 1.92 mmol), and 2-chlorobenzothiazole (0.277 mL, 2.13 mmol) in DMF (3 mL) was stirred under argon at 120° C. for 18 h. The mixture was allowed to cool to room temperature, diluted with EtOAc (20 mL), washed with water (2×15 mL), brine (15 mL), dried over anhydrous $MgSO_4$, filtered, and the solvent was removed under reduced pressure. The residue was purified by flash chromatography (20% EtOAc in Hex) to yield 0.492 g of Compound 120 as an oil.

Example 21

Preparation of Compound 121

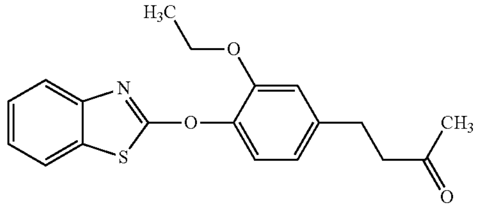

(120)

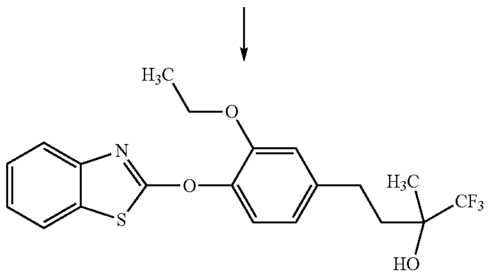

(121)

To a stirred mixture of Compound 120 (0.100 g, 0.281 mmol) and $K_2CO_3$ (0.018 g) in DMF (2 mL) under argon was added $CF_3$TMS (0.100 mL, 0.678 mmol). The reaction mixture was stirred for 18 h at room temperature and then was diluted with EtOAc (15 mL) and washed with brine (2×15 mL). The organic layer was dried over anhydrous $MgSO_4$, filtered, and the solvent was removed under reduced pressure. The residue was taken-up in MeOH (5 mL) and stirred with conc. HCl (0.250 mL) for 1 h. The solvent was removed under reduced pressure, the residue was taken-up in EtOAc (20 mL) and washed with brine (2×20 mL). The organic layer was dried over anhydrous $MgSO_4$, filtered, and the solvent was removed under reduced pressure. The residue was purified by flash chromatography (20% EtOAc in Hex) to yield 72 mg of Compound 121 as a colourless oil.

Example 22

Preparation of Compound 122

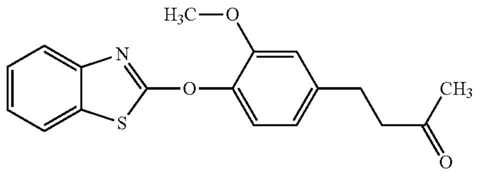

(110)

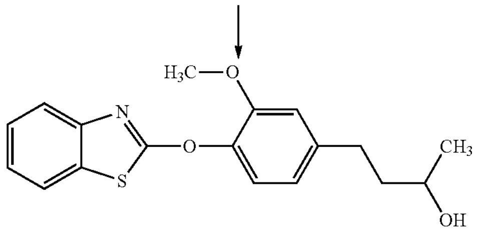

(122)

Following general procedure for reductions, Compound 122 was prepared from Compound 110 (0.46 mmol, prepared as in Example 10), sodium borohydride (0.91 mmol), and methanol (3 mL). Flash column chromatography of the crude mixture on silica gel (40% EtOAc in Hex) yielded 0.156 g of Compound 122 as an oil.

Example 23

Preparation of Compound 123

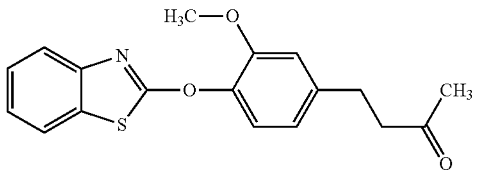

(110)

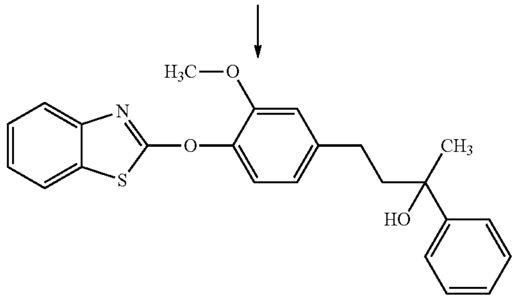

(123)

Following General Procedure for Grignard Additions, Compound 123 was prepared from Compound 110 (0.150 g, 0.46 mmol, prepared as in Example 10), THF (3.0 mL), and phenyl magnesium bromide (0.30 mL, 3 M in $Et_2O$). Flash column chromatography of the crude mixture on silica gel (30% EtOAc in Hex) yielded 0.204 g of Compound 123 as an oil.

Example 24

Preparation of Compound 124

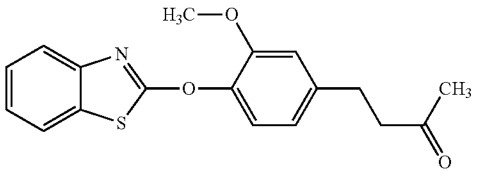

(110)

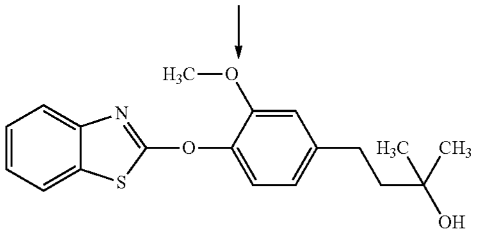

(124)

Following General Procedure for Grignard Additions, Compound 124 was prepared from Compound 110 (0.100 g, 0.305 mmol, prepared as in Example 10), THF (1.0 mL), and methyl magnesium bromide (0.20 mL, 3 M in $Et_2O$). Flash column chromatography of the crude mixture on silica gel (50-70% EtOAc in Hex) yielded 0.115 g of Compound 124 as an oil.

Example 25

Preparation of Compound 125

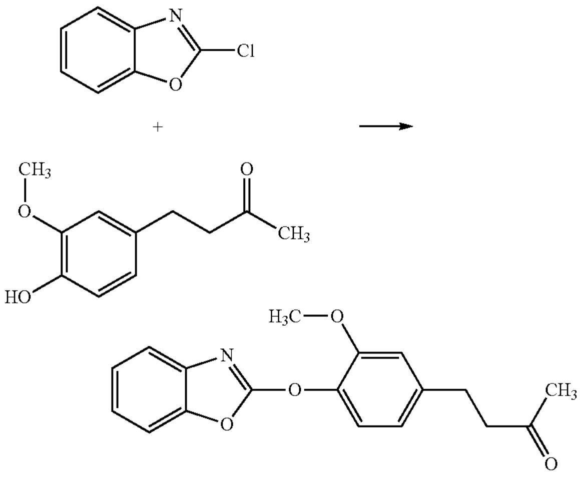

(125)

To a solution of vanillyl acetone (0.621 g, 3.20 mmol) in DMF (8 mL) under argon was added 2-chlorobenzoxazole (300 μL, 2.62 mmol) and $K_2CO_3$ (0.511 g, 3.70 mmol). The reaction mixture was stirred at 140° C. for 18 hours. The reaction mixture was diluted with water and EtOAc. The organic layer was then washed with 5% aqueous NaOH (2×30 mL) and brine (20 mL). The organic layer was dried over $MgSO_4$, filtered, and the solvent was removed under reduced pressure. Flash column chromatography on silica gel (40% EtOAc in Hex) yielded 0.483 g of Compound 125 as a white solid.

Example 26

Preparation of Compound 126

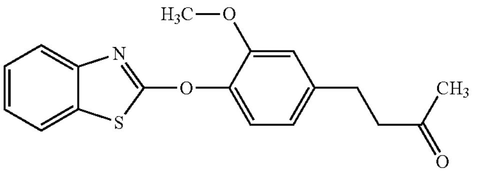

(125)

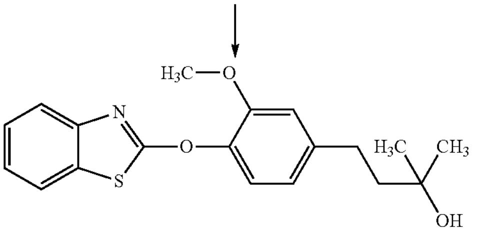

(126)

Following General Procedure for Grignard Additions, methyl magnesium bromide (0.180 mL, 3 M in $Et_2O$) was added to a flask which had been cooled in an ice-water bath and contained a stirring mixture of Compound 125 (0.095 g, 0.305 mmol) in THF (3.0 mL). The ice-bath was removed and the mixture was allowed to stir for 70 minutes at room temperature. $H_2O$ (5 mL) was added followed by EtOAc (10 mL) and brine (5 mL). The layers were separated and the aqueous layer was extracted with EtOAc (2×10 mL). The combined organic layers were washed with brine, dried over $MgSO_4$, filtered and the filtrate concentrated. Flash column chromatography of the crude mixture on silica gel (30% EtOAc in Hex) yielded 0.090 g of Compound 126 as a colourless oil.

Example 27

Preparation of Compound 127

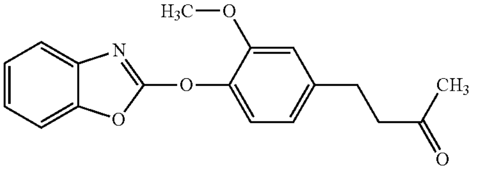

(125)

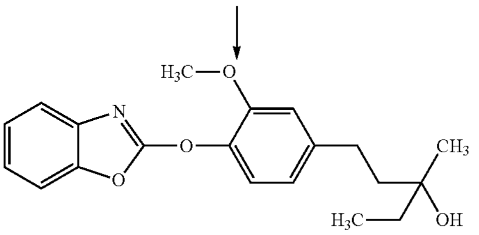

(127)

Following General Procedure for Grignard Additions, ethyl magnesium bromide (0.180 mL, 3 M in $Et_2O$) was added to a flask which has been cooled in an ice-water bath and contained a stirring mixture of Compound 125 (0.101 g, 0.325 mmol) in THF (3.0 mL). The ice-bath was removed and the mixture was allowed to stir for 70 minutes at room temperature. $H_2O$ (5 mL) was added followed by EtOAc (10 mL) and brine (5 mL). The layers were separated and the aqueous layer was extracted with EtOAc (2×10 mL). The combined organic layers were washed with brine, dried over $MgSO_4$, filtered and the filtrate concentrated. Flash column chromatography of the crude mixture on silica gel (40% EtOAc in Hex) yielded 0.066 g of Compound 127 as a colourless oil.

Example 28

Preparation of Compound 128

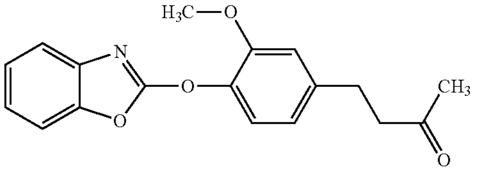

(125)

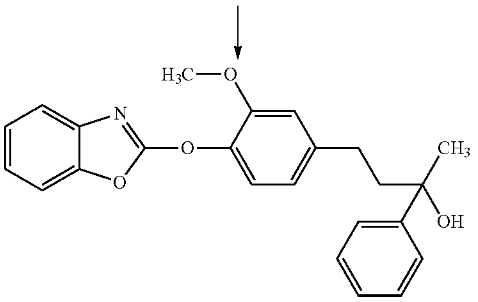

(128)

Following General Procedure for Grignard Additions, phenyl magnesium bromide (0.180 mL, 3 M in $Et_2O$) was added to a flask which had been cooled in an ice-water bath and contained a stirring mixture of Compound 125 (0.097 g, 0.314 mmol) in THF (3.0 mL). The ice-bath was removed and the mixture was allowed to stir for 70 minutes at room temperature. $H_2O$ (5 mL) was added followed by EtOAc (10 mL) and brine (5 mL). The layers were separated and the aqueous layer was extracted with EtOAc (2×10 mL). The combined organic layers were washed with brine, dried over $MgSO_4$, filtered and the filtrate concentrated. Flash column chromatography of the crude mixture on silica gel (40% EtOAc in Hex) yielded 0.080 g of Compound 128 as a colourless oil.

Example 29

Preparation of Compound 129

To a stirred solution of 3-ethoxy-4-hydroxybenzaldehyde (2.00 g, 12.0 mmol) and 85% KOH (3.00 g, 45.4 mmol) in MeOH (17 mL)/H2O (2.5 mL), acetophenone (4.5 mL, 38.6 mmol) was added. The mixture was stirred at room temperature while monitoring by TLC. Upon completion, standard workup and concentration provided a residue which was carried forward to the next step without further purification. The residue was dissolved in EtOAc (30 mL), 10% Pd/C (320 mg) was added and the mixture was stirred under hydrogen for 1 h. The mixture was filtered and the filtrate concentrated to yield 1.2 g of 3-(3-ethoxy-4-hydroxyphenyl)-1-phenylpropan-1-one as a yellow solid.

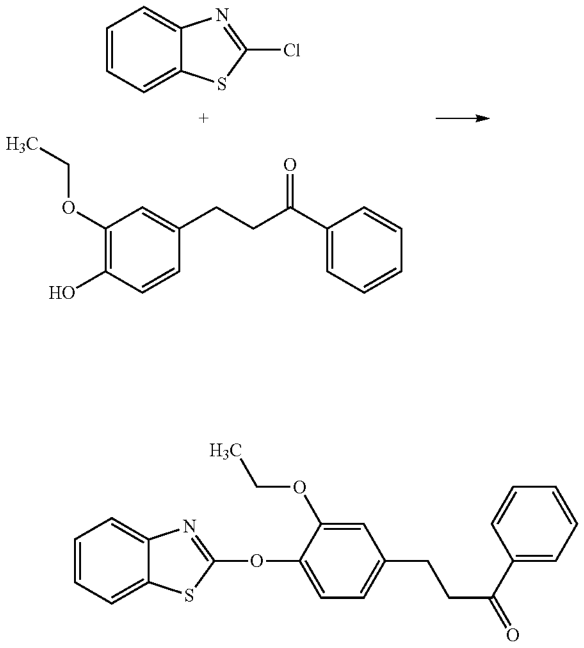

(129)

To a solution of 3-(3-ethoxy-4-hydroxyphenyl)-1-phenylpropan-1-one (1.20 g, 4.44 mmol) in DMF (8 mL) under argon was added 2-chlorobenzothiazole (682 µL, 5.26 mmol) and $K_2CO_3$ (0.648 g, 4.70 mmol). The reaction mixture was stirred at 140° C. for 18 hours. The reaction mixture was diluted with water and ethyl acetate. The organic layer was then washed with brine. The organic layer was dried ($MgSO_4$), filtered, and the solvent was removed under reduced pressure. Flash column chromatography on silica gel (15-20% EtOAc in Hex) yielded 1.11 g of Compound 129 as an oil.

Example 30

Preparation of Compound 130

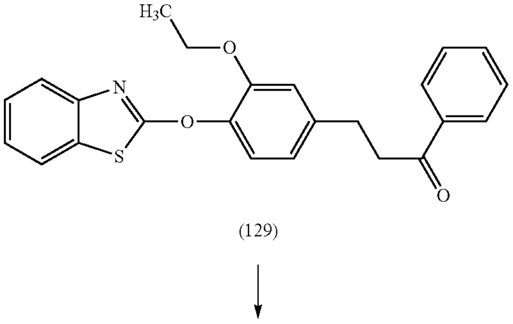

(129)

-continued

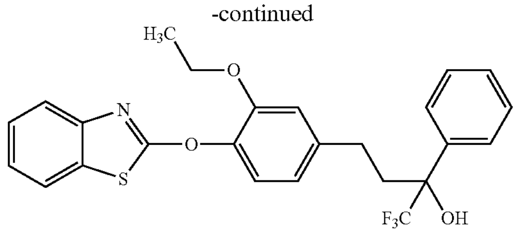

(130)

To a stirred mixture of Compound 129 (0.200 g, 0.5 mmol) and $K_2CO_3$ (0.015 g, 0.11 mmol) in DMF (3 mL) under argon was added $CF_3TMS$ (0.172 mL, 1.16 mmol) dropwise. The reaction mixture was stirred at room temperature for 18 h. The mixture was diluted with EtOAc (15 mL) and washed with brine (2×15 mL). The organic layer was concentrated and the residue was taken-up in MeOH (5 mL) and stirred with conc. HCl (0.25 mL) for 1 h. The mixture was diluted with EtOAc (20 mL) and washed with brine (2×20 mL). The organic layer was dried over anhydrous $MgSO_4$, filtered, and the solvent was removed under reduced pressure. The residue was purified by flash chromatography (20% EtOAc in Hex) to yield 178 mg of Compound 130 as an oil.

Example 31

Preparation of Compound 131

A mixture of vanillin (2.00 g, 13.1 mmol), acetophenone (5.00 mL, 42.9 mmol), and KOH (6 g, 106.5 mmol) in MeOH (20 mL)/$H_2O$ (58 mL) in a sealed tube was warmed up to 60° C. with stirring, and stirred at 60° C. for 4 h. The reaction mixture was allowed to cool to room temperature, quenched with aq. HCl (10 mL conc. HCl in 100 mL water), and extracted with EtOAc (100 mL). The organic layer was washed with water (2×100 mL) and brine (20 mL), dried over anhydrous $MgSO_4$, filtered, and the solvent was removed under reduced pressure. The residue was purified by flash chromatography (15% to 40% EtOAc in Hex) to yield 3.8 g of 3-(4-hydroxy-3-methoxyphenyl)-1-phenylprop-2-en-1-one.

A mixture of 3-(4-hydroxy-3-methoxyphenyl)-1-phenylprop-2-en-1-one (1.27 g, 4.99 mmol), and 10% Pd/C (139 mg) in EtOAc (10 mL) and $Et_3N$ (1.3 mL) was stirred under hydrogen for 2 h, and then was filtered. The solvent was removed under reduced pressure, and the residue was purified by flash chromatography (20% EtOAc in Hex, 30% EtOAc in Hex) to yield 311 mg of 3-(4-hydroxy-3-methoxyphenyl)-1-phenylpropan-1-one.

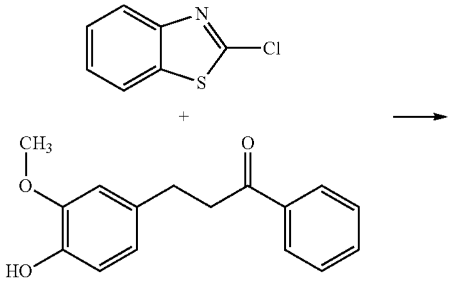

-continued

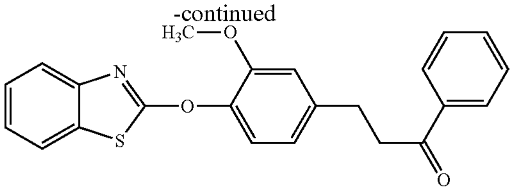

(131)

A mixture of 3-(4-hydroxy-3-methoxyphenyl)-1-phenyl-propan-1-one (768 mg, 3 mmol), $K_2CO_3$ (414 mg, 3 mmol) and 2-chlorobenzothiazole (429 μL, 3.2 mmol) in DMF (5 mL) was warmed to 100° C. with stirring, and was stirred at 100° C. for 18 h. The reaction mixture was allowed to cool to room temperature, diluted with EtOAc (30 mL) and washed with brine (3×30 mL), dried over anhydrous $MgSO_4$, filtered, and the solvent was removed under reduced pressure to yield 813 mg of Compound 131 as a white solid.

Example 32

Preparation of Compound 132

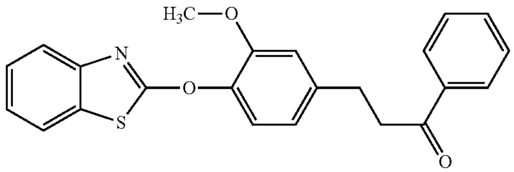

(131)

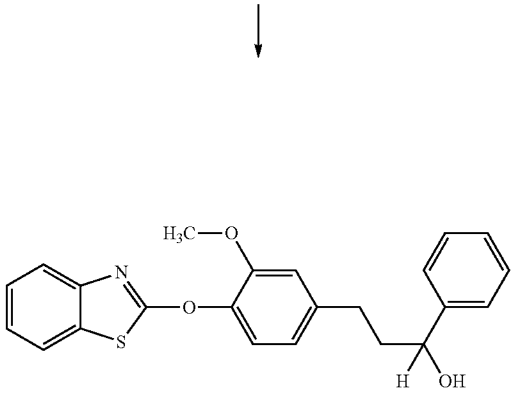

(132)

Compound 131 (100 mg, 0.257 mmol) and $NaBH_4$ (46 mg, 1.22 mmol) in MeOH (3 mL) was stirred at room temperature under argon for 1 h. The reaction was quenched with EtOAc (25 ml) and 5% aq. HCl (25 mL), and the aqueous layer was extracted with EtOAc (15 mL). The combined organic layer was washed with brine (2×20 mL), dried over anhydrous $MgSO_4$, filtered, and the solvent was removed under reduced pressure. The residue was purified by flash chromatography (30% EtOAc in Hex) to yield 114 mg of Compound 132 as a colourless oil.

Example 33

Preparation of Compound 133

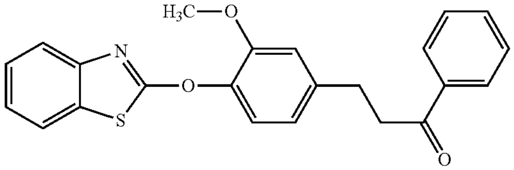

(131)

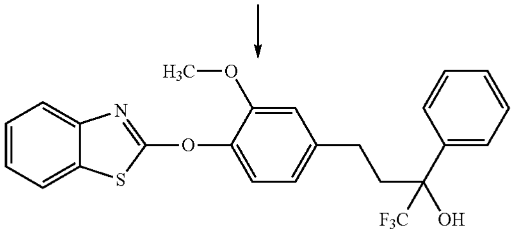

(133)

To a stirred mixture of Compound 131 (250 mg, 0.642 mmol) and $K_2CO_3$ (18 mg, 0.130 mmol) in DMF (3 mL) under argon was added $CF_3$TMS (200 μL, 1.35 mmol). The reaction mixture was stirred at room temperature for 24 h, and then was diluted with EtOAc (35 mL) and washed with brine (3×30 mL). The organic layer was dried over anhydrous $MgSO_4$, filtered, and the solvent was removed under reduced pressure. The residue was taken-up in MeOH (10 mL) and stirred with conc. HCl (0.25 mL) for 2 h. The solvent was removed under reduced pressure, and the residue was taken-up in EtOAc (30 mL), washed with water (2×20 mL) and brine (20 mL), dried over anhydrous $MgSO_4$, filtered, and the solvent was removed under reduced pressure. The residue was purified by flash chromatography (20% EtOAc in Hex) to yield 264 mg of Compound 133 as a yellowish oil.

Example 34

Preparation of Compound 134

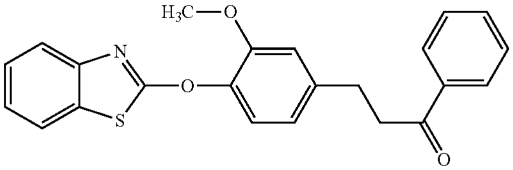

(131)

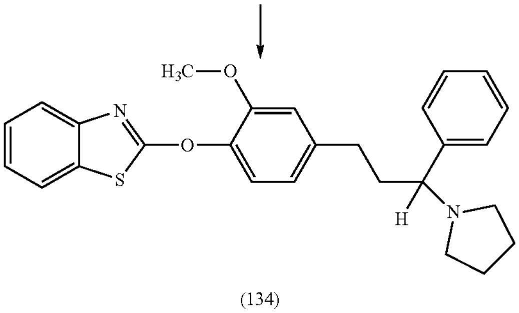

(134)

To a stirred solution of Compound 131 (167 mg, 0.429 mmol) in THF (8 mL) at room temperature under argon was added $Ti(OiPr)_4$ (150 μL, 0.507 mmol), followed by pyrrolidine (50 μL, 0.609 mmol). The reaction mixture was stirred at reflux for 16 h, and then was allowed to cool to room temperature. $NaBH_4$ (24 mg, 0.634 mmol) was added, the reaction mixture was stirred for 3 h, and then was quenched with water (25 mL) and extracted with EtOAc (2×35 mL). The organic layer was washed with water (35 mL), dried over anhydrous $MgSO_4$, filtered, and the solvent was removed under reduced pressure. The residue was purified by flash chromatography (EtOAc/MeOH/Et3N, 9:1:0.1) to yield 108 mg of Compound 134 as a yellow foam.

Example 35

Preparation of Compound 135

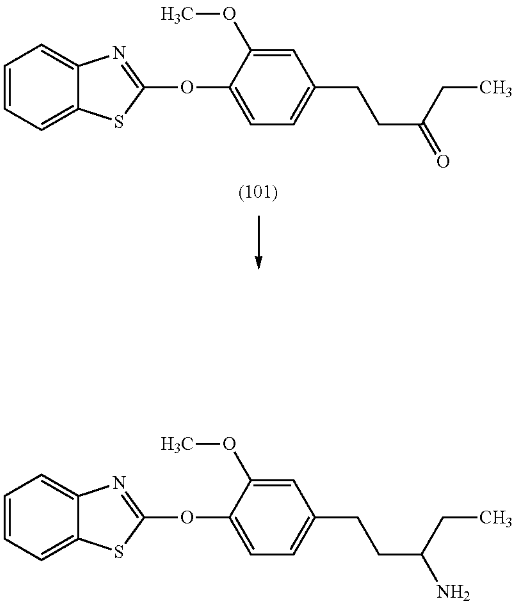

(101)

(135)

To a stirred mixture of $NH_4Cl$ (313 mg, 5.85 mmol) in MeOH (6 mL) at room temperature under argon were added $Et_3N$ (820 μL, 5.88 mmol), Compound 101 from Example 1 (200 mg, 0.586 mmol), and Ti(OiPr)4 (350 μL, 1.18 mmol). The milk-like reaction mixture was stirred for 18 h. $Et_3N$ (820 μL) and $NH_4Cl$ (313 mg) were added, and the reaction mixture was stirred for 3 h. $NaBH_4$ (45 mg) was added, and the reaction mixture was stirred for 1.5 h. Another portion of $NaBH_4$ (23 mg) was added, and the reaction mixture was stirred for 1 h. The reaction was quenched with water (35 mL) and extracted with EtOAc (40 mL). The organic layer was washed with water (2×35 mL), dried over anhydrous $MgSO_4$, filtered, and the solvent was removed under reduced pressure. The residue was purified by flash chromatography (10% MeOH in EtOAc, then EtOAc/MeOH/$Et_3N$, 9:1:0.1) to yield 62 mg of Compound 135 as a yellowish oil.

Example 36

Preparation of Compound 136

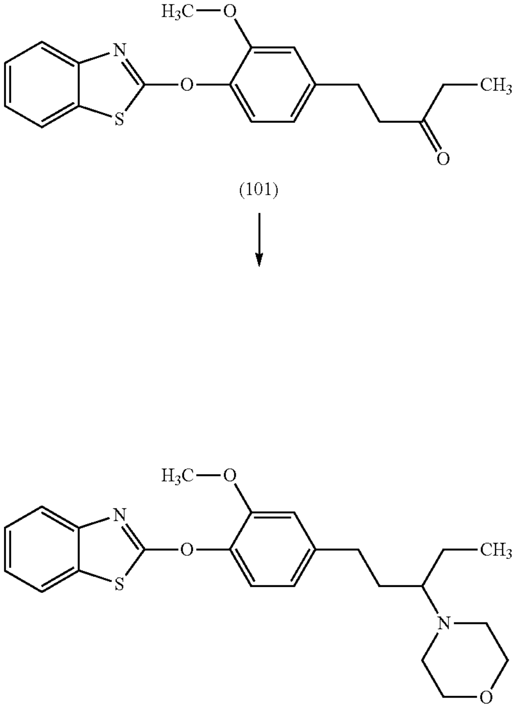

(101)

(136)

To AcOH (5.00 mL, 87.4 mmol) in toluene (70 mL) at 0° C. under argon was added $NaBH_4$ (1.00 g, 26.4 mmol), portionwise over 30 minutes. The cooling bath was removed, and the reaction mixture was stirred for 1 h, filtered, and the insoluble material was washed with ether and dried to yield 3.19 g of $NaBH(OAc)_3$.

To a stirred mixture of Compound 101 (150 mg, 0.439 mmol, prepared as in Example 1) in DCE (3 mL) at room temperature under argon were added 4 Å molecular sieves powder (150 mg), AcOH (100 μL), morpholine (50 μL, 0.578 mmol), and $NaBH(OAc)_3$ (190 mg, 0.896 mmol), prepared as described above. The reaction mixture was stirred for 18 h. An additional quantity of morpholine (50 μL) was added, and stirring was continued for 2 h. The reaction mixture was quenched with saturated aqueous $NaHCO_3$ (25 mL) and extracted with $CH_2Cl_2$ (2×35 mL). The combined organic layer was dried over anhydrous $MgSO_4$, filtered, and the solvent was removed under reduced pressure. The residue was purified by flash chromatography (EtOAc/MeOH/$Et_3N$, 9:1:0.1) to yield 30 mg of a colourless oil. The oil was taken up in $CH_2Cl_2$ (3 mL) and stirred with 1.25 M HCl in MeOH (100 μL) for 1 h. The solvents were removed under reduced pressure to yield 30 mg of the hydrochloride salt of Compound 136 as a white foam.

Example 37

Preparation of Compound 137

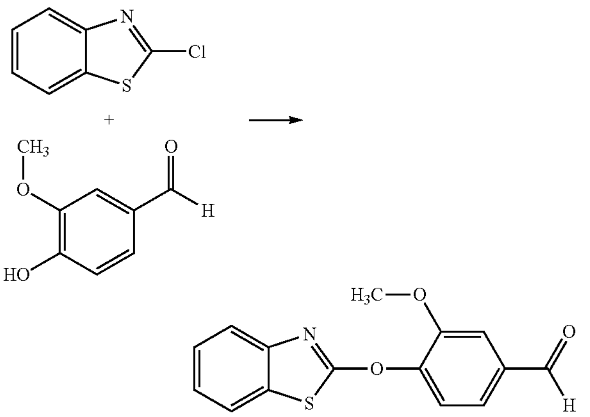

A mixture of vanillin (250 mg, 1.64 mmol), $K_2CO_3$ (341 mg, 2.47 mmol), and 2-chlorobenzothiazole (260 μL, 2.00 mmol) in DMF (5 mL) was stirred in a sealed tube at 100° C. for 18 h. The mixture was allowed to cool to room temperature, diluted with EtOAc (35 mL), washed with water (3×25 mL), dried over anhydrous $MgSO_4$, filtered, and the solvent was removed under reduced pressure. The residue was purified by flash chromatography (20% EtOAc in Hex) to yield 407 mg of 4-(1,3-benzothiazol-2-yloxy)-3-methoxybenzaldehyde as a white solid.

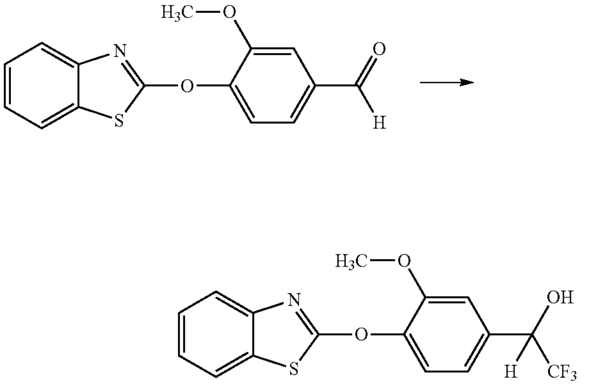

(137)

To a stirred mixture of 4-(1,3-benzothiazol-2-yloxy)-3-methoxybenzaldehyde (200 mg, 0.701 mmol) and $K_2CO_3$ (10 mg, 0.072 mmol) in DMF (3 mL) under argon was added $CF_3TMS$ (155 μL, 1.05 mmol). The reaction mixture was stirred at room temperature for 42 h, and then was diluted with EtOAc (40 mL) and washed with water (2×25 mL). The organic layer was dried over anhydrous $MgSO_4$, filtered, and the solvent was removed under reduced pressure. The residue was taken-up in MeOH (3 mL) and stirred with conc. HCl (0.15 mL) for 1 h. The mixture was diluted with EtOAc (40 mL) and washed with water (2×25 mL). The organic layer was dried over anhydrous $MgSO_4$, filtered, and the solvent was removed under reduced pressure. The residue was purified by flash chromatography (20% EtOAc in Hex) to yield 109 mg of Compound 137 as a white solid.

Example 38

Preparation of Compound 138

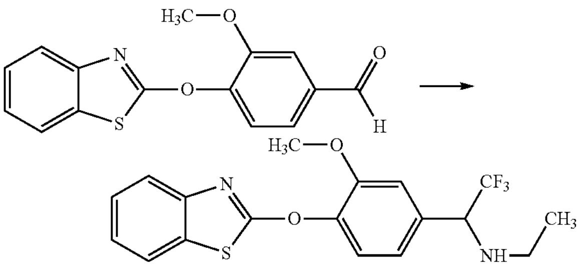

(138)

To a stirred mixture of 4-(1,3-benzothiazol-2-yloxy)-3-methoxybenzaldehyde (250 mg, 0.876 mmol, prepared as in Example 37) and anhydrous $Na_2SO_4$ (1 g) at room temperature under argon was added ethylamine (2.0 M solution in THF, 2.0 mL, 4.0 mmol). The reaction mixture was stirred for 18 h and then was filtered to remove the solid. The solvent was removed under reduced pressure to yield a yellowish oil. To the oil and $KHF_2$ (51 mg, 0.653 mmol) in MeCN (3 mL) and DMF (203 μL, 2.62 mmol) at 0° C. under argon was added TFA (84 μL, 1.10 mmol). The mixture was stirred for 5 minutes, and $CF_3TMS$ (194 μL, 1.31 mmol) was added. The cooling bath was removed, and the reaction mixture was stirred for 18 h. The mixture was diluted with saturated aq. $Na_2CO_3$ (40 mL) and extracted with EtOAc (40 mL). The organic layer was washed with water (2×25 mL), dried over anhydrous $MgSO_4$, filtered, and the solvent was removed under reduced pressure. The residue was purified by flash chromatography (15% EtOAc in Hex) to yield 61 mg of Compound 138 as an off-white solid.

Example 39

Preparation of Compound 139

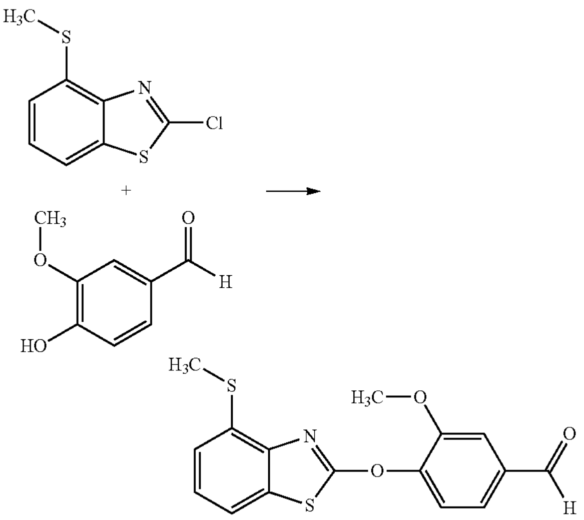

A mixture of vanillin (150 mg, 0.985 mmol), $K_2CO_3$ (204 mg, 1.48 mmol) and 2-chloro-4-(methylthio)benzothiazole (266 mg, 1.23 mmol) in DMF (3 mL) was stirred in a sealed tube at 100° C. for 18 h, and then was allowed to cool to room temperature, diluted with EtOAc (35 mL) and washed with 1 M NaOH (2x25 mL) and water (25 mL). The organic layer was dried over anhydrous $MgSO_4$, filtered, and the solvent was removed under reduced pressure. The residue was purified by flash chromatography (20% EtOAc in Hex) to yield 256 mg of 3-methoxy-4-{[4-(methylsulfanyl)-1,3-benzothiazol-2-yl]oxy}benzaldehyde as a white solid.

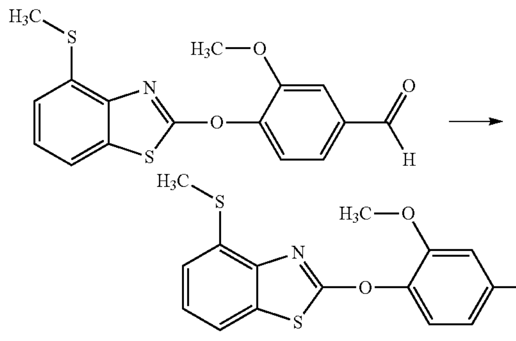

(139)

To a stirred mixture of 3-methoxy-4-{[4-(methylsulfanyl)-1,3-benzothiazol-2-yl]oxy}benzaldehyde (256 mg, 0.772 mmol) and $K_2CO_3$ (11 mg, 0.080 mmol) in DMF (3 mL) under argon was added $CF_3$TMS (171 μL, 1.16 mmol). The reaction mixture was stirred at room temperature for 42 h, and then was diluted with EtOAc (35 mL) and washed with water (2x25 mL). The organic layer was dried over anhydrous $MgSO_4$, filtered, and the solvent was removed under reduced pressure. The residue was taken up in MeOH (3 mL) and stirred with conc. HCl (0.3 mL) for 1 h. The mixture was diluted with EtOAc (35 mL) and washed with water (2x25 mL). The organic layer was dried over anhydrous $MgSO_4$, filtered, and the solvent was removed under reduced pressure. The residue was purified by flash chromatography (20% EtOAc in Hex) to yield 192 mg of Compound 139 as a yellowish solid.

Example 40

Preparation of Compound 140

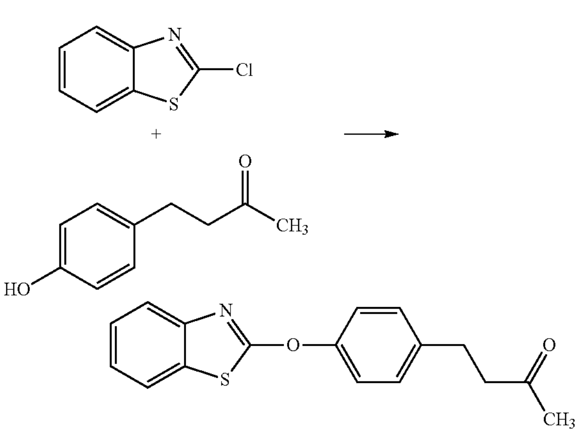

To a solution of 4-(4-hydroxyphenyl)-2-butanone (1.5 g, 9.1 mmol) in DMF (8 mL) under argon was added 2-chlorobenzothiazole (1.34 mL, 10.3 mmol) and $K_2CO_3$ (1.27 g, 9.2 mmol). The reaction mixture was stirred at 140° C. for 20 hours. The reaction mixture was allowed to cool to room temperature, and then was diluted with water (20 mL) and extracted with EtOAc (3x20 mL). The organic layer was washed with 5% aqueous NaOH (2x20 mL) and brine (2x2 mL). The organic layer was dried ($MgSO_4$), filtered, and the solvent was removed under reduced pressure. Flash column chromatography on silica gel (30% EtOAc in Hex) yielded 1.72 g of 4-[4-(1,3-benzothiazol-2-yloxy)phenyl]butan-2-one.

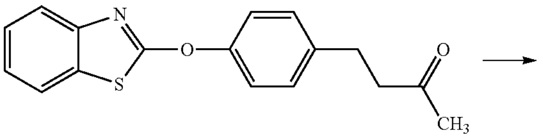

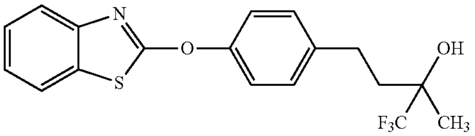

(140)

Following General Procedure for $CF_3$TMS Additions as disclosed herein, Compound 140 was prepared from 4-[4-(1,3-benzothiazol-2-yloxy)phenyl]butan-2-one (135 mg, 0.45 mmol), $CF_3$TMS (200 μL, 1.35 mmol), $K_2CO_3$ (20 mg, 0.14 mmol) and DMF (3 mL). Flash column chromatography of the crude mixture on silica gel (30% EtOAc in Hex) yielded 137 mg of Compound 140 as an oil.

Example 41

Preparation of Compound 141

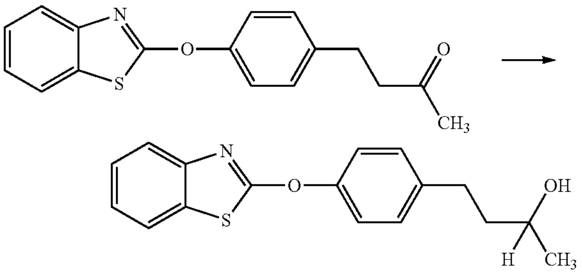

(141)

Following General Procedure for Reductions as disclosed herein, Compound 141 was prepared from 4-[4-(1,3-benzothiazol-2-yloxy)phenyl]butan-2-one (113 mg, 0.38 mmol, prepared as in Example 40), $NaBH_4$ (25 mg, 0.59 mmol), $CeCl_3x7H_2O$ (125 mg, 0.34 mmol), and MeOH (3 mL). Flash column chromatography of the crude mixture on silica gel (50% EtOAc in Hex) yielded 100 mg of Compound 141 as a colourless oil.

Example 42

Preparation of Compound 142

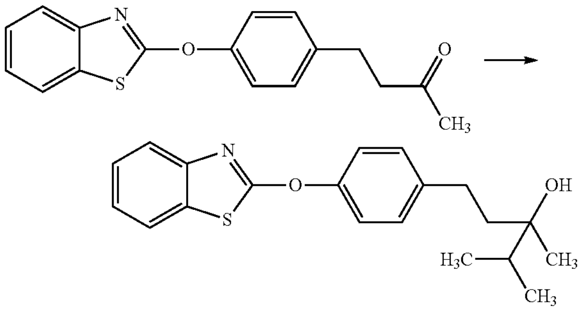

(142)

Following General Procedure for Grignard Additions, Compound 142 was prepared from 4-[4-(1,3-benzothiazol-2-yloxy)phenyl]butan-2-one (128 mg, 0.43 mmol, prepared as in Example 40), THF (2.0 mL), and isopropyl magnesium bromide (0.45 mL, 2 M in THF). Flash column chromatography of the crude mixture on silica gel (30% EtOAc in Hex) yielded 52 mg of Compound 142 as an oil.

Example 43

Preparation of Compound 143

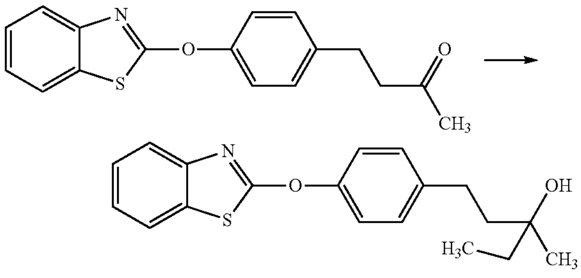

(143)

Following General Procedure for Grignard Additions, Compound 143 was prepared from 4-[4-(1,3-benzothiazol-2-yloxy)phenyl]butan-2-one (195 mg, 0.66 mmol, prepared as in Example 40), THF (2.0 mL), and ethyl magnesium bromide (0.32 mL, 3 M in $Et_2O$). Flash column chromatography of the crude mixture on silica gel (30% EtOAc in Hex) yielded 168 mg of Compound 143.

Example 44

Preparation of Compound 144

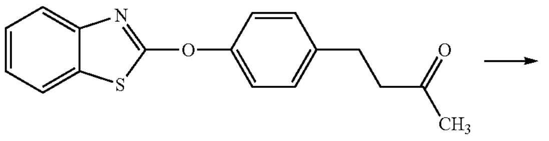

-continued

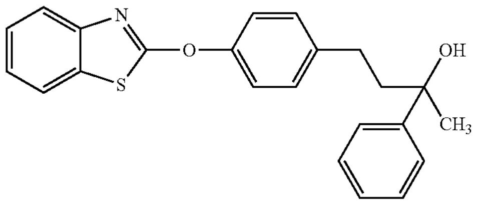

(144)

Following General Procedure for Grignard Additions, Compound 144 was prepared from 4-[4-(1,3-benzothiazol-2-yloxy)phenyl]butan-2-one (195 mg, 0.66 mmol, prepared as in Example 40), THF (2.0 mL), and phenyl magnesium bromide (0.32 mL, 3 M in $Et_2O$). Flash column chromatography of the crude mixture on silica gel (30% EtOAc in Hex) yielded 222 mg of Compound 144 as an oil.

Example 45

Preparation of Compound 145

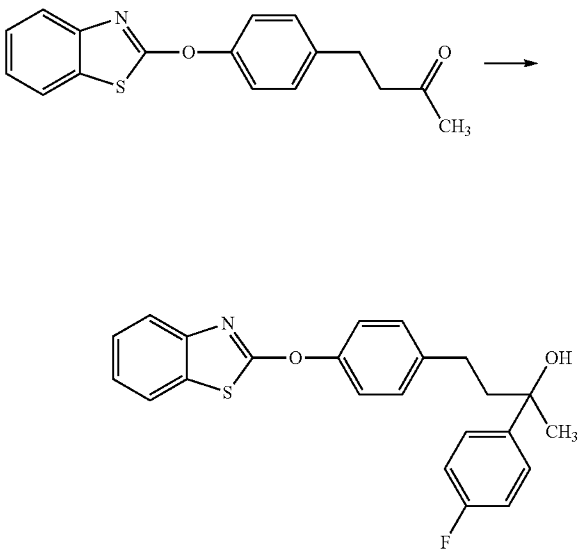

(145)

Following General Procedure for Grignard Additions, Compound 145 was prepared from 4-[4-(1,3-benzothiazol-2-yloxy)phenyl]butan-2-one (220 mg, 0.74 mmol, prepared as in Example 40), THF (9.0 mL), and 4-fluorophenyl magnesium bromide (0.8 mmol). 4-Fluorophenyl magnesium bromide was prepared following General Procedure for the Preparation of Grignard Reagents using 1-bromo-4-fluorobenzene (0.8 mmol) and magnesium (2.2 mmol). Flash column chromatography of the crude mixture on silica gel (30% EtOAc in Hex) yielded 323 mg of Compound 145 as a colourless oil.

Example 46

Preparation of Compound 146

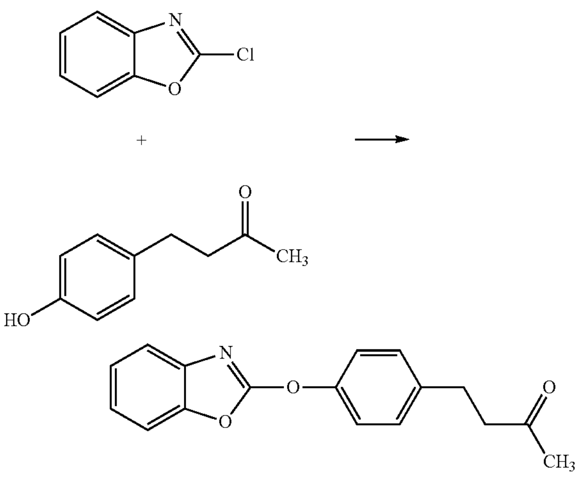

To a solution of 4-(4-hydroxyphenyl)-2-butanone (518 mg, 3.2 mmol) in DMF (8 mL) under argon was added 2-chlorobenzoxazole (300 μL, 2.6 mmol) and $K_2CO_3$ (496 mg, 3.6 mmol). The reaction mixture was stirred at 130° C. for 15 hours. The reaction mixture was diluted with water (20 mL), brine (20 mL), and EtOAc (30 mL). The layers were separated, the aqueous layer was extracted with EtOAc (20 mL) and the combined organic layers were washed with brine (20 mL). The organic layer was dried ($MgSO_4$), filtered, and the solvent was removed under reduced pressure. Flash column chromatography on silica gel (30% EtOAc in Hex) yielded 605 mg of 4-[4-(1,3-benzoxazol-2-yloxy)phenyl]butan-2-one as a colourless oil.

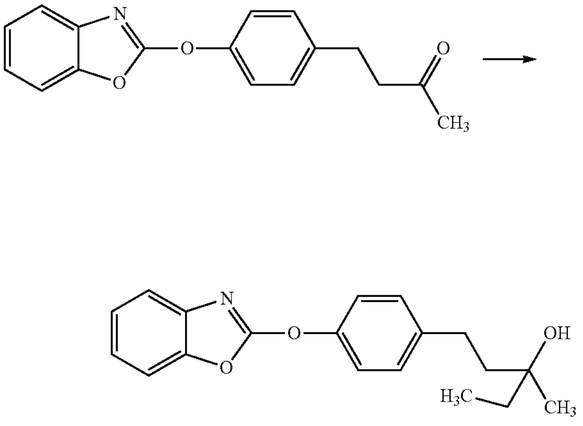

(146)

Following General Procedure for Grignard Additions, Compound 146 was prepared from 4-[4-(1,3-benzoxazol-2-yloxy)phenyl]butan-2-one (101 mg, 0.36 mmol), THF (3.0 mL), and ethyl magnesium bromide (0.150 mL, 3 M in $Et_2O$). Flash column chromatography of the crude mixture on silica gel (30% EtOAc in Hex) yielded 80 mg of Compound 146.

Example 47

Preparation of Compound 147

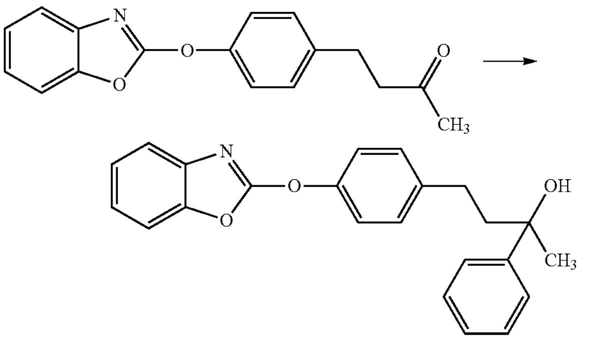

(147)

Following General Procedure for Grignard Additions, Compound 147 was prepared from 4-[4-(1,3-benzoxazol-2-yloxy)phenyl]butan-2-one (101 mg, 0.36 mmol, prepared as in Example 46), THF (3.0 mL), and phenyl magnesium bromide (0.2 mL, 3 M in $Et_2O$). Flash column chromatography of the crude mixture on silica gel (30% EtOAc in Hex) yielded 96 mg of Compound 83.

Example 48

Preparation of Compound 148

To a mixture of 4-hydroxybenzaldehyde (2.0 g, 16.4 mmol) in MeOH (17 mL)/$H_2O$ (2.5 mL) 2-butanone (10 mL, 111 mmol) was added, followed by KOH (3.0 g, 45.4 mmol). The mixture was stirred at room temperature for 3 days. The reaction was quenched with 10% aq. HCl (15 mL) and extracted with EtOAc (40 mL). The organic layer was washed with water (2×30 mL), then brine (1×30 mL), dried over anhydrous $MgSO_4$, filtered, and the solvent was removed under reduced pressure. The residue was triturated with ether/Hex (40 mL, 1:1) to yield 1.29 g of 1-(4-hydroxyphenyl)pent-1-en-3-one as a solid.

To a stirred solution of 1-(4-hydroxyphenyl)pent-1-en-3-one (1.25 g, 7.17 mmol) in EtOAc (12 mL) 10% Pd/C (125 mg) was added. The reaction mixture was stirred under hydrogen for 1 h. The mixture was filtered and the solvent was removed under reduced pressure. The residue was purified by flash chromatography (20% to 40% EtOAc in Hex) to yield 650 mg of 1-(4-hydroxyphenyl)pentan-3-one.

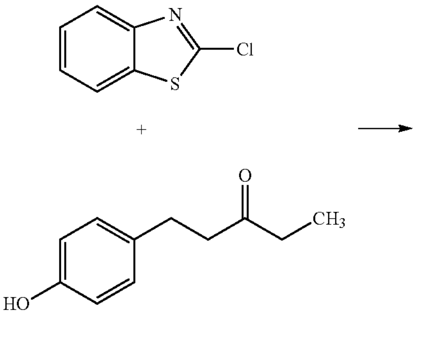

-continued

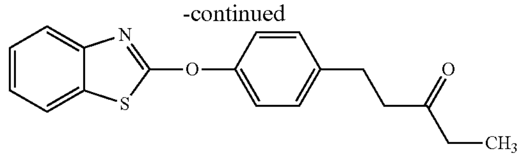

(148)

A mixture of 1-(4-hydroxyphenyl)pentan-3-one (200 mg, 1.12 mmol), $K_2CO_3$ (154 mg, 1.11 mmol), and 2-chlorobenzothiazole (0.160 mL, 1.23 mmol) in DMF (3 mL) was stirred in a sealed tube at 120° C. for 18 h. The mixture was allowed to cool to room temperature, diluted with EtOAc (10 mL), washed with brine (3×10 mL), dried over anhydrous $MgSO_4$, filtered, and the solvent was removed under reduced pressure. The residue was purified by flash chromatography (25% EtOAc in Hex) to yield 303 mg of Compound 148 as an oil.

Example 49

Preparation of Compound 149

To a stirred solution of 3-chloro-4-hydroxybenzaldehyde (0.250 g, 1.60 mmol) in MeOH (2 mL)/$H_2O$ (0.32 mL) 2-butanone (0.60 mL, 6.66 mmol) was added, followed by KOH (0.422 g, 6.39 mmol). The mixture was stirred at 75° C. for 2 hours. The reaction was allowed to cool to room temperature. EtOAc (35 mL) and 10% aq HCl (25 mL) were added. The layers were separated and the organic layer was washed with water (25 mL), dried over anhydrous $MgSO_4$, filtered, and the solvent was removed under reduced pressure. The residue was purified by flash chromatography (10-20% EtOAc in Hex) to yield 0.290 g of 1-(3-chloro-4-hydroxyphenyl)pent-1-en-3-one as a yellow oil.

To a stirred solution of 1-(3-chloro-4-hydroxyphenyl)pent-1-en-3-one (0.690 g, 1.38 mmol) in EtOAc (15 mL) 10% Pd/C (29 mg) was added. The reaction mixture was stirred under hydrogen for 1 h. The reaction mixture was filtered. The solvent was removed under reduced pressure, and the residue was purified by flash chromatography (20% EtOAc in Hex) to yield 0.090 g of 1-(3-chloro-4-hydroxyphenyl)pentan-3-one as a yellow oil.

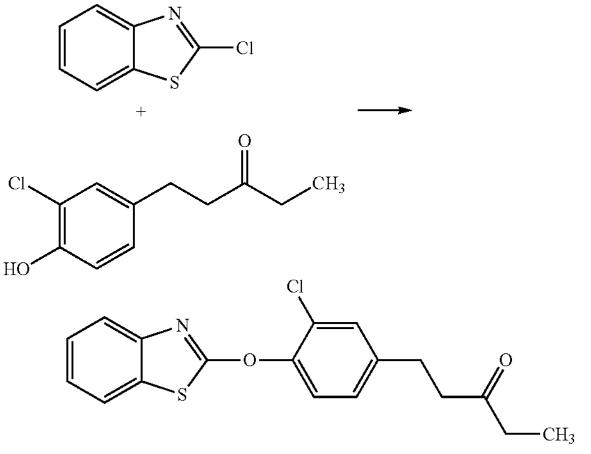

(149)

A mixture of 1-(3-chloro-4-hydroxyphenyl)pentan-3-one (199 mg, 0.936 mmol), $K_2CO_3$ (194 mg, 1.40 mmol), and 2-chlorobenzothiazole (0.150 mL, 1.15 mmol) in DMF (4 mL) was stirred in a sealed tube at 100° C. for 18 h. The mixture was allowed to cool to room temperature, diluted with EtOAc (35 mL), washed with water (3×25 mL), dried over anhydrous $MgSO_4$, filtered, and the solvent was removed under reduced pressure. The residue was purified by flash chromatography (20% EtOAc in Hex) to yield 165 mg of Compound 149 as a yellow oil Example 50

Preparation of Compound 150

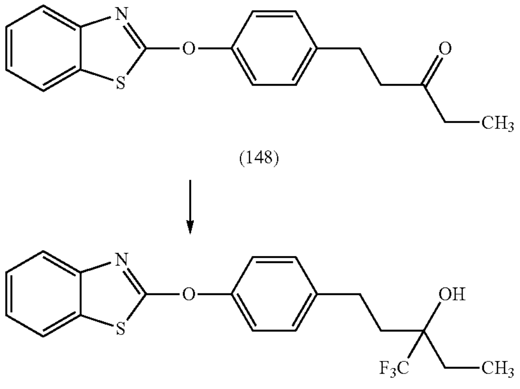

(148)

(150)

A mixture of Compound 148 (100 mg, 0.321 mmol, prepared as in Example 48), $K_2CO_3$ (15 mg, 0.108 mmol) and $CF_3TMS$ (0.100 mL, 0.677 mmol) in DMF (2 mL) was stirred at room temperature under argon for 18 h. The mixture was diluted with EtOAc (415 mL) and washed with brine (2×15 mL). The organic layer was concentrated under reduced pressure. The residue was taken-up in MeOH (5 mL) and stirred with conc. HCl (0.25 mL) for 1 h. The mixture was diluted with EtOAc (20 mL) and washed with brine (2×20 mL). The organic layer was dried over anhydrous $MgSO_4$, filtered, and the solvent was removed under reduced pressure. The residue was purified by flash chromatography (30% EtOAc in Hex) to yield 111 mg of Compound 150 as an oil.

Example 51

Preparation of Compound 151

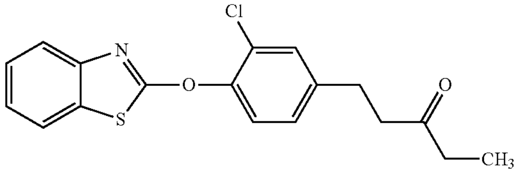

(149)

-continued

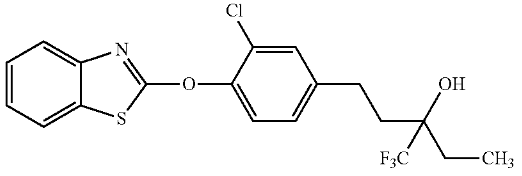

(151)

A mixture of Compound 149 (153 mg, 0.442 mmol; prepared as in Example 49), $K_2CO_3$ (6 mg, 0.043 mmol) and $CF_3TMS$ (0.091 mL, 0.616 mmol) in DMF (2 mL) was stirred at room temperature under argon for 18 h. The mixture was diluted with EtOAc (35 mL) and washed with water (2×25 mL). The organic layer was dried over anhydrous $MgSO_4$, filtered, and the solvent was removed under reduced pressure. The residue was taken-up in MeOH (4.5 mL) and stirred with conc. HCl (0.07 mL) for 1 h. The mixture was diluted with EtOAc (35 mL) and washed with water (2×25 mL). The organic layer was dried over anhydrous $MgSO_4$, filtered, and the solvent was removed under reduced pressure. The residue was isolated as a colourless oil that solidified upon standing at room temperature to yield 0.093 g of Compound 151 as a white solid.

Example 52

Preparation of Compound 152

A mixture of 3-fluoro-4-hydroxybenzaldehyde (250 mg, 1.78 mmol), benzyl bromide (320 μL, 2.69 mmol) and $K_2CO_3$ (372 mg, 2.69 mmol) in acetone (5 mL) was stirred at reflux for 16 h, and then was allowed to cool to room temperature, filtered and washed with acetone. The filtrate was concentrated under reduced pressure, and the residue was purified by flash chromatography (20% EtOAc in Hex) to yield 212 mg of 4-(benzyloxy)-3-fluorobenzaldehyde as a white solid.

A mixture of 4-(benzyloxy)-3-fluorobenzaldehyde (212 mg, 0.921 mmol), 2-butanone (80 μL, 0.888 mmol) and 85% KOH (182 mg, 2.76 mmol) in MeOH (3 mL) and water (0.6 mL) was stirred in a sealed tube at 75° C. for 1 h. The reaction was allowed to cool to room temperature and filtered. The solid was washed with water, MeOH, and dried to yield 146 mg of 1-[4-(benzyloxy)-3-fluorophenyl]pent-1-en-3-one as a white solid.

1-[4-(benzyloxy)-3-fluorophenyl]pent-1-en-3-one (146 mg, 0.514 mmol) and 10% Pd on C (15 mg) were combined in EtOAc (14 mL) under argon. AcOH (14 drops) was added. The flask was evacuated and back-filled with hydrogen (balloon). The reaction mixture was stirred for 20 h, and then was filtered and washed with EtOAc. The filtrate was concentrated under reduced pressure to yield 96 mg of 1-[4-(benzyloxy)-3-fluorophenyl]pentan-3-one as a white solid.

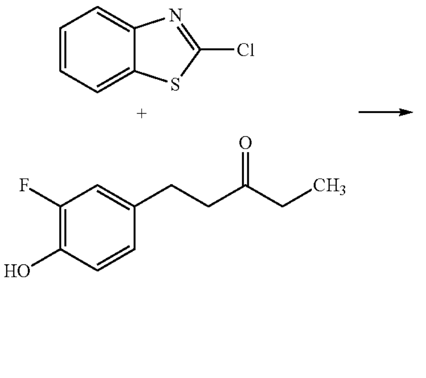

-continued

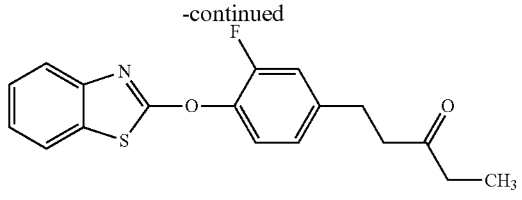

(152)

A mixture of 1-[4-(benzyloxy)-3-fluorophenyl]pentan-3-one (96 mg, 0.489 mmol), $K_2CO_3$ (101 mg, 0.731 mmol), and 2-chlorobenzothiazole (100 □L, 0.768 mmol) in DMF (2 mL) was stirred in a sealed tube at 100° C. for 16 h. The mixture was allowed to cool to room temperature, diluted with EtOAc (50 mL) and washed with water (3×25 mL). The organic layer was dried over anhydrous $MgSO_4$, filtered, and the solvent was removed under reduced pressure. The residue was purified by flash chromatography (20% EtOAc in Hex) to yield 102 mg of Compound 152 as a colourless oil.

Example 53

Preparation of Compound 153

A mixture of 4-hydroxy-3-(trifluoromethyl)benzaldehyde (250 mg, 1.31 mmol), benzyl bromide (230 μL, 1.94 mmol) and $K_2CO_3$ (272 mg, 1.97 mmol) in acetone (5 mL) was stirred at reflux for 16 h, and then was allowed to cool to room temperature, filtered and washed with acetone. The filtrate was concentrated under reduced pressure, and the residue was purified by flash chromatography (20% EtOAc in Hex) to yield 161 mg of 4-(benzyloxy)-3-(trifluoromethyl)benzaldehyde as a white solid.

A mixture of 4-(benzyloxy)-3-(trifluoromethyl)benzaldehyde (161 mg, 0.574 mmol), 2-butanone (50 μL, 0.555 mmol) and 85% KOH (114 mg, 1.73 mmol) in MeOH (2 mL) and water (0.4 mL) was stirred in a sealed tube at 75° C. for 1 h. The reaction was allowed to cool to room temperature, diluted with EtOAc (35 mL) and washed with water (2×25 mL). The organic layer was dried over anhydrous $MgSO_4$, filtered, and the solvent was removed under reduced pressure. The residue was purified by flash chromatography (10% EtOAc in Hex) to yield 38 mg of 1-[4-(benzyloxy)-3-(trifluoromethyl)phenyl]pent-1-en-3-one as a white solid.

1-[4-(benzyloxy)-3-(trifluoromethyl)phenyl]pent-1-en-3-one (38 mg, 0.114 mmol) and 10% Pd on C (4 mg) were combined in EtOAc (3 mL) under argon. AcOH (3 drops) was added. The flask was evacuated and back-filled with hydrogen (balloon). The reaction mixture was stirred for 32 h, and then was filtered and washed with EtOAc. The filtrate was concentrated under reduced pressure to yield 22 mg of 1-[4-(benzyloxy)-3-(trifluoromethyl)phenyl]pentan-3-one as a colourless oil.

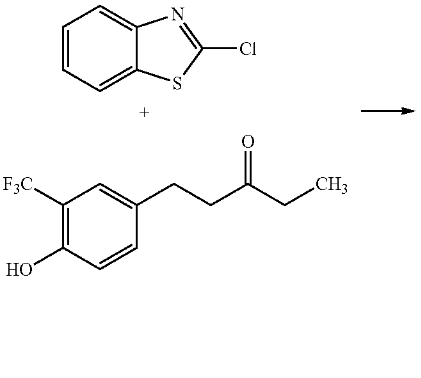

-continued

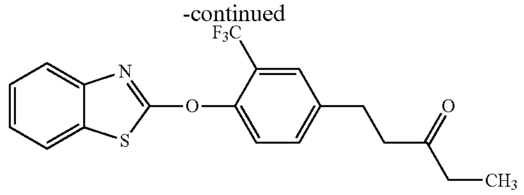

(153)

A mixture of 1-[4-(benzyloxy)-3-(trifluoromethyl)phenyl]pentan-3-one (22 mg, 0.089 mmol), $K_2CO_3$ (20 mg, 0.145 mmol), and 2-chlorobenzothiazole (20 □L, 0.154 mmol) in DMF (1 mL) was stirred in a sealed tube at 100° C. for 16 h. The mixture was allowed to cool to room temperature, diluted with EtOAc (50 mL) and washed with water (3x25 mL). The organic layer was dried over anhydrous $MgSO_4$, filtered, and the solvent was removed under reduced pressure. The residue was purified by flash chromatography (20% EtOAc in Hex) to yield 22 mg of Compound 153 as a colourless oil.

Example 54

Preparation of Compound 154

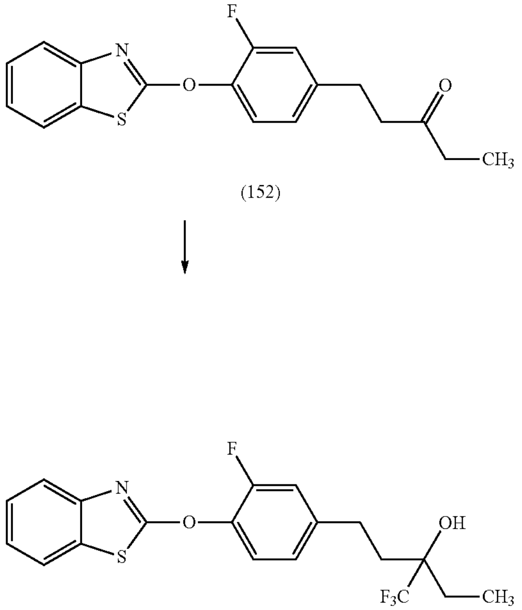

(152)

(154)

To a stirred mixture of Compound 152 (94 mg, 0.285 mmol) and $K_2CO_3$ (4 mg, 0.029 mmol) in DMF (2 mL) under argon was added $CF_3TMS$ (60 μL, 0.406 mmol). The reaction mixture was stirred at room temperature for 18 h, and then was diluted with EtOAc (35 mL) and washed with water (2x25 mL). The organic layer was dried over anhydrous $MgSO_4$, filtered, and the solvent was removed under reduced pressure. The residue was taken up in MeOH (3 mL) and stirred with conc. HCl (0.1 mL) for 1 h. The mixture was concentrated under reduced pressure, and the residue was purified by flash chromatography (20% EtOAc in Hex) to yield 86 mg of Compound 154 as a colourless gum.

Example 55

Preparation of Compound 155

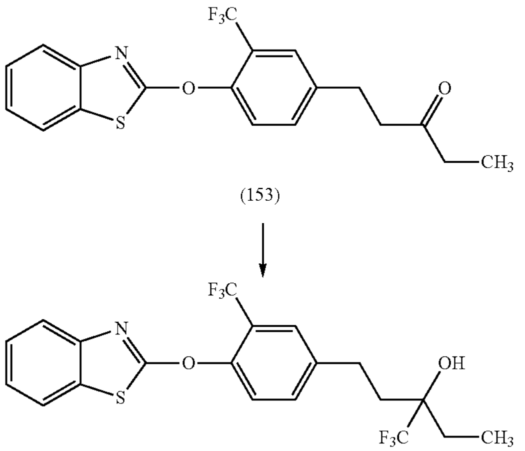

(153)

(155)

To a stirred mixture of Compound 153 (22 mg, 0.058 mmol) and $K_2CO_3$ (1 mg, 0.007 mmol) in DMF (1 mL) under argon was added $CF_3TMS$ (12 μL, 0.081 mmol). The reaction mixture was stirred at room temperature for 18 h, and then was diluted with EtOAc (35 mL) and washed with water (2x25 mL). The organic layer was dried over anhydrous $MgSO_4$, filtered, and the solvent was removed under reduced pressure. The residue was taken up in MeOH (3 mL) and stirred with conc. HCl (0.1 mL) for 1 h. The mixture was concentrated under reduced pressure, and the residue was purified by flash chromatography (20% EtOAc in Hex) to yield 18 mg of Compound 155 as a colourless oil.

Example 56

Preparation of Compound 156

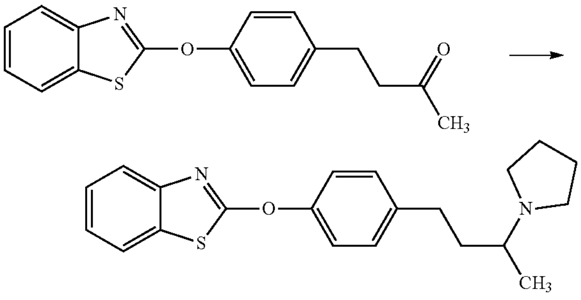

(156)

To a stirred solution of 4-[4-(1,3-benzothiazol-2-yloxy)phenyl]butan-2-one prepared as in Example 40 (150 mg, 0.504 mmol) in THF (3 mL) at room temperature under argon was added $Ti(O^iPr)_4$ (200 μL, 0.676 mmol), followed by pyrrolidine (100 μL, 1.22 mmol). The reaction mixture was stirred at reflux for 18 h, and then was allowed to cool to room temperature. $NaBH_4$ (28 mg, 0.740 mmol) was added, the reaction mixture was stirred for 1 h, and then was quenched with water (25 mL) and extracted with EtOAc (35 mL). The organic layer was dried over anhydrous $MgSO_4$, filtered, and the solvent was removed under reduced pressure. The residue was purified by flash chromatography (EtOAc/MeOH/$Et_3N$, 9:1:0.1) to yield 60 mg of Compound 156 as a yellow oil.

Example 57

Preparation of Compound 157

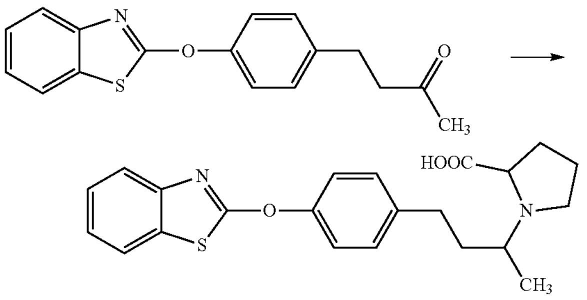

(157)

To a stirred solution of 4-[4-(1,3-benzothiazol-2-yloxy)phenyl]butan-2-one prepared as in Example 40 (150 mg, 0.504 mmol) in DCE (3 mL) at room temperature under argon was added 4A molecular sieves powder (150 mg), L-proline (75 mg, 0.651 mmol), AcOH (100 μL, 1.75 mmol), followed by $NaBH(OAc)_3$ (214 mg, 1.01 mmol). The reaction mixture was stirred for 18 h and then was quenched with water (25 mL) and extracted with EtOAc (35 mL) and $CH_2Cl_2$ (2x35 mL). The combined organic layer was dried over anhydrous $MgSO_4$, filtered, and the solvent was removed under reduced pressure. The residue was purified by flash chromatography (10% MeOH in $CH_2Cl_2$+1% AcOH) to yield 80 mg of Compound 157 as a wax.

Example 58

Preparation of Compound 158

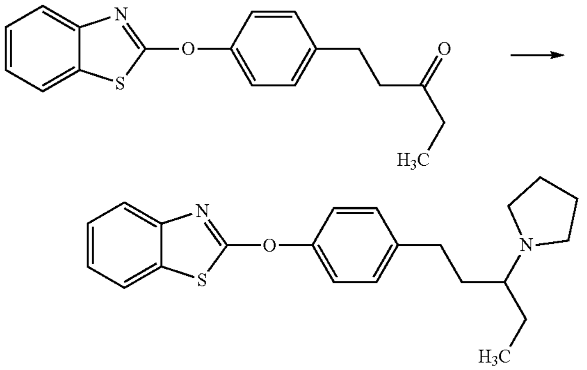

(158)

To a stirred solution of Compound 148 prepared as in Example 48 (150 mg, 0.482 mmol) in DCE (3 mL) at room temperature under argon was added 4A molecular sieves powder (150 mg), pyrrolidine (50 μL, 0.609 mmol), AcOH (55 μL, 0.961 mmol), followed by $NaBH(OAc)_3$ (204 mg, 0.962 mmol). The reaction mixture was stirred for 18 h, and then was quenched with water (25 mL) and extracted with $CH_2Cl_2$ (3x35 mL). The combined organic layer was dried over anhydrous $MgSO_4$, filtered, and the solvent was removed under reduced pressure. The residue was purified by flash chromatography (EtOAc/MeOH/$Et_3N$, 9:1:0.1) to yield 160 mg of Compound 158 as colourless wax.

Example 59

Preparation of Compound 159

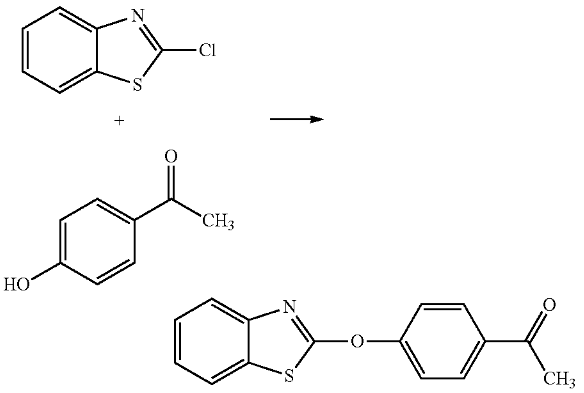

(159)

A mixture of 4-hydroxyacetophenone (109, 500 mg, 3.67 mmol), $K_2CO_3$ (435 mg, 3.15 mmol), and 2-chlorobenzothiazole (525 μL, 4.04 mmol) in DMF (5 mL) was stirred at 140° C. for 18 h. The mixture was allowed to cool to room temperature, diluted with $H_2O$ (10 mL) and EtOAc (30 mL), separated, and the organic layer was washed with 5% NaOH (2x20 mL), then brine (3x30 mL), dried over anhydrous $MgSO_4$, filtered, and the solvent was removed under reduced pressure. The residue was purified by flash chromatography (30% EtOAc in Hex) to yield 979 mg of Compound 159 as a yellow solid.

Example 60

Preparation of Compound 160

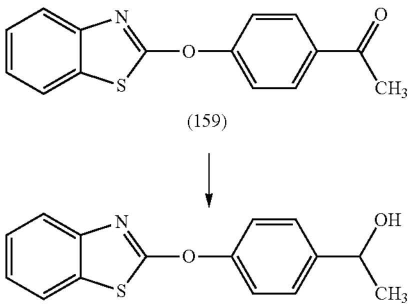

(159)

(160)

To a stirred solution of Compound 159 (100 mg, 0.371 mmol, prepared as in Example 59) in MeOH (2 mL) at room temperature under argon was added $NaBH_4$ (21 mg, 0.555 mmol). The reaction mixture was stirred for 2 h and then was quenched with water (25 mL) and extracted with $CH_2Cl_2$ (3x25 mL). The combined organic layer was dried over anhydrous $MgSO_4$, filtered, and the solvent was removed under reduced pressure. The residue was purified by flash chromatography (30% EtOAc in Hex) to yield 40 mg of Compound 160 as a white solid.

Example 61

Preparation of Compound 161

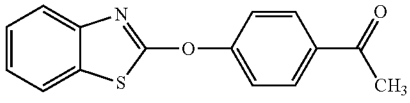

(159)

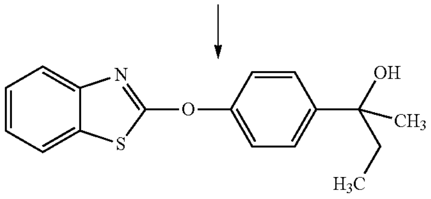

(161)

Following the general procedure for Grignard Additions as disclosed herein, Compound 161 was prepared from Compound 159 (233 mg, 0.865 mmol, prepared as in Example 59), THF (4.0 mL), and ethyl magnesium bromide (0.57 mL, 3 M in $Et_2O$). Flash column chromatography of the crude mixture on silica gel (30% EtOAc in Hex) yielded 169 mg of Compound 161 as a yellow oil.

Example 62

Preparation of Compound 162

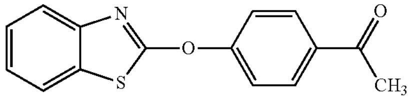

(159)

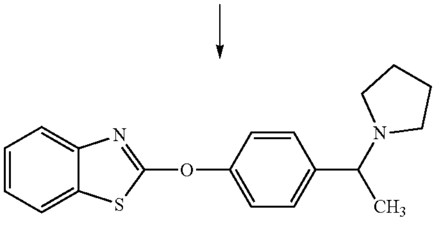

(162)

To a stirred solution of Compound 159 (200 mg, 0.743 mmol, prepared as in Example 91) in THF (8 mL) at room temperature under argon was added $Ti(OiPr)_4$ (265 μL, 0.895 mmol), followed by pyrrolidine (85 μL, 1.04 mmol). The reaction mixture was stirred at reflux for 16 h, and then was allowed to cool to room temperature. $NaBH_4$ (42 mg, 1.11 mmol) was added, the reaction mixture was stirred for 1.5 h, and then was quenched with water (25 mL) and extracted with EtOAc (2×35 mL). The organic layer was washed with water (35 mL), dried over anhydrous $MgSO_4$, filtered, and the solvent was removed under reduced pressure. The residue was purified by flash chromatography ($EtOAc/MeOH/Et_3N$, 9:1:0.1) to yield 88 mg of Compound 162 as a yellow oil.

Example 63

Preparation of Compound 163

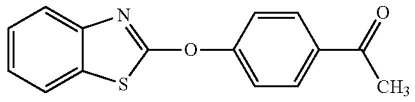

(159)

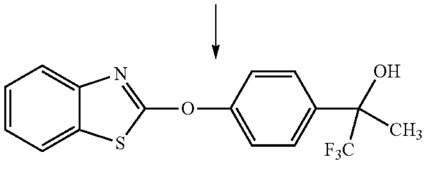

(163)

To a stirred mixture of Compound 159 (125 mg, 0.464 mmol, prepared as in Example 59) and $K_2CO_3$ (6 mg, 0.043 mmol) in DMF (2 mL) under argon was added $CF_3TMS$ (90 μL, 0.610 mmol). The reaction mixture was stirred at room temperature for 18 h, and then was diluted with EtOAc (35 mL) and washed with water (2×25 mL). The organic layer was dried over anhydrous $MgSO_4$, filtered, and the solvent was removed under reduced pressure. The residue was taken-up in MeOH (2 mL) and stirred with conc. HCl (0.1 mL) for 1 h. The solvent was removed under reduced pressure, and the residue was purified by flash chromatography (10% EtOAc in Hex) to yield 26 mg of Compound 163 as an off-white solid.

Example 64

Preparation of Compound 164

A mixture of 4-hydroxybenzaldehyde (84, 200 mg, 1.64 mmol), $K_2CO_3$ (340 mg, 2.46 mmol), and 2-chlorobenzothiazole (260 μL, 2.00 mmol) in DMF (3 mL) was stirred in a sealed tube at 100° C. for 16 h. The mixture was allowed to cool to room temperature, diluted with EtOAc (35 mL), washed with water (3×25 mL), dried over anhydrous $MgSO_4$, filtered, and the solvent was removed under reduced pressure. The residue was purified by flash chromatography (20% EtOAc in Hex) to yield 354 mg of 4-(1,3-benzothiazol-2-yloxy)benzaldehyde as a white solid.

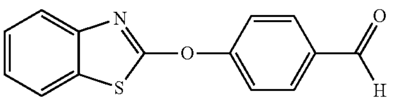

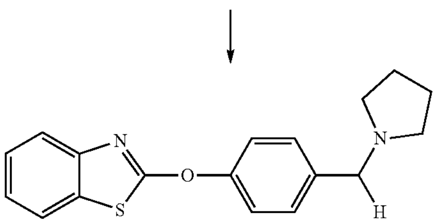

(164)

To a stirred mixture of 4-(1,3-benzothiazol-2-yloxy)benzaldehyde (150 mg, 0.588 mmol) in DCE (3 mL) at room temperature under argon was added pyrrolidine (60 μL, 0.730 mmol), followed by $NaBH(OAc)_3$ (190 mg, 0.896 mmol). The reaction mixture was stirred for 18 h, and then was quenched with water (25 mL) and extracted with $CH_2Cl_2$ (3x35 mL). The combined organic layer was dried over anhydrous $MgSO_4$, filtered, and the solvent was removed under reduced pressure. The residue was purified by flash chromatography (EtOAc/MeOH/$Et_3N$, 9:1:0.1) to yield 153 mg of Compound 164 as a colourless oil.

Example 65

Preparation of Compound 165

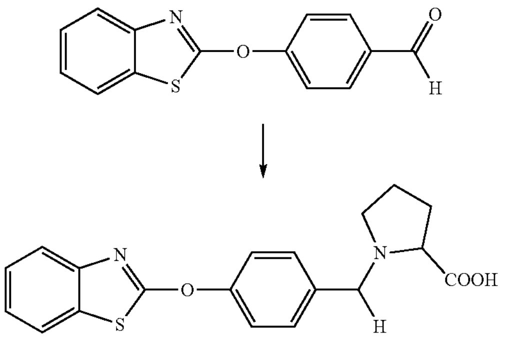

(165)

Following the procedure previously described for making Compound 157, and making non-critical variations to use L-proline (81 mg, 0.704 mmol), 4-(1,3-benzothiazol-2-yloxy)benzaldehyde (150 mg, 0.588 mmol) in DCE (3 mL) at room temperature under argon and $NaBH(OAc)_3$ (190 mg, 0.896 mmol) and purification using 10% MeOH in $CH_2Cl_2$+1.5% AcOH as eluent yielded 132 mg of Compound 165 as a white solid.

Example 66

Preparation of Compound 166

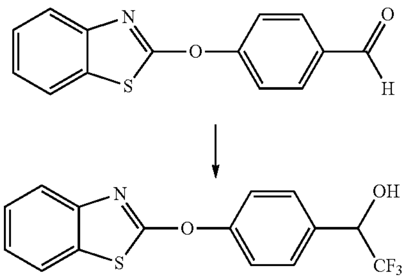

(166)

To a stirred mixture of 4-(1,3-benzothiazol-2-yloxy)benzaldehyde (125 mg, 0.490 mmol) and $K_2CO_3$ (7 mg, 0.051 mmol) in DMF (2 mL) under argon was added $CF_3TMS$ (94 μL, 0.655 mmol). The reaction mixture was stirred at room temperature for 18 h, and then was diluted with EtOAc (35 mL) and washed with water (2x25 mL). The organic layer was dried over anhydrous $MgSO_4$, filtered, and the solvent was removed under reduced pressure. The residue was taken-up in MeOH (2 mL) and stirred with conc. HCl (0.1 mL) for 1 h. The solvent was removed under reduced pressure, and the residue was purified by flash chromatography (20% EtOAc in Hex) to yield 94 mg of Compound 166 as white solid.

Example 67

Preparation of Compound 167

A mixture of 3-chloro-4-hydroxybenzothiazole (250 mg, 1.60 mmol), $K_2CO_3$ (332 mg, 2.40 mmol), and 2-chlorobenzothiazole (260 μL, 2.00 mmol) in DMF (3 mL) was stirred in a sealed tube at 100° C. for 18 h. The mixture was allowed to cool to room temperature, diluted with EtOAc (35 mL), washed with water (3x25 mL), dried over anhydrous $MgSO_4$, filtered, and the solvent was removed under reduced pressure. The residue was purified by flash chromatography (20% EtOAc in Hex) to yield 187 mg of 4-(1,3-benzothiazol-2-yloxy)-3-chlorobenzaldehyde as a white solid.

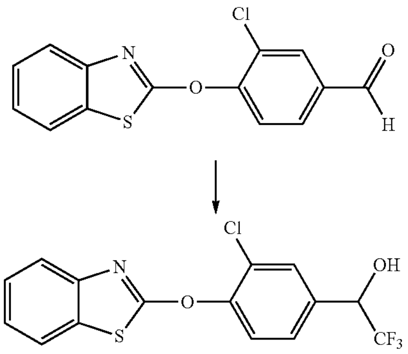

(167)

To a stirred mixture of 4-(1,3-benzothiazol-2-yloxy)-3-chlorobenzaldehyde (187 mg, 0.645 mmol) and $K_2CO_3$ (9 mg, 0.065 mmol) in DMF (2 mL) under argon was added $CF_3TMS$ (143 μL, 0.968 mmol). The reaction mixture was stirred at room temperature for 4 days, and then was diluted with EtOAc (40 mL) and washed with water (2x25 mL). The organic layer was dried over anhydrous $MgSO_4$, filtered, and the solvent was removed under reduced pressure. The residue was taken-up in MeOH (3 mL) and stirred with conc. HCl (0.2 mL) for 1 h. The mixture was diluted with EtOAc (40 mL) and washed with water (2x25 mL). The organic layer was dried over anhydrous $MgSO_4$, filtered, and the solvent was removed under reduced pressure. The residue was purified by flash chromatography (20% EtOAc in Hex) to yield 90 mg of Compound 167 as a white solid.

Example 68

Preparation of Compound 168

A mixture of 4-(1,3-benzothiazol-2-yloxy)benzaldehyde (300 mg, 1.18 mmol, prepared as in Example 64), 4A molecular sieves (600 mg) and ethylamine (2.0 M solution in THF, 3.0 mL, 6.0 mmol) was stirred under argon at room temperature for 3 h. The reaction mixture was filtered, and the solvent was removed under reduced pressure to yield crude 1-[4-(1,3-benzothiazol-2-yloxy)phenyl]-N-ethylmethanimine.

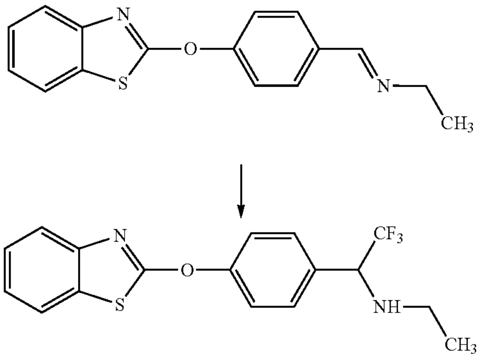

(168)

To 1-[4-(1,3-benzothiazol-2-yloxy)phenyl]-N-ethylmethanimine (1.18 mmol) and $KHF_2$ (69 mg, 0.883 mmol) in MeCN (4 mL) and DMF (274 μL) at 0° C. under argon was added TFA (113 μL, 1.48 mmol). The mixture was stirred for 5 minutes, and then $CF_3TMS$ (261 μL, 1.78 mmol) was added. The cooling bath was removed, and the reaction mixture was stirred for 18 h. It was diluted with saturated aqueous $Na_2CO_3$ (40 mL) and extracted with EtOAc (40 mL). The organic layer was washed with water (25 mL), dried over anhydrous $MgSO_4$, filtered, and the solvent was removed under reduced pressure. The residue was purified by flash chromatography (5% EtOAc in Hex) to yield 294 mg of a yellow oil.

To further purify the desired compound, to the oil in MeOH (2 mL) was added $NaBH_4$ (30 mg), and the mixture was stirred under argon for 30 minutes. The reaction was quenched with water (25 mL) and extracted with EtOAc (35 mL). The organic layer was dried over anhydrous $Na_2SO_4$, filtered, and the solvent was removed under reduced pressure. The residue was purified by flash chromatography (10% EtOAc in Hex) to yield 133 mg of Compound 168 as a colourless oil.

Example 69

Preparation of Compound 169

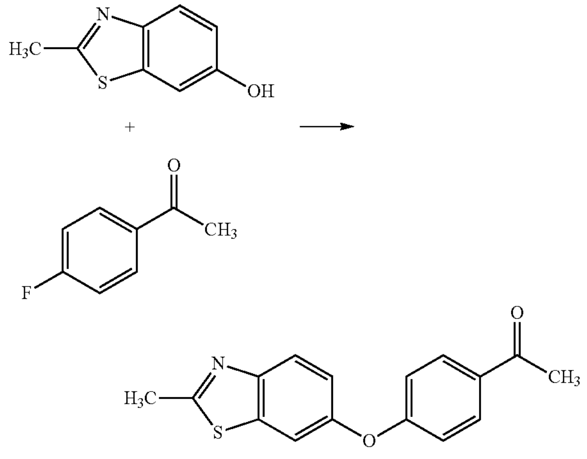

(169)

A mixture of 4'-fluoroacetophenone (177, 150 μL, 1.24 mmol), 2-methyl-5-benzothiazolol (205 mg, 1.24 mmol) and $K_2CO_3$ (514 mg, 3.72 mmol) in DMSO (3 mL) was stirred in a sealed tube at 100° C. for 18 h, and then was allowed to cool to room temperature, diluted with EtOAc (35 mL), washed with 1 M NaOH (2x25 mL) and water (25 mL). The organic layer was dried over anhydrous $Na_2SO_4$, filtered, and the solvent was removed under reduced pressure. The residue was purified by flash chromatography (20% EtOAc in Hex) to yield 306 mg of Compound 169 as an off-white solid.

Example 70

Preparation of Compound 170

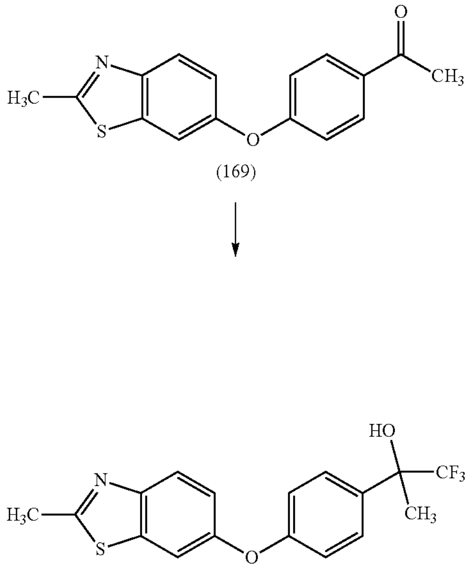

(169)

(170)

To a stirred mixture of Compound 169 (150 mg, 0.529 mmol, prepared as in Example 69) and $K_2CO_3$ (7 mg, 0.051 mmol) in DMF (3 mL) under argon was added $CF_3TMS$ (195 μL, 1.32 mmol). The reaction mixture was stirred at room temperature for 5 days, and then was diluted with EtOAc (35 mL) and washed with water (2x25 mL). The organic layer was dried over anhydrous $Na_2SO_4$, filtered, and the solvent was removed under reduced pressure. The residue was taken-up in MeOH (3 mL) and stirred with conc. HCl (0.3 mL) for 1 h. The mixture was diluted with EtOAc (35 mL) and washed with saturated aqueous solution of $Na_2CO_3$ (2x25 mL). The organic layer was dried over anhydrous $Na_2SO_4$, filtered, and the solvent was removed under reduced pressure.

To further purify the desired compound, to the residue in MeOH (3 mL) was added 20 mg of $NaBH_4$. The reaction was stirred for 1 h, and then was quenched with water (25 mL) and extracted with EtOAc (35 mL). The organic layer was washed with water (25 mL), dried over anhydrous $Na_2SO_4$, filtered, and the solvent was removed under reduced pressure. The residue was purified by flash chromatography (30% EtOAc in Hex) to yield 52 mg of Compound 170 as an off-white solid.

Example 71

Preparation of Compound 171

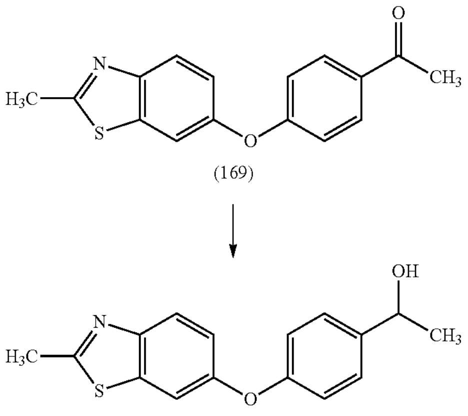

(169)

(171)

To a suspension of Compound 169 prepared as in Example 69 (75 mg, 0.265 mmol) in MeOH (2 mL) was added $NaBH_4$ (15 mg, 0.396 mmol). The mixture was stirred under argon for 1 h, after which time 10 mg of $NaBH_4$ was added. The mixture was stirred for 30 minutes, after which time a clear solution was observed. The reaction was quenched with water (25 mL) and extracted with EtOAc (35 mL). The organic layer was washed with water (25 mL), dried over anhydrous $Na_2SO_4$, filtered, and the solvent was removed under reduced pressure to yield 40 mg of Compound 171 as a yellowish oil.

Example 72

Preparation of Compound 172

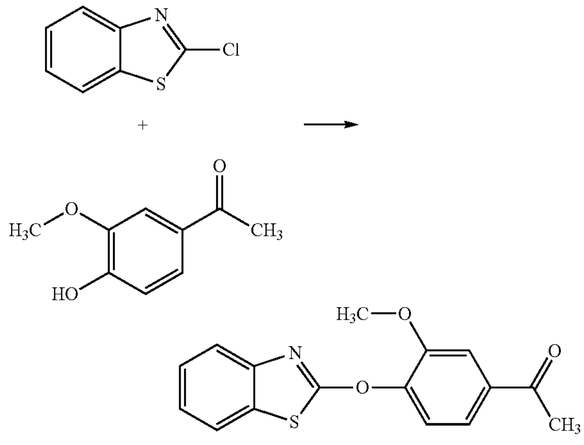

(172)

To a solution of acetovanillone (250 mg, 1.50 mmol) in DMF (5 mL) under argon was added 2-chlorobenzothiazole (235 μL, 1.80 mmol) and $K_2CO_3$ (311 mg, 2.25 mmol). The reaction mixture was stirred in a sealed tube at 100° C. for 18 hours. The reaction mixture was diluted with ethyl acetate (35 mL). The organic layer was then washed with 1M aqueous NaOH (2×25 mL) and water (25 mL). The organic layer was dried over $Na_2SO_4$, filtered, and the solvent was removed under reduced pressure. Flash column chromatography on silica gel (20% EtOAc in Hex yielded 437 mg of Compound 172 as a white solid.

Example 73

Preparation of Compound 173

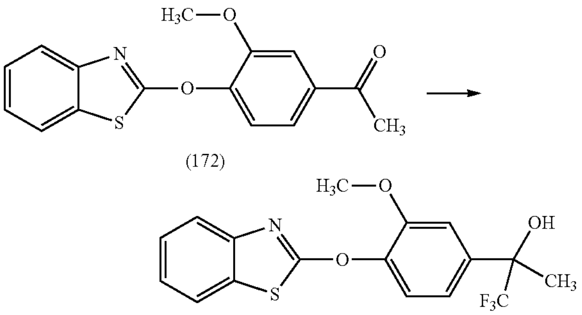

(172)

(173)

To a stirred mixture of Compound 172 (150 mg, 0.501 mmol) and $K_2CO_3$ (7 mg, 0.051 mmol) in DMF (3 mL) under argon was added $CF_3$TMS (111 μL, 0.752 mmol). The reaction mixture was stirred at room temperature for 44 hours then additional $CF_3$TMS (222 μL, 1.54 mmol) was added and stirring continued for 3 days. The mixture was then diluted with EtOAc (35 mL) and washed with water (25 mL). The organic layer was dried over anhydrous $Na_2SO_4$, filtered, and the solvent was removed under reduced pressure. The residue was taken-up in MeOH (3 mL) and stirred with conc. HCl (0.3 mL) for 1 hour. The mixture was diluted with EtOAc (35 mL) and washed with water (25 mL). The organic layer was dried over anhydrous $Na_2SO_4$, filtered, and the solvent was removed under reduced pressure.

In order to separate the product from by-products the residue was taken-up in MeOH (3 mL), $NaBH_4$ (22 mg) was added and the mixture was stirred for 30 minutes. The mixture was diluted with EtOAc (35 mL) and washed with water (25 mL). The organic layer was dried over anhydrous $Na_2SO_4$, filtered, and the solvent was removed under reduced pressure. The residue was purified by flash chromatography (20% EtOAc in Hex) to yield 56 mg of Compound 173 as a white solid.

Example 74

Preparation of Compound 174

To a stirred solution of 3-chloro-4-hydroxybenzaldehyde (900 mg, 5.75 mmol) in Acetone (10 mL)/$H_2O$ (10 mL) was added NaOH (1 g, 25 mmol). The mixture was stirred at room temperature for 18 h. The reaction was quenched with the addition of 5% aq. HCl (10 mL) and extracted with EtOAc (15 mL). The organic layer was washed with water (2×10 mL), brine (10 mL), dried over anhydrous $MgSO_4$, filtered, and the solvent was removed under reduced pressure to yield 1.1 g of 4-(3-chloro-4-hydroxyphenyl)but-3-en-2-one as a yellow oil.

To a stirred solution of 4-(3-chloro-4-hydroxyphenyl)but-3-en-2-one (626 mg, 3.18 mmol) in EtOAc (12 mL) was added 10% Pd/C (100 mg). The reaction mixture was stirred under hydrogen for 1.5 h after. The mixture was filtered, the solvent was removed under reduced pressure, and the residue was purified by flash chromatography (25% EtOAc in Hex) to yield 333 mg of 4-(3-chloro-4-hydroxyphenyl) butan-2-one as an oil.

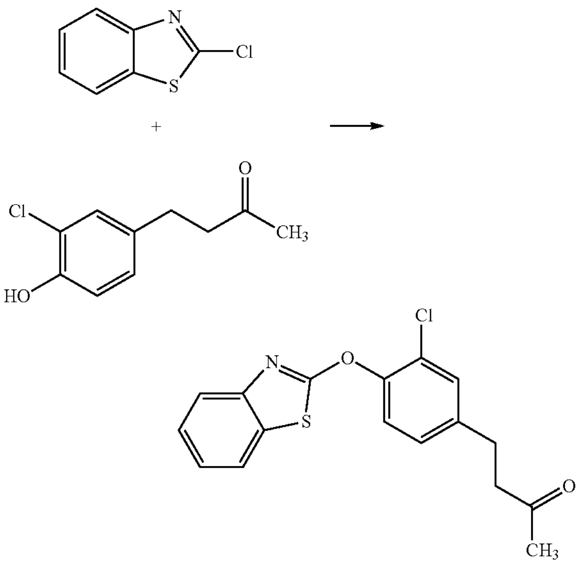

(174)

To a solution of 4-(3-chloro-4-hydroxyphenyl)butan-2-one (333 mg, 1.67 mmol) in DMF (5 mL) under argon was added 2-chlorobenzothiazole (239 μL, 1.84 mmol) and $K_2CO_3$ (231 mg, 1.67 mmol). The reaction mixture was stirred at 140° C. for 18 hours. The reaction mixture was allowed to cool to room temperature, and then was diluted with water (30 mL) and extracted with EtOAc (40 mL). The organic layer was washed with brine (3x40 mL). The organic layer was dried ($MgSO_4$), filtered, and the solvent was removed under reduced pressure. Flash column chromatography on silica gel (25% EtOAc in Hex) yielded 429 mg of Compound 174 as a yellow oil.

Example 75

Preparation of Compound 175

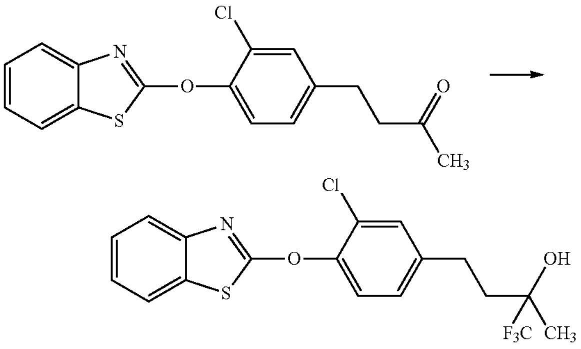

(175)

Following General Procedure for $CF_3$TMS Additions as disclosed herein, Compound 175 was prepared from Compound 174 (105 mg, 0.36 mmol), $CF_3$TMS (97 μL, 0.65 mmol), $K_2CO_3$ (15 mg, 0.11 mmol) and DMF (2 mL) then MeOH (5 mL) and HCl (250 μL). Flash column chromatography of the crude mixture on silica gel (20% EtOAc in Hex) yielded 109 mg of Compound 175 as an oil.

Example 76

Preparation of Compound 176

A mixture of 4-hydroxyacetophenone (150 mg, 1.10 mmol), $K_2CO_3$ (228 mg, 1.65 mmol), and 2-chloro-4-(methylthio)-benzothiazole (297 mg, 1.38 mmol) in DMF (3 mL) was stirred at 100° C. for 18 h in a sealed tube. The mixture was allowed to cool to room temperature, diluted with $H_2O$ (10 mL) and EtOAc (30 mL), separated, and the organic layer was washed with 5% NaOH (2x20 mL), then brine (3x30 mL), dried over anhydrous $MgSO_4$, filtered, and the solvent was removed under reduced pressure. The residue was purified by flash chromatography (20% EtOAc in Hex) to yield 338 mg of 1-(4-{[4-(methylsulfanyl)-1,3-benzothiazol-2-yl]oxy}phenyl)ethan-1-one as a white solid.

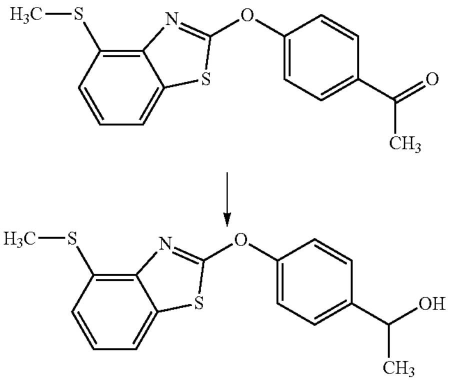

(176)

To a stirred solution of 1-(4-{[4-(methylsulfanyl)-1,3-benzothiazol-2-yl]oxy}phenyl)ethan-1-one (150 mg, 0.476 mmol) in MeOH (10 mL) at room temperature under argon was added $NaBH_4$ (27 mg, 0.714 mmol). The reaction mixture was stirred for 1 h and then was quenched with water (25 mL) and extracted with EtAOc (35 mL). The organic layer was dried over anhydrous $MgSO_4$, filtered, and the solvent was removed under reduced pressure. The residue was purified by flash chromatography (20% EtOAc in Hex) to yield 134 mg of Compound 176 as a colorless oil.

Example 77

Preparation of Compound 177

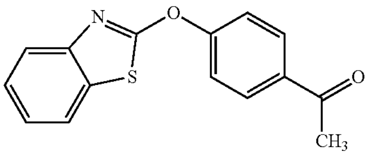

(159)

-continued

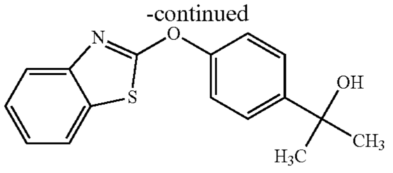

(177)

To a stirred solution of Compound 159 (150 mg, 0.557 mmol) in diethyl ether (9 mL) at 0° C. under argon was added 3.0M MeMgBr in ether (0.3 mL, 0.9 mmol). The reaction mixture was stirred for 10 minutes at 0° C. The cooling bath was removed and the reaction was stirred for 1 hour then quenched with water (10 mL), diluted with 5% HCl (10 mL) and extracted with EtAOc (35 mL). The organic layer was washed with water (20 mL), dried over anhydrous $MgSO_4$, filtered, and the solvent was removed under reduced pressure. The residue was purified by flash chromatography (20% EtOAc in Hex) to yield 93 mg of Compound 177 as a colorless oil.

Example 78

Preparation of Compound 178

A mixture of 4-(1,3-benzothiazol-2-yloxy)benzaldehyde (300 mg, 1.18 mmol, prepared as in Example 64), 4A molecular sieves (600 mg), methylamine (2.0 M solution in THF, 3.0 mL, 6.0 mmol) and anhydrous DCE (3.0 mL) was stirred under argon at room temperature for 18 h. The reaction mixture was filtered and the solvent was removed under reduced pressure to yield crude 1-[4-(1,3-benzothiazol-2-yloxy)phenyl]-N-methylmethanimine.

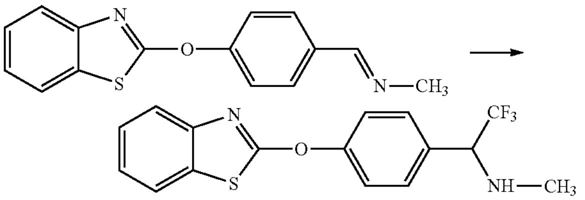

(178)

To 1-[4-(1,3-benzothiazol-2-yloxy)phenyl]-N-methylmethanimine (1.18 mmol) and $KHF_2$ (69 mg, 0.883 mmol) in MeCN (4 mL) and DMF (274 μL) at 0° C. under argon was added TFA (113 μL, 1.48 mmol). The mixture was stirred for 5 minutes, and then $CF_3TMS$ (261 μL, 1.78 mmol) was added. The cooling bath was removed, and the reaction mixture was stirred for 20 h. It was diluted with saturated aqueous $Na_2CO_3$ (40 mL) and extracted with EtOAc (40 mL). The organic layer was washed with water (25 mL), dried over anhydrous $Na_2SO_4$, filtered, and the solvent was removed under reduced pressure.

The residue was taken-up in MeOH (2 mL), $NaBH_4$ (45 mg) was added, and the mixture was stirred under argon for 30 minutes. The reaction was quenched with water (25 mL) and extracted with EtOAc (35 mL). The organic layer was dried over anhydrous $Na_2SO_4$, filtered, and the solvent was removed under reduced pressure. The residue was purified by flash chromatography (20% EtOAc in Hex) to yield 109 mg of Compound 178 as a colourless oil.

Example 79

Preparation of Compound 179

A mixture of 4-hydroxybenzaldehyde (100 mg, 0.819 mmol), $K_2CO_3$ (170 mg, 1.23 mmol), and 2-chloro-4,6-difluoro-benzothiazole (168 mg, 0.817 mmol) in DMF (3 mL) was stirred in a sealed tube at 100° C. for 18 h. The mixture was allowed to cool to room temperature, diluted with EtOAc (35 mL), washed with 1M NaOH (2x25 mL) and water (25 mL), dried over anhydrous $Na_2SO_4$, filtered, and the solvent was removed under reduced pressure to yield 216 mg of 4-(4,6-difluoro-1,3-benzothiazol-2-yloxy)benzaldehyde as a white solid.

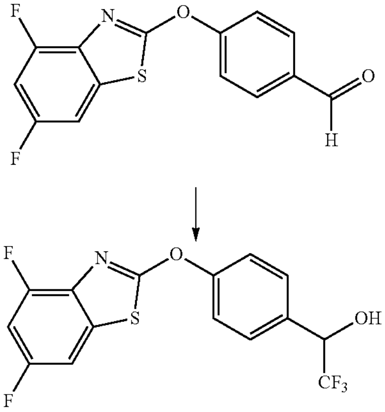

(179)

To a stirred mixture of 4-(4,6-difluoro-1,3-benzothiazol-2-yloxy)benzaldehyde (216 mg, 0.742 mmol) and $K_2CO_3$ (10 mg, 0.072 mmol) in DMF (2 mL) under argon was added $CF_3TMS$ (220 μL, 1.49 mmol). The reaction mixture was stirred at room temperature for 20 h, and then was diluted with EtOAc (35 mL) and washed with water (25 mL). The organic layer was dried over anhydrous $Na_2SO_4$, filtered, and the solvent was removed under reduced pressure. The residue was taken-up in MeOH (3 mL) and stirred with conc. HCl (0.3 mL) for 1 h. EtOAc (35 mL) was added and the mixture was washed with water (25 mL). The organic layer was dried over anhydrous $Na_2SO_4$, and filtered. The solvent was removed under reduced pressure and the residue was purified by flash chromatography (20% EtOAc in Hex) to yield 116 mg of Compound 179 as a white solid.

Example 80

Preparation of Compound 180

A mixture of 4-hydroxyacetophenone (150 mg, 1.10 mmol), $K_2CO_3$ (228 mg, 1.65 mmol), and 2-chloro-4,6-difluoro-benzothiazole (226 mg, 1.10 mmol) in DMF (3 mL) was stirred at 100° C. for 18 h in a sealed tube. The mixture was allowed to cool to room temperature, diluted with EtOAc (35 mL), separated, and the organic layer was washed with 1M NaOH (2x25 mL), then water (25 mL), dried over anhydrous $Na_2SO_4$, filtered, and the solvent was removed under reduced pressure to yield 335 mg of 1-[4-(4,6-difluoro-1,3-benzothiazol-2-yloxy)phenyl]ethan-1-one as a light brown solid.

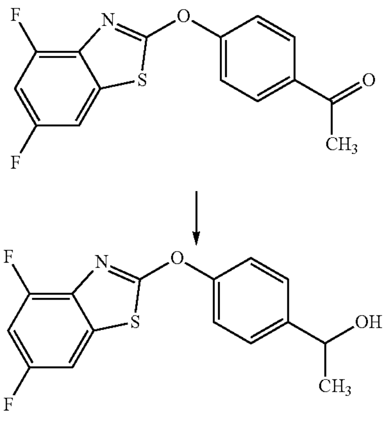

(180)

To a stirred solution of 1-[4-(4,6-difluoro-1,3-benzothiazol-2-yloxy)phenyl]ethan-1-one (100 mg, 0.328 mmol) in MeOH (2 mL) at room temperature under argon was added $NaBH_4$ (18 mg, 0.476 mmol). The reaction mixture was stirred for 1 h and then was quenched with water (25 mL) and extracted with EtOAc (35 mL). The organic layer was dried over anhydrous $Na_2SO_4$, filtered, and the solvent was removed under reduced pressure. The residue was purified by flash chromatography (30% EtOAc in Hex) to yield 80 mg of Compound 180 as a colourless oil.

Example 81

Preparation of Compound 181

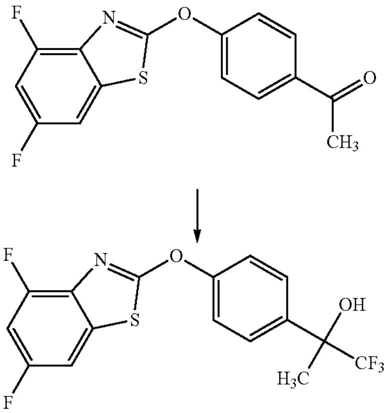

(181)

To a stirred solution of 1-[4-(4,6-difluoro-1,3-benzothiazol-2-yloxy)phenyl]ethan-1-one (150 mg, 0.491 mmol) and $K_2CO_3$ (7 mg, 0.051 mmol) in DMF (3 mL) under argon was added $CF_3TMS$ (145 μL, 0.982 mmol). The reaction mixture was stirred at room temperature for 4 days then diluted with EtOAc (35 mL) and washed with water (25 mL). The organic layer was dried over anhydrous $Na_2SO_4$, filtered, and the solvent was removed under reduced pressure. The residue was taken-up in MeOH (3 mL) and stirred with conc. HCl (0.3 mL) for 1 h. EtOAc (35 mL) was added and the mixture was washed with water (25 mL). The residue was taken-up in MeOH (3 mL), $NaBH_4$ (27 mg) was added and the mixture was stirred for 1 h. EtOAc (35 mL) was added and the mixture was washed with water (25 mL). The organic layer was dried over anhydrous $Na_2SO_4$, and filtered. The solvent was removed under reduced pressure and the residue was purified by flash chromatography (20% EtOAc in Hex) to yield 27 mg of Compound 181 as a white solid.

Example 82

Preparation of Compound 182

A mixture of 4-hydroxy-2-methoxybenzaldehyde (250 mg, 1.64 mmol), $K_2CO_3$ (340 mg, 2.46 mmol), and 2-chlorobenzothiazole (215 μL, 1.65 mmol) in DMF (5 mL) was stirred in a sealed tube at 100° C. for 18 h. The mixture was allowed to cool to room temperature, diluted with EtOAc (35 mL), washed with 1M NaOH (2×25 mL) and water (25 mL), dried over anhydrous $Na_2SO_4$, filtered, and the solvent was removed under reduced pressure and the residue was purified by flash chromatography (20% EtOAc in Hex) to yield 457 mg of 4-(1,3-benzothiazol-2-yloxy)-2-methoxybenzaldehyde as a white solid.

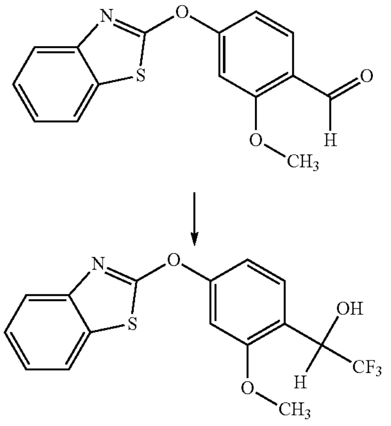

(182)

To a stirred mixture of 4-(1,3-benzothiazol-2-yloxy)-2-methoxybenzaldehyde (200 mg, 0.701 mmol) and $K_2CO_3$ (10 mg, 0.072 mmol) in DMF (3 mL) under argon was added $CF_3TMS$ (207 μL, 1.402 mmol). The reaction mixture was stirred at room temperature for 20 h then was diluted with EtOAc (35 mL) and washed with water (25 mL). The organic layer was dried over anhydrous $Na_2SO_4$, filtered, and the solvent was removed under reduced pressure. The residue was taken-up in MeOH (3 mL) and stirred with conc. HCl (0.3 mL) for 1 h. EtOAc (35 mL) was added and the mixture was washed with water (25 mL). The organic layer was dried over anhydrous $Na_2SO_4$, and filtered. The solvent was removed under reduced pressure and the residue was purified by flash chromatography (20% EtOAc in Hex) to yield 172 mg of Compound 182 as a white solid.

Example 83

Preparation of Compound 183

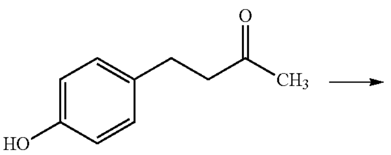

-continued

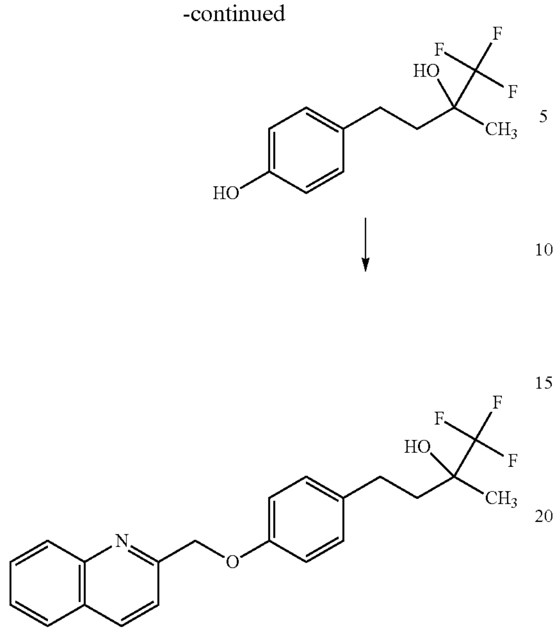

(183)

To a stirred mixture of 4-(4-hydroxyphenyl)-2-butanone (150 mg, 0.914 mmol) and $K_2CO_3$ (13 mg, 0.094 mmol) in DMF (2 mL) at 0° C. under argon was added $CF_3TMS$ (340 D L, 2.30 mmol) dropwise. The reaction mixture was stirred at room temperature for 42 hours. The mixture was diluted with EtOAc (20 mL), washed with water (2×20 mL), dried over anhydrous $Na_2SO_4$, filtered, and the solvent was removed under reduced pressure. To the residue were added MeOH (3 mL) and 6N aqueous HCl (0.3 mL), and the reaction was stirred for 1 hour. The reaction was diluted with EtOAc (20 mL), washed with saturated aqueous $NaHCO_3$ solution (2×20 mL), water (20 mL), dried over anhydrous $Na_2SO_4$, filtered, and the solvent was removed under reduced pressure. The residue was purified by flash chromatography (20% EtOAc in hexane) to yield 145 mg of 4-(4,4,4-trifluoro-3-hydroxy-3-methylbutyl)phenol as a white solid.

In analogy to the procedure of Example 97, 173 mg of Compound 183 was prepared as a white solid from 4-(4,4,4-trifluoro-3-hydroxy-3-methylbutyl)phenol (145 mg, 0.619 mmol), 2-(chloromethyl)quinoline hydrochloride (146 mg, 0.682 mmol), and $K_2CO_3$ (342 mg, 2.47 mmol) in DMF (2 mL).

Example 84

Preparation of Compound 184

A mixture of vanillylacetone (250 mg, 1.52 mmol), $K_2CO_3$ (377 mg, 2.73 mmol), and 2-(chloromethyl)quinoline hydrochloride (343 mg, 1.60 mmol) in DMF (6 mL) was stirred in a sealed tube at 130° C. for 22 h. The mixture was allowed to cool to room temperature. Water (20 mL) was added and the mixture was extracted with EtOAc (3×20 mL). The combined organic layers were dried over $Na_2SO_4$, filtered, and the solvent was removed under reduced pressure. The residue was purified by flash chromatography (25% EtOAc in Hex) to yield 344 mg of 4-{3-methoxy-4-[(quinoline-2-yl)methoxy]phenyl}butan-2-one as a yellow oil.

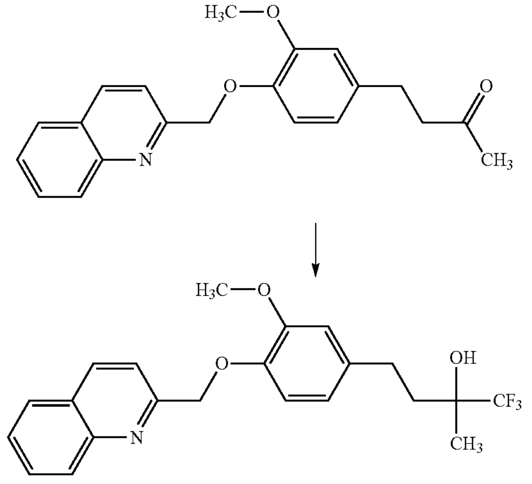

(184)

To a stirred mixture of 4-{3-methoxy-4-[(quinoline-2-yl)methoxy]phenyl}butan-2-one (120 mg, 0.36 mmol) and $K_2CO_3$ (33 mg, 0.24 mmol) in DMF (3 mL) under argon was added $CF_3TMS$ (175 µL, 1.18 mmol). The reaction mixture was stirred at room temperature for 21 h then was diluted with EtOAc (25 mL) and washed with brine (25 mL). The organic layer was dried over anhydrous $Na_2SO_4$, filtered, and the solvent was removed under reduced pressure. The residue was taken-up in MeOH (5 mL) and stirred with conc. HCl (0.2 mL) for 75 minutes. The solvent was removed under reduced pressure, EtOAc (25 mL) was added and the mixtures was washed with water (25 mL), dried over $Na_2SO_4$, filtered, and concentrated, The residue was purified by flash chromatography (25% EtOAc in Hex) to yield 100 mg of Compound 184 as an off-white solid.

Example 85

Preparation of Compound 185

A mixture of 1-(4-hydroxyphenyl)pentan-3-one (175 mg, 0.98 mmol, prepared as in Example 48), $K_2CO_3$ (150 mg, 1.09 mmol), and 2-(chloromethyl)quinoline hydrochloride (150 mg, 0.70 mmol) in DMF (3 mL) was stirred in a sealed tube at 140° C. for 20 h. The mixture was allowed to cool to room temperature, water (25 mL) was added and the mixture was extracted with EtOAc (3×25 mL). The combined organic layers were washed with brine (25 mL), dried over $Na_2SO_4$, filtered, and the solvent was removed under reduced pressure. The residue was purified by flash chromatography (25% EtOAc in Hex) to yield 254 mg of 1-{4-[(quinoline-2-yl)methoxy]phenyl}pentan-3-one as a yellow oil.

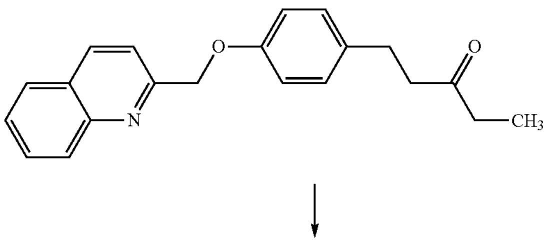

-continued

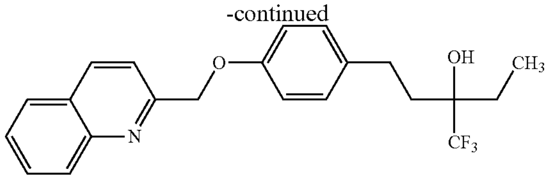

(185)

To a stirred mixture of 1-{4-[(quinoline-2-yl)methoxy]phenyl}pentan-3-one (135 mg, 0.42 mmol) and $K_2CO_3$ (40 mg, 0.29 mmol) in DMF (3 mL) under argon was added $CF_3TMS$ (200 μL, 1.35 mmol). The reaction mixture was stirred at room temperature for 20 h then was diluted with EtOAc (35 mL), washed with water (2×50 mL) and brine (15 mL). The organic layer was dried over anhydrous $Na_2SO_4$, filtered, and the solvent was removed under reduced pressure. The residue was taken-up in MeOH (5 mL) and stirred with conc. HCl (0.2 mL) for 1 h. The solvent was removed under reduced pressure, EtOAc (25 mL) was added and the mixture was washed with water (25 mL), dried over $Na_2SO_4$, filtered, and concentrated. The residue was purified by flash chromatography (25% EtOAc in Hex) to yield 83 mg of Compound 185.

Example 86

Preparation of Compound 186

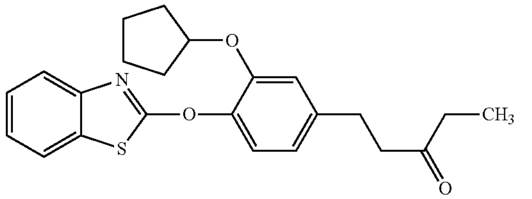

(113)

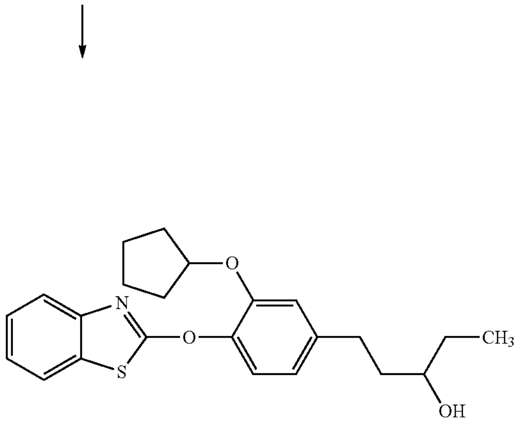

(186)

Following general procedure for reductions, Compound 186 was prepared from Compound 113 (105 mg, 0.265 mmol, prepared as in Example 13), sodium borohydride (20 mg, 0.529 mmol), and methanol (2 mL). Flash column chromatography of the crude mixture on silica gel (20% EtOAc in Hex) yielded 0.083 g of Compound 186 as a colourless glass.

Example 87

Preparation of Compound 187

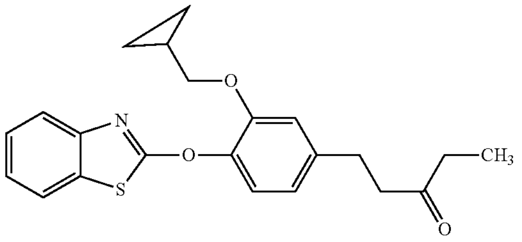

(114)

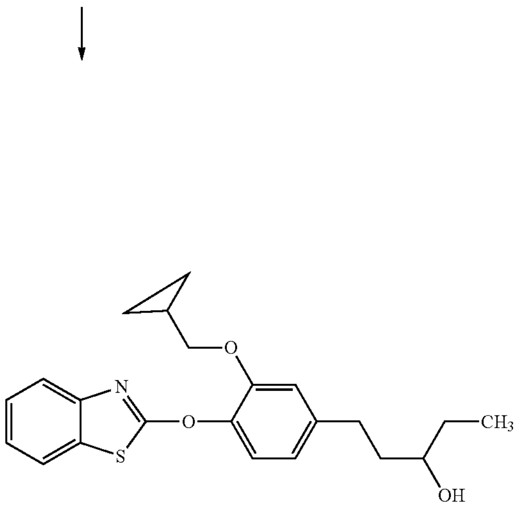

(187)

Following general procedure for reductions, Compound 187 was prepared from Compound 114 (115 mg, 0.301 mmol, prepared as in Example 14), sodium borohydride (23 mg, 0.608 mmol), and methanol (2 mL). Flash column chromatography of the crude mixture on silica gel (20% EtOAc in Hex) yielded 0.080 g of Compound 187 as a colourless glass.

Example 88

Preparation of Compound 188

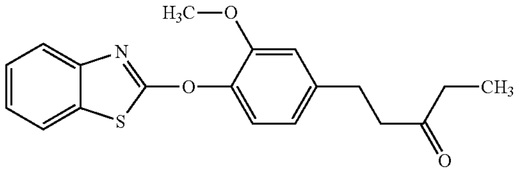

(101)

-continued

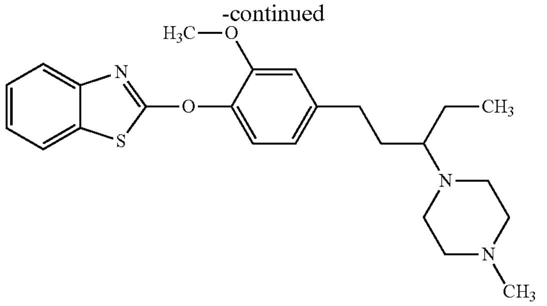

(188)

To a stirred solution of Compound 101 prepared as in Example 1 (150 mg, 0.439 mmol) in DCE (3 mL) at room temperature under argon was added 4A molecular sieves powder (156 mg), 1-methylpiperazine (70 μL, 0.631 mmol), AcOH (100 μL, 1.75 mmol), followed by $NaBH(OAc)_3$ (190 mg, 0.896 mmol). The reaction mixture was stirred for 18 h, and then was quenched with saturated $NaHCO_3$ (25 mL) and extracted with $CH_2Cl_2$ (2×35 mL). The combined organic layer was dried over anhydrous $MgSO_4$, filtered, and the solvent was removed under reduced pressure. The residue was purified by flash chromatography (EtOAc/MeOH/$Et_3N$, 9:1:0.1) to yield 24 mg of Compound 188 as colourless oil. Compound 188 was then taken-up in $CH_2CL_2$ (2 mL) and stirred with 1.25M HCl in MeOH (0.15 mL) for 1 h. The mixture was evaporated under reduced pressure to give the hydrochloride salt of Compound 188 as a colourless foam (27 mg).

Example 89

Preparation of Compound 189

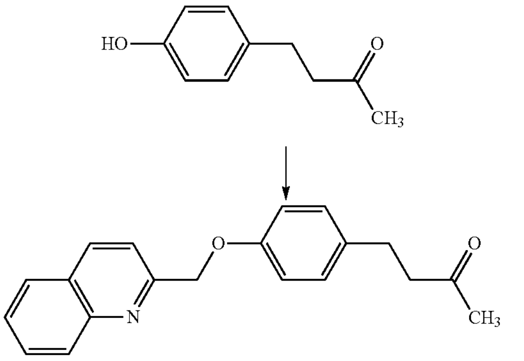

(189)

A mixture of 4-(4-hydroxyphenyl)-2-butanone (500 mg, 3.04 mmol), $K_2CO_3$ (443 mg, 3.21 mmol), and 2-(chloromethyl)quinoline hydrochloride (400 mg, 1.866 mmol) in DMF (6 mL) was stirred in a sealed tube at 150° C. for 20 h. The mixture was allowed to cool to room temperature. Water (20 mL) was added and the mixture was extracted with EtOAc (3×20 mL). The combined organic layers were dried over $MgSO_4$, filtered, and the solvent was removed under reduced pressure. The residue was purified by flash chromatography (20% EtOAc in Hex) to 603 mg of Compound 189 as a yellow oil.

Example 90

Preparation of Compound 190

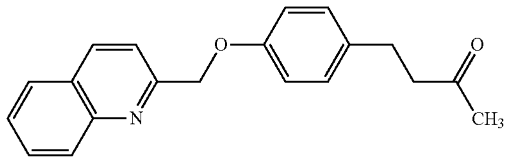

(189)

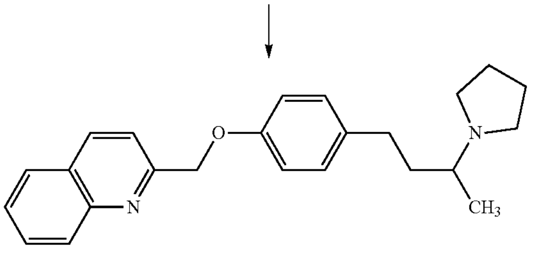

(190)

To a stirred solution of Compound 189 (115 mg, 0.378 mmol, prepared as in Example 89) in DCE (3 mL) at room temperature under argon was added glacial acetic acid (0.050 mL), $NaBH(OAc)_3$ and pyrrolidine (40 μL, 1.04 mmol). The reaction mixture was stirred at room temperature for 20 h. The reaction was quenched with water (20 mL) and extracted with $CH_2CL_2$ (2×20 mL). The organic layer was washed with brine (20 mL), dried over anhydrous $MgSO_4$, filtered, and the solvent was removed under reduced pressure. The residue was purified by flash chromatography (EtOAc/MeOH/$Et_3N$, 9:1:0.1) to yield Compound 190 as a yellow oil.

Example 91

Preparation of Compound 191

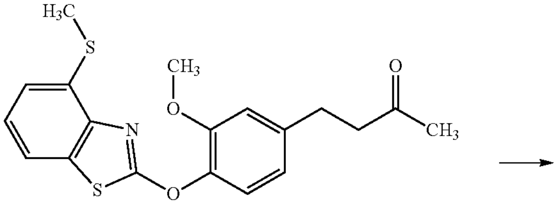

(118)

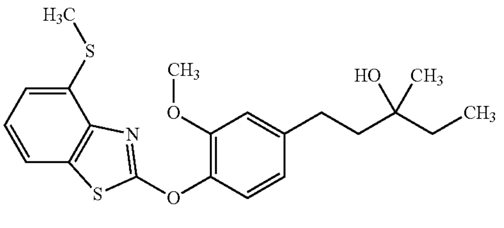

(191)

To a stirred solution of Compound 118 (154 mg, 0.431 mmol) in anhydrous THF at 0° C. under argon was added 3.0

M solution of EtMgBr in ether (180 □L, 0.540 mmol) dropwise. The reaction mixture was stirred at 0° C. for 10 minutes, after which time the cooling bath was removed, and the stirring was continued at room temperature for 1 hour. The reaction was quenched with saturated aqueous $NH_4Cl$ solution (10 mL) and extracted with EtOAc (15 mL). The organic layer was washed with water (10 mL), dried over anhydrous $Na_2SO_4$, filtered, and the solvent was removed under reduced pressure. The residue was purified by flash chromatography (30% EtOAc in hexane) to yield 114 mg of Compound 191 as a yellow oil.

The two enantiomers of Compound 191 were separated by HPLC using the following conditions: ChiralPak AD™ column, 5 □m particle size, 4.6x250 mm column dimensions; mobile phase: 90% i-PrOH in hexane; flow rate: 1 mL/min; injection volume: 50 DL; sample concentration: 1 mg/mL; run time: 22 minutes; number of injections: 1. Each peak was manually collected to create two pools of fractions. 50 DL samples from each pool were separately injected into the HPLC column, using the same mobile phase and run time as mentioned above. Enantiomer 1 had a retention time of 17.014 min and >99% purity. Enantiomer 2 had a retention time of 18.709 min and >99% purity.

Example 92

Preparation of Compound 192

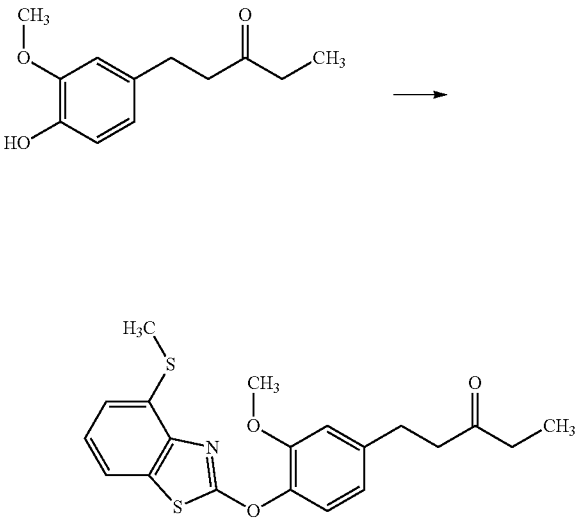

(192)

A mixture of 1-(4-hydroxy-3-methoxyphenyl)pentan-3-one (343 mg, 1.65 mmol), $K_2CO_3$ (342 mg, 2.47 mmol), and 2-chloro-4-(methylthio)benzothiazole (392 mg, 1.82 mmol) in DMF (4 mL) was stirred under argon in a sealed tube at 100° C. for 20 h. The mixture was allowed to cool to room temperature, diluted with EtOAc (25 mL), washed with water (2x25 mL), dried over anhydrous $Na_2SO_4$, filtered, and the solvent was removed under reduced pressure. The residue was purified by flash chromatography (20% EtOAc in Hex) to yield 400 mg of Compound 192 as a white solid.

Example 93

Preparation of Compound 193

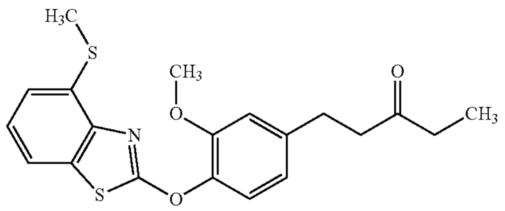

(192)

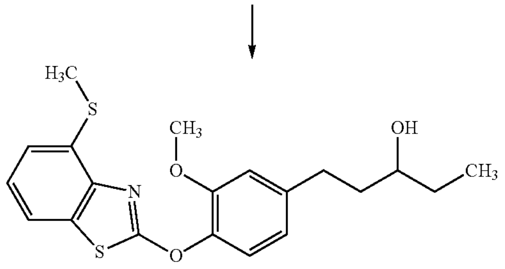

(193)

To a stirred suspension of Compound 192 (150 mg, 0.39 mmol) in MeOH (5 mL) under argon was added $NaBH_4$ (22 mg, 0.58 mmol). The reaction mixture was stirred for 30 minutes, after which time another 22 mg of $NaBH_4$ was added. The reaction mixture was stirred for 30 minutes, and then was diluted with EtOAc (30 mL), washed with water (2x20 mL), dried over anhydrous $Na_2SO_4$, filtered, and the solvent was removed under reduced pressure. The residue was triturated with EtOAc/hexane to yield 70 mg of Compound 193 as a white solid.

Example 94

Preparation of Compound 194

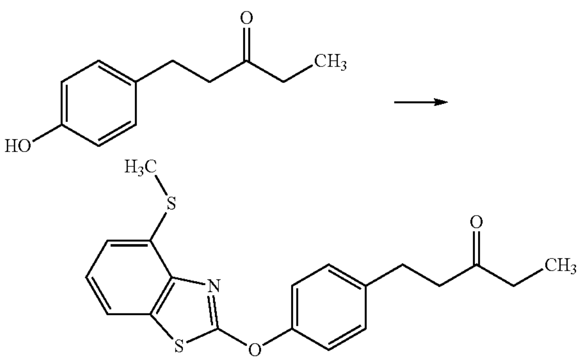

(194)

In analogy to the procedure of Example 92, 613 mg of Compound 194 was prepared as an off-white solid from 1-(4-hydroxyphenyl)pentan-3-one (390 mg, 2.19 mmol), 2-chloro-4-(methylthio)benzothiazole (520 mg, 2.41 mmol), and $K_2CO_3$ (454 mg, 3.28 mmol) in DMF (5 mL).

Example 95

Preparation of Compound 195

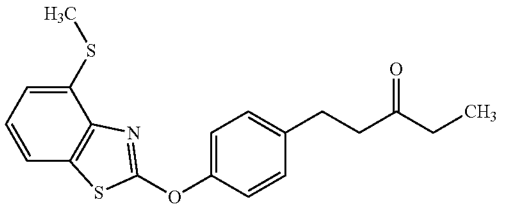

(194)

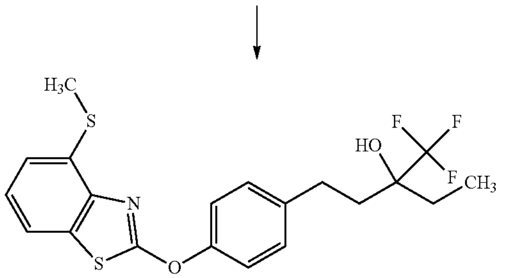

(195)

To a stirred mixture of Compound 194 (150 mg, 0.42 mmol) and $K_2CO_3$ (6 mg, 0.04 mmol) in DMF (3 mL) at 0° C. under argon was added $CF_3TMS$ (160 □L, 1.08 mmol) dropwise. The reaction mixture was stirred at room temperature for 42 hours. The mixture was diluted with EtOAc (25 mL), washed with water (2×25 mL), dried over anhydrous $Na_2SO_4$, filtered, and the solvent was removed under reduced pressure. To the residue were added MeOH (2 mL) and 6N aqueous HCl (0.2 mL), and the reaction was stirred for 1 hour. The reaction was diluted with EtOAc (25 mL), washed with water (2×25 mL), dried over anhydrous $Na_2SO_4$, filtered, and the solvent was removed under reduced pressure. To the residue were added MeOH (2 mL) and $NaBH_4$ (10 mg), and the reaction was stirred for 45 minutes. The solvent was removed under reduced pressure, and the residue was purified by flash chromatography (20% EtOAc in hexane) to yield 95 mg of Compound 195 as a colorless oil.

Example 96

Preparation of Compound 196

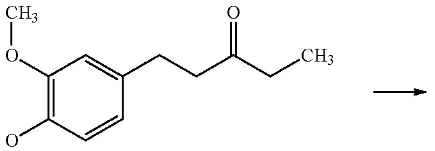

-continued

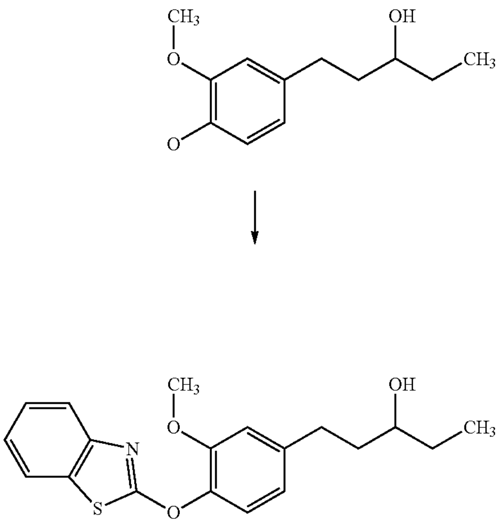

(196)

To 1-(4-hydroxy-3-methoxyphenyl)pentan-3-one (1.72 g, 8.26 mmol) in MeOH (20 mL) at 0° C. under argon was added $NaBH_4$ (469 mg, 12.4 mmol) in portions over 15 minutes. The reaction mixture was stirred at room temperature for 1 hour, and then was quenched with water (35 mL) and extracted with EtOAc (50 mL). The organic layer was washed with water (35 mL), dried over anhydrous $Na_2SO_4$, filtered, and the solvent was removed under reduced pressure to yield 1.17 g of 4-(3-hydroxypentyl)-2-methoxyphenol as a light yellow oil.

In analogy to the procedure of Example 92, 113 mg of Compound 196 was prepared as a colorless wax from 4-(3-hydroxypentyl)-2-methoxyphenol (100 mg, 0.48 mmol), 2-chlorobenzothiazole (70 □L, 0.54 mmol), and $K_2CO_3$ (199 mg, 1.44 mmol) in DMF (2 mL).

Example 97

Preparation of Compound 197

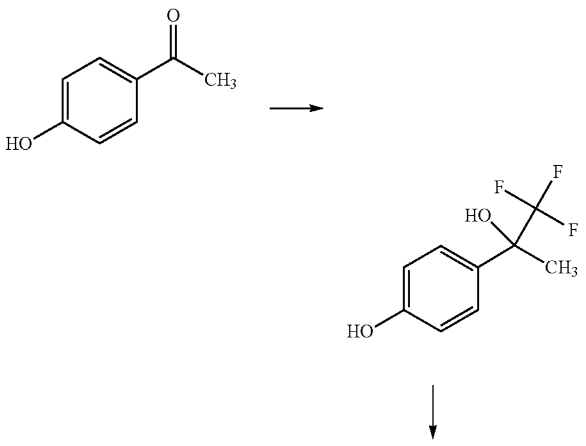

-continued

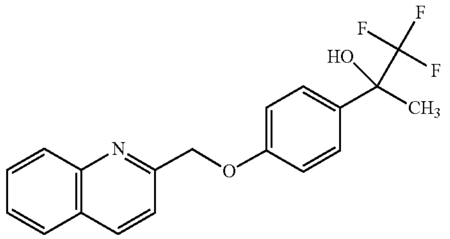

(197)

To a stirred mixture of 4'-hydroxyacetophenone (150 mg, 1.10 mmol) and $K_2CO_3$ (15 mg, 0.11 mmol) in DMF (2 mL) at 0° C. under argon was added $CF_3TMS$ (410 □L, 2.78 mmol) dropwise. The reaction mixture was stirred at room temperature for 90 hours. The mixture was diluted with EtOAc (20 mL), washed with water (2×20 mL), dried over anhydrous $Na_2SO_4$, filtered, and the solvent was removed under reduced pressure. To the residue were added MeOH (3 mL) and 6N aqueous HCl (0.3 mL), and the reaction was stirred for 1 hour. The reaction was diluted with EtOAc (20 mL), washed with saturated aqueous $NaHCO_3$ solution (2×20 mL), water (20 mL), dried over anhydrous $Na_2SO_4$, filtered, and the solvent was removed under reduced pressure. The residue was purified by flash chromatography (30% EtOAc in hexane) to yield 135 mg of 4-(1,1,1-trifluoro-2-hydroxypropan-2-yl)phenol as a white solid.

A mixture of 4-(1,1,1-trifluoro-2-hydroxypropan-2-yl) phenol (135 mg, 0.655 mmol), $K_2CO_3$ (362 mg, 2.62 mmol), and 2-(chloromethyl)quinoline hydrochloride (154 mg, 0.719 mmol) in DMF (2 mL) was stirred in a sealed tube at 80° C. for 18 hours. The mixture was allowed to cool to room temperature, diluted with EtOAc (20 mL), washed with water (2×20 mL), dried over anhydrous $Na_2SO_4$, filtered, and the solvent was removed under reduced pressure. The residue was purified by flash chromatography (20% EtOAc in Hex) to yield 156 mg of Compound 197 as a yellowish solid.

Example 98

Preparation of Compound 198

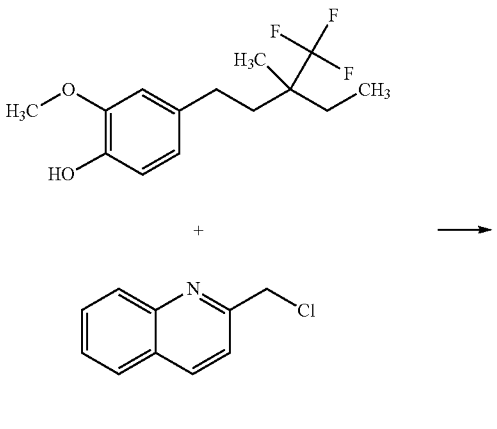

-continued

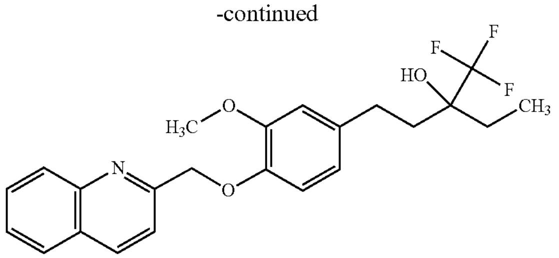

(198)

A mixture of 4-[3-hydroxy-3-(trifluoromethyl)pentyl]-2-methoxyphenol (189 mg, 0.679 mmol), $K_2CO_3$ (375 mg, 2.71 mmol), and 2-(chloromethyl)quinoline hydrochloride (160 mg, 0.747 mmol) in anhydrous acetone (4 mL) was stirred in a sealed tube at 60° C. for 18 hours. The mixture was allowed to cool to room temperature, filtered, washed with acetone, and the solvent was removed under reduced pressure. The residue was purified by 2 successive flash columns (20% EtOAc in Hex, then by 10% EtOAc in $CH_2Cl_2$) to yield 75 mg of Compound 198 as a colorless glass.

Example 99

Preparation of Compound 199

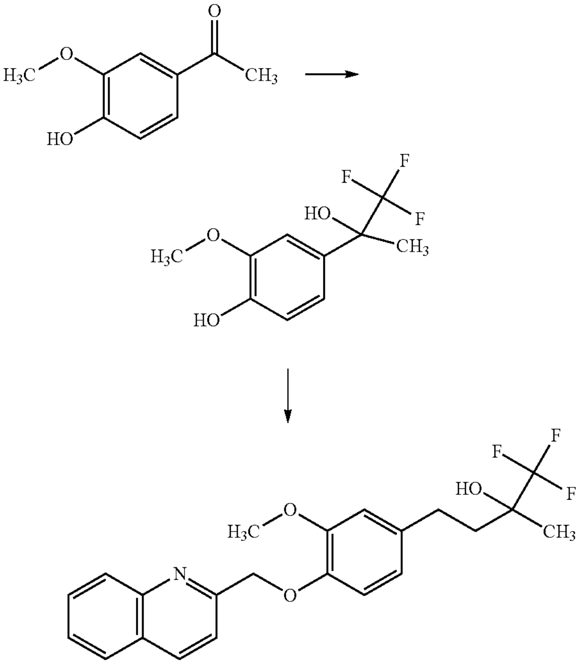

(199)

In analogy to the method for the procedure of 4-(1,1,1-trifluoro-2-hydroxypropan-2-yl)phenol, 132 mg of 2-methoxy-4-(1,1,1-trifluoro-2-hydroxypropan-2-yl)phenol was prepared from 4'-hydroxy-3'-methoxyacetophenone (150 mg, 0.903 mmol), $CF_3TMS$ (340 □L, 2.30 mmol), and $K_2CO_3$ (12 mg, 0.087 mmol) in DMF (2 mL).

Following the procedure of Example 97, 161 mg of Compound 199 was prepared as a white solid from 2-methoxy-4-(1,1,1-trifluoro-2-hydroxypropan-2-yl)phenol (132 mg, 0.560 mmol), 2-(chloromethyl)quinoline hydrochloride (132 mg, 0.620 mmol), and $K_2CO_3$ (310 mg, 2.24 mmol) in DMF (2 mL).

Example 100

MC/9 HPLC Assay

Cultured MC/9 cells (3×10ˆ6 cells) in 1 mL HBSS were pre-incubated with a series of concentrations of compound solubilized in DMSO for 30 minutes. Production of leukotrienes were stimulated with the addition of 1 µM calcium ionophore (A23187), diluted from a 4 mM DMSO stock in HBSS, and incubated at room temperature for 20 minutes. The reaction was stopped with the addition of 500 µL of methanol containing 20 ng/mL prostaglandin B2 as an internal standard. Samples were collected and stored at −20° C. at least 2 hr or overnight before centrifuged at 13,000 rpm for 15 minutes and loaded onto C18 SEP-PAK columns (Canadian Lifesciences IS12000) for solid phase extraction. The leukotrienes were analyzed by HPLC using an ACE C18 column (4.5 mm×150 mm, 5 m) eluted with acetonitrile/methanol/water mixture with $H_3PO_4$, pH 3.5 (37:26:37) with a flow rate of 1.8 mL/min. The amount of $LTB_4$ (Cayman Chemical, 20110) and $LTC_4$ (Cayman Chemical, 20210) were calculated based on reference standards and the level of inhibition of $LTB_4$ production induced by the test compounds was calculated relative to control samples. The results are provided in Table 2, where Compound No. refers to the compounds identified in Table 1.

TABLE 2

| Compound No. | % Inhibition LTC4 (3 µM) | % Inhibition LTB4 | % Inhibition LTC4 | % Inhibition LTB4 |
|---|---|---|---|---|
| 101 | | | <10% | <10% |
| 102 | | | 10-30% | >90% |
| 103 | >90% | >90% | 50-70% | 50-70% |
| 104 | >90% | >90% | >90% | >90% |
| 105 | 70-90% | 30-50% | 30-50% | |
| 106 | 30-50% | 10-30% | 10-30% | 10-30% |
| 107 | >90% | >90% | 70-90% | >90% |
| 108 | 50-70% | >90% | 70-90% | >90% |
| 109 | | | 50-70% | 70-90% |
| 110 | | | <10% | <10% |
| 111 | 70-90% | 70-90% | | |
| 115 | <10% | >90% | <10% | <10% |
| 116 | | | <10% | <10% |
| 117 | | | 30-50% | 70-90% |
| 119 | >90% | >90% | >90% | >90% |
| 120 | 70-90% | 70-90% | | |
| 121 | | | 50-70% | 50-70% |
| 122 | | | 30-50% | 30-50% |
| 123 | | | 10-30% | 50-70% |
| 124 | | | 10-30% | |
| 126 | | | <10% | 10-30% |
| 127 | | | <10% | <10% |
| 128 | <10% | <10% | <10% | <10% |
| 130 | | | <10% | 10-30% |
| 131 | 50-70% | <10% | | |
| 132 | | | 70-90% | >90% |
| 133 | | | <10% | 30-50% |
| 134 | | | 10-30% | 10-30% |
| 135 | | | 10-30% | 30-50% |
| 136 | 10-30% | <10% | | |
| 137 | 50-70% | 30-50% | | 10-30% |
| 138 | 70-90% | 70-90% | 30-50% | 10-30% |
| 139 | >90% | >90% | | |
| 140 | | | <10% | <10% |
| 141 | | | 10-30% | >90% |
| 143 | | | 10-30% | >90% |
| 144 | | | 10-30% | >90% |
| 146 | | | 10-30% | >90% |

TABLE 2-continued

| Compound No. | % Inhibition LTC4 (3 µM) | % Inhibition LTB4 | % Inhibition LTC4 | % Inhibition LTB4 |
|---|---|---|---|---|
| 147 | | | 30-50% | >90% |
| 149 | | | 30-50% | 50-70% |
| 150 | 70-90% | >90% | 10-30% | 50-70% |
| 151 | | | 10-30% | 10-30% |
| 152 | 30-50% | 30-50% | 30-50% | 50-70% |
| 154 | <10% | 10-30% | 30-50% | 50-70% |
| 155 | | | <10% | 10-30% |
| 156 | | | <10% | >90% |
| 157 | | | <10% | 70-90% |
| 158 | <10% | >90% | 10-30% | >90% |
| 159 | 10-30% | 30-50% | | |
| 160 | <10% | 50-70% | | |
| 161 | <10% | 10-30% | | |
| 162 | <10% | 70-90% | | |
| 163 | 10-30% | 50-70% | | |
| 164 | <10% | >90% | | |
| 165 | <10% | 70-90% | | |
| 166 | 30-50% | 50-70% | | |
| 167 | 10-30% | 10-30% | 10-30% | 10-30% |
| 168 | <10% | 10-30% | | |
| 170 | >90% | >90% | | |
| 171 | 70-90% | 70-90% | | |
| 173 | 30-50% | | | |
| 176 | <10% | <10% | | |
| 177 | | 30-50% | | |
| 178 | <10% | <10% | | |
| 179 | 10-30% | 10-30% | | |
| 180 | <10% | 10-30% | | |
| 181 | <10% | 10-30% | | |
| 182 | 10-30% | | | |
| 183 | >90% | >90% | >90% | >90% |
| 184 | | >90% | | |
| 185 | 70-90% | >90% | | |
| 186 | 70-90% | 50-70% | | |
| 187 | 50-70% | 50-70% | | |
| 188 | 10-30% | <10% | | |
| 189 | 70-90% | >90% | | |
| 190 | 30-50% | 30-50% | | |
| 191 | >90% | >90% | | |
| 193 | 70-90% | >90% | >90% | >90% |
| 195 | >90% | >90% | | |
| 196 | >90% | >90% | | |
| 197 | >90% | >90% | | |
| 198 | 30-50% | 70-90% | | |
| 199 | 30-50% | 50-70% | | |

The enantiomers of Compound 104 had divergent potency with respect to inhibiting LTC4 and LTB4. Notably, Enantiomer 1 demonstrated enhanced % inhibition of LTC4 (0.3 µM—74%) compared to Enantiomer 2 (0.3 µM—10%). Also notably, Enantiomer 1 demonstrated enhanced inhibition of LTB4 (0.3 µM—83%) compared to enantiomer 2 (0.3 µM—24%).

Notably, Compound 104 demonstrated enhanced % inhibition LTC4 (1 µM) (90%) compared to Compound 103 (50-70%). Also notably, Compound 104 demonstrated enhanced % inhibition LTB4 (1 µM) (90%) compared to Compound 103 (50-70%). Structurally, Compounds 103 and 104 differ only in the presence of an —S-alkyl substitutent on the Ar ring of compound 104, and more specifically a —S—$CH_3$ group.

Accordingly, in one embodiment, the present disclosure provides compounds of formula (1) having an —S-alkyl substituent on Ar, and more specifically compounds of formula (1)

(1)

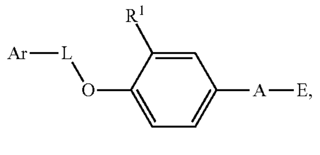

and pharmaceutically acceptable salts thereof, wherein: Ar is a 9- or 10-membered bicyclic aromatic ring system, where Ar is substituted with one, two or three substituents including at least one —S-alkyl, where —S-alkyl may be —S—$C_1$-$C_6$alkyl, e.g., —S-methyl; L is selected from a direct bond and methylene; $R^1$ is selected from hydrogen, halide, $C_1$-$C_6$alkyl, $C_1$-$C_6$haloalkyl and $C_1$-$C_6$alkoxy; A is selected from a direct bond, —$CH_2$— and —$CH_2CH_2$—; E is selected from —C(O)—$R^2$, C($OR^3$)$R^4R^5$ and CH($R^6$)$NR^7R^8$; $R^2$ is selected from methyl, ethyl and phenyl; $R^3$ is selected from H, alkyl and substituted alkyl; $R^4$ is selected from hydrogen, alkyl and phenyl; $R^5$ is selected from $C_1$-$C_7$alkyl, $C_1$-$C_7$haloalkyl, phenyl and substituted phenyl; $R^6$ is selected from hydrogen, methyl, halogenated methyl and ethyl; $R^7$ is hydrogen; and $R^8$ is hydrogen, methyl or ethyl; with the proviso that together, $R^7$ and $R^8$ may form a 5 or 6-membered, optionally substituted, heterocycle. As to the Ar group, optionally Ar is a mono-substituted 9-membered bicyclic aromatic ring; or optionally Ar is a di-substituted 9-membered bicyclic aromatic ring; or optionally Ar is a tri-substituted 9-membered bicyclic aromatic ring; or optionally Ar is a mono-substituted 10-membered bicyclic aromatic ring; or optionally Ar is a di-substituted 10-membered bicyclic aromatic ring; or optionally Ar is a tri-substituted 10-membered bicyclic aromatic ring; or optionally Ar is selected from 1,3-benzoxazole and 1,3-benzothiazole; or optionally Ar is naphthalene or a nitrogen-substituted analog thereof selected from 1,5-naphthyridine, 1,6-naphthyridine, 1,7-naphthyridine, 1,8-naphthyridine, isoquinoline, phthalazine, 2,6-naphthyridine and 2,7-naphthyridine. As to the other substituents, any one or more of the following may be used to further described the compounds of the embodiment: L is a direct bond; L is methylene; $R^1$ is hydrogen; $R^1$ is halogen; $R^1$ is $C_1$-$C_6$alkyl; $R^1$ is $C_1$-$C_6$haloalkyl; $R^1$ is $C_1$-$C_6$alkoxy; A is a direct bond; A is —$CH_2$—; A is —$CH_2CH_2$—; E is —C(O)—$R^2$; $R^2$ is methyl; $R^2$ is ethyl; $R^2$ is phenyl; E is —C($OR^3$)$R^4R^5$; $R^3$ is hydrogen; $R^3$ is alkyl; $R^3$ is substituted alkyl; $R^4$ is hydrogen; $R^4$ is alkyl; $R^4$ is phenyl; $R^5$ is $C_1$-$C_7$alkyl; $R^5$ is $C_1$-$C_7$haloalkyl, e.g., $R^5$ is trifluoromethyl; $R^5$ is phenyl; $R^5$ is substituted phenyl; E is —CH($R^6$)$NR^7R^8$; $R^6$ is hydrogen; $R^6$ is methyl; $R^6$ is halogenated methyl; $R^6$ is ethyl; $R^8$ is hydrogen; $R^8$ is methyl; $R^8$ is ethyl; $R^7$ and $R^8$ together form a 5 membered heterocycle; $R^7$ and $R^8$ together form a substituted 5 membered heterocycle; $R^7$ and $R^8$ together form a 6 membered heterocycle; and/or $R^7$ and $R^8$ together form a substituted 6 membered heterocycle.

Notably, comparing the performance of Compound 103 to Compound 150, Compound 103 demonstrated % Inhibition LTC4 (1 μM) of 50-70% and % Inhibition LTB4 (1 μM) of 50-70%, i.e., there was no detectable difference in performance. However, Compound 150 demonstrated % Inhibition LTC4 (1 μM) of 10-30% and % Inhibition LTB4 (1 μM) of 50-70%, i.e., there was a detectable difference in performance. Structurally, Compounds 103 and 150 differ only in the presence of an —O-alkyl substituent on the benzene ring of compound 103, and more specifically a —O—$CH_3$ group as the $R_1$ substituent.

Accordingly, in one embodiment, the present disclosure provides compounds of formula (1) wherein $R^1$ is O-alkyl, and more specifically compounds of formula (1)

(1)

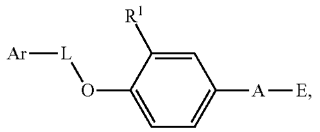

and pharmaceutically acceptable salts thereof, wherein: Ar is a 9- or 10-membered bicyclic aromatic ring system, where Ar is substituted with one, two or three substituents; L is selected from a direct bond and methylene; $R^1$ is $C_1$-$C_6$alkoxy; A is selected from a direct bond, —$CH_2$— and —$CH_2CH_2$—; E is selected from —C(O)—$R^2$, C($OR^3$)$R^4R^5$ and CH($R^6$)$NR^7R^8$; $R^2$ is selected from methyl, ethyl and phenyl; $R^3$ is selected from H, alkyl and substituted alkyl; $R^4$ is selected from hydrogen, alkyl and phenyl; $R^5$ is selected from $C_1$-$C_7$alkyl, $C_1$-$C_7$haloalkyl, phenyl and substituted phenyl; $R^6$ is selected from hydrogen, methyl, halogenated methyl and ethyl; $R^7$ is hydrogen; and $R^8$ is hydrogen, methyl or ethyl; with the proviso that together, $R^7$ and $R^1$ may form a 5 or 6-membered, optionally substituted, heterocycle. As to the Ar group, optionally Ar is an unsubstituted 9-membered bicyclic aromatic ring; or optionally Ar is a mono-substituted 9-membered bicyclic aromatic ring; or optionally Ar is a di-substituted 9-membered bicyclic aromatic ring; or optionally Ar is a tri-substituted 9-membered bicyclic aromatic ring; or optionally Ar is an unsubstituted 10-membered bicyclic aromatic ring; or optionally Ar is a mono-substituted 10-membered bicyclic aromatic ring; or optionally Ar is a di-substituted 10-membered bicyclic aromatic ring; or optionally Ar is a tri-substituted 10-membered bicyclic aromatic ring; or optionally Ar is selected from 1,3-benzoxazole and 1,3-benzothiazole; or optionally Ar is naphthalene or a nitrogen-substituted analog thereof selected from 1,5-naphthyridine, 1,6-naphthyridine, 1,7-naphthyridine, 1,8-naphthyridine, isoquinoline, phthalazine, 2,6-naphthyridine and 2,7-naphthyridine. As to the other substituents, any one or more of the following may be used to further described the compounds of the embodiment: L is a direct bond; L is methylene; A is a direct bond; A is —$CH_2$—; A is —$CH_2CH_2$—; E is —C(O)—$R^2$; $R^2$ is methyl; $R^2$ is ethyl; $R^2$ is phenyl; E is —C($OR^3$)$R^4R^5$; $R^3$ is hydrogen; $R^3$ is alkyl; $R^3$ is substituted alkyl; $R^4$ is hydrogen; $R^4$ is alkyl; $R^4$ is phenyl; $R^5$ is $C_1$-$C_7$alkyl; $R^5$ is $C_1$-$C_7$haloalkyl, e.g., $R^5$ is trifluoromethyl; $R^5$ is phenyl; $R^5$ is substituted phenyl; E is —CH($R^6$)$NR^7R^8$; $R^6$ is hydrogen; $R^6$ is methyl; $R^6$ is halogenated methyl; $R^6$ is ethyl; $R^8$ is hydrogen; $R^8$ is methyl; $R^8$ is ethyl; $R^7$ and $R^8$ together form a 5 membered heterocycle; $R^7$ and $R^8$ together form a substituted 5 membered heterocycle; $R^7$ and $R^8$ together form a 6 membered heterocycle; and/or $R^7$ and $R^8$ together form a substituted 6 membered heterocycle.

Example 101

Whole Blood HPLC Assay

Porcine or human whole blood (1 mL) was pre-incubated with a series of concentrations of compound solubilized in DMSO for 30 minutes. Production of leukotrienes were stimulated with the addition of 20 μM calcium ionophore (A23187), diluted from a 4 mM DMSO stock in HBSS, and incubated at room temperature for 20 minutes. In porcine blood 20 μM arachidonic acid was added in addition to the calcium ionophore. The blood was centrifuged at 2,000 rpm for 15 minutes, and the plasma fraction removed for further processing. Plasma samples were diluted with 500 μL acidified water (HCl pH 3.0) and loaded onto C18 SEP-PAK columns (Canadian Lifesciences IS12000) for solid phase extraction. The leukotrienes were analyzed by HPLC using an ACE C18 column (4.5 mm×150 mm, 5 m) eluted with acetonitrile/methanol/water mixture with $H_3PO_4$, pH 3.5 (37:26:37) with a flow rate of 1.8 mL/min. The amount of $LTB_4$ (Cayman Chemical, 20110) was calculated based on reference standards and the level of inhibition of $LTB_4$ production induced by the test compounds was calculated relative to control samples. The results provided in Table 3 are $IC_{50}$ values calculated based on a 5 point curve, where Compound No. refers to the compounds identified in Table 1.

TABLE 3

| Compound No. | Whole Blood $IC_{50}$ |
|---|---|
| 103 | 1-10 μM |
| 104 | 0.1-1 μM |
| 106 | >10 μM |
| 107 | >10 μM |
| 108 | 1-10 μM |
| 115 | >10 μM |
| 117 | >10 μM |
| 119 | 1-10 μM |
| 132 | >10 μM |
| 137 | >10 μM |
| 138 | 1-10 μM |
| 139 | 1-10 μM |
| 141 | 1-10 μM |
| 146 | 1-10 μM |
| 150 | 1-10 μM |
| 155 | >10 μM |
| 156 | 0.1-1 μM |
| 157 | 1-10 μM |
| 158 | 0.1-1 μM |
| 160 | >10 μM |
| 163 | >10 μM |
| 164 | 0.1-1 μM |
| 166 | 0.1-1 μM |
| 167 | >10 μM |
| 183 | 0.1-1 μM |
| 184 | 0.1-1 μM |
| 185 | 0.1-1 μM |
| 197 | 0.1-1 μM |
| 198 | 0.1-1 μM |
| 199 | >10 μM |

Example 102

Amino-Peptidase Assay—Alanine-4-Nitroanalide

A series of compound concentrations were pre-incubated in the absence of light with 0.5 μg of recombinant human leukotriene A4 hydrolase enzyme (Cayman Chemical 10007817) in 50 μL assay buffer (50 mM Tris-HCl, 100 mM KCl). The reaction was stimulated by adding 50 μL 6 mM alanine-4-nitroanilide (Sigma Aldrich A9325) in assay buffer. The amount of amino-peptidase activity was measured by determining the change in absorbance at 405 nm due to 4-nitroanaline production and comparing the rate of change to a reference standard (Sigma Aldrich 185310). Amino-peptidase activity was compared to control samples and the level of inhibition was calculated. Compounds that augment peptidase activity are represented by negative values. The results are shown in Table 4, where Compound No. refers to the compounds listed in Table 1.

Example 103

Amino-Peptidase Assay—PGP

A series of compound concentrations were pre-incubated with 50 ng of recombinant human leukotriene $A_4$ hydrolase enzyme (Cayman Chemical, 10007817) in 50 L assay buffer (50 mM Tris-HCl, 100 mM KCl). The reaction was stimulated by adding 50 L 1 mM proline-glycine-proline (Bachem, H-7284) and incubated for 30 minutes at 37° C. The reaction was stopped with the addition of 150 μL of glacial acetic acid. The amount of free proline released from the peptide was detected through a reaction with ninhydrin. 150 μL of 25 mg/mL ninhydrin (BDH, B10132) in 60:40 acetic acid/water was added to each sample, and boiled for 30 minutes at 100° C. and once samples had cooled to room temperature, 350 μL of toluene was added to extract the ninhydrin reaction product. The amount of free proline was determined by comparing the absorbance at 520 nm to the L-proline (Sigma Aldrich, 81709) reference standard. Inhibition of free proline production was calculated based on control samples. The results are shown in Table 4, where Compound No. refers to the compounds listed in Table 1.

TABLE 4

| Compound No. | % Inhibition aminopeptidase-Alanine-4-nitroanalide activity of LTA4H (3 μM) | % Inhibition aminopeptidase-PGP activity of LTA4H |
|---|---|---|
| 102 | −0-50% | |
| 104 | −50-100% | |
| 105 | 75% | |
| 109 | −0-50% | |
| 112 | | <25% |
| 121 | −0-50% | |
| 123 | 25-50% | |
| 128 | <25% | |
| 146 | <25% | |
| 147 | 50-75% | 25-50% |
| 148 | <25% | |
| 149 | <25% | 25-50% |
| 150 | 25-50% | <25% |
| 152 | <25% | 25-50% |
| 154 | >75% | |
| 158 | 50-75% | |
| 164 | >75% | |
| 165 | 50-75% | |
| 166 | <25% | |
| 167 | >75% | |
| 173 | −0-50% | |
| 175 | 50-75% | |
| 176 | <25% | |
| 177 | >75% | |
| 178 | 70-90% | 70-90% |
| 179 | >75% | >75% |
| 180 | 50-75% | |
| 181 | −0-50% | >75% |
| 182 | <25% | |
| 183 | >75% | >75% |
| 184 | <25% | 25-50% |
| 186 | >75% | >75% |
| 187 | >75% | 50-75% |
| 188 | <25% | 25-50% |
| 190 | <25% | 25-50% |

Example 104

Arachidonic Acid (AA) Induced Mouse Ear Edema Model

The mouse model of arachidonic acid induced ear edema is an acute model of inflammation of the skin exhibiting redness and swelling in response to application of the stimulus to the skin. One group serves as a control and receives 20 μL of vehicle applied to the pinna of each ear (10

μL to the inside and 10 μL to the outside of the pinna). One or more additional groups serve as test groups. The test compound was applied to the pinna of one ear of the mouse in a 20 μL volume (10 μL to the inside and 10 μL to the outside of the pinna). Test compound or control vehicle (acetone/1% DMSO) was applied topically to the right ear 4 and 1 hour before the application of 2 mg/ear AA as a stimulus to both the inner and outer surfaces of CD-1 mice. The left ears received vehicle (acetone/1% DMSO) alone.

The animal was lightly anesthetized again using isofluorane to enable application of the stimulus. For the control group, arachidonic acid (2 mg/ear) was applied as the stimulus to the pinna of one ear only, in a total volume of 20 μL of acetone (10 μL applied to the inside and 10 μL to the outside of the pinna). The other ear received 20 μL of acetone. This served to determine the increase in ear weight due to arachidonic acid in the absence of test compounds. For the test groups, arachidonic acid (2 mg/ear) was applied as the stimulus to the pinna of each ear, in a total volume of 20 μL of acetone (10 μL applied to the inside and 10 μL to the outside of the pinna). The animal was allowed to recover after application of the stimulus in each case. After 60 minutes the animal was euthanized and a standard biopsy sample was taken from each ear using a 6 mm skin biopsy punch (Acuderm). Ear edema was determined by the increase in weight of the tissue due to accumulation of fluid as a result of plasma extravasation. The ears were weighed separately using a balance suitable to record 0.1 mg. For the control group, the difference in ear weights was determined by subtracting the weight of the unstimulated ear from the stimulated ear, and this was a measure of the increase in ear weight due to edema. The percentage increase in ear weight was determined by dividing the increase in stimulated ear weight by the unstimulated ear weight and multiplying by 100. For the test groups, the difference in ear weights was determined by subtracting the weight of the untreated ear from the weight of the ear treated with test compound. The percent inhibition of the increase in ear weight for ears treated with the test compound was estimated by first subtracting the mean ear weight of the untreated controls from each tissue to determine the increase in tissue weight due to application of the arachidonic acid.

The percent inhibition=1−(test drug stimulated ear (mg)/control stimulated ear (mg))×100.

In Table 5, the data from inhibition of AA-induced ear edema in mice by topical application of compounds is provided. Compounds (0.3 or 1 mg/ear) were applied topically to the ear 4 hrs and 1 hr prior to application of arachidonic acid (AA; 2 mg/ear). Representative data from 4-6 mice per treatment group is shown, where Compound No. refers to the compounds listed in Table 1.

TABLE 5

| Compound No. | % Inhibition AA-Induced ear edema (1 mg/ear) | % Inhibition AA-Induced ear edema (0.3 mg/ear) |
|---|---|---|
| 103 | 70-90% | 30-50% |
| 158 | 10-30% | |
| 108 | 30-50% | <10% |
| 104 | 50-70% | 30-50% |
| 183 | >90% | 30-50% |
| 119 | 50-70% | 30-50% |

Example 105

Lipopolysaccharide (LPS) Mouse Lung Inflammation Model

In this model, LPS was instilled into the lungs of mice to induce a neutrophilia in the lung tissue. The neutrophilia can be measured in the BAL fluid during lung lavage at various times after challenge with LPS. The neutrophilia develops with a significant increase in cells in the BAL after 6 hrs and achieves a maximum response by 24 hrs.

CD-1 mice received lipopolysaccharide (LPS) 2.5 mg/kg in phosphate buffered saline (PBS) or PBS in a volume of 50 μL by intracheal instillation into the lung. The animals were lightly anesthetized using isofluorane to enable application of the LPS. When anesthetized the animals were placed on a board at an angle of 45°. The tongue was rolled to one side and LPS was administered directly into the trachea in a volume of 50 μL. The animal remained in position for 1-2 minutes to ensure the LPS remained in the lung. At the end of the LPS challenge time, animals were euthanized by an overdose of isofluorane. The trachea was exposed and the lungs were intubated using a 21 G catheter tube. The lungs were lavaged with 2×1 mL of PBS at room temperature. The recovered bronchiolar lavage fluid (BAL) was placed on ice and centrifuged at 2500 rpm (desktop centrifuge) for 5 min to pellet the recovered cells. The BAL supernatant was removed and the cell pellet was resuspended in 150 μL of PBS. The differential cell counts were determined using an automated cell counter (Abraxia) set to measure mouse cells. Cell concentration of the resuspended sample was expressed as total cells recovered in the total volume of recovered BAL.

Animals receive test drug or vehicle (polyethylene glycol 200 (PEG200) with 1% DMSO) at doses of 10-30 mg/kg orally at various times prior to and after instillation of LPS. For example, test drug may be administered 30 minutes prior to LPS, and again 2 hours after LPS, or may be co-administered with LPS and again 2 hrs and 4 hrs after LPS.

The resulting data is shown in FIG. 1, which shows the effect of Compound 104 on LPS-induced neutrophil infiltration into the lung. Animals were treated orally with either 10 mg/kg of Compound 104, 1 mg/kg Dexamethasone or dosing vehicle (PEG 200 with 1% DMSO) 1 hr before and 2 hrs after 2.5 mg/kg LPS was administered intratracheally. Animals were euthanized 6 hr post-LPS and the BAL was collected from the lung. The results demonstrating inhibitory effect of Compound 104 are shown in FIG. 1, which represent the mean±standard deviation, n=7-10 animals per group.

Example 106

Rat Endotoxin Induced Uveitis (EIU) Model

The endotoxin induced uveitis (EIU) model employs an injection of LPS into the hind footpad of the rat with assessment of inflammation in the eye 24 hrs later. EIU can be induced by systemic injection of lipopolysaccharide (LPS), which generates inflammatory responses largely in the anterior uvea and mild responses in the posterior segments of the eye, mimicking the pathological conditions in human acute anterior uveitis.

In general, cellular inflammation in EIU starts 4 hrs after injection of LPS, with maximum infiltration after 18-24 hrs. Inflammation in the eye is determined by assessment of the clinical score, and determination of cell content and protein content in the aqueous and vitreous humor of the each eye. Aqueous and vitreous humor from normal control animals have few detectable cells present, and low levels of protein, with organized tissues layers under histological examination. In contrast, after LPS the aqueous humor has elevated cell content and protein content, extravasation into the anterior space manifested by the ability to remove a larger volume of fluid for assessment. Similar effects are observed in the vitreous humor, with a large vitreous humor mass which is easily extracted for evaluation. Histologically structures within the tissue are less well organized showing evidence of inflammatory cell infiltrate, large amount of protein matrix in the aqueous humor, and disorganization and inflammatory cell infiltration associated with the iris-ciliary body.

Rats received an injection of 75 μg LPS, prepared in 100 μL saline, into the hind footpad to initiate disease. The level of inflammation in the eye was evaluated by assessment of the clinical score which assesses iris hyperemia, pupil dilation, exudate and hypopyon, and determination of cell content and protein content in the aqueous and vitreous humor of the each eye through histological examination of tissue sections.

Animals received test drug or vehicle (PEG 200 with 1% DMSO) at doses of 30 mg/kg orally at various times prior to and after injection of LPS. Animals may also receive test drug topically where the test drug was administered as a 10 μL drop directly to the eye, using a dose solution up to 1% test drug in a formulation consisting of 20% hydroxypropyl beta-cyclodextrin, 0.5% hydroxypropyl methyl cellulose and 1.6 mM EDTA in PBS, directly to the eye at various times before and after LPS administration.

Figure 2:
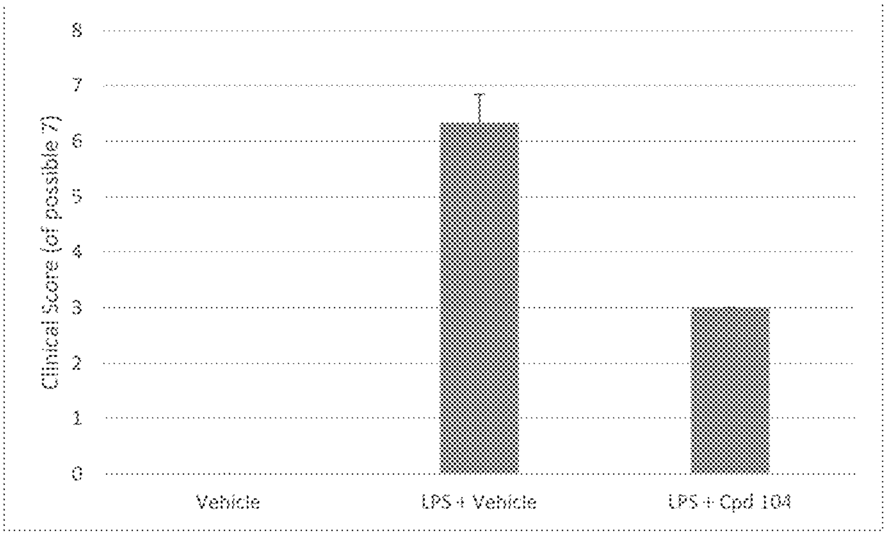
FIG. 2 shows the effect of Compound 104 on clinical scores in the EIU rat model. Animals were treated with 30 mg/kg of Compound 104 or dosing vehicle orally 15 min before and 5 hrs after 75 μg of LPS from *Salmonella Typhimurium* in saline 2.5 mg/kg LPS was administered subcutaneously in the hind foot pad of each foot. Mean clinical scores were determined at 24 hrs post LPS dose. Values represent the mean±standard deviation, n=3 per group.

The results for oral dosing of test drug are provided in FIG. 2. FIG. 2 shows the effect of Compound 104 on clinical scores in the EIU rat model. Animals were treated with 30 mg/kg of Compound 104 or dosing vehicle (PEG 200 with 1% DMSO) orally 15 min before and 5 hrs after 75 μg of LPS from *Salmonella typhimurium* in 100 μL saline was administered subcutaneously in the hind foot pad of each foot. Mean clinical scores were determined at 24 hrs post LPS dose. Values shown in FIG. 2 represent the mean±standard deviation, n=3 per group.

Example 107

Rat Ocular Distribution Model

Eye drops were prepared by adding compounds at a theoretical concentration of 10 mg/mL to a 2 mL microcentrifuge tube before adding a stir bar and the selected formulation that consisted of (w/v) hydroxypropyl β-cyclodextrin (Trappsol) (20%), hydroxyl propyl methylcellulose (0.5%) and EDTA (1.6 mM) in phosphate buffered saline. Tubes containing compound in eye drop formulation were heated to 60-65° C. and stirred at least 4 hours to overnight. The tubes were removed from the heat bath and centrifuged at 10,000 ref for 5 minutes to clear the solution of any residual drug not in solution. The supernatant was removed from the tubes and one 10 μL sample was removed for HPLC analysis of solubilized by HPLC using an ACE C18 column (4.5 mm×150 mm, 5 m), eluted with acetonitrile/methanol/water mixture with $H_3PO_4$, pH 3.5 (50:30:20) with a flow rate of 2.5 mL/min. The solubilized concentration of each compound was calculated by interpolation from a standard curve based on reference standards solubilized in methanol when the assay was validated.

Compounds were applied as a single 10 μL drop to rats and the aqueous humor, and the posterior segment of the eye (vitreous body and retina) were collected from each eye at the time point assigned after the eye was irrigated to remove any residual formulation present. Tissues were collected in pre-weighed collection tubes and the tissue weight was determined for each sample. An internal standard (IS) mixture containing a reference compound at a ratio of 1 μL to 4 mg tissue was added to samples, mixed and then diluted× 4.25 in acetonitrile:methanol (9:1). Aqueous humour samples were vortex mixed for 10 s. The vitreous body & retina were vortex mixed 2 times each for 10 s, and further mixed for 6 min on a tabletop shaker at 750 rpm followed by final vortex mixing (10 s). All samples were centrifuged to pellet any particulate matter and the supernatant was transferred to LC vials. A 10 μL sample was then applied to the HPLC during LC/MS/MS analysis. A calibration curve for compounds (0.588-176.471 ng/mL) was prepared in rat plasma to estimate concentrations of compounds in each of the matrices analyzed using the area under curve (AUC) normalized to internal standard AUC for determining response. The assumption was made that 1 mg tissue is equivalent to 1 μL plasma. Concentrations measured in each tissue were then normalized to the amount of drug applied to account for differences in solubilized drug in each formulation. The average concentration and the standard deviation was determined based on "n"=number of eyes assessed, rather than the number of animals.

In Table 6, the data from distribution studies performed in Lewis rats show the concentration of each compound present in the retina 0.5 hr after the administration of a 10 μL drop of each topical formation is provided. Compounds were paired and individual formulations mixed at a ratio to make a mixture that contained ~2.5 mg/mL of each compound. Representative data from 2 eyes is shown, where Compound No. refers to the compounds listed in Table 1.

TABLE 6

| Compound No. | Concentration of compound in formulation (ng/mL) | Concentration of compound in retina 0.5 hr after administration (ng/mL) per mg compound applied (Avg ± SD) n = 2 |
|---|---|---|
| 104 | 2.86 | 3340 ± 1061 |
| 191 | 1.65 | 4872 ± 1672 |
| 193 | 2.53 | 15690 ± 9863 |
| 195 | 3.64 | 3343 ± 2.4 |

Figure 3:
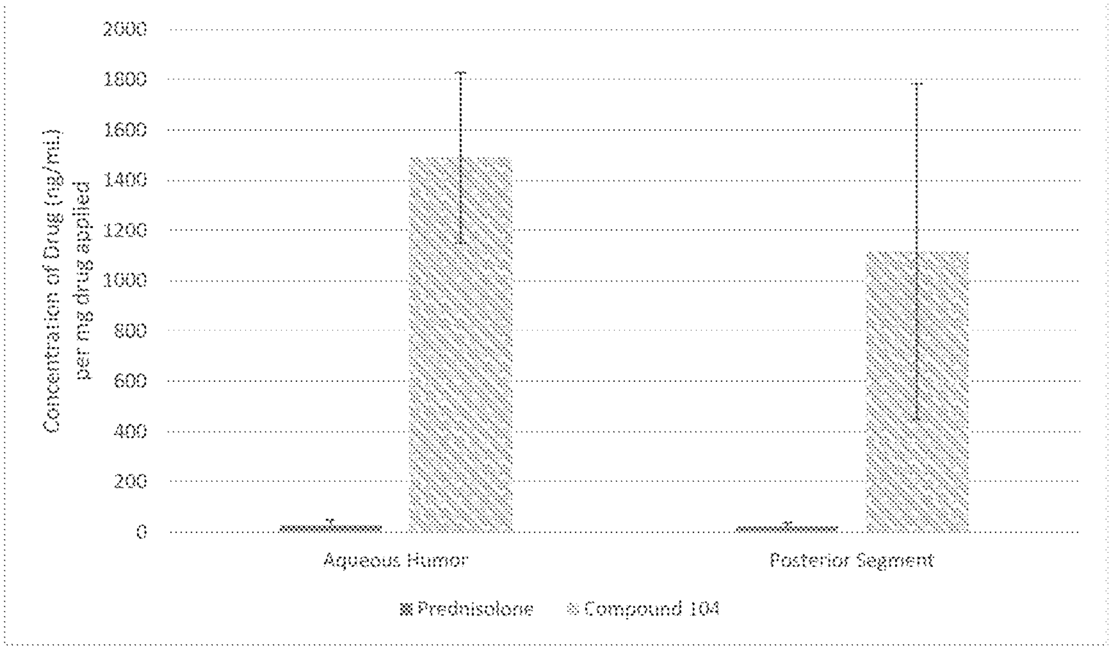
FIG. 3. shows the superior ability of Compound 104 to distribute to the posterior section (vitreous+retina) of the eye compared to standard of care Prednisolone. Sprague Dawley rats received a 10 μL drop of either Compound 104 (0.4%) or commercially available ophthalmic prednisolone acetate (1%) and tissues were removed 2 hours post administration to measure compound concentration. The resulting data in FIG. 3, which represent the mean±standard deviation, n=5 eyes per drug, shows that Compound 104 was absorbed into the posterior segment at levels approximately 50 times that of prednisolone 2 hours after administration.

In another study, Sprague Dawley rats received a 10 μL drop of either Compound 104 (0.4%) or commercially available ophthalmic prednisolone acetate (1%) and tissues were removed 2 hours post administration to measure compound concentration by LC/MS/MS. The resulting data in FIG. 3, which represent the mean±standard deviation, n=5 eyes per drug, shows that Compound 104 was absorbed into the posterior segment at levels 50× that of prednisolone 2 hours after administration.

Example 108

Rat Experimental Autoimmune Uveitis (EAU) Model

Experimental autoimmune uveitis is an organ specific T-cell mediated autoimmune disease that targets neural retinal and related tissues that is induced by immunization with retinal antigens. Histologically it involves inflammatory cell infiltration of the retina leading to photoreceptor damage, extending to the inner nuclear layer, leading to edema and retinal detachment at the peak of severity. In additional to changes in the eye posteriorly, inflammatory cell infiltration is prominent in the anterior segment of the eye, with vascular engorgement, loss of red reflex, and haziness in anterior chamber.

The experimental autoimmune uveitis (EAU) model is initiated by injection of Complete Freund's Adjuvant (CFA) containing a heat killed form of a laboratory strain of tuberculosis bacteria and a peptide directed towards toward a retinal protein that causes inflammation in the eye in susceptible animals such as the Lewis rat. At approximately 6-7 days after injection of the CFA and retinal protein, clinical signs of ocular inflammation are visible, which peak at approximately 10-14 days, and are mostly resolved within 21 days.

Lewis rats were injected with an emulsion of retinal peptide (<100 μg) and Complete Freund's Adjuvant (2-3 mg/ml) subcutaneously with 100 μL injection at the base of the tail and an additional 50 μL in each thigh. This was undertaken in a biological safety cabinet, and throughout the study the animals remain in containment housing. The animal was lightly anesthetized using isofluorane to enable administration of the stimulus. Starting at day 6-8 after immunization, rats were lightly anesthetized using isofluorane to enable administration of the dose of test drug as 10 μL drop directly to the eye, using a dose solution up to 1% test drug in a formulation consisting of 20% hydroxypropyl beta-cyclodextrin, 0.5% hydroxypropyl methyl cellulose and 1.6 mM EDTA in PBS, and continue to be treated as the disease develops over several days. Disease symptoms were scored to assess blood vessel dilation, engorgement of blood vessels, change in red reflex and haziness of anterior chamber and proptosis (scale 0-4) (Agarwal et al Autoimmunity: Methods and Protocols, Methods in Molecular Biology, vol. 900, Ch 22). Animals were euthanized by isoflurane and $CO_2$ and the eye excised and evaluated histologically for structural changes and inflammatory cell infiltrate within the eye and scored based on pathological changes (Gadjanski et al./Experimental Eye Research 93 (2011) 82e90). Retinal thickness measurements were performed on histological sections using Aperio ImageScope (Leica Biosystems) from the retinal pigment epithelial layer to the internal limiting membrane.

Figure 4A:
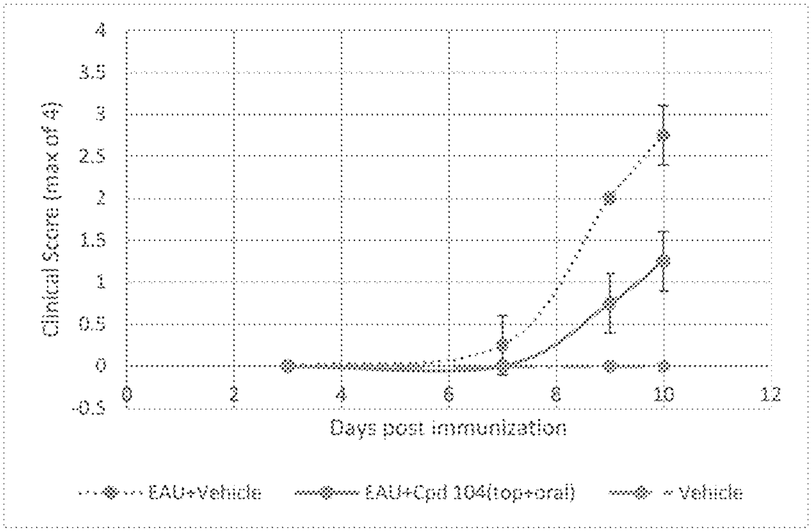
FIG. 4A shows the effect of Compound 104 on clinical scores and histological evaluation in the EAU rat model. Animals were immunized with 30 μg of peptide in an emulsion containing 2 mg/mL Complete Freunds Adjuvant on day 0. From day 6 post immunization, animals received 10 μL of 0.5% wt/vol Compound 104 or vehicle topically in each eye every 3 hours for four doses each day, and once orally (30 mg/kg) immediately after the last topical dose each day. Animals were treated daily until euthanized 10 days post-immunization and tissues collected for histological examination. Values represent the mean±standard deviation of 4 eyes, n=2 per group. In this Figure, 4A the mean clinical scores were determined at various times post immunization as indicated.
Figure 4B:
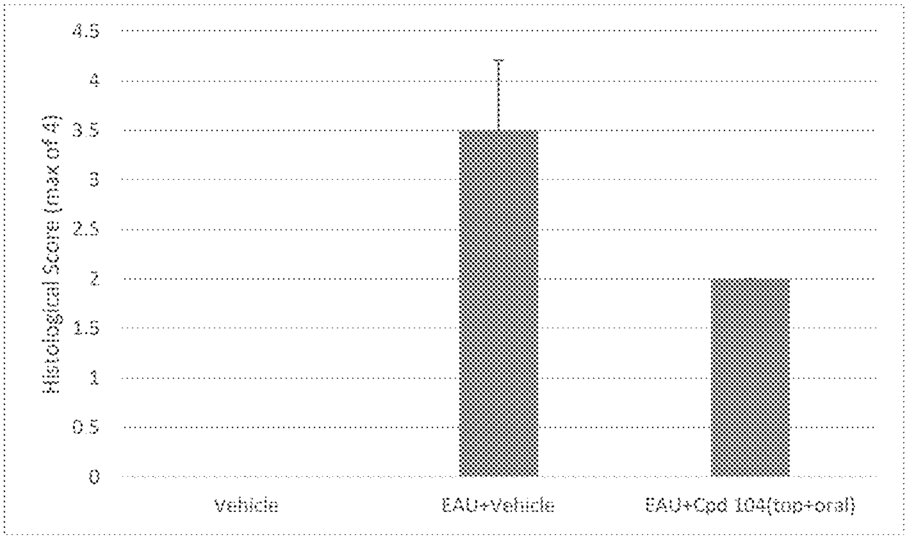
FIG. 4B is data taken from the same experiment as described for FIG. 4A, where
Figure 4C:
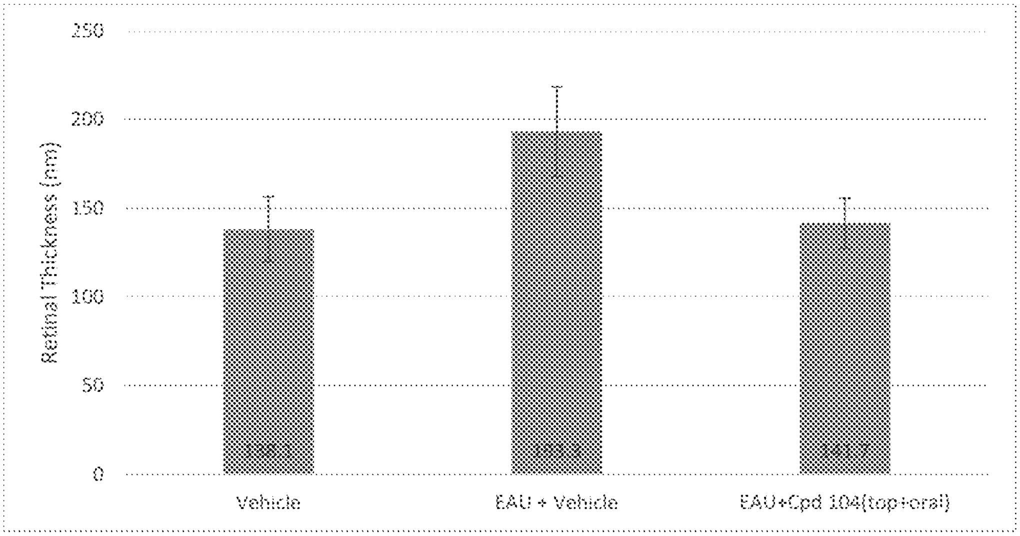
FIG. 4C is data taken from the same experiments as described for FIG. 4A, where

The results from this example are shown in FIG. 4A, FIG. 4B and FIG. 4C. In these figures, the effect of Compound 104 on clinical scores and histological evaluation in the EAU rat model is shown. Animals were immunized with 30 μg of peptide in an emulsion containing 2 mg/mL Complete Freunds Adjuvant on day 0. From day 6 post immunization, animals received 10 μL of 0.5% wt/vol Compound 104 or vehicle (liquid formulation containing of 20% hydroxypropyl beta-cyclodextrin, 0.5% hydroxypropyl methyl cellulose and 1.6 mM EDTA in PBS) topically in each eye every 3 hours for four doses each day, and once orally (30 mg/kg) immediately after the last topical dose each day. Animals were treated daily until euthanized 10 days post-immunization and tissues collected for histological examination. Values represent the mean±standard deviation of 4 eyes, n=2 per group. FIG. 4A shows the mean clinical scores which were determined at various times post immunization. FIG. 4B shows histological scores which were obtained 10 days post immunization. FIG. 4C shows the results of retinal thickness measurements which were determined from histological slides 10 days post immunization.

For selected compounds prepared according to the previous examples, $^1$H nuclear magnetic resonance spectroscopy was performed to obtain $^1$H NMR spectra, which are characterized as described and provided in Table 7.

TABLE 7

| Compound No. | NMR data |
|---|---|
| 101 | $^1$H NMR (300 MHz, $CDCl_3$): δ 7.74 (d, 1H), 7.64 (d, 1H), 7.44-7.18 (m, 3H), 6.93-6.79 (m, 2H), 3.80 (s, 3H), 2.94 (t, 2H), 2.78 (t, 2H), 2.45 (q, 2H), 1.07 (t, 3H). |
| 103 | $^1$H NMR (300 MHz, $CDCl_3$): δ 7.75 (d, 1H), 7.64 (d, 1H), 7.46-7.20 (m, 3H), 6.93-6.82 (m, 2H), 3.81 (s, 3H), 2.83-2.71 (m, 2H), 2.12-1.97 (m, 2H), 1.85 (q, 2H), 1.05 (t, 3H). |
| 104 | $^1$H NMR (300 MHz, $CDCl_3$): δ 7.44-7.37 (m, 1H), 7.26 (d, 1H), 7.23-7.16 (m, 2H), 6.88-6.80 (m, 2H), 3.82 (s, 3H), 2.77 (t, 2H), 2.55 (s, 3H), 2.08-1.97 (m, 2H), 1.94 (s, 1H), 1.90-1.78 (m, 2H), 1.06 (t, 3H). |
| 105 | $^1$H NMR (300 MHz, $CDCl_3$): δ 7.55-7.50 (m, 1H), 7.27 (d, 1H), 7.24-7.20 (m, 1H), 7.19-7.14 (m, 2H), 6.86-6.80 (m, 2H), 3.78 (s, 3H), 3.75 (s, 3H), 2.74 (t, 2H), 2.08-1.95 (m, 3H), 1.90-1.76 (m, 2H), 1.05 (t, 3H). |
| 106 | $^1$H NMR (400 MHz, $CDCl_3$): δ 8.28 (d, 1H), 7.92 (dd, 1H), 7.85 (d, 1H), 7.24 (d, 1H), 6.91-6.85 (m, 2H), 3.82 (s, 3H), 3.08 (s, 3H), 2.78 (t, 2H), 2.08-2.00 (m, 2H), 1.97 (s, 1H), 1.91-1.79 (m, 2H), 1.06 (t, 3H). |
| 107 | $^1$H NMR (400 MHz, $CDCl_3$): δ 7.24 (d, 1H), 7.18-7.13 (m, 1H), 6.94-6.82 (m, 3H), 3.82 (s, 3H), 2.77 (t, 2H), 2.06-1.98 (m, 2H), 1.95 (s, 1H), 1.89-1.80 (m, 2H), 1.06 (t, 3H). |
| 108 | $^1$H NMR (300 MHz, $CDCl_3$): δ 7.66 (dd, 1H), 7.34 (dd, 1H), 7.30-7.20 (m, 1H), 7.16-7.05 (m, 1H), 6.93-6.82 (m, 2H), 3.82 (s, 3H), 2.83-2.72 (m, 2H), 2.04-1.79 (m, 5H), 1.06 (t, 3H). |
| 111 | $^1$H NMR (400 MHz, $CDCl_3$): δ 7.72 (d, 1H), 7.64 (d, 1H), 7.39-7.33 (m, 1H), 7.27-7.21 (m, 2H), 6.89-6.82 (m, 2H), 3.82 (s, 3H), 2.90-2.73 (m, 2H), 2.12-1.94 (m, 3H), 1.45 (s, 3H). |
| 115 | $^1$H NMR (400 MHz, $CDCl_3$): δ 7.71 (d, 1H), 7.64 (d, 1H), 7.39-7.34 (m, 1H), 7.27-7.21 (m, 2H), 6.89-6.81 (m, 2H), 4.58-4.48 (m, 1H), 2.74 (t, 2H), 2.07-1.97 (m, 2H), 1.95 (s, 1H), 1.92-1.78 (m, 2H), 1.21 (d, 6H), 1.05 (t, 3H). |
| 116 | $^1$H NMR (400 MHz, $CDCl_3$): δ 7.70 (d, 1H), 7.64 (d, 1H), 7.38-7.33 (m, 1H), 7.27-7.19 (m, 2H), 6.86-6.78 (m, 2H), 4.78 (p, 1H), 2.74 (t, 2H), 2.06-1.99 (m, 2H), 1.95 (s, 1H), 1.87-1.80 (m, 2H), 1.78-1.70 (m, 4H), 1.52-1.39 (m, 4H), 1.05 (t, 3H). |
| 117 | $^1$H NMR (400 MHz, $CDCl_3$): δ 7.71 (d, 1H), 7.64 (d, 1H), 7.39-7.33 (m, 1H), 7.27-7.20 (m, 2H), 6.87-6.81 (m, 2H), 3.83 (d, 2H), 2.74 (t, 2H), 2.05-1.98 (m, 2H), 1.95 (s, 1H), 1.88-1.80 (m, 2H), 1.05 (t, 4H), 0.43-0.36 (m, 2H), 0.15-0.10 (m, 2H). |
| 119 | $^1$H NMR (400 MHz, $CDCl_3$): δ 7.44-7.38 (m, 1H), 7.26 (d, 1H), 7.22-7.17 (m, 2H), 6.90-6.82 (m, 2H), 3.82 (s, 3H), 2.87-2.76 (m, 2H), 2.54 (s, 3H), 2.08-1.94 (m, 3H), 1.46 (s, 3H). |

TABLE 7-continued

| Compound No. | NMR data |
|---|---|
| 121 | $^1$H NMR (300 MHz, $CDCl_3$): δ 7.76 (d, 1H), 7.64 (d, 1H), 7.39 (t, 1H), 7.32-7.19 (m, 2H), 6.92-6.80 (m, 2H), 4.05 (q, 2H), 2.82-2.70 (m, 2H), 2.50 (broad s, 1H), 2.11-1.97 (m, 2H), 1.92-1.78 (m, 2H), 1.23 (t, 3H), 1.05 (t, 3H). |
| 122 | $^1$H NMR (300 MHz, $CDCl_3$): δ 7.75 (d, 1H), 7.64 (d, 1H), 7.48-7.19 (m, 3H), 7.01-6.82 (m, 2H), 3.98-3.78 (m, 1H), 3.80 (s, 3H), 2.92-2.64 (m, 2H), 2.00-1.75 (m, 3H), 1.27 (d, 3H). |
| 123 | $^1$H NMR (300 MHz, $CDCl_3$): δ 7.74 (d, 1H), 7.63 (d, 1H), 7.55-7.14 (m, 8H), 6.85-6.72 (m, 2H), 3.77 (s, 3H), 2.77-2.40 (m, 2H), 2.27-2.12 (m, 2H), 2.01 (broad s, 1H), 1.65 (s, 3H). |
| 124 | $^1$H NMR (300 MHz, $CDCl_3$): δ 7.74 (d, 1H), 7.64 (d, 1H), 7.38 (t, 1H), 7.31-7.19 (m, 2H), 6.95-6.81 (m, 2H), 3.81 (s, 3H), 2.86-2.69 (m, 2H), 1.93-1.73 (m, 3H), 1.32 (s, 6H). |
| 126 | $^1$H NMR (300 MHz, $CDCl_3$): δ 7.51 (d, 1H), 7.41 (d, 1H), 7.32-7.17 (m, 3H), 6.92-6.82 (m, 2H), 3.81 (s, 3H), 2.79-2.68 (m, 2H), 1.88-1.66 (m, 3H), 1.32 (s, 6H). |
| 127 | $^1$H NMR (300 MHz, $CDCl_3$): δ 7.50 (d, 1H), 7.41 (d, 1H), 7.33-7.16 (m, 3H), 6.95-6.80 (m, 2H), 3.81 (s, 3H), 2.77-2.66 (m, 2H), 1.86-1.73 (m, 2H), 1.58 (q, 2H), 1.25 (s, 3H), 0.96 (t, 3H). |
| 128 | $^1$H NMR (300 MHz, $CDCl_3$): δ 7.61-7.16 (m, 10H), 6.85-6.73 (m, 2H), 3.77 (s, 3H), 2.75-2.38 (m, 2H), 2.30-2.01 (m, 3H), 1.64 (s, 3H). |
| 129 | $^1$H NMR (300 MHz, $CDCl_3$): δ 7.98 (d, 2H), 7.81-7.20 (m, 8H), 6.98-6.84 (m, 2H), 4.04 (q, 2H), 3.34 (t, 2H), 3.09 (t, 2H), 1.23 (t, 3H). |
| 130 | $^1$H NMR (300 MHz, $CDCl_3$): δ 7.75 (s, 1H), 7.68-7.57 (m, 3H), 7.53-7.34 (m, 4H), 7.32-7.16 (m, 2H), 6.82-6.71 (m, 2H), 4.00 (q, 2H), 2.80-2.33 (m, 5H), 1.21 (t, 3H). |
| 132 | $^1$H NMR (300 MHz, $CDCl_3$): δ 7.76 (d, 1H), 7.64 (d, 1H), 7.51-7.17 (m, 8H), 6.97-6.80 (m, 2H), 4.83-4.70 (m, 1H), 3.79 (s, 3H), 2.95-2.64 (m, 2H), 2.35-2.06 (m, 3H). |
| 133 | $^1$H NMR (300 MHz, $CDCl_3$): δ 7.79 (d, 1H), 7.67-7.59 (m, 3H), 7.49-7.24 (complex m), 7.19 (d, 1H), 6.79-6.73 (m, 2H), 3.78 (s, 3H), 2.77-2.69 (m, 1H), 2.59-2.51 (m, 1H), 2.42-2.36 (m, 2H). |
| 134 | $^1$H NMR (400 MHz, $CDCl_3$): δ 7.71 (d, 1H), 7.64 (d, 1H), 7.40-7.27 (m, 6H), 7.26-7.20 (m, 1H), 7.18 (d, 1H), 6.76-6.71 (m, 2H), 3.76 (s, 3H), 3.24-3.14 (m, 1H), 2.58 (broad s, 2H), 2.48-2.06 (m, 6H), 1.83-1.69 (m, 4H). |
| 136 | $^1$H NMR (400 MHz, $CDCl_3$): δ 12.8 (broad s, 1H), 7.70 (d, 1H), 7.64 (d, 1H), 7.39-7.33 (m, 1H), 7.27-7.19 (m, 2H), 7.00 (s, 1H), 6.85 (dd, 1H), 4.56-4.40 (m, 2H), 4.02-3.92 (m, 2H), 3.84 (s, 3H), 3.37-3.23 (m, 2H), 3.08-2.79 (m, 5H), 2.52-2.39 (m, 1H), 2.15-1.94 (m, 2H), 1.86-1.69 (m, 1H), 1.16 (t, 3H). |
| 137 | $^1$H NMR (400 MHz, $CDCl_3$): δ 7.72 (d, 1H), 7.67 (d, 1H), 7.41-7.32 (m, 2H), 7.30-7.23 (m, 1H), 7.20 (s, 1H), 7.09 (d, 1H), 5.03-4.96 (m, 1H), 3.84 (s, 3H), 3.10 (d, 1H). |
| 138 | $^1$H NMR (400 MHz, DMSO-$d_6$): δ 7.91 (d, 1H), 7.67 (d, 1H), 7.45 (d, 1H), 7.43-7.38 (m, 2H), 7.34-7.28 (m, 1H), 7.18 (d, 1H), 4.51-4.41 (m, 1H), 3.79 (s, 3H), 2.94-2.85 (m, 1H), 2.58-2.48 (m, 1H), 1.04 (t, 3H). |
| 139 | $^1$H NMR (400 MHz, $CDCl_3$): δ 7.44 (dd, 1H), 7.40 (d, 1H), 7.23-7.18 (m, 3H), 7.10 (d, 1H), 5.12-5.04 (m, 1H), 3.85 (s, 3H), 2.76 (d, 1H), 2.53 (s, 3H). |
| 140 | $^1$H NMR (300 MHz, $CDCl_3$): δ 7.74 (d, 1H), 6.67 (s, 1H), 7.47-7.23 (m, 6H), 2.95-2.70 (m, 2H), 2.16-1.93 (m, 2H), 1.46 (s, 3H). |
| 141 | $^1$H NMR (300 MHz, $CDCl_3$): δ 7.75 (d, 1H), 7.66 (d, 1H), 7.48-7.13 (m, 6H), 3.95-3.78 (m, 1H), 2.91-2.63 (m, 2H), 1.92-1.74 (m, 2H), 1.26 (d, 3H). |
| 142 | $^1$H NMR (300 MHz, $CDCl_3$): δ 7.75 (d, 1H), 7.66 (d, 1H), 7.45-7.23 (m, 6H), 2.86-2.65 (m, 2H), 1.93-1.74 (m, 3H), 1.18 (s, 3H), 1.07-0.89 (m, 6H). |
| 143 | $^1$H NMR (300 MHz, $CDCl_3$): δ 7.75 (d, 1H), 7.66 (d, 1H), 7.45-7.09 (m, 6H), 2.82-2.65 (m, 2H), 1.90-1.73 (m, 2H), 1.69-1.51 (m, 3H), 1.24 (s, 3H), 0.952 (t, 3H). |
| 144 | $^1$H NMR (300 MHz, $CDCl_3$): δ 7.74 (d, 1H), 7.65 (s, 1H), 7.56-7.10 (m, 11H), 2.75-2.40 (m, 2H), 2.24-2.06 (m, 3H), 1.64 (s, 3H). |
| 145 | $^1$H NMR (300 MHz, $CDCl_3$): δ 7.74 (d, 1H), 7.66 (d, 1H), 7.66 (d, 1H), 7.55-6.99 (m, 10H), 2.73-2.38 (m, 2H), 2.22-2.08 (m, 2H), 1.63 (s, 3H). |
| 146 | $^1$H NMR (300 MHz, $CDCl_3$): δ 7.67-7.21 (m, 8H), 2.81-2.66 (m, 2H), 1.88-1.67 (m, 3H), 1.58 (q, 2H), 1.24 (s, 3H), 0.95 (t, 3H). |
| 147 | $^1$H NMR (300 MHz, $CDCl_3$): δ 7.63-7.11 (m, 13H), 2.74-2.60 (m, 1H), 2.53-2.40 (m, 1H), 2.22-2.08 (m, 2H), 1.64 (s, 3H). |
| 148 | $^1$HNMR (300 MHz, $CDCl_3$): δ 7.72 (d, 1H), 7.64 (d, 1H), 7.46-7.19 (m, 6H), 3.02-2.88 (m, 2H), 2.83-2.70 (m, 2H), 2.51-2.36 (m, 2H), 1.13-1.00 (m, 3H). |
| 149 | $^1$H NMR (400 MHz, $CDCl_3$): δ 7.71 (d, 1H), 7.68 (d, 1H), 7.42-7.32 (m, 3H), 7.28 (d, 1H), 7.18 (dd, 1H), 2.93 (t, 2H), 2.77 (t, 2H), 2.44 (q, 2H), 1.08 (t, 3H). |
| 150 | $^1$H NMR (300 MHz, $CDCl_3$): δ 7.75 (d, 1H), 7.67 (d, 1H), 7.49-7.24 (m, 6H), 2.77 (t, 2H), 2.13 (broad s, 1H), 2.08-1.97 (m, 2H), 1.92-1.78 (m, 2H), 1.05 (t, 3H). |
| 151 | $^1$H NMR (400 MHz, $CDCl_3$): δ 7.72 (d, 1H), 7.68 (d, 1H), 7.41-7.33 (m, 3H), 7.30-7.25 (m, 1H), 7.19 (dd, 1H), 2.80-2.73 (m, 2H), 2.04-1.98 (m, 2H), 1.94 (s, 1H), 1.90-1.78 (m, 2H), 1.05 (t, 3H). |
| 154 | $^1$H NMR (400 MHz, DMSO-$d_6$): δ 7.96 (d, 1H), 7.68 (d, 1H), 7.53 (t, 1H), 7.46-7.31 (m, 3H), 7.20 (d, 1H), 5.82 (s, 1H), 2.72 (t, 2H), 1.99-1.63 (m, 4H), 0.95 (t, 3H). |
| 158 | $^1$H NMR (400 MHz, $CDCl_3$): δ 7.73 (d, 1H), 7.66 (d, 1H), 7.43-7.33 (m, 1H), 7.33-7.12 (m, 5H), 3.05-2.38 (m, 7H), 2.09-1.52 (m, 8H), 1.01 (t, 3H). |
| 160 | $^1$H NMR (400 MHz, $CDCl_3$): δ 7.74 (d, 1H), 7.68 (d, 1H), 7.47 (d, 2H), 7.43-7.32 (m, 3H), 7.31-7.25 (m, 1H), 4.96 (q, 1H), 1.85 (s, 1H), 1.53 (d, 3H). |
| 161 | $^1$H NMR (400 MHz, $CDCl_3$): δ 7.75 (d, 1H), 7.67 (d, 1H), 7.52 (d, 2H), 7.43-7.36 (m, 1H), 7.33 (d, 2H), 7.30-7.24 (m, 1H), 1.92-1.80 (m, 2H), 1.74 (broad s, 1H), 1.58 (s, 3H), 0.843 (t, 3H). |

TABLE 7-continued

| Compound No. | NMR data |
|---|---|
| 163 | $^1$H NMR (400 MHz, $CDCl_3$): δ 7.75 (d, 1H), 7.72-7.64 (m, 3H), 7.46-7.36 (m, 3H), 7.29 (t, 1H), 2.45 (broad s, 1H), 1.82 (s, 3H). |
| 164 | $^1$H NMR (400 MHz, $CDCl_3$): δ 7.74 (d, 1H), 7.67 (d, 1H), 7.53 (d, 2H), 7.44-7.32 (m, 3H), 7.31-7.23 (m, 1H), 3.82 (s, 2H), 2.76 (broad s, 4H), 2.00-1.83 (m, 4H). |
| 165 | $^1$H NMR (400 MHz, $CDCl_3$): δ 8.00-7.52 (m, 4H), 7.50-7.08 (m, 4H), 4.44 (broad s, 2H), 4.06 (broad s, 1H), 3.72 (broad s, 1H), 3.07 (broad s, 1H), 2.54-1.86 (m, 4H). |
| 166 | $^1$H NMR (400 MHz, $CDCl_3$): δ 7.74 (d, 1H), 7.70 (s, 1H), 7.57 (d, 2H), 7.46-7.36 (m, 3H), 7.30 (t, 1H), 5.09-5.01 (m, 1H), 2.88 (d, 1H). |
| 167 | $^1$H NMR (400 MHz, $CDCl_3$): δ 7.75-7.68 (m, 2H), 7.66 (s, 1H), 7.54-7.36 (m, 3H), 7.34-7.28 (m, 1H), 5.05-4.96 (m, 1H), 3.14 (d, 1H). |
| 168 | $^1$H NMR (400 MHz, $CDCl_3$): δ 7.75 (d, 1H), 7.69 (d, 1H), 7.50 (d, 2H), 7.45-7.37 (m, 3H), 7.32-7.26 (m, 1H), 4.19 (q, 1H), 2.65 (q, 2H), 1.13 (t, 3H). |
| 170 | $^1$H NMR (400 MHz, $CDCl_3$): δ 7.77 (d, 1H), 7.57-7.51 (m, 3H), 7.12 (dd, 1H), 7.04 (d, 2H), 2.83 (s, 3H), 2.52 (d, 1H), 1.78 (s, 3H). |
| 171 | $^1$H NMR (400 MHz, $CDCl_3$): δ 7.74 (d, 1H), 7.53 (d, 1H), 7.36 (d, 2H), 7.10 (dd, 1H), 7.02 (d, 2H), 4.91 (q, 1H), 2.82 (s, 3H), 1.79 (broad s, 1H), 1.51 (d, 3H). |
| 173 | $^1$H NMR (400 MHz, $CDCl_3$): δ 7.72 (d, 1H), 7.66 (d, 1H), 7.41-7.31 (m, 3H), 7.29-7.22 (m, 1H), 7.18 (d, 1H), 3.85 (s, 3H), 2.50 (s, 1H), 1.82 (s, 3H). |
| 183 | $^1$H NMR (400 MHz, $CDCl_3$): δ 8.36-8.17 (m, 2H), 7.88 (d, 1H), 7.84-7.70 (m, 2H), 7.61 (t, 1H), 7.12 (d, 2H), 6.97 (d, 2H), 5.48 (s, 2H), 2.79-2.63 (m, 2H), 2.04-1.85 (m, 3H), 1.42 (s, 3H). |
| 184 | $^1$H NMR (400 MHz, $CDCl_3$): δ 8.17 (d, 1H), 8.08 (d, 1H), 7.81 (d, 1H), 7.76-7.68 (m, 2H), 7.54 (t, 1H), 6.84 (d, 1H), 6.76 (d, 1H), 6.65 (dd, 1H), 5.44 (s, 2H), 3.93 (s, 3H), 2.78-2.62 (m, 2H), 2.04-1.85 (m, 3H), 1.42 (s, 3H). |
| 185 | $^1$H NMR (400 MHz, $CDCl_3$): δ 8.18 (d, 1H), 8.08 (d, 1H), 7.83 (d, 1H), 7.71-7.71 (m, 1H), 7.67 (d, 1H), 7.55 (t, 1H), 7.11 (d, 2H), 6.96 (d, 2H), 5.37 (s, 2H), 2.66 (t, 2H), 1.99-1.91 (m, 2H), 1.89 (broad s, 1H), 1.85-1.76 (m, 2H), 1.02 (t, 3H). |
| 191 | $^1$H NMR (400 MHz, $CDCl_3$): δ [7.93 (dd), 7.75 (dd), 7.48 (t), 7.43-7.38 (m), 2H], 7.24-7.17 (m, 2H), 6.90-6.81 (m, 2H), 3.81 (s, 3H), [2.95 (s), 2.55 (s), 3H], 2.78-2.68 (m, 2H), 1.84-1.76 (m, 2H), 1.62-1.55 (m, 2H), [1.26 (s), 1.25 (s), 3H], 1.00-0.93 (m, 3H). |
| 193 | $^1$H NMR (400 MHz, CDCl3): δ [7.92 (dd), 7.75 (dd), 7.48 (t), 7.44-7.38 (m), 2H], 7.25-7.17 (m, 2H), 6.92-6.81 (m, 2H), 3.81 (s, 3H), 3.64-3.55 (m, 1H), [2.94 (s), 2.56 (s), 3H], 2.90-2.80 (m, 1H), 2.77-2.66 (m, 1H), 1.90-1.72 (m, 2H), 1.62-1.45 (m, 2H), 1.02-0.94 (m, 3H). |
| | $^1$H NMR (400 MHz, DMSO-d6): δ 7.63 (d, 1H), 7.32 (d, 1H), 7.28 (t, 1H), 7.25-7.21 (m, 1H), 7.10 (d, 1H), 6.89 (dd, 1H), 4.45 (br s, 1H), 3.77 (s, 3H), 2.82-2.72 (m, 1H), 2.68-2.58 (m, 1H), 2.49 9s, 3H), 1.76-1.55 (m, 2H), 1.49-1.31 (m, 2H), 0.88 (t, 3H). |
| 195 | $^1$H NMR (400 MHz, CDCl3): δ [7.94 (d), 7.78 (d), 7.50 (t), 7.44 (dd), 2H], 7.36-7.20 (m, 5H), [2.93 (s), 2.56 (s), 3H], 2.84-2.72 (m, 2H), 2.08-1.96 (m, 2H), 1.91-1.79 (m, 2H), 1.10-1.01 (m, 3H). |
| 196 | $^1$H NMR (400 MHz, CDCl3): δ 7.79 (d, 1H), 7.64 (d, 1H), 7.39 (t, 1H), 7.29-7.24 (m, 1H), 7.22 (d, 1H), 6.90 9d, 1H), 6.86 (dd, 1H), 3.81 (s, 3H), 3.64-3.56 (m, 1H), 2.90-2.80 (m, 1H), 2.76-2.67 (m, 1H), 1.89-1.71 (m, 2H), 1.63-1.46 (m, 2H), 0.98 (t, 3H). |
| 197 | $^1$H NMR (400 MHz, $CDCl_3$): δ 8.28 (d, 1H), 8.21 (broad s, 1H), 7.87 (d, 1H), 7.79 (t, 1H), 7.73 (d, 1H), 7.60 (t, 1H), 7.50 (d, 2H), 7.05 (d, 2H), 5.47 (s, 2H), 1.76 (s, 3H). |
| 198 | $^1$H NMR (400 MHz, $CDCl_3$): δ 8.36-8.16 (m, 2H), 7.90-7.72 (m, 3H), 7.61 (t, 1H), 6.88 (d, 1H), 6.76 (d, 1H), 6.66 (dd, 1H), 5.55 (s, 2H), 3.92 (s, 3H), 2.66 (t, 2H), 1.99-1.92 (m, 2H), 1.85-1.76 (m, 2H), 1.02 (t, 3H). |
| 199 | $^1$H NMR (400 MHz, $CDCl_3$): δ 8.33 (br s, 2H), 7.93-7.77 (m, 3H), 7.63 (t, 1H), 7.20 (s, 1H), 7.03-6.93 (m, 2H), 5.60 (s, 2H), 3.94 (s, 3H), 1.75 (s, 3H). |

Although any methods and materials similar or equivalent to those described herein can also be used in the practice or testing of the present invention, a limited number of the exemplary methods and materials are described herein. Generally, unless otherwise indicated, the materials for making the invention and/or its components may be selected from appropriate starting materials.

Where a range of values is provided herein, it is understood that each intervening value, to the tenth of the unit of the lower limit unless the context clearly dictates otherwise, between the upper and lower limit of that range and any other stated or intervening value in that stated range is encompassed within the disclosure. The upper and lower limits of these smaller ranges may independently be included in the smaller ranges is also encompassed within the disclosure, subject to any specifically excluded limit in the stated range. Where the stated range includes one or both of the limits, ranges excluding either or both of those included limits are also included in the disclosure.

For example, any concentration range, percentage range, ratio range, or integer range provided herein is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means ±20% of the indicated range, value, or structure, unless otherwise indicated.

All of the U.S. patents, U.S. patent application publications, U.S. patent applications, foreign patents, foreign patent applications and non-patent publications referred to in this specification and/or listed in the Application Data Sheet are incorporated herein by reference, in their entirety. Such documents may be incorporated by reference for the purpose of describing and disclosing, for example, materials and methodologies described in the publications, which might be used in connection with the presently described invention. The publications discussed above and throughout the text are provided solely for their disclosure prior to the filing date of the present application. Nothing herein is to be construed as an admission that the inventors are not entitled to antedate any referenced publication by virtue of prior invention.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A compound of formula (1)

(1)

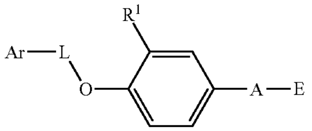

or a pharmaceutically acceptable enantiomer, diastereomer, salt, or solvate thereof, wherein:

Ar is a 9- or 10-membered bicyclic aromatic ring system, where Ar is substituted with one, two or three substituents, wherein Ar is substituted with at least one —S—$CH_3$;

L is selected from a direct bond and methylene;

$R^1$ is selected from hydrogen, halide, $C_1$-$C_6$alkyl, $C_1$-$C_6$haloalkyl, $C_1$-$C_6$alkoxy, $C_3$-$C_6$cycloalkoxy and $C_1$-$C_6$alkoxy substituted with $C_3$-$C_6$cycloalkyl;

A is selected from a direct bond, —$CH_2$— and —$CH_2CH_2$—;

E is $C(OR^3)R^4R^5$;

$R^3$ is selected from H, alkyl and substituted alkyl;

$R^4$ is selected from hydrogen, alkyl and phenyl; and $R^5$ is selected from $C_1$-$C_7$alkyl, $C_1$-$C_7$haloalkyl, phenyl and substituted phenyl.

2. The compound of claim 1 wherein Ar is a mono-substituted 9-membered bicyclic aromatic ring.

3. The compound of claim 1 wherein Ar is a mono-substituted 10-membered bicyclic aromatic ring.

4. The compound of claim 1 wherein Ar is selected from 1,3-benzoxazole, 2-methylquinoline, and 1,3-benzothiazole.

5. The compound of claim 1 wherein Ar is naphthalene or a nitrogen-substituted analog thereof selected from 1,5-naphthyridine, 1,6-naphthyridine, 1,7-naphthyridine, 1,8-naphthyridine, isoquinoline, phthalazine, 2,6-naphthyridine and 2,7-naphthyridine.

6. The compound of claim 1 wherein L is a direct bond.

7. The compound of claim 1 wherein $R^1$ is $C_1$-$C_6$alkoxy.

8. The compound of claim 1 wherein E is —$C(OR^3)R^4R^5$.

9. The compound of claim 1 wherein $R^3$ is hydrogen.

10. The compound of claim 1 wherein $R^4$ is alkyl.

11. The compound of claim 1 wherein $R^5$ is $C_1$-$C_7$haloalkyl.

12. A pharmaceutical composition comprising a compound according to claim 1, or a pharmaceutically acceptable enantiomer, salt or solvate thereof, and at least one pharmaceutically acceptable carrier, diluent, excipient and/or adjuvant.

13. A method of treating an inflammatory disease or inflammatory condition comprising administrating to a subject in need thereof an effective amount of a compound of claim 1.

14. A method of treating an autoimmune disease or autoimmune condition comprising administrating to a subject in need thereof an effective amount of a compound of claim 1.

15. A method of treating an allergic disease comprising administrating to a subject in need thereof an effective amount of a compound of claim 1.

16. A method of treating a conjunctivitis comprising administrating to a subject in need thereof an effective amount of a compound of claim 1.

17. A method of treating uveitis comprising administrating to a subject in need thereof an effective amount of a compound of claim 1.

18. A method of treating atopic dermatitis comprising administrating to a subject in need thereof an effective amount of a compound of claim 1.

19. A method of treating dry eye comprising administrating to a subject in need thereof an effective amount of a compound of claim 1.

20. A method of treating allergic conjunctivitis comprising administrating to a subject in need thereof an effective amount of a compound of claim 1.

* * * * *